US012630563B2

(12) United States Patent
Lamotte et al.

(10) Patent No.: US 12,630,563 B2
(45) Date of Patent: May 19, 2026

(54) MACROCYCLIC RIP2-KINASE INHIBITORS

(71) Applicant: Oncodesign S.A., Dijon Cedex (FR)

(72) Inventors: Yann Lamotte, Villebon sur Yvette (FR); Nérina Dodic, Les Ulis cedex (FR); Aurélien Tap, Saulx les Chartreux (FR); Alexis Denis, Paris (FR); Jean-Marie Brusq, Dampierre en Yvelines (FR); Mourad Daoubi Khamlichi, Murcia (ES); Pascal André René Benderitter, St Apollinaire (FR)

(73) Assignee: Oncodesign S.A., Dijon (FR)

( * ) Notice: Subject to any disclaimer, the term of this patent is extended or adjusted under 35 U.S.C. 154(b) by 833 days.

(21) Appl. No.: 17/759,644

(22) PCT Filed: Feb. 1, 2021

(86) PCT No.: PCT/EP2021/052255
§ 371 (c)(1),
(2) Date: Jul. 28, 2022

(87) PCT Pub. No.: WO2021/152165
PCT Pub. Date: Aug. 5, 2021

(65) Prior Publication Data

US 2023/0126352 A1 Apr. 27, 2023

(30) Foreign Application Priority Data

Jan. 31, 2020 (EP) .................................... 20154852

(51) Int. Cl.
*C07D 498/22* (2006.01)
*A61P 29/00* (2006.01)
*C07F 7/08* (2006.01)

(52) U.S. Cl.
CPC ............ *C07D 498/22* (2013.01); *A61P 29/00* (2018.01); *C07F 7/0834* (2013.01); *C07B 2200/05* (2013.01); *C07B 2200/07* (2013.01)

(58) Field of Classification Search
CPC .................................................... C07D 498/22
See application file for complete search history.

(56) References Cited

FOREIGN PATENT DOCUMENTS

| | | | |
|---|---|---|---|
| WO | 2014140235 | A1 | 9/2014 |
| WO | 2014140299 | A1 | 9/2014 |
| WO | 2015136073 | A1 | 9/2015 |
| WO | 2016042087 | A1 | 3/2016 |
| WO | 2016042089 | A1 | 3/2016 |

OTHER PUBLICATIONS

Canning et al. (Chemistry & Biology, 2015, 22, 1174-1184).*

International Search Report and Written Opinion mailed Feb. 26, 2021 in reference to co-pending European Application No. PCT/EP2021/052255 filed Feb. 1, 2021.

Tigno-Aranjuez, et al., "In Vivo Inhibition of RIPK2 Kinase Alleviates Inflammatory Disease", Journal of Biological Chemistry, vol. 289, No. 43, Sep. 11, 2014, pp. 29651-29664, XP055191179.

Danker, et al., "early identification of hERG liability in drug discovery programs by automated patch clamp", Frontiers in Pharmacology, vol. 5, Article 203, pp. 1-11, Sep. 2014.

Duggan, et al., Tyrosine kinase inhibitors of Ropk2 attenuate bacterial cell wall-mediated lipolysis, inflammation and dysglycermia, Scientific Reports, vol. 7, pp. 1-13, 2017.

Franca, et al., "Expression and activity of NOD1 and NOD2/RIPK2 signalling in mononuclear cells from patients with rehumatoid arthritis", Scan J. Rheumatol, pp. 1-5, 2015.

Gambnino, et al., "A Three-Dimensional Lymphatic Endothelial Cell Tube Formation Assay to Identify Novel Kinases Involved in Lymphatic Vessel Remodeling", Assay and Drug Development Technologies, vol. 15, No. 1, pp. 30-43, Jan. 2017.

Girardin, et al., "CARD4/Nod1 mediates NF-κB and JNK activation by invasive Shigella flexneri", Scientific Report, vol. 2, No. 81, pp. 736-742, 2001.

Haile, et al., "Discovery of a First-in-Class Receptor Interacting Protein 2 (RIP2) Kinase Specific Clinical Candidate, 2-((2-4-(Benzo[d]thiazol-5-ylamino)-6-(tert-butylsulfonyl)quinazolin-7-yl)oxy)ethyl Dihyrdrogen Phosphate, for the Treatment of Inflammatory Diseases", Journal of Medicinal Chemistry, pp. A-M, 2019.

Hysi, et al., "NOD1 variation, immunoglobulin E and asthma", Human Molecular Genetics, vol. 14, No. 7, pp. 935-941, 2005.

Mcovern, et al., "Association between a complex insertion/deletion polymorphism in NOD1 (CAD4) and susceptibility to inflammatory bowel disease", Human Molecular Genetics, vol. 14, No. 10, pp. 1245-1250, 2005.

(Continued)

*Primary Examiner* — Susanna Moore
(74) *Attorney, Agent, or Firm* — Dinsmore & Shohl LLP

(57) ABSTRACT

The present invention relates to macrocyclic compounds and compositions containing said compounds acting as kinase inhibitors, in particular as inhibitors of RIP2-kinase, and/or mutants thereof, for use in the diagnosis, prevention and/or treatment of RIP2-kinase associated diseases. Moreover, the present invention provides methods of using said compounds, for instance as a medicine or diagnostic agent. In particular, the present disclosure relates to a compound according to Formula(I):

(I)

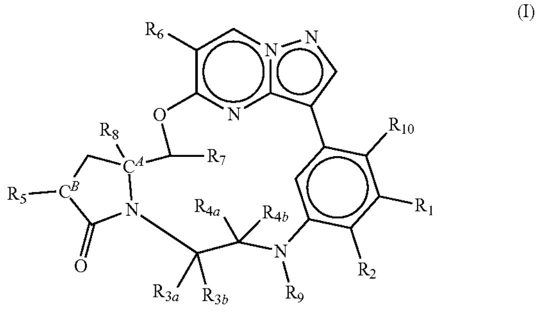

or a stereoisomer, tautomer, racemate, salt, hydrate, N-oxide form, or solvate thereof.

10 Claims, No Drawings

(56) References Cited

OTHER PUBLICATIONS

Inaki, et al., "Systems consequences of amplicon formation in human breast cancer", Genome Research, vol. 24, pp. 1559-1571, Jun. 3, 2016.
Vieira, et al., "Joint NOD2/RIPK2 Signaling Regulates IL-17 Axis and Contributes to the Development of Experimental Arthritis", The Journal of Immunology, vol. 188, pp. 5116-5122, Apr. 2012.
Inohara, et al., "An Induced Proximity Model for NF-κB Activation in the Nod1/RICK and RIP Signaling Pathways", The Journal of Biological Chemistry, vol. 275, No. 36, pp. 27823-27831, Sep. 8, 2000.
Hollenbach, et al., "Inhibition of TICK/Nuclear Factor-κB and p38 Signaling Attenuates the Inflammatory Response in a Murine Model of Crohn Disease", The Journal of Biological Chemistry, vol. 280, No. 15, pp. 14981-14988, Apr. 15, 2005.
Jaafar, et al., "RIP2 enhances cell survival by activation of NF-κB in triple negative breast cancel cells", Biochemical and Biophysical Research Communications, pp. 1-7, 2018.
Kabesch, et al., "Association between polymorphisms in caspase recruitment domain containing protein 15 and allergy in two German populations", Mechanisms of allergy, vol. 111, No. 4, pp. 813-817, 2003.
Borchardt, "Drug Design with ADME in Mind: Recent Paradigm Shifts in Drug Discovery", Toward Drugs of the Future, IOS Press, pp. 53-74, 2009.
Lesage, et al., "CARD15/NOD2 Mutational Analysis and Genotype-Phenotype Correlation in 612 Patients with Inflammatory Bowel Disease", American Journal Human Genet., vol. 70, pp. 845-857, 2002.
Liu, et al., "Non-canonical NF-κB Plays a Pivotal Role in Non-Hodgkin's Lymphoma", Cell Biochem Biophys, vol. 72, pp. 681-685, 2015.
Maloney, et al., "Gefitinib Blocks Macrophage-Promoted Invasion of Osteosarcoma via Inhibition of Receptor-Interacting Protein Kinase 2 (RIPK2) and Prevents Progression of Pulmonary Micrometastases", J. Am. Coll. Surg., Scientific Forum Abstracts, p. S150, 2017.
Mertins, et al., "Proteogenomics connects somatic mutations to signalling in breast cancer", Nature Article, vol. 534, pp. 55-73, Jun. 2, 2016.
Brief Communications, "CARD15 mutations in Blau syndrome", Nature Publishing Group, vol. 29, pp. 19-20, Sep. 2001.
Negroni, et al., "Activation of NOD2-mediated Intestinal Pathway in a Pediatric Population with Crohn's Disease", Original Article, Inflamm. Bowel Dis., vol. 15, No. 15, pp. 1145-1154, Aug. 2009.
Zhou, et al., "Increased NOD1, but Not NOD2, Activity in Subcutaneous Adipose Tissue from Patients with Metabolic Syndrome", Obesity Biology and Integrated Physiology, vol. 23, pp. 1394-1400, 2015.
Chen, et al., "Fusobacterium nucleatum Promotes Metastasis in Colorectal Cancer by Activating Autophagy Signaling via the Upregulation of CARD3 Expression", Theranostics, vol. 10, Issue 1, pp. 323-339, 2020.
Singel, et al., "Receptor-interacting protein kinase 2 promotes triple-negative breast cancer cell migration and invasion via activation of nuclear factor-kappaB and c-Jun N-terminal kinase pathways", Breast Cancer Research, vol. 16, pp. 1-14, 2014.
Som, et al., "Immune checkpoint inhibitor-induced colitis: A comprehensive review", World Journal of Clinical Cases, vol. 7, No. 4, pp. 405-418, Feb. 2019.
Strober, et al., "Signalling pathways and molecular interactions of NOD1 and NOD2", Nature Review Immunology, vol. 6, pp. 9-20, Jan. 2006.
Stronati, et al., "Altered expression of innate immunity genes in different intestinal sites of children with ulcerative colitis", Digestive and liver Disease, vol. 42, pp. 848-853, 2010.
Brooks, "Erlotinib and Gefitinib, Epidermal Growth Factor Receptor Kinase Inhibitors, May Treat Non-Cancer-Related Tumor Necrosis Factor-x-Mediated Inflammatory Diseases", The Oncologist, pp. e3-e5, 2013.
Uehara, et al., "PR3-ANCA in Wegener's granulomatosis prime human mononuclear cells for enhanced activation via TLRs and NOD1/2", Diagnostic Pathology, vol. 4, No. 23, pp. 1-10, 2009.
Zhao, et al., "RIP2 deficiency attenuates cardiac hypertrophy, inflammation and fibrosis in pressure overload induced mice", Biochemical and Biophysical Research Communications, pp. 1-20, 2017.
Wiken, et al., "Higher Monocyte Expression of TLR2 and TLR4, and Enhanced Pro-inflammatory Synergy of TLR2 with NOD2 Stimulation in Sarcoidosis", Journal Clinical Immunology, vol. 29, pp. 78-79, 2009.
Yamamoto, et al., "Role of Nod2 in the development of Crohn's disease", Microbes Infect., vol. 11, No. 12, pp. 912-918, 2009.
Yang, et al., "Coronary Artery Remodeling in a Model of Left Ventricular Pressure Overload Is Influenced by Platelets and Inflammatory Cells", PLOS One, vol. 7, Issue 8, pp. 1-12, Aug. 2012.
Zare, et al., "RIPK2: New Elements in Modulating Inflammatory Breast Cancer Pathogenesis", Cancers, vol. 10, No. 184, pp. 1-17, 2018.
Jun et al., "RIP2 activity in inflammatory disease and implications for novel therapeutics," Journal of Leukocyte Biology, 94(5):927-32 (2013).
Axelrad et al., "Inflammatory bowel disease and cancer: The role of inflammation, immunosuppression, and cancer treatment," World J. Gastroenterol, 22(20):4794-4801 (2016).
Chen et al., "A novel enhancer regulates MGMT expression and promotes temozolomide resistance in glioblastoma," Nat. Commun., 9(1):2949 (2018).
Fox et al., "The serine/threonine kinase PIM-2 is a transcriptionally regulated apoptotic inhibitor," Genes and Dev., 17 (15): 1841-54 (2003).
Wu et al., "Correct Interpretation of Comprehensive Phosphorylation Dynamics Requires Normalization by Protein Expression Changes," Molecular & Cellular Proteomics, pp. 1-12 (2011).

* cited by examiner

MACROCYCLIC RIP2-KINASE INHIBITORS

CROSS REFERENCES TO RELATED APPLICATIONS

This application is a national-stage application under 35 U.S.C. § 371 of International Application No. PCT/EP2021/052255, filed Feb. 1, 2021, which International Application claims benefit of priority to European Patent Application No. 20154852.6, filed Jan. 31, 2020.

FIELD OF THE INVENTION

The present invention relates to macrocyclic compounds and compositions containing said compounds acting as kinase inhibitors, in particular as inhibitors of RIP2-kinase, and/or mutants thereof, for use in the diagnosis, prevention and/or treatment of RIP2-kinase associated diseases. Moreover, the present invention provides methods of using said compounds, for instance as a medicine or diagnostic agent.

BACKGROUND TO THE INVENTION

Protein kinases constitute a large family of structurally related enzymes that are responsible for the control of a wide variety of signal transduction processes in the cell. They have been shown to be key regulators in most cellular functions including proliferation, cell metabolism, cell survival, apoptosis, DNA damage repair, cell motility . . . Uncontrolled signaling due to defective control of protein phosphorylation has been implicated in a number of diseases, including, for example, cancer, inflammation, allergies, immune diseases, CNS disorders, angiogenesis . . . .

Amongst the families of protein kinases, one particular example is the Receptor-Interacting Serine/Threonine Kinases including RIP2. RIP2 (Receptor-Interacting Protein 2) is also referred to as Card-Containing Ice-Associated Kinase (CARDIAK), CARD3 (C-terminal CAspase-Recruitment Domain 3), Receptor-Interacting Protein Kinase 2 (RIPK2), or Rip-Like Interacting Clarp Kinase (RICK). RIP2 kinase is composed of an N-terminal kinase domain and a C-terminal caspase-recruitment domain (CARD) linked via an intermediate (IM) region (Chin et al., Curr. Med. Chem. 2005 4 1:35-42). The CARD domain of RIP2 kinase mediates interaction with other CARD-containing proteins, such as the Nucleotide Oligomerization Domain Proteins, NOD1 and NOD2 (Inohara et al., J. Biol. Chem. 2000 36:27823-31 and Girardin et al., EMBO Rep. 2001 2:736-742). NOD1 and NOD2 are cytoplasmic receptors which are activated by specific bacterial peptidoglycan motifs and play a key role in innate immune surveillance. Upon intracellular bacterial exposure, NOD1 or NOD2 binds to the protein kinase RIP2 to coordinate NF-κB (nuclear factor κ B)-mediated cytokine responses. Once associated with NOD1/2, RIP2 undergoes autophosphorylation on Tyr 474 (Y474), and acts as a molecular scaffold to bring together other kinases (TAK1, IKKβ involved in NF-κB and MAPK activation (Strober et al., Nat. Rev. Immunol. 2006 1:9-20).

Both NOD1/2 and RIP2 are NF-κB regulated genes, and as such, their activation causes a positive feedback loop in which activation of NOD1/2:RIP2 stimulates further activation and further inflammation. Additionally, NOD1/2 and RIP2 expression are stimulated by a variety of mediators of inflammation, including TNF (Tumor Necrosis Factor) and IFN (Interferon). In addition to NF-κB pathway activation, the NOD1/2:RIP2 complex stimulates autophagy, bactericidal activity, MHC Class II presentation and MAPK (Mitogen-Activated Protein Kinase) activation. Overall, this pathway modulates the innate immune system to help tailor the adaptive immune response to eradicate the offending pathogen.

Dysregulation of RIP2-dependent signaling has been linked to autoinflammatory diseases. Patients with loss-of-function NOD2 alleles are prone to the development of Crohn's disease, an inflammatory disorder of the gastrointestinal tract (Lesage et al., Am. J. Hum. Genet. 2002 70:845-857 and Yamamoto et al., Microbes & Infections 2009 12:912-918). Several groups showed that the NOD2/RIPK2 pathway is involved in the pathogenesis of IBD (Negroni et al., Inflamm. Bowel. Dis. 2009 8:1145-1154; Stronati et al., Digestive and Liver Disease 2010 12:848-853; Haile et al., J. Med. Chem. 2019 14:6482-6494; Chen et al., J. Pathol. 2020 250 2:170-182). Negroni showed for the first time an upregulation of both NOD2 and RIPK in colon biopsies from CD patients (Negroni et al., Inflamm. Bowel Dis. 2009 8:1145-1154). Stronati confirmed this finding in a UC pediatric population. Interestingly, beyond RIPK2 and NOD2 upregulations and the subsequent cytokines increase this group also suggested that HD5 and HD6 upregulation (two human defensins, acting as a major component of epithelial innate immune system) could be attributed to NOD2/RIPK2 (Stronati et al., Digestive and Liver Disease 2010 12:848-853). Finally, Haile et al. showed that a selective RIPK2 inhibitor could block the spontaneous pro-inflammatory cytokines secretion from UC/CD patient's biopsies. This result underlines that RIPK2 activation in the UC/CD patient's mucosa leads to the pro-inflammatory status of these biopsies (Haile et al., J. Med. Chem. 2019 14:6482-6494). Also, Chen et al. studies on links between *Fusobacterium nucleatum* (*F. nucleatum*) and ulcerative colitis shed a new light on RIK2 role in the epithelial damage. In this paper the authors concluded that, *F. nucleatum* targeted CARD3 through NOD2 to activate the IL-17F/NF-κB pathway in-vivo. Thus, *F. nucleatum* orchestrates a molecular network involving CARD3 and IL-17F to control the UC process (Chen et al., J. Pathol. 2020 250 2:170-182). Another cause of IBD is called IMC (for immune mediated colitis). IMC is a side effect of immune-checkpoint inhibition (ICI). All immune-checkpoint inhibitors (anti-CTLA-4, anti-PD-1 and anti-PD-L1) are at risk for immune-related adverse events. The incidence of IMC ranges from 0.3% to 7% and occur 5 weeks to 10 weeks after the 2nd or 3rd doses of ICI (Som et al., World J. Clin. Cases 2019 4:405-418). Current treatment are oral corticosteroids (mild to moderate stages) and systemic corticosteroids for severe grade. However, about half of IMC patients have a corticosteroid-refractory colitis. Then, anti-TNFα inhibitor treatment is an option. RIPK2 inhibition could be an additional treatment option with a new mechanism of action.

Viera et al. (Vieira et al., J. Immunol. 2012 10:5116-5122) have first described another indication when they pointed out the role of NOD2/RIPK2 in the development of experimental arthritis.

Franca et al. (Franca et al., Scand. J. Rheumatol. 2016 45:8-12) confirmed these findings on rheumatoid arthritis (RA) patients. They showed that NOD2/RIPK2 pathway was up-regulated in immune cells of RA patients suggesting that RIPK2 inhibition could be beneficial in this population.

Gain-of-function NOD2 mutations have been genetically linked to other inflammatory diseases, such as Blau Syndrome/Early Onset Sarcoidosis (EOS), a pediatric granulomateous disease characterized by uveitis, dermatitis, and arthritis (Miceli-Richard et al., Nature Genetics 2001 29:19-

20 and Becker et al., Curr. Rheum. Reports 2005 7:427-433). Broad genotyping of young patients suffering from allergic rhinitis and atopic dermatitis highlighted common NOD2 polymorphism with Crohn's disease (Kabesh et al., J. Allergy Clin. Immunol. 2003 4:813-7) as probable leading cause of the excessive immune response against skin tissues observed.

Mutations in NOD1 have been associated with asthma (Hysi et al., Hum. Mol. Genet. 2005 14:935-941), and early-onset and extra-intestinal inflammatory bowel disease (McGovern et al., Hum. Mol. Genet. 2005 14:1245-1250). Genetic and functional studies have also suggested a role for RIP2-dependent signaling in a variety of other granulomateous disorders, such as sarcoidosis (Wiken et al., J. Clin. Immunol. 2009 29:78-89) and Wegner's Granulomatosis (Uehara et al., Diag. Path. 2009 4:23).

Metabolic syndrome, a pathology closely related to obesity and overweight, results from a chronic inflammation and is characterized by hypertension, hyperglycemia and lipolysis dysfunction. Activation of the immune system through NOD1 pathway was observed in patients suffering from metabolic syndrome (Zhou et al., Obesity 2015 7:1394-1400). A recent functional study highlighting the impact of RIPK2 inhibitors on lipolysis suggested a role for RIP2-dependent signaling in dysglycemia and lipolysis (Duggan et al., Scientific reports 2017 7:1578).

In cardiac hypertrophy, a complex and multifactorial pathology, inflammation was shown as important hallmark of the disease, notably through the activation of NF-kB signaling (Yang et al., PLoS One 2012 8:e40196). Knockout studies of RIPK2 on hypertrophic heart mice models subjected suggested a role in the regulation of the inflammation and subsequent tissue fibrosis and hypertrophy (Zhao et al., Biochem. Biophys. Res. Commun. 2017 2:1151-1158).

Beyond immuno-inflammatory diseases, RIPK2 modulation has also been described in several cancers. In triple negative breast cancer (TNBC), RIPK2 high expression has been associated to worse progression-free survival (Singel et al., Breast Cancer Res. 2014 16:R28) as well as a worse overall survival (Jaafar et al., Biochem. Biophys. Res. Commun. 2018 1:115-121). In the first study, authors showed that RIPK2 knockdown increases docetaxel sensitivity and decreases tumor and lung metastasis. Another group studied a new cancer gene cassette on breast cancer patients' chromosome 8 (Inaki et al., Genome Research 2014 24: 1559). They discovered RIPK2 coamplification with other tested oncogenes (such as MYC). In 2016, Mertins et al., studied TNBC biopsies in order to find druggable kinases beyond HER2. It turned-out that RIPK2 was hyper-phosphorylated in basal-like and luminal B breast cancer biopsies suggesting that this pathway could be activated in these type of TNBC (Mertins et al., Nature 2016 7605:55-62).

More recently, phospho-RIPK2 levels as well as NF-kB activity were shown elevated in biopsies of Inflammatory Breast Cancer (Zare et al., Cancers 2018 10:184). Using 34 head and neck squamous cell carcinoma cell lines, Wu et al. showed that RIPK2 knockdown led to cell death, indicating central roles of the protein for cell survival (Wu et al., Mol. Cell. Proteomics 2011 10: 1-14). While others claimed that RIPK2 promotes glioma cell growth by regulating TRAF3 and activating the NF-kB pathway and p38 signaling (Cai et al., Oncology Reports 2018 39:2915-2923).

Taken together these data strongly support the development of RIPK2 inhibitors in oncology. In 2017, Maloney et al. described a new role for RIPK2 in osteosarcoma invasion showing that Gefitinib, via RIPK2 inhibition, prevented progression of pulmonary metastasis (Maloney et al., J. Am. Col. Surg. 2017 4(S1):S150). Moreover, Liu et al. discovered that non-canonical NF-κB plays a pivotal role in non-Hodgkin's lymphoma (Liu et al., Cell. Biochem. Biophys. 2015 72 3:681-5). Finally, using a three-dimensional lymphatic endothelial cell tube formation, Gambino et al. identified RIPK2 as a kinase involved in lymphatic vessel remodeling, a key factor for the metastatic spread of cancer (Gambino et al., Assay Drug. Dev. Technol. 2017 15 1:30-43).

The fact that both loss-of-function polymorphisms and gain-of-function mutations cause inflammatory diseases is likely due to the fact that NOD2 functions a possible function of NOD2 as a rheostat to help maintain normal immunologic homeostasis. Lack of coordination between inflammatory signaling pathways influences the development of inflammatory disorders, and the NOD1/2:RIP2 activation equilibrium is central to this coordination. Treatments for Crohn's disease and sarcoidosis currently rely on broad, non-specific immunologic inhibition (e.g., corticosteroids) or on specific cytokine inhibition (e.g., anti-TNF therapies) with significant costs and side effects. Treatment is less than ideal, however, because not all agents are equally efficacious, the diseases occur over long time frames, and not all agents remain efficacious in the same patient. The RIP2 Y474 autophosphorylation event has been shown to be necessary for effective NOD2 signaling and does not occur in the presence of the most common loss-of-function Crohn's disease-associated NOD2 allele. This autophosphorylation is inhibited by non highly selective kinase inhibitors, Gefitinib and Erlotinib, suggesting that RIP2's tyrosine kinase activity could be targeted specifically in the treatment of inflammatory diseases (Tigno-Aranjuez et al., Genes Dev 2010 1:2666-77). Several clinical cases were reported about Gefitinib or Erlotinib treatment being efficient to clear psoriasis or reduce arthritic symptoms or insulin-resistant type 2 diabetes associated with metabolic syndrome (Brooks, The Oncologist 2013 1:e3-e5). In mouse established models of chronic inflammatory bowel diseases, inhibition of RIP2 activity by the small molecule SB203580 is efficacious to reduce induced-colitis (Hollenbach et al., JBC, 2005, 280: 14981-8). None of these small molecules however, primarily and selectively targets RIP2. It was therefore an object of the present invention to provide a potent, selective, small molecule inhibitor of RIP2 kinase activity which can block specifically RIP2-dependent pro-inflammatory signaling and thereby provides a therapeutic benefit in auto-inflammatory diseases characterized by increased and/or dysregulated RIP2 kinase activity.

We have now found that the macrocyclic compounds and pharmaceutically acceptable compositions according to this invention are useful for the treatment of inflammatory disorders, in particular Crohn's disease, bowel disease, sarcoidosis, psoriasis, atopic dermatitis, allergic rhinitis, rheumatoid arthritis, asthma, insulin-resistant type 2 diabetes, obesity metabolic syndrome, cardiac hypertrophy, ulcerative colitis, lupus, uveitis, Blau syndrome, granulomatous inflammation, in particular Behget's disease, immune-mediated colitis, multiple sclerosis, and diseases associated with RIP2 kinase activity (i.e. RIP2-kinase associated diseases). Our macrocyclic compounds and pharmaceutically acceptable compositions according to this invention are also useful in oncology, in particular to treat breast cancers (including Inflammatory Breast Cancer), head and neck cancers and gliomas.

In a previously published patent application WO2016/042087 was disclosed a series of macrocyclic pyrazolopyrimidine with nanomolar RIPK2 inhibition, determined by a biochemical assay. Representatives of the series are the two examples 04 and 011.

Example O4

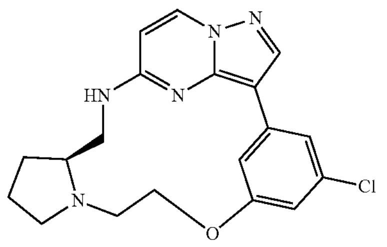

Example O11

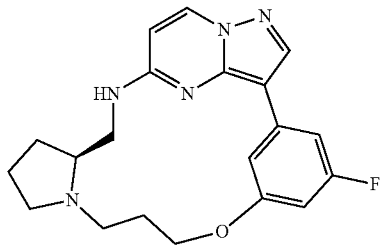

SUMMARY OF THE INVENTION

We have surprisingly found a specific combination of several structural modifications of the macrocyclic compounds described herein, such as introduction of substitutions on the pyrrolidine moiety and the replacement of X1=—NH—$C_{1-6}$alkyl and X2=O—$C_{1-6}$alkyl by X1=O—$C_{1-6}$alkyl and X2=—NH—$C_{1-6}$alkyl (X1 and X2 referring to the Markush formula I described in patent WO2016/042087), which led to drastic improvement of key developability and safety parameters, such as human protein binding, human microsomal metabolic stability and hERG channel inhibition. In more details, as depicted in the Comparative Table between some representative compounds of WO2016/042087 and the compounds of the present invention (see end of experimental part), the compounds described in the present invention display improved human protein binding free fraction (Assay A), a higher metabolic stability (Assay B), and a lower hERG inhibition liability (Assay C). Plasma protein binding, metabolic stability and hERG liability have been recognized in the last 15 years as key developability parameters to optimize in addition to potency and specificity (*Towards Drugs of the Future*, IOS Press, 2009, 9:53-74). For example, hERG link to cardiotoxicity was recognized as key developability parameter to address, as published by Danker et al (Danker et al, Front. Pharmacol. 2014, 5:203).

Accordingly, in a first aspect, the present invention provides a compound of Formula I or a stereoisomer, tautomer, racemic, salt, hydrate, N-oxide form, or solvate thereof,

I

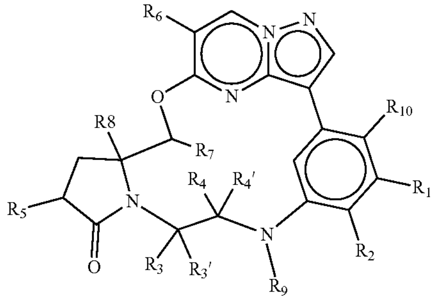

Wherein $R_1$ is selected from -Halo, —O—$C_{1-6}$alkyl, -Alkynyl, —$C_{1-6}$alkyl, —$C_{3-6}$-cycloalkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH; each of said -Alkynyl being optionally substituted with one substituent selected from —$C_{1-6}$alkyl, and —$CH_2$—O—$C_{1-6}$alkyl;

$R_2$ and $R_{10}$ are each independently selected from —H, and -Halo;

$R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;

wherein when $R_3$ and/or $R_{3'}$ is —$C_{1-6}$alkyl, then $R_4$ and $R_{4'}$ are each —H;

wherein when $R_4$ and/or $R_{4'}$ is —$C_{1-6}$alkyl, then $R_3$ and $R_{3'}$ are each —H;

$R_5$ is selected from —OH, —$NR_cR_{c'}$, —NHC(O)$R_c$, —NC(O)$R_cR_{c'}$, —NC(O)O$R_c$, —NHS($O_2$)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -Halo, —$C_{1-6}$alkyl, —O—$C_{1-6}$ alkyl, and -$Het_3$; each of said —$C_{1-6}$alkyl being optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl; each of said —$C_{1-6}$alkyl being optionally substituted with one or more substituents selected from -D, and —$C_{1-6}$alkyl;

$R_b$ is selected from —H, —$C_{1-6}$alkyl, and —O—$C_{1-6}$ alkyl; each of said —$C_{1-6}$alkyl being optionally substituted with one or more substituents selected from -D, —$C_{1-6}$alkyl, and —$C_{3-5}$-cycloalkyl;

$R_c$ and $R_{c'}$ are each independently selected from —H, and —$C_{1-6}$alkyl; each of said —$C_{1-6}$alkyl being optionally substituted with one or more substituents selected from -D, and —$C_{1-6}$alkyl;

$Het_1$ and $Het_3$ are each independently selected from a 5 or 6-membered aromatic heterocycle having from 1 to 3 heteroatoms selected from O, N and S, wherein each of said $Het_1$ or $Het_3$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH;

$Het_2$ is selected from a 4 to 6-membered saturated heterocycle having from 1 to 3 heteroatoms selected from O and N; wherein each of said $Het_2$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH.

Alternatively, in a first aspect, the present invention provides a compound of Formula I or a stereoisomer, tautomer, racemic, salt, hydrate, N-oxide form, or solvate thereof,

I

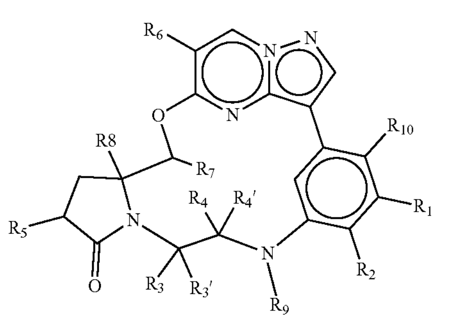

Wherein $R_1$ is selected from -Halo, —O—$C_{1-6}$alkyl, -Alkynyl, —$C_{1-6}$alkyl, —$C_{3-6}$-cycloalkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH; each of said -Alkynyl being optionally substituted with one substituent selected from —$C_{1-6}$alkyl, and —$CH_2$—O—$C_{1-6}$alkyl;

$R_2$ and $R_{10}$ are each independently selected from —H, and -Halo;

$R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;

wherein when $R_3$ and/or $R_{3'}$ is —$C_{1-6}$alkyl, then $R_4$ and $R_{4'}$ are each —H;

wherein when $R_4$ and/or $R_{4'}$ is —$C_{1-6}$alkyl, then $R_3$ and $R_{3'}$ are each —H;

$R_5$ is selected from —OH, —$NR_cR_{c'}$; —NHC(O)$R_c$, —NC(O)$R_cR_{c'}$, —NC(O)O$R_c$, —NHS($O_2$)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl; each of said —$C_{1-6}$alkyl being optionally substituted with one or more substituents selected from -D, and —$C_{1-6}$alkyl;

$R_b$ is selected from —H, —$C_{1-6}$alkyl, and —O—$C_{1-6}$ alkyl; each of said —$C_{1-6}$alkyl being optionally substituted with one or more substituents selected from -D, —$C_{1-6}$alkyl, and —$C_{3-5}$-cycloalkyl;

$R_c$ and $R_{c'}$ are each independently selected from —H, and —$C_{1-6}$alkyl; each of said —$C_{1-6}$alkyl being optionally substituted with one or more substituents selected from -D, and —$C_{1-6}$alkyl;

$Het_1$ and $Het_3$ are each independently selected from a 5 or 6-membered aromatic heterocycle having from 1 to 3 heteroatoms selected from O, N and S, wherein each of said $Het_1$ or $Het_3$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH;

$Het_2$ is selected from a 4 to 6-membered saturated heterocycle having from 1 to 3 heteroatoms selected from O and N; wherein each of said $Het_2$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH.

In a specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —$C_{3-6}$-cycloalkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH;

$R_2$ and $R_{10}$ are each independently selected from —H, and -Halo;

$R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;

wherein when $R_3$ and/or $R_{3'}$ is —$C_{1-6}$alkyl, then $R_4$ and $R_{4'}$ are each —H;

wherein when $R_4$ and/or $R_{4'}$ is —$C_{1-6}$alkyl, then $R_3$ and $R_{3'}$ are each —H;

$R_5$ is selected from —OH, —$NR_cR_{c'}$; —NHC(O)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -Halo, —$C_{1-6}$alkyl, —O—$C_{1-6}$alkyl, —O-$Het_4$, and -$Het_3$; each of said —$C_{1-6}$alkyl being optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl;

$R_b$ is selected from —H, —$C_{1-6}$alkyl, and —O—$C_{1-6}$ alkyl;

$R_c$ and $R_{c'}$ are each independently selected from —H, and —$C_{1-6}$alkyl;

$Het_1$ and $Het_3$ are each independently selected from a 5 or 6-membered aromatic heterocycle having from 1 to 3 heteroatoms selected from O and N, wherein each of said $Het_1$ and $Het_3$ is optionally substituted with from 1 to 3 —$C_{1-6}$alkyl;

$Het_2$ is selected from a 4 to 6-membered saturated heterocycle having from 1 to 3 O atoms $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In another specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —$C_{3-6}$-cycloalkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH;

$R_2$ and $R_{10}$ are each independently selected from —H, and -Halo;

$R_3$, $R_{3'}$, $R_4$, $R_{4'}$, $R_7$, and $R_8$ are each —H;

$R_5$ is selected from —OH, -Halo, —O—$C_{1-6}$alkyl, —O—$C_{3-5}$-cycloalkyl, and —$C_{1-6}$alkyl; each of said —$C_{1-6}$alkyl being optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl;

$R_b$ is selected from —H, —$C_{1-6}$alkyl, and —O—$C_{1-6}$ alkyl; each of said —$C_{1-6}$alkyl being optionally substituted with one or more;

$Het_1$ and $Het_3$ are each independently selected from a 5 or 6-membered aromatic heterocycle having from 1 to 3 heteroatoms selected from O and N, wherein each of said $Het_1$ and $Het_3$ is optionally substituted with from 1 to 3 —$C_{1-6}$alkyl;

$Het_2$ is selected from a 4 to 6-membered saturated heterocycle having from 1 to 3 O atoms $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In yet a further specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —$C_{3-6}$-cycloalkyl, —C(O)—$C_{1-6}$-alkyl, —C(O)—$NR_aR_b$, -$Het_1$ and —CN; each of said —$C_{1-6}$ alkyl being optionally substituted with one or more substituents selected from -D, -Halo, and —O—$C_{1-3}$ alkyl;

$R_2$ is selected from —H, and -Halo;

$R_{10}$ is —H;

$R_3$, $R_{3'}$, $R_4$, $R_{4'}$, $R_7$, and $R_8$ are each —H $R_5$ is selected from —OH, -Halo, —O—$C_{1-6}$alkyl, —O—$C_{3-5}$-cycloalkyl, and —$C_{1-6}$alkyl; each of said —$C_{1-6}$alkyl being optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more —O—$C_{1-6}$alkyl;

$R_9$ is —H;

$R_a$ is selected from —H, and —$C_{1-6}$alkyl;

$R_b$ is selected from —H, —$C_{1-6}$alkyl, and —O—$C_{1-6}$ alkyl;

$Het_1$ is a 5-membered aromatic heterocycle having from 1 to 3 heteroatoms selected from O and N, wherein said $Het_1$ is optionally substituted with from 1 to 3 —$C_{1-6}$ alkyl $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In a more specific embodiment, the present invention provides a selected from any of the tables disclosed herein.

In another specific embodiment, in the compounds of the present invention, the carbon atom bearing the $R_8$ substituent may be in the S-configuration.

In a further specific embodiment, in the compounds of the present invention, the carbon atom bearing the $R_5$ substituent may be in the R-configuration.

The present invention further provides a pharmaceutical composition comprising a compound according to this invention.

In a further aspect, the present invention provides a compound or a composition according to this invention, for use as a medicine.

In a particular embodiment, the present invention provides a compound or composition according to this invention for use in the diagnosis, prevention and/or treatment of a RIP2-kinase associated disease. Said RIP2-kinase associated disease may in particular be an inflammatory disorder, in particular selected from the list comprising: Crohn's disease, bowel disease, sarcoidosis, psoriasis, atopic dermatitis, allergic rhinitis, rheumatoid arthritis, asthma, insulin-resistant type 2 diabetes, obesity metabolic syndrome, cardiac hypertrophy, ulcerative colitis, lupus, uveitis, Blau syndrome, granulomatous inflammation, Behget's disease, immune-mediated colitis, and multiple sclerosis. Alternatively, said RIP2-kinase associated disease may be cancer, more in particular selected from breast cancers (including Inflammatory Breast Cancer), head and neck cancers and gliomas.

Furthermore, the present invention provides the use of a compound or composition according to this invention, suitable for inhibiting the activity of a kinase; in particular a RIP2 kinase; or for the diagnosis, prevention and/or treatment of a RIP2-kinase associated disease.

Finally, the present invention provides a method for prevention and/or treatment of a RIP2-kinase associated disease; said method comprising administering to a subject in need thereof a compound or a composition according to the present invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides a compound of Formula I or a stereoisomer, tautomer, racemic, salt, hydrate, N-oxide form, or solvate thereof,

I

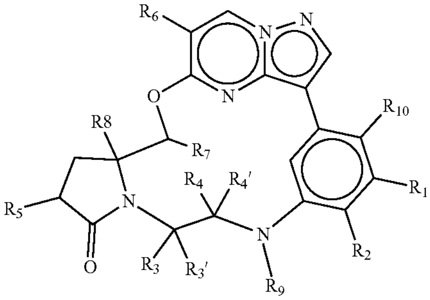

Wherein

- $R_1$ is selected from -Halo, —O—$C_{1-6}$alkyl, -Alkynyl, —$C_{1-6}$alkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH; each of said -Alkynyl being optionally substituted with one substituent selected from —$C_{1-6}$alkyl, and —$CH_2$—O—$C_{1-6}$alkyl;
- $R_2$ and $R_{10}$ are each independently selected from —H, and -Halo;
- $R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;
  - wherein when $R_3$ and/or $R_{3'}$ is —$C_{1-6}$alkyl, then $R_4$ and $R_{4'}$ are each —H;
  - wherein when $R_4$ and/or $R_{4'}$ is —$C_{1-6}$alkyl, then $R_3$ and $R_{3'}$ are each —H;
- $R_5$ is selected from —OH, —$NR_cR_{c'}$; —NHC(O)$R_c$, —NC(O)$R_cR_{c'}$, —NC(O)O$R_c$, —NHS($O_2$)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;
- $R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more substituents selected from -D, and —O—$C_{1-6}$alkyl;
- $R_9$ is selected from —H, —$C_{1-6}$alkyl, —C(O)—$C_{1-6}$alkyl, and —C(O)—O—$C_{1-6}$alkyl;
- $R_a$ is selected from —H, and —$C_{1-6}$alkyl; each of said —$C_{1-6}$alkyl being optionally substituted with one or more substituents selected from -D, and —$C_{1-6}$alkyl;
- $R_b$ is selected from —H, —$C_{1-6}$alkyl, and —O—$C_{1-6}$ alkyl; each of said —$C_{1-6}$alkyl being optionally substituted with one or more substituents selected from -D, —$C_{1-6}$alkyl, and —$C_{3-5}$-cycloalkyl;
- $R_c$ and $R_{c'}$ are each independently selected from —H, and —$C_{1-6}$alkyl; each of said —$C_{1-6}$alkyl being optionally substituted with one or more substituents selected from -D, and —$C_{1-6}$alkyl;
- $Het_1$ and $Het_3$ are each independently selected from a 5 or 6-membered aromatic heterocycle having from 1 to 3 heteroatoms selected from O, N and S, wherein each of said $Het_1$ or $Het_3$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH;
- $Het_2$ is selected from a 4 to 6-membered saturated heterocycle having from 1 to 3 heteroatoms selected from O and N; wherein each of said $Het_2$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH;
- $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$alkyl, and —OH.

In any of the herein disclosed embodiments, $R_6$ may alternatively be selected from —H, -Halo, —$C_{1-6}$alkyl, —O—$C_{1-6}$alkyl, and -$Het_3$; each of said —$C_{1-6}$alkyl being optionally substituted with one or more substituents selected from -D, and —O—$C_{1-6}$alkyl; in which case $Het_4$ is absent.

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. $C_1$-$C_6$ alkyl includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -D, -halo, —OH, primary and secondary amides, —O—$C_{1-6}$alkyl, heteroaryl, aryl, cycloalkyl, heterocyclyl and the like.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond.

Examples of alkynyl radicals include ethynyl, E- and Z-propynyl, isopropynyl, E- and Z-butynyl, E- and Z-isobutynyl, E- and Z-pentynyl, E, Z-hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having a cyclic structure.

Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms.

Examples of cycloalkyl groups include but are not limited to cyclopropyl, cyclobutyl, cyclopentyl, Cyclohexane.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a $C_3$ alkylene group may be for example $*—CH_2CH_2CH_2—*$, $*—CH(—CH_2CH_3)—*$, or $*—CH_2CH(—CH_3)—*$.

The term "heterocycle" as used herein by itself or as part of another group refers to aromatic, non-aromatic, fully saturated or partially unsaturated cyclic groups (for example, 3 to 6 membered monocyclic ring systems, or 8-10 membered bicyclic rings) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary non-aromatic heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, oxetanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrahydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, tetrahydrofuranyl, 7-10 Membered heterocyclic groups are also meant to include spiro-groups, which are bicyclic compounds with both rings connected through a single atom, such as for example spiro[4.5]decane, which is a spiro compound consisting of a cyclohexane ring and a cyclopentane ring. Other examples include oxaspiro[3.3]heptan, which is a spiro compound consisting of a $C_4$ cycloalkyl and an oxetane ring.

The term "aryl" as used herein refers to a polyunsaturated, aromatic hydrocarbyl group having from 5-10 atoms. Aryl is also intended to include the partially hydrogenated derivatives of the carbocyclic systems enumerated herein. Non-limiting examples of aryl comprise phenyl, biphenylyl, biphenylenyl, 1- or 2-naphthyl, 1-, 2-, or 3-indenyl, 1- 2-, 3-, 4-, or 5-acenaphtylenyl, 1- or 2-pentalenyl, 4- or 5-indanyl, 5-, 6-, 7-, or 8-tetrahydronaphthyl, 1,2,3,4-tetrahydronaphthyl, 1,4-dihydronaphthyl and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring, alternatively, such ring structure is also referred to as an aromatic heterocyle.

The term "heteroaryl" or "aromatic heterocycle" as used herein by itself or as part of another group refers but is not limited to 5 to 10 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[2,3-d]imidazolyl, tetrazolo[1,5-a]pyridinyl, indolyl, indolizinyl, isoindolyl, benzofuranyl, isobenzofuranyl, indazolyl, benzimidazolyl, 1,3-benzoxazolyl, 1,2-benzisoxazolyl, 2,1-benzisoxazolyl, 1,3-benzothiazolyl, benzotriazolyl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

The term "oxo" as used herein refers to the group =O.

The term "alkoxy" or "alkyloxy" as used herein refers to a radical having the Formula $—OR^b$ wherein $R^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent.

Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as 2H (Deuterium), $^{3}H$, $^{11}C$, $^{13}N$, $^{14}C$, $^{15}O$ and $^{18}F$. Such isotopically-labelled compounds of formula (I) are useful in drug and/or substrate tissue distribution assays. For example, $^{2}H$ (Deuterium) are particularly useful, when well positioned on the chemical structure, to decrease metabolism, hence improving pharmacokinetic profile of the deuterated analog in animals and humans (Uttamsingh et al., CTP-656 Phase 1 study results). For example, $^{11}C$ and $^{18}F$ isotopes are particularly useful in PET (Positron Emission Tomography). PET is useful as a diagnostic or treatment follow-up tool that can be applied in a translational manner in a preclinical and clinical setting. It also has applications in PK determination of compounds, including biodistribution. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a particular embodiment, the present invention provides a compound of Formula I or a stereoisomer, tautomer, racemic, salt, hydrate, N-oxide form, or solvate thereof; wherein one or more of the following applies:

$R_1$ is selected from -Halo, —O—$C_{1-6}$alkyl, -Alkynyl, —$C_{1-6}$alkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH; each of said -Alkynyl being optionally substituted with one substituent selected from —$C_{1-6}$alkyl, and —$CH_2$—O—$C_{1-6}$alkyl;

$R_2$ and $R_{10}$ are each independently selected from —H, and -Halo;

$R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;

wherein when $R_3$ and/or $R_{3'}$ is —$C_{1-6}$alkyl, then $R_4$ and $R_{4'}$ are each —H;

wherein when $R_4$ and/or $R_{4'}$ is —$C_{1-6}$alkyl, then $R_3$ and $R_{3'}$ are each —H;

$R_5$ is selected from —OH, —$NR_cR_{c'}$; —NHC(O)$R_c$, —NC(O)$R_cR_{c'}$, —NC(O)O$R_c$, —NHS($O_2$)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl; each of said —$C_{1-6}$alkyl being optionally substituted with one or more substituents selected from -D, and —$C_{1-6}$alkyl;

$R_b$ is selected from —H, —$C_{1-6}$alkyl, and —O—$C_{1-6}$ alkyl; each of said —$C_{1-6}$alkyl being optionally substituted with one or more substituents selected from -D, —$C_{1-6}$alkyl, and —$C_{3-5}$-cycloalkyl;

$R_c$ and $R_{c'}$ are each independently selected from —H, and —$C_{1-6}$alkyl; each of said —$C_{1-6}$alkyl being optionally substituted with one or more substituents selected from -D, and —$C_{1-6}$alkyl;

$Het_1$ and $Het_3$ are each independently selected from a 5 or 6-membered aromatic heterocycle having from 1 to 3 heteroatoms selected from O, N and S, wherein each of said $Het_1$ or $Het_3$ is optionally substituted with from 1 to 3 —$C_{1-6}$ alkyl; each of said —$C_{1-6}$alkyl being optionally substituted with one or more substituents selected from -D, -halo, —O—$C_{1-3}$alkyl, and —OH;

$Het_2$ is selected from a 4 to 6-membered saturated heterocycle having from 1 to 3 heteroatoms selected from O and N; wherein each of said $Het_2$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In a specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH;

$R_2$ and $R_{10}$ are each independently selected from —H, and -Halo;

$R_3$, $R_{3'}$, $R_4$, $R_{4'}$, $R_7$, and $R_8$ are each independently selected from —H, and —$C_{1-6}$alkyl; wherein each of said —$C_{1-6}$alkyl may optionally be substituted with one or more —O—$C_{1-6}$alkyl;

wherein when $R_3$ and/or $R_{3'}$ is —$C_{1-6}$alkyl, then $R_4$ and $R_{4'}$ are each —H;

wherein when $R_4$ and/or $R_{4'}$ is —$C_{1-6}$alkyl, then $R_3$ and $R_{3'}$ are each —H;

$R_5$ is selected from —OH, —$NR_cR_{c'}$; —NHC(O)$R_c$, -Halo, —O—$C_{1-6}$alkyl, —O—$C_{3-5}$-cycloalkyl, —O-$Het_2$, —$C_{1-6}$alkyl, and —CN; each of said —$C_{1-6}$alkyl being optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl;

$R_b$ is selected from —H, —$C_{1-6}$alkyl, and —O—$C_{1-6}$ alkyl;

$R_c$ and $R_{c'}$ are each independently selected from —H, and —$C_{1-6}$alkyl;

$Het_1$ and $Het_3$ are each independently selected from a 5 or 6-membered aromatic heterocycle having from 1 to 3 heteroatoms selected from 0 and N, wherein each of said $Het_1$ and $Het_3$ is optionally substituted with from 1 to 3 —$C_{1-6}$alkyl;

$Het_2$ is selected from a 4 to 6-membered saturated heterocycle having from 1 to 3 O atoms $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In another specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —C(O)—$C_{1-6}$-alkyl, —C(O)—$C_{1-6}$cycloalkyl, —C(O)—$Het_2$, —C(O)—$NR_aR_b$, -$Het_1$ and —CN; each of said —$C_{1-6}$alkyl being optionally substituted with one or more substituents selected from -D, -Halo, —O—$C_{1-3}$alkyl, —$C_{3-6}$-cycloalkyl, -Ph, -$Het_1$, -$Het_2$, and —OH;

$R_2$ and $R_{10}$ are each independently selected from —H, and -Halo;

$R_3$, $R_{3'}$, $R_4$, $R_{4'}$, $R_7$, and $R_8$ are each —H;

$R_5$ is selected from —OH, -Halo, —O—$C_{1-6}$alkyl, —O—$C_{3-5}$-cycloalkyl, and —$C_{1-6}$alkyl; each of said —$C_{1-6}$alkyl being optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$R_a$ is selected from —H, and —$C_{1-6}$alkyl;

$R_b$ is selected from —H, —$C_{1-6}$alkyl, and —O—$C_{1-6}$ alkyl; each of said —$C_{1-6}$alkyl being optionally substituted with one or more;

$Het_1$ and $Het_3$ are each independently selected from a 5 or 6-membered aromatic heterocycle having from 1 to 3 heteroatoms selected from O and N, wherein each of said $Het_1$ and $Het_3$ is optionally substituted with from 1 to 3 —$C_{1-6}$alkyl;

$Het_2$ is selected from a 4 to 6-membered saturated heterocycle having from 1 to 3 O atoms;

$Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In yet a further specific embodiment, the present invention provides a compound of Formula I or a stereoisomer, tautomer, racemic, salt, hydrate, N-oxide form, or solvate thereof, wherein $R_1$ is selected from -Halo, —O—$C_{1-6}$alkyl, -Alkynyl, —$C_{1-6}$alkyl, —C(O)—$C_{1-6}$-alkyl, —C(O)—$NR_aR_b$, -$Het_1$ and —CN; each of said —$C_{1-6}$alkyl being optionally substituted with one or more substituents selected from -D, -Halo, and —O—$C_{1-3}$alkyl;

$R_2$ is selected from —H, and -Halo;

$R_{10}$ is —H;

$R_3$, $R_{3'}$, $R_4$, $R_{4'}$, $R_7$, and $R_8$ are each —H $R_5$ is selected from —OH, -Halo, —O—$C_{1-6}$alkyl, —O—$C_{3-5}$-cycloalkyl, and —$C_{1-6}$alkyl; each of said —$C_{1-6}$alkyl being optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more —O—$C_{1-6}$alkyl;

$R_9$ is —H;

$R_a$ is selected from —H, and —$C_{1-6}$alkyl;

$R_b$ is selected from —H, —$C_{1-6}$alkyl, and —O—$C_{1-6}$ alkyl;

$Het_1$ is a 5-membered aromatic heterocycle having from 1 to 3 heteroatoms selected from O and N, wherein said $Het_1$ is optionally substituted with from 1 to 3 —$C_{1-6}$ alkyl $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In yet a further embodiment, the present invention provides a compound of Formula I or a stereoisomer, tautomer, racemic, salt, hydrate, N-oxide form, or solvate thereof, wherein one or more of the following applies:

$R_1$ is selected from -Halo, —O—$C_{1-6}$alkyl, -Alkynyl, —$C_{1-6}$alkyl, —C(O)—$C_{1-6}$-alkyl, —C(O)—$NR_aR_b$, -$Het_1$ and —CN; each of said —$C_{1-6}$alkyl being optionally substituted with one or more substituents selected from -D, -Halo, and —O—$C_{1-3}$alkyl;

$R_2$ is selected from —H, and -Halo;

$R_{10}$ is —H;

$R_3$, $R_{3'}$, $R_4$, $R_{4'}$, $R_7$, and $R_8$ are each —H $R_5$ is selected from —OH, -Halo, —O—$C_{1-6}$alkyl, —O—$C_{3-5}$-cycloalkyl, and —$C_{1-6}$alkyl; each of said —$C_{1-6}$alkyl being optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -Halo, —$C_{1-6}$alkyl, —O—$C_{1-6}$ alkyl, —O-$Het_4$, and -$Het_3$; each of said —$C_{1-6}$alkyl being optionally substituted with one or more —O—$C_{1-6}$alkyl;

$R_9$ is —H;

$R_a$ is selected from —H, and —$C_{1-6}$alkyl;

$R_b$ is selected from —H, —$C_{1-6}$alkyl, and —O—$C_{1-6}$ alkyl;

$Het_1$ is a 5-membered aromatic heterocycle having from 1 to 3 heteroatoms selected from O and N, wherein said $Het_1$ is optionally substituted with from 1 to 3 —$C_{1-6}$ alkyl $Het_4$ is selected from a 4 to 10-membered saturated heterocycle having from 1 to 3 heteroatoms selected from O and N; wherein each of said $Het_4$ is optionally substituted with from 1 to 3 —$C_{1-6}$alkyl; each of said —$C_{1-6}$alkyl being optionally substituted with one or more substituents selected from -D, -halo, —O—$C_{1-3}$ alkyl, and —OH.

In a more specific embodiment, the present invention provides a compound selected from any of the tables disclosed herein.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

The present invention further provides a pharmaceutical composition comprising a compound according to this invention.

In a further aspect, the present invention provides a compound or a composition according to this invention, for use as a human or veterinary medicine.

In a particular embodiment, the present invention provides a compound or composition according to this invention for use in the diagnosis, prevention and/or treatment of a RIP2-kinase associated disease.

Said RIP2-kinase associated disease may in particular be inflammatory disorders, in particular Crohn's disease, bowel disease, sarcoidosis, psoriasis, atopic dermatitis, allergic rhinitis, rheumatoid arthritis, asthma, insulin-resistant type 2 diabetes, obesity metabolic syndrome, cardiac hypertrophy, ulcerative colitis, lupus, uveitis, Blau syndrome, granulomatous inflammation, Behget's disease, immune-mediated colitis, and multiple sclerosis.

Alternatively, said RIP2-kinase associated disease may be cancer, more in particular selected from breast cancers (including Inflammatory Breast Cancer), head and neck cancers and gliomas.

Furthermore, the present invention provides the use of a compound or composition according to this invention, suitable for inhibiting the activity of a kinase; in particular a RIP2 kinase; or for the diagnosis, prevention and/or treatment of a RIP2-kinase associated disease.

Finally, the present invention provides a method for prevention and/or treatment of a RIP2-kinase associated disease; said method comprising administering to a subject in need thereof a compound or a composition according to the present invention.

Method of Treatment

Compounds of formula (I) or (Ia) a stereoisomer, tautomer, racemic, metabolite, pro- or pre-drug, salt, hydrate, N-oxide form, or solvate thereof, are inhibitors of RIP2 kinase activity and are thus believed to be of potential use in the diagnosis, prevention and/or treatment of inflammatory disorders, or cancer.

As used herein, the terms "inflammatory disorder" or "inflammatory disease" can refer to a disorder or disease characterized by aberrant activation of the immune system that leads to or causes pathogenesis of several acute and chronic conditions including, for example, Crohn's disease, bowel disease, Sarcoidosis, psoriasis, rheumatoid arthritis, asthma, ulcerative colitis, lupus, uveitis, Blau syndrome, granulomatous inflammation, in particular Behget's disease, multiple sclerosis and insulin-resistant type 2 diabetes. An inflammatory disease can include a state in which there is a response to tissue damage, cell injury, an antigen, an infectious disease, and/or some unknown cause. Symptoms of inflammation may include, but are not limited to, cell infiltration and tissue swelling.

As used herein, the term "cancer" can refer to a disorder or disease characterized by abnormal cell growth with the potential to invade or spread to different parts of the body; such as for example breast cancers (including Inflammatory Breast Cancer), head and neck cancers and gliomas.

In the invention, particular preference is given to compounds of Formula I or any subgroup thereof that in the inhibition assay for RIP2 described below inhibit kinase activity with an $IC_{50}$ value of less than 10 μM, preferably less than 1 μM, most preferably less than 100 nM.

Said inhibition may be effected in vitro and/or in vivo, and when effected in vivo, is preferably effected in a selective manner, as defined above.

The term "RIP2 kinase-mediated condition" or "disease", as used herein, means any disease or other deleterious condition in which the RIP2 kinase and/or mutants thereof is/are known to play a role. The term "RIP2 kinase-mediated condition" or "disease" also means those diseases or conditions that are alleviated by treatment with a RIP2 kinase inhibitor.

Accordingly, another embodiment of the present invention relates to treating or lessening the severity of one or more diseases in which the RIP2 kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations. The formulations can optionally contain other pharmaceutically active substances (which may or may not lead to a synergistic effect with the compounds of the invention) and other substances that are commonly used in pharmaceutical formulations. The compositions may also be formulated so as to provide rapid, sustained or delayed release of the active compound(s) contained therein.

For local administration, the compounds may advantageously be used in the form of a spray, ointment or transdermal patch or another suitable form for topical, transdermal and/or intradermal administration.

Composition

Compounds of Formula (1) or pharmaceutically acceptable salts thereof may be formulated into pharmaceutical compositions prior to administration to a subject. According to one aspect, the invention provides a pharmaceutical composition comprising a compound of Formula (1) or a pharmaceutically acceptable salt thereof and a pharmaceutically acceptable excipient. According to another aspect, the invention provides a process for the preparation of a pharmaceutical composition comprising admixing a compound of Formula (1) or a pharmaceutically acceptable salt thereof, with a pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of Formula (1) will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of formula (1) for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a pharmaceutically acceptable salt or solvate, etc., may be determined as a proportion of the therapeutically effective amount of the compound of Formula (1) perse. It is envisaged that similar dosages would be appropriate for treatment of the other diseases referred to above.

The pharmaceutical compositions of the invention may contain one or more compounds of Formula (1) or a pharmaceutically acceptable said thereof. In some embodiments, the pharmaceutical compositions may contain more than one compound of the invention. For example, in some embodiments, the pharmaceutical compositions may contain two or more compounds of Formula (1) or a pharmaceutically acceptable salt thereof. In addition, the pharmaceutical compositions may optionally further comprise one or more additional active pharmaceutical ingredients (APIs).

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The invention will now be illustrated by means of the following synthetic and biological examples, which do not limit the scope of the invention in any way.

Abbreviations

The following abbreviations are employed herein:

Ph=phenyl
Ac=Acetate
Bn=benzyl
t-Bu=tertiary butyl
n-Bu=linear butyl
Me=methyl
Et=ethyl
Pr=propyl
iPr=isopropyl
Bu=Butyl
TMS=trimethylsilyl
TBS=tert-butyldimethylsilyl
THE=tetrahydrofuran
DMF=dimethyl formamide
AA=acetic acid
TFA=trifluoroacetic acid
i-$Pr_2NEt$ or DIPEA=diisopropylethylamine
TEA=triethylamine
DMAP=4-dimethylaminopyridine
Pd/C=palladium on carbon
KOH=potassium hydroxide
NaOH=sodium hydroxide
LiOH=lithium hydroxide
Ar=argon
$N_2$=nitrogen
EDC=3-ethyl-3'-(dimethylamino)propyl-carbodiimide hydrochloride (or 1-[(3-(dimethyl)amino)propyl])-3-ethylcarbodiimide hydrochloride)
HOBT=1-hydroxybenzotriazole hydrate
DIC=1,3-dipropylcarbodiimide
BOP=(benzotriazol-1-yloxy)tris(dimethylamino)phosphonium hexafluorophosphate
PyBOP=benzotriazol-1-yloxy-tripyrrolidino phosphonium hexafluorophosphate
HATU=1-[bis(dimethylamino)methylene]-1H-1,2,3-triazolo[4,5-b]pyridinium 3-oxid hexafluorophosphate
LiHMDS=lithium bis(trimethylsilyl)amide
LAH=Lithium Aluminium Hydride
Boc=tert-butoxycarbonyl
Cbz=Carboxybenzyl
LDA=lithium diisopropylamide
NBS=N-bromosuccinimide
ACN=Acetonitrile
min=minute(s)
h or hr=hour(s)
L=liter
mL=milliliter
μL=microliter
g=gram(s)
mg=milligram(s)
mol=moles
mmol=millimole(s)
meq=milliequivalent
rt=room temperature
RT=retention time
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The compounds of the present invention may be synthesized by many methods available to those skilled in the art of organic chemistry (Maffrand, J. P. et al., *Heterocycles,* 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

General Schemes:

As indicated herein before, the present invention in general provides compounds according to formula I, (I)

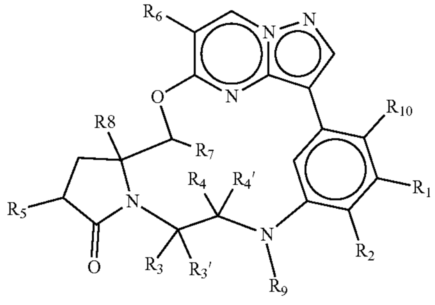

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC or preparative SFC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

Compounds of this invention with the formula (I) can be prepared by the methods illustrated in the following schemes.

As shown in Scheme 1a, Compound P1a (commercially available) can undergo alkylation reaction either using silver oxide or sodium hydride to afford compound P1b. The expected compound Pic can be obtained by reduction of the acid or ester moiety in presence of a reductive agent (such as LAH, Sodium borohydride or $BH_3.SMe_2$).

Scheme 1a

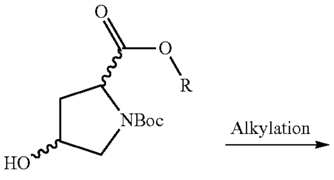

P1a

-continued

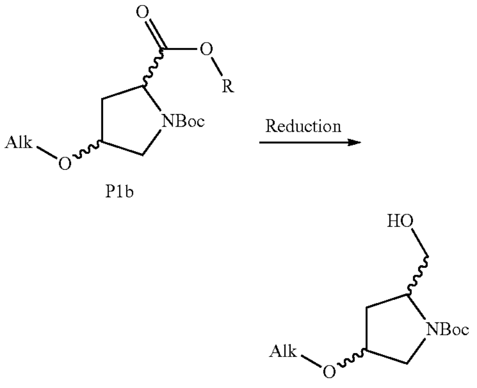

P1b

P1c

R = H, Me
Alk = Alkyl

As shown in Scheme 1b, Compound P1a (commercially available) can undergo silylation reaction in presence of weak base (such as Imidazole) to afford compound P2a. The ether P2b can be obtained by reaction with an aldehyde or a ketone in presence of $BiBr_3$ and Triethylsilane. The sequential hydrogenation in presence of Pd/C, Boc protection and ester reduction in presence of Borohydride reagent can afford the expected compound P2e.

Scheme 1b

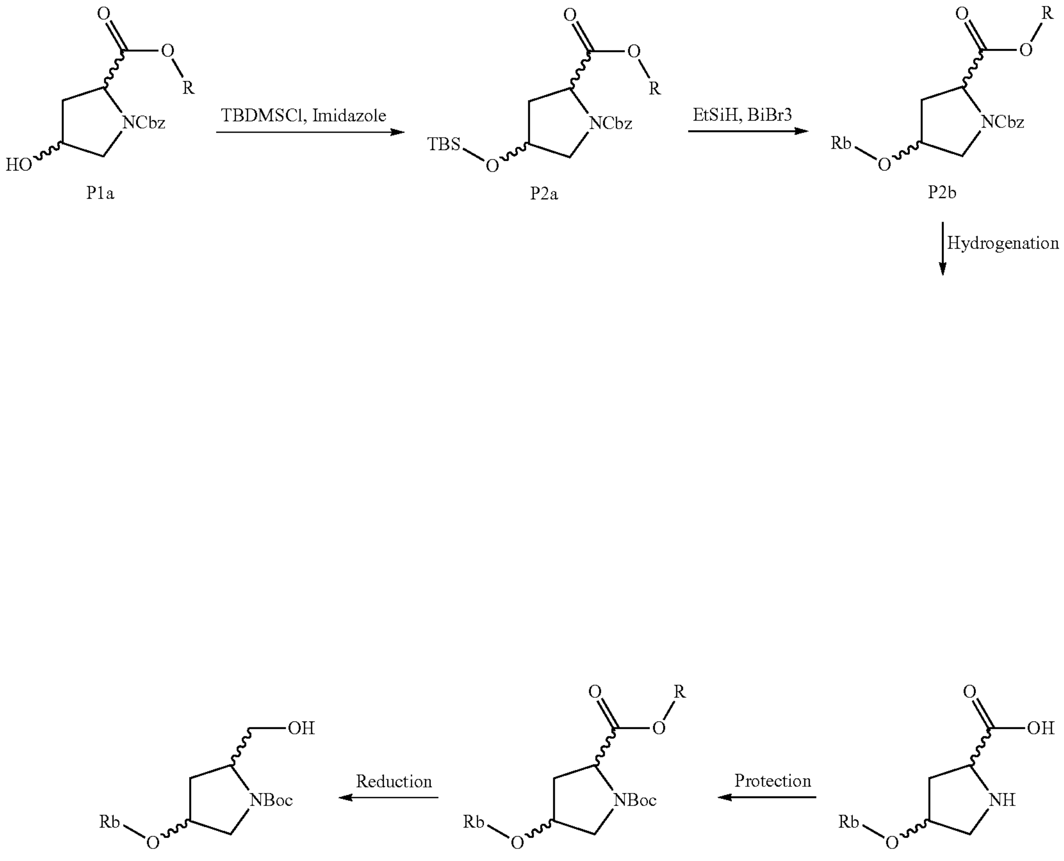

P1a P2a P2b

P2e P2d P2c

As shown in Scheme 1c, Compound P1a (commercially available) can undergo a reaction in presence of TMSOTf to afford the enolate P3b. The cyclopropanation can be achieved in presence of Diethyl Zinc afforded P3c. 2-step transprotection can be achieved by sequential deprotection of Cbz in presence of Palladium on charcoal, followed by $Boc_2O$ reaction to obtain P3e. A final reduction in presence of Borohydride reagent can afford the expected compound P3f.

Scheme 1c

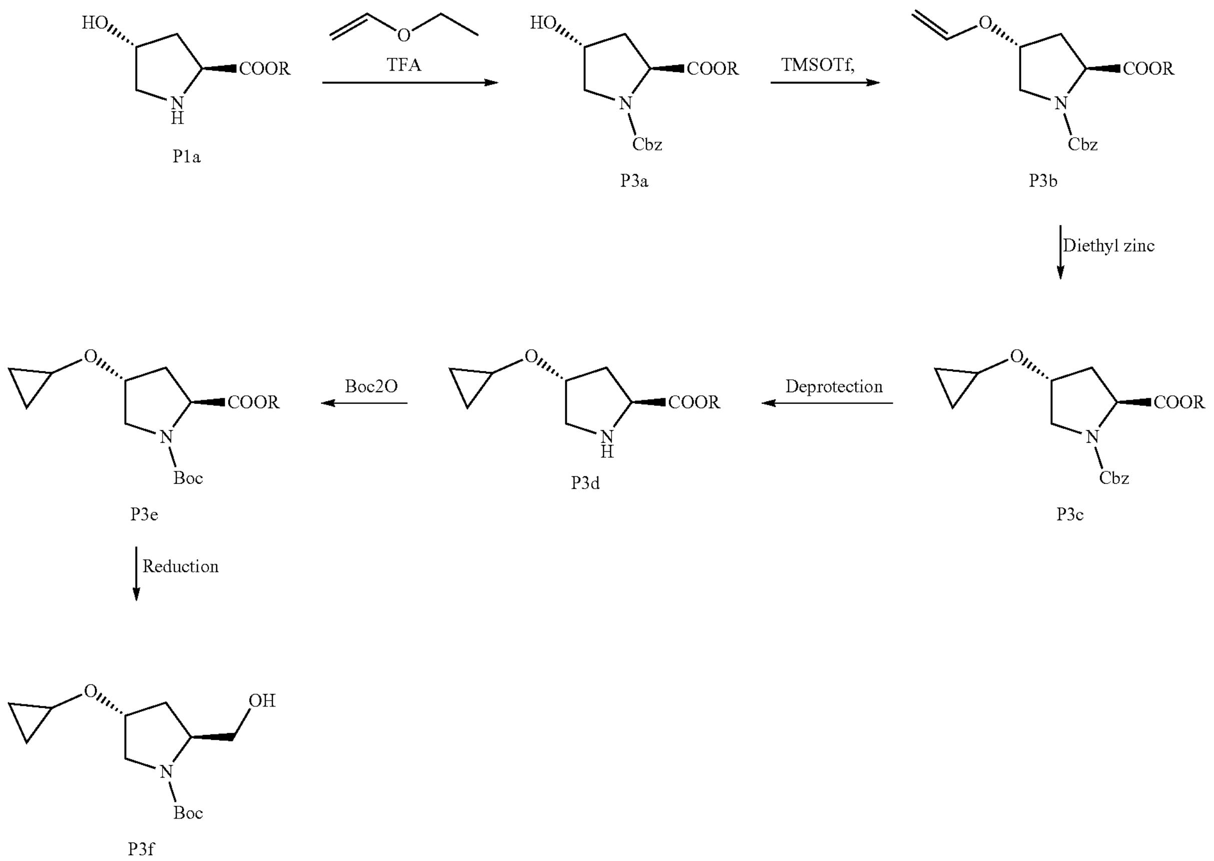

As shown in Scheme 1d, Compound P1a (commercially available) can undergo reduction reaction in presence of a borane reagent (such as $BH_3.SMe_2$) to afford compound P4a. The primary alcohol can be protected in presence of TBDPSCl, followed by a Dess-Martin oxidation to afford the ketone P4c. The enolate P4d can be obtained by Wittig reaction, followed by a reduction of the double bond by hydrogenation. The expected compound P4f can be obtained by deprotection of the silyl group, for example in presence of a fluorine-containing reagent.

Scheme 1d

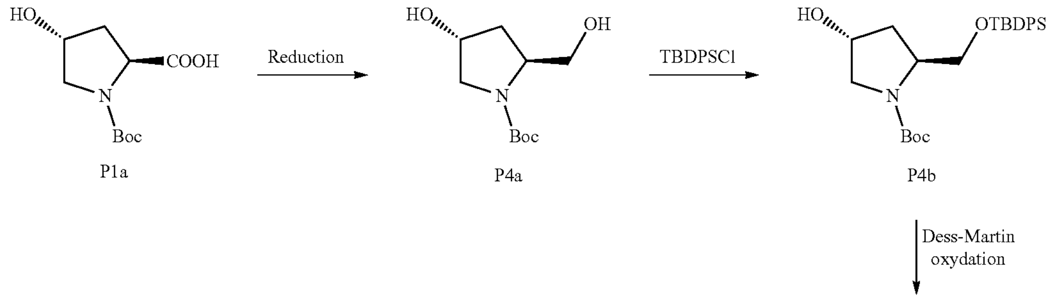

-continued

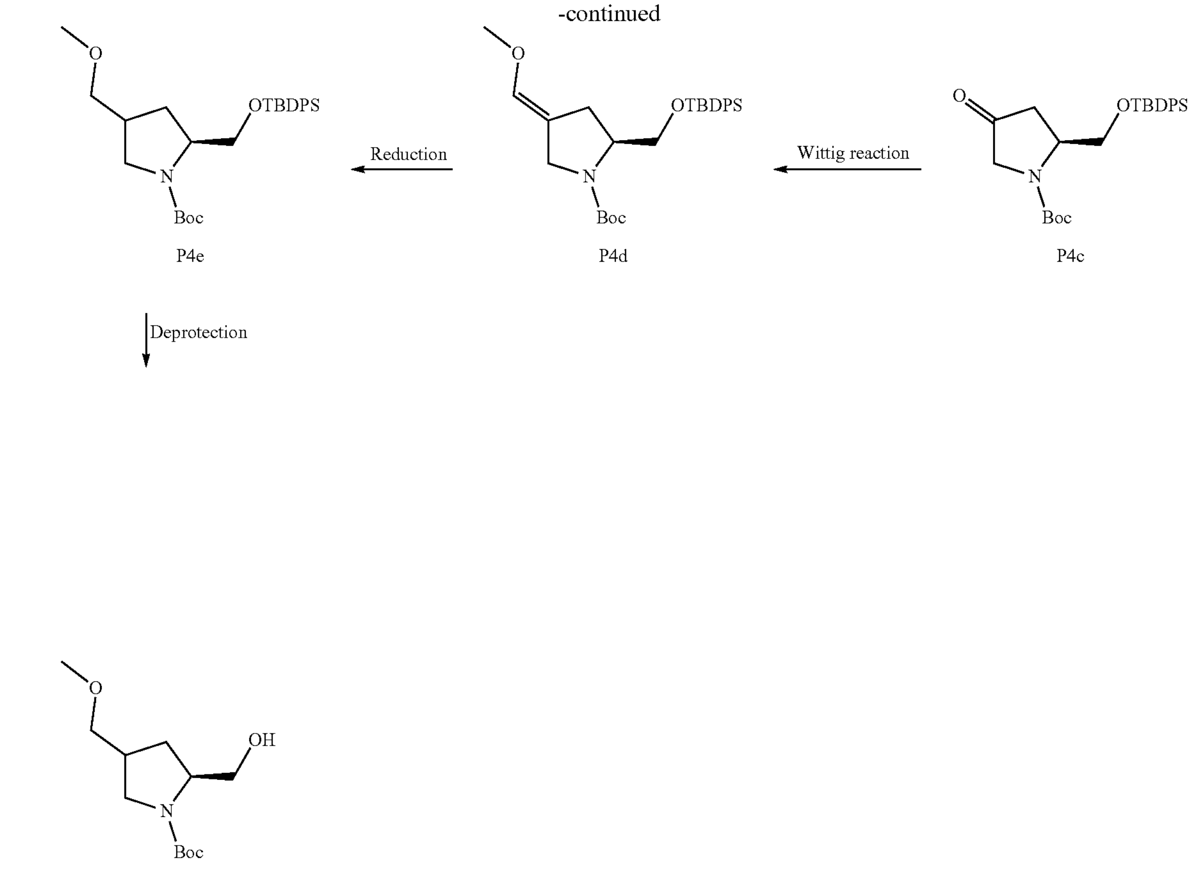

P4e P4d P4c

P4f

As shown in Scheme 1e, Compound P1b can undergo alkylation reaction in presence of strong base (such as LDA) to afford compound P2a. The reduction of the ester moiety in presence of Sodium borohydride can afford the expected compound P2b.

Scheme 1e

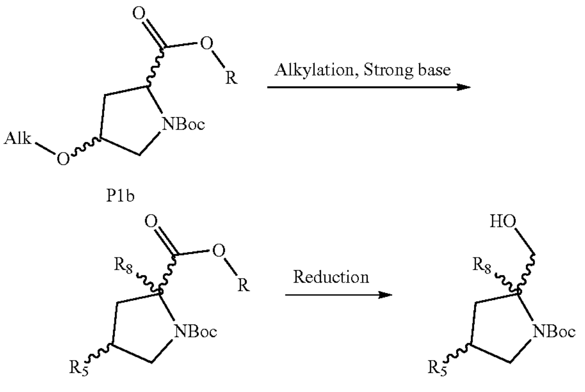

P1b

P3a P3b

As shown in Scheme 1f, Compound Pic can undergo oxidation under Swern conditions followed by strong alkylating agent (such as alkylmagnesium bromide) to afford the Pyrrolidine P4b.

Scheme 1f

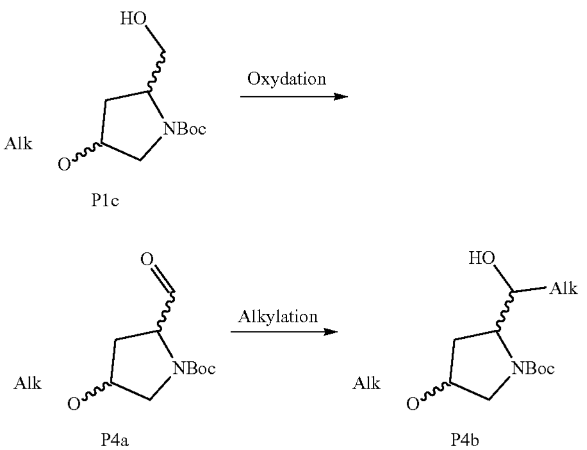

P1c

P4a P4b

As shown in Scheme 2a, Compound S1a can undergo cyclization reaction in presence of amino-pyrazole S1b. The intermediate S1c can be sequential treated by Phosphorous oxychloride followed by N-bromosuccinimide to give the intermediate S1e. An aromatic nucleophilic substitution can be achieved in presence of Ammonia to afford compound S1f. The scaffold S1g is obtained by diazotation reaction in presence of isopentyl nitrite, followed by elimination in a one-pot reaction.

Scheme 2a

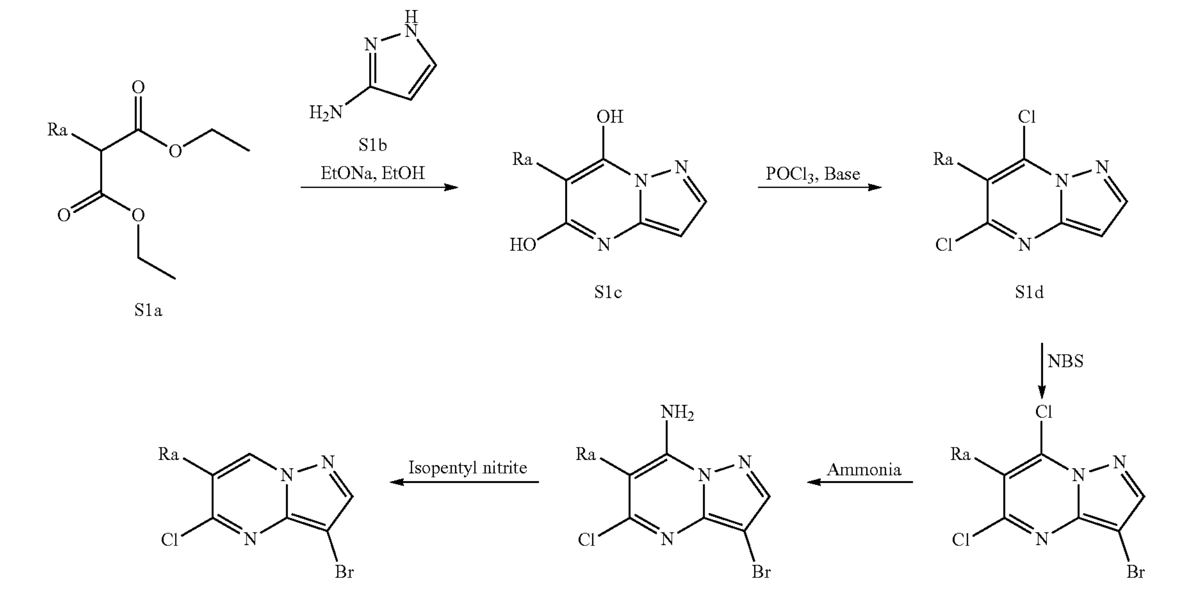

S1a S1b S1c S1d S1e S1f S1g

As shown in Scheme 2b, Compound S1g can undergo a bromination in presence of N-bromosuccinimide to afford compound S2a. The expected compound S2b can be obtained by alkylation of the scaffold by Sodium alcoholates.

Scheme 2b

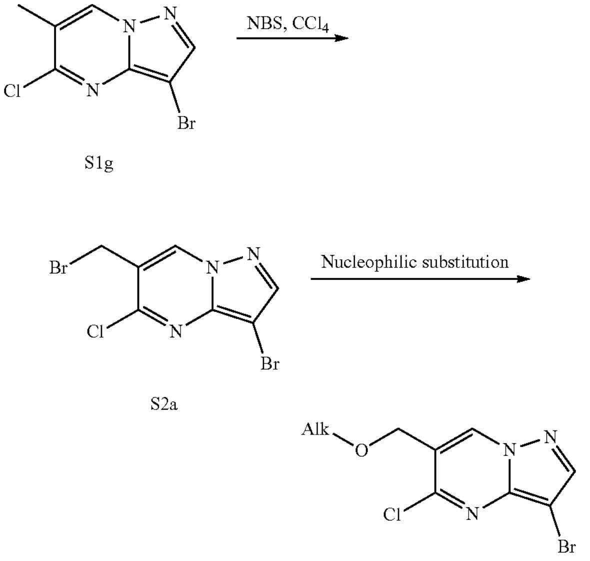

S1g S2a S2b

Alk = Alkyl

As shown in Scheme 2c, Compound S1g can undergo a bromination in presence of N-bromosuccinimide to afford compound S3a. The expected compound S3b can be obtained by alkylation of the scaffold by Sodium alcoholates.

Scheme 2c

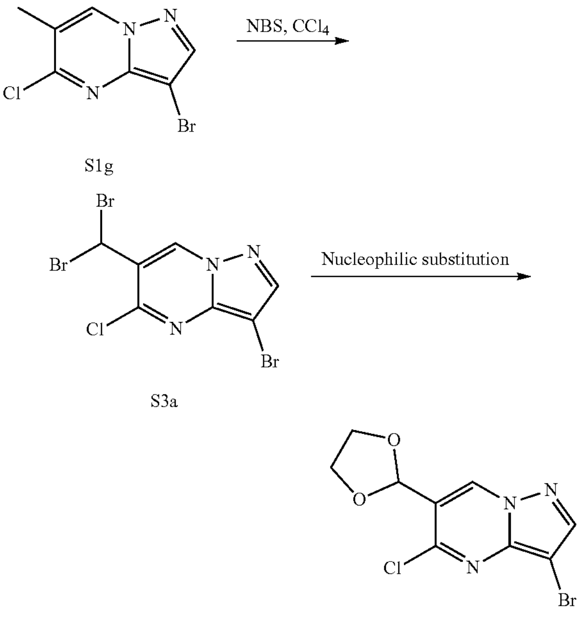

S1g S3a S3b

As shown in Scheme 2d, Compound S4a can undergo esterification in presence of MeOH and Acetyl Chloride, followed by reaction with Ethyl formate in presence of a strong base. Intermediate S4c was converted to the enol ester S4d. The subsequent cyclization reaction can be achieved in presence of amino-pyrazole S1b. The intermediate S4e can be sequential treated by Phosphorous oxychloride followed by N-bromosuccinimide to afford the expected compound S4 g.

Scheme 2d
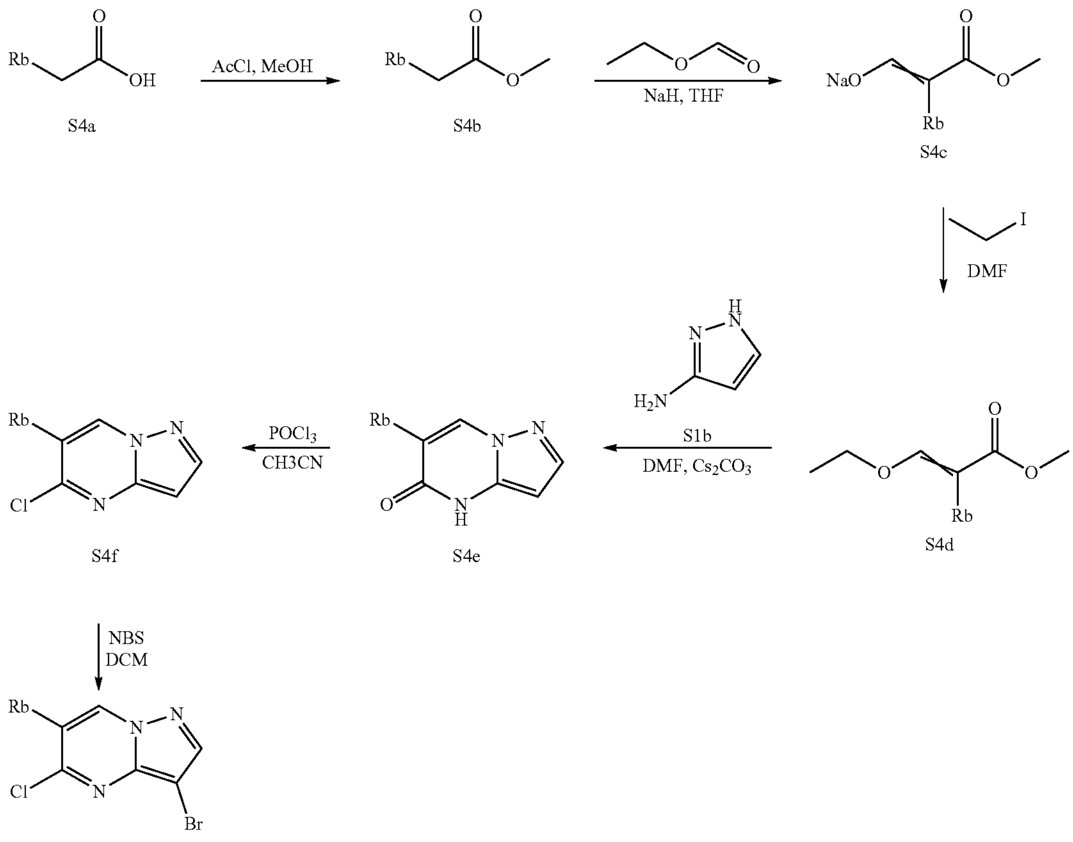
S4a S4b S4c S4d S4e S4f S4g
As shown in Scheme 3a, Compound A1a can undergo Miyaura borylation reaction to afford A1b.
Scheme 3a
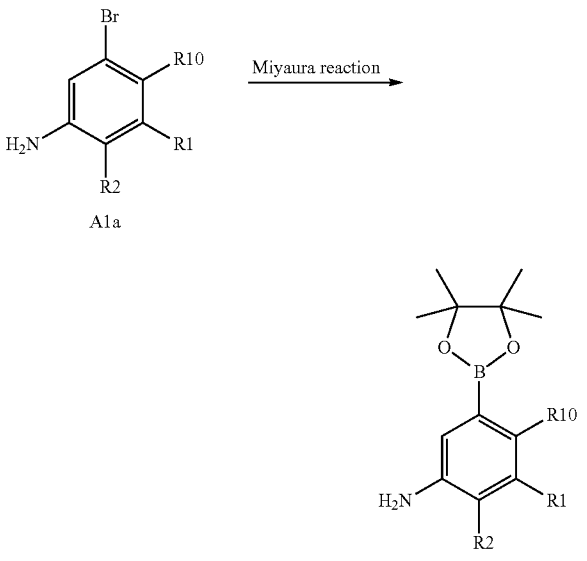
A1a
A1b
As shown in Scheme 3b, Compound A1a can undergo alkylation in presence of alkyl halide to afford the intermediate A2a. The aniline A2b can be obtained by Miyaura borylation reaction.
Scheme 3b
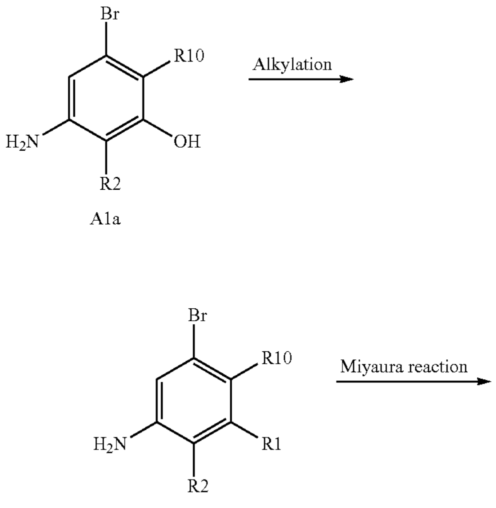
A1a
A2a -continued

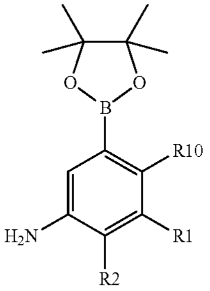

A2b

As shown in Scheme 3c, Compound A3a can undergo Bocylation, followed by a Sonogashira to obtain intermediate A3c. The Bromide can be converted to the free aniline A3d using strong acid (such as HCl), which can undergo Miyaura borylation reaction to afford A3e.

Scheme 3c

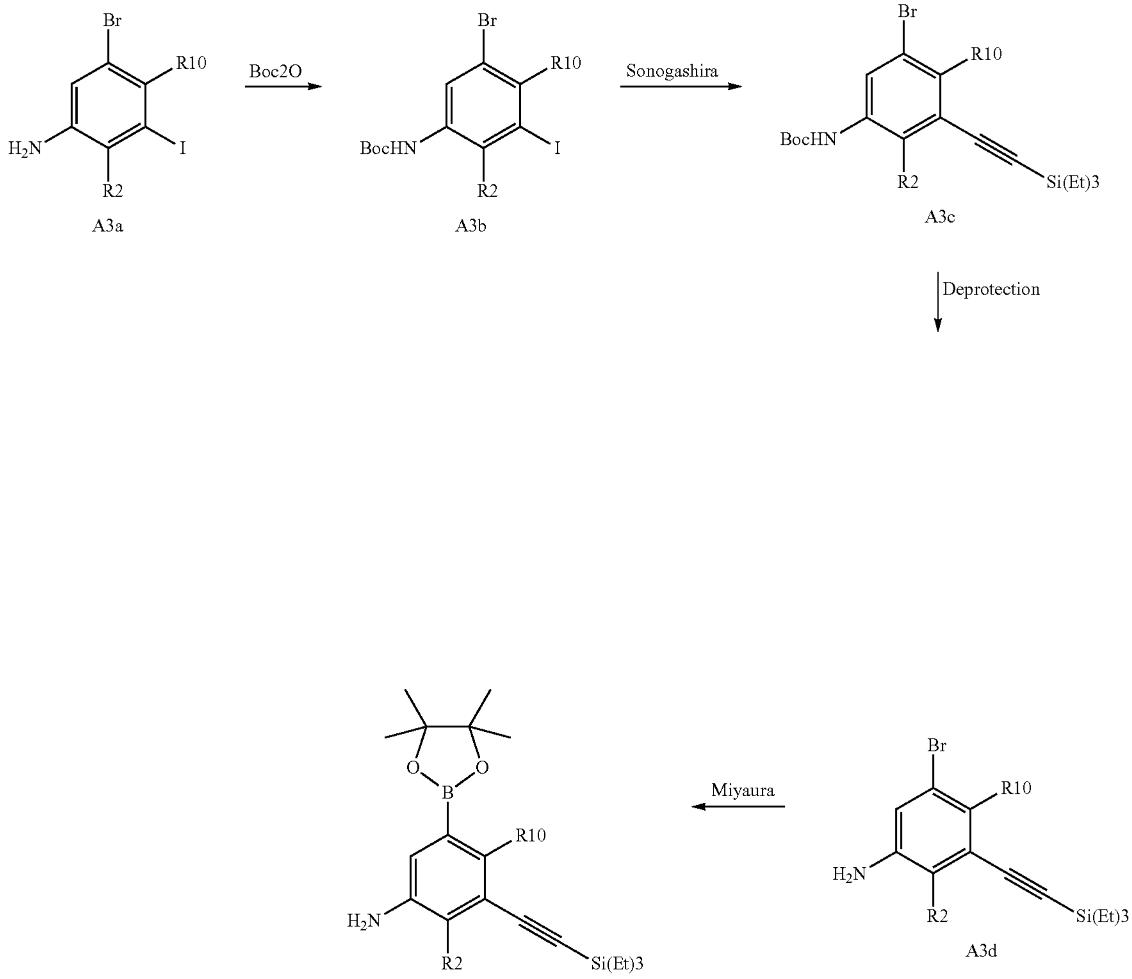

A3a A3b A3c A3d A3e

As shown in Scheme 3d, Compound A4a can undergo Bocylation, followed by Boc deprotection (purification process) to afford intermediate A4c. The compound A4d can be obtained by Miyaura borylation reaction.

Scheme 3d

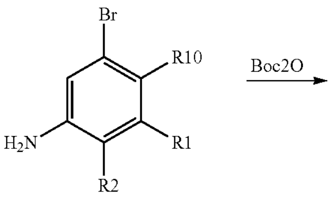

A4a

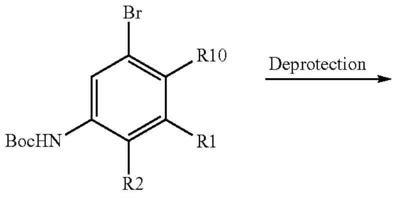

A4b

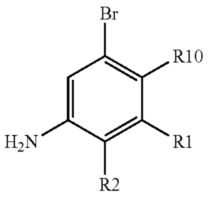

A4c

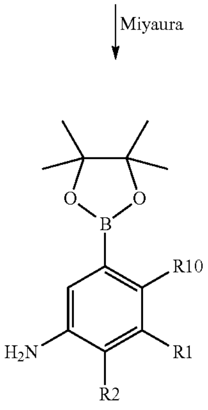

A4d

As shown in Scheme 3e, Compound A5a can undergo Copper-catalyzed cross-coupling reaction followed by nitro reduction (for example using Iron and Ammonium Chloride) to afford intermediate A5c. The compound A5d can be obtained by Miyaura borylation reaction.

Scheme 3e

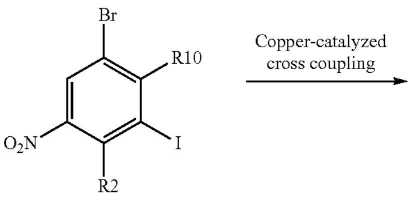

A5a

-continued

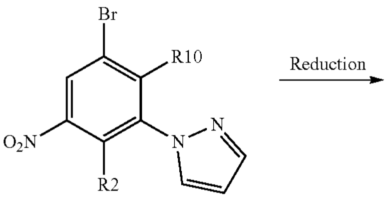

A5b

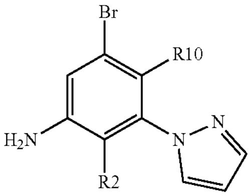

A5c

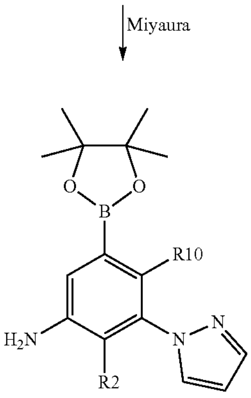

A5d

As shown in Scheme 3f, Compound A6a can undergo Copper-catalyzed cross-coupling reaction followed by Miyaura borylation reaction to afford the boronate A6c.

Scheme 3f

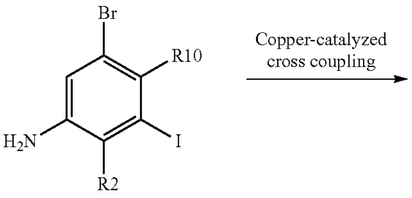

A6a

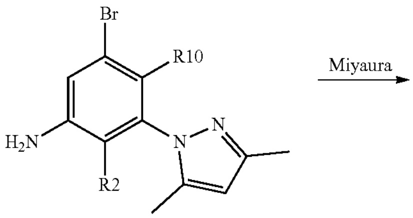

A6b

-continued

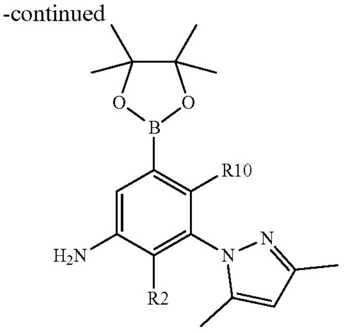

A6c

As shown in Scheme 3 g, Compound A5a can undergo Copper-catalyzed cross-coupling reaction followed by Boc hydrolysis to afford the boronate A6c. The hydrazine derivative can be converted to the pyrazole A7c. The intermediate can be decarboxylated in presence of strong acid, followed by nitro reduction in presence using Iron and Ammonium chloride to afford A7e. The boronate A7f can be obtained by Miyaura borylation reaction.

As shown in Scheme 3h, Compound A8a can undergo esterification followed by Miyaura borylation reaction to afford the boronate A8c.

Scheme 3h

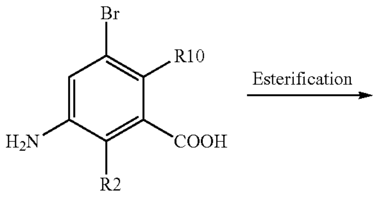

A8a

Scheme 3g

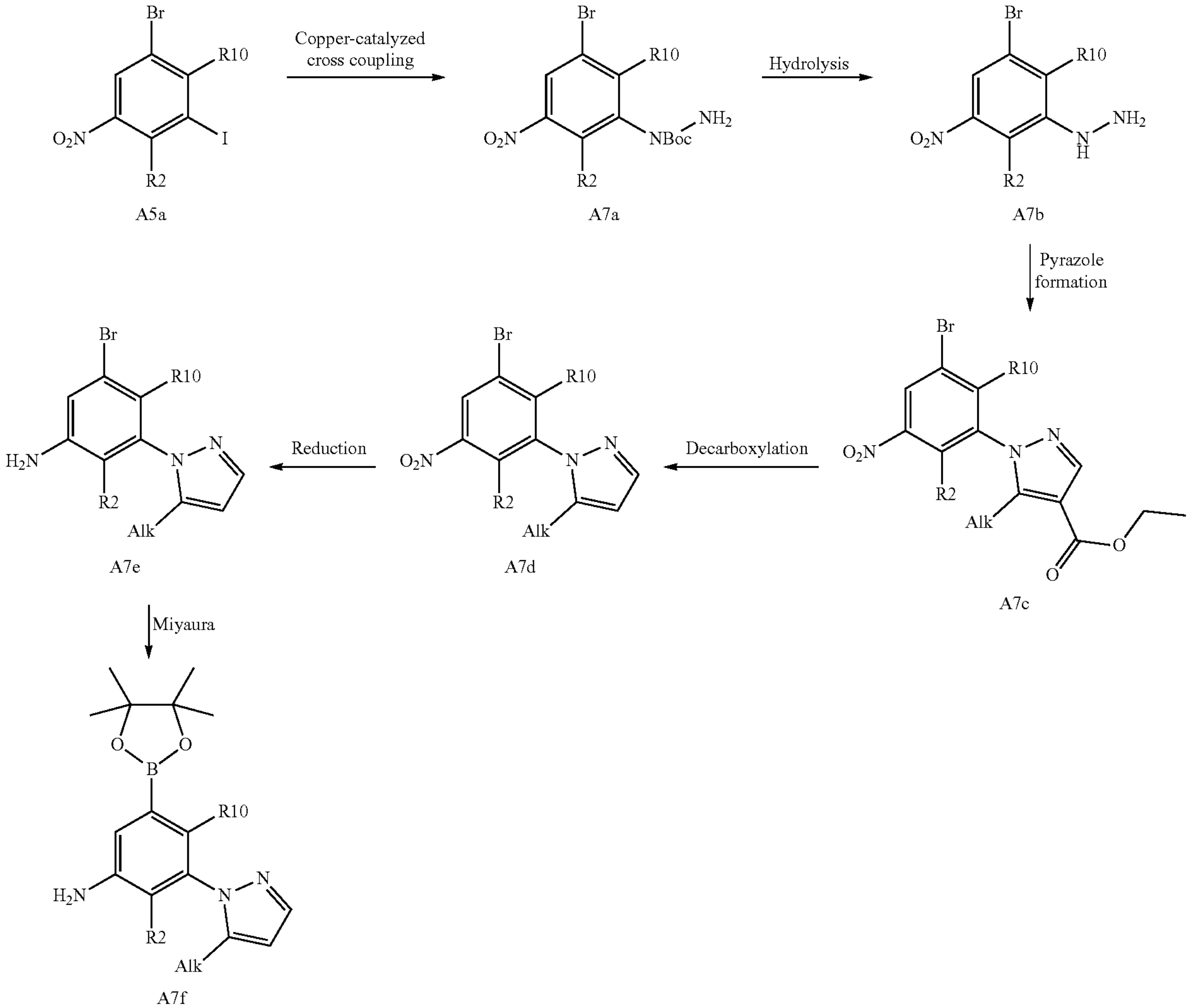

A5a A7a A7b A7c A7d A7e A7f

-continued

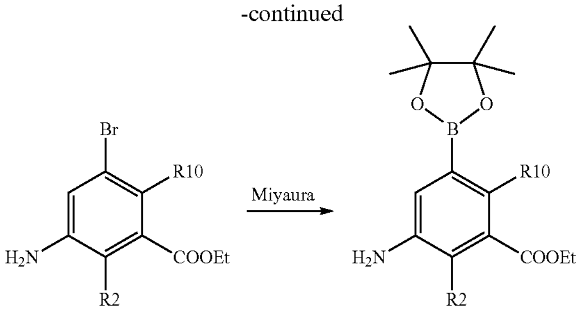

A8b A8c

As shown in Scheme 3i, Compound A3a can undergo Suzuki coupling followed by a silylation protection by TBDPS to obtain intermediate A9c. The compound can be converted to a free aniline using strong acid (for example HCl) followed by Miyaura borylation reaction to afford the boronate A9d.

Scheme 3i

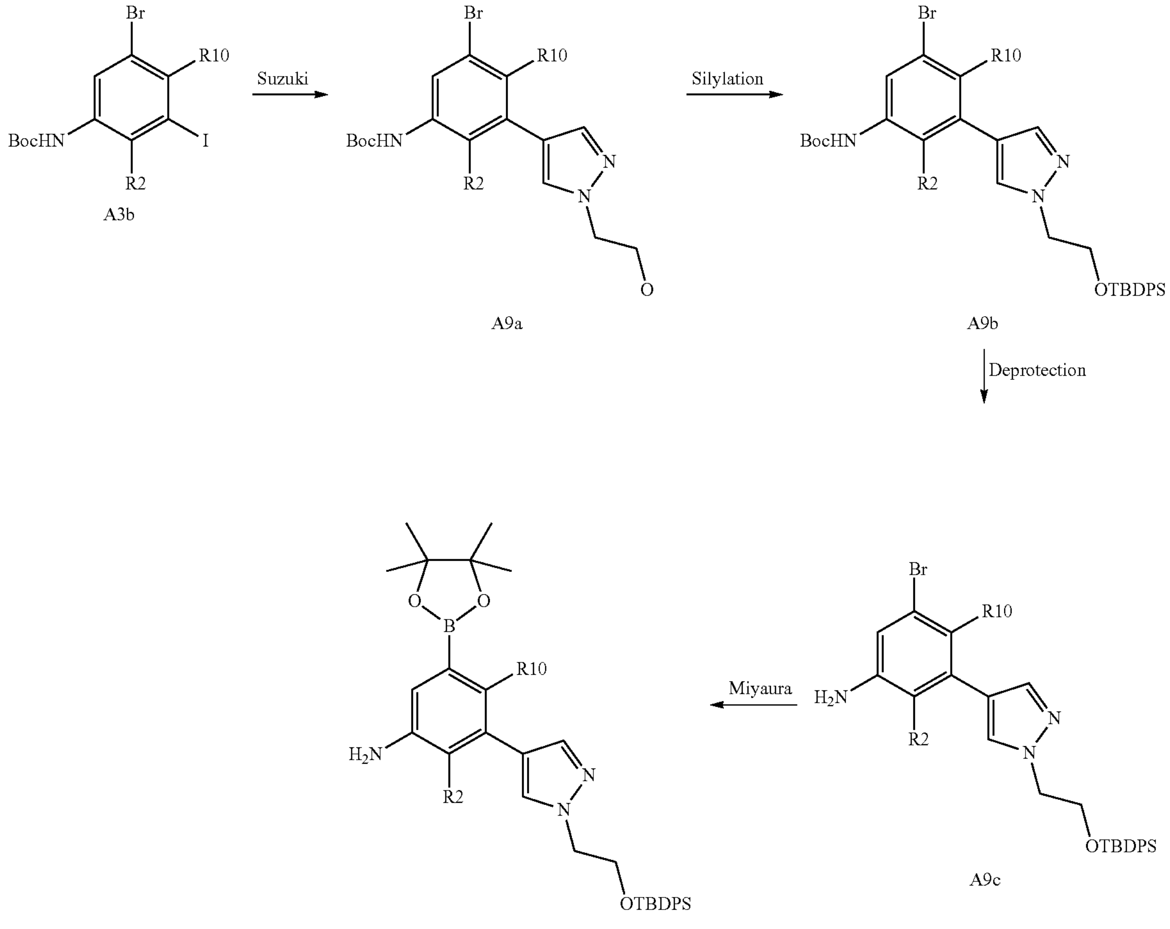

A3b A9a A9b A9c A9d

As shown in Scheme 3j, Compound A10a can undergo Curtius reaction followed by a Suzuki coupling to obtain intermediate A10c. The compound can be converted to a free aniline using strong acid (for example HCl) followed by Miyaura borylation reaction to afford the boronate A10e.

Scheme 3j

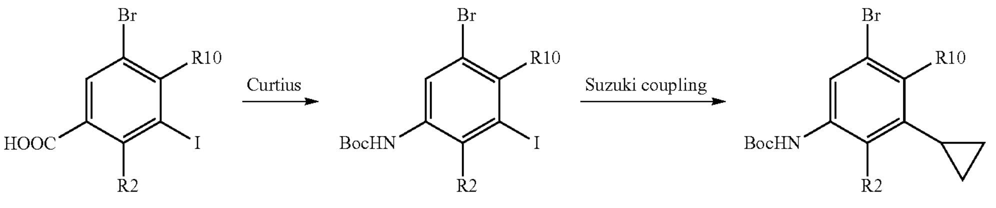

A10a A10b A10c

Deprotection

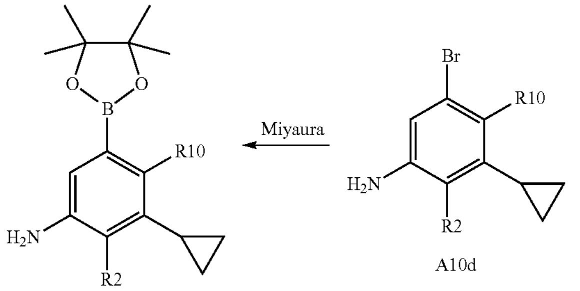

A10e A10d

As shown in Scheme 1, Compound 1a, accounting for intermediates such as Pic or P2b, can undergo aromatic nucleophilic substitution by reaction with 1b. The Boronic ester 1d, prepared from its corresponding Bromophenyl by Borylation, can be introduced by transition metal catalyzed cross coupling to afford 1e. Sequential Nosyl protection of the aniline, its alkylation and deprotection of the Boc group can lead to the amine 1h. Macrocyclization can be performed using Finkelstein conditions to give 1i, which can be followed by oxidation in presence of iodine to afford 1j. Nosyl deprotection can provide final compound 1k.

Scheme 1

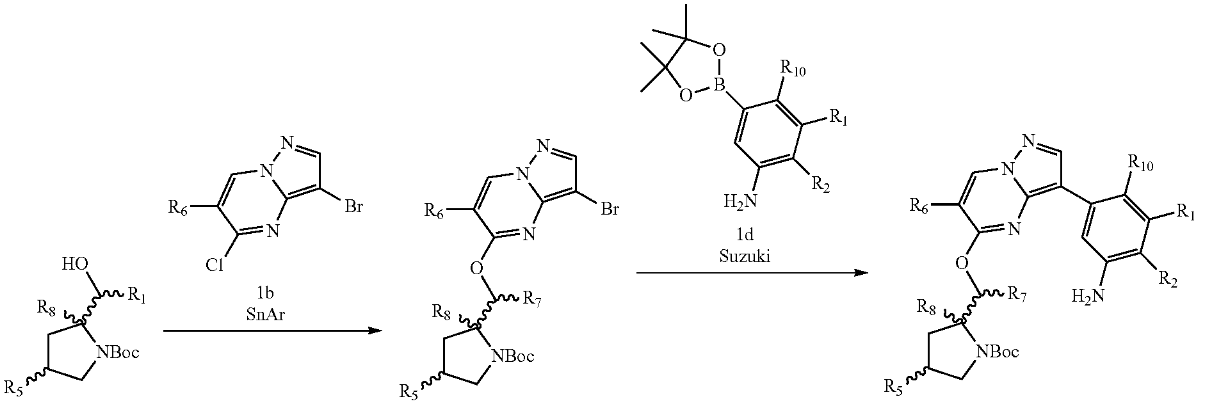

1a 1c 1e

NsCl, Pyridine

-continued

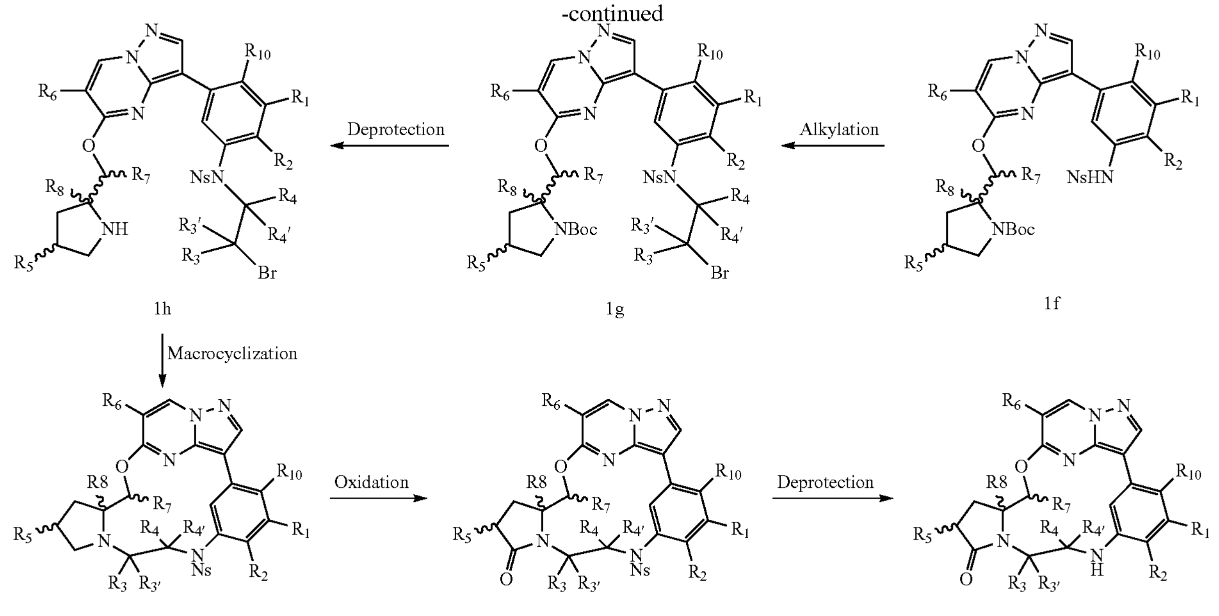

1h 1g 1f 1i 1j 1k

As shown in Scheme 2, compound 1j, containing $R_1$=OBn, can be deprotected in presence of TFA and Anisole to afford the phenol 2a. Subsequent and sequential alkylation and deprotection of the Nosyl provides final compound 2c.

Scheme 2

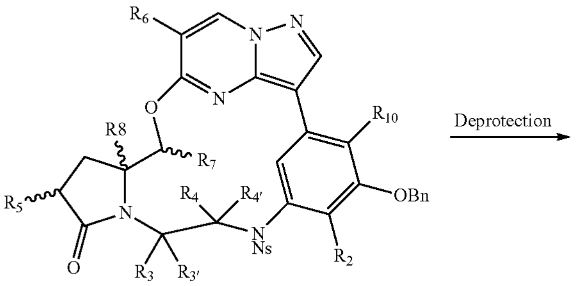

1j

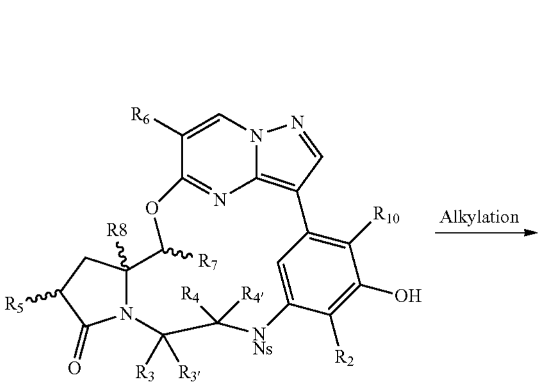

2a

-continued

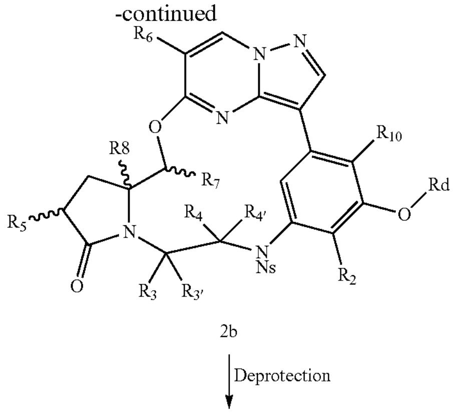

2b

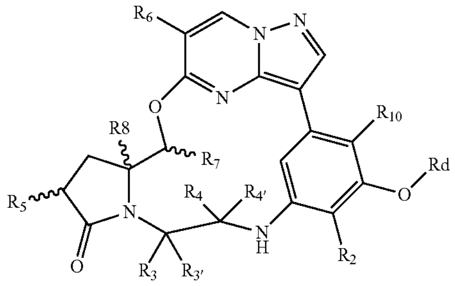

2c

As shown in Scheme 3, the phenol 2a can be converted to the triflate 3a. Acyl moieties was introduced by transition metal catalyzed cross coupling to afford 3b. Subsequent deprotection of the Nosyl provides final compound 3c.

Scheme 3

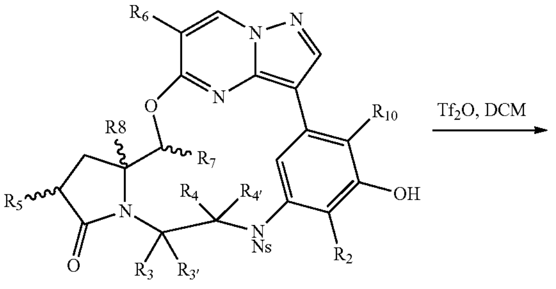

2a

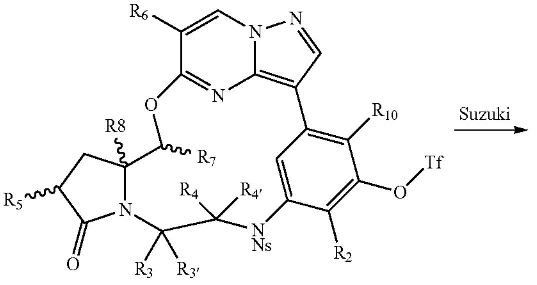

3a

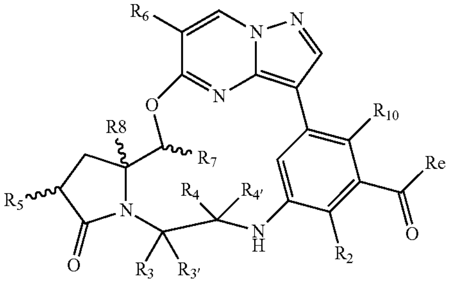

3b

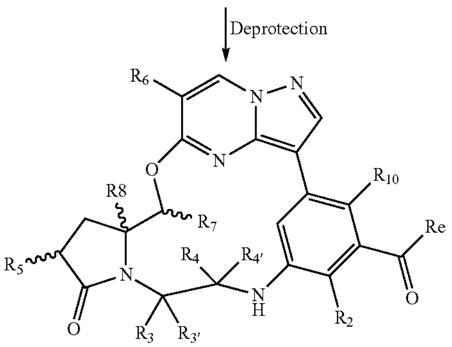

3c

As shown in Scheme 4, the final compound 4b could be obtained by sequential deprotection of the Nosyl group then by removal of the silyl moiety in presence of Methanol and a base from the compound 1j.

Scheme 4

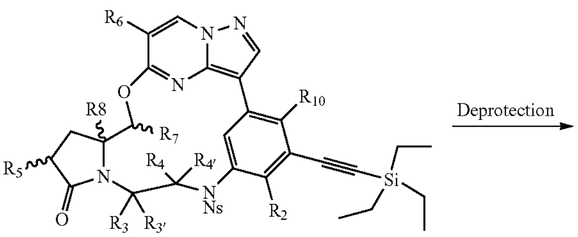

1j

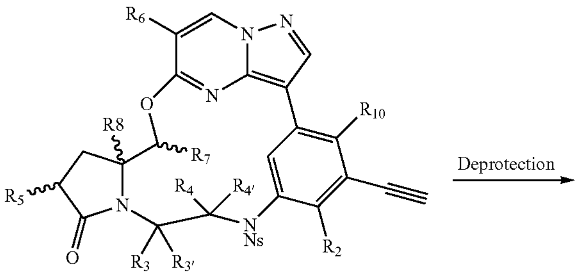

4a

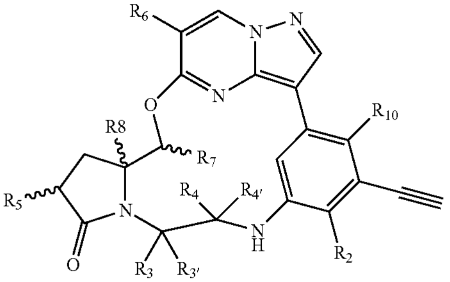

4b

As shown in Scheme 5, compound 1j, containing $R_6$=OBn, can undergo a deprotection of the benzylic moiety in presence of TFA and Anisole to afford the phenol 5a. Following the formation of a triflate in presence of Triflate anhydride and Pyridine, a saturated heterocycle was introduced by a transition metal catalyzed cross coupling to afford the compound 5c. The Nosyl group was removed in presence of Thiophenol to afford the final compound 5d.

Scheme 5
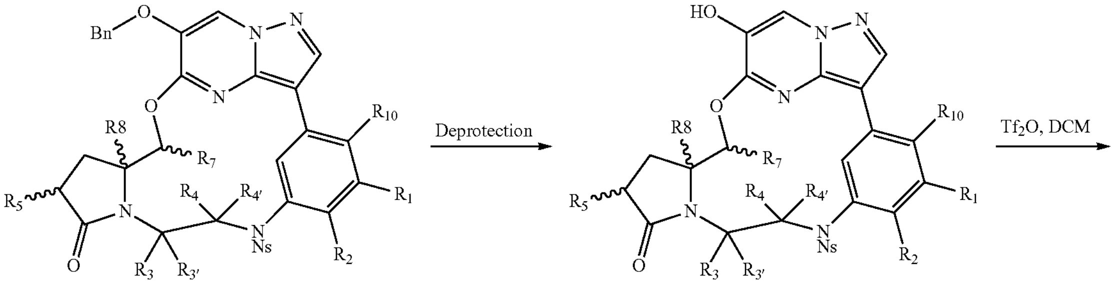
1j 5a
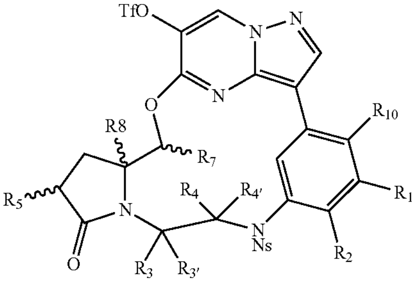
5b
Suzuki
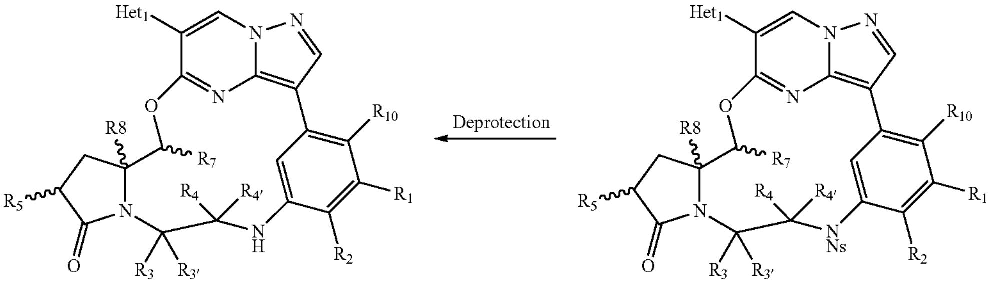
5d 5c

As shown in Scheme 6, compound 1j, containing $R_1$=COOMe, can undergo hydrolysis to the compound 6a. Following a saponification in presence of a base to the compound 6b, a peptidic coupling can afford the final compound 6c.

Scheme 6

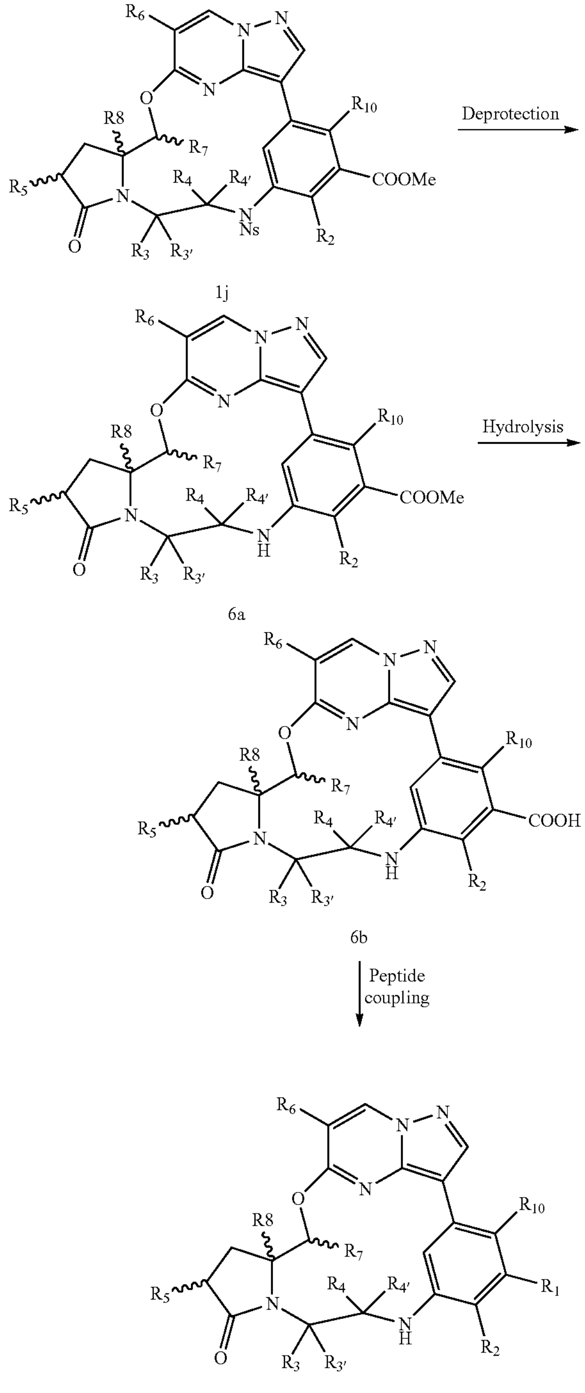

1j

6a

6b

6c

As shown in Scheme 7, compound 6b can undergo reduction in presence of Borane dimethyl sulfide to afford the final compound 7a.

Scheme 7

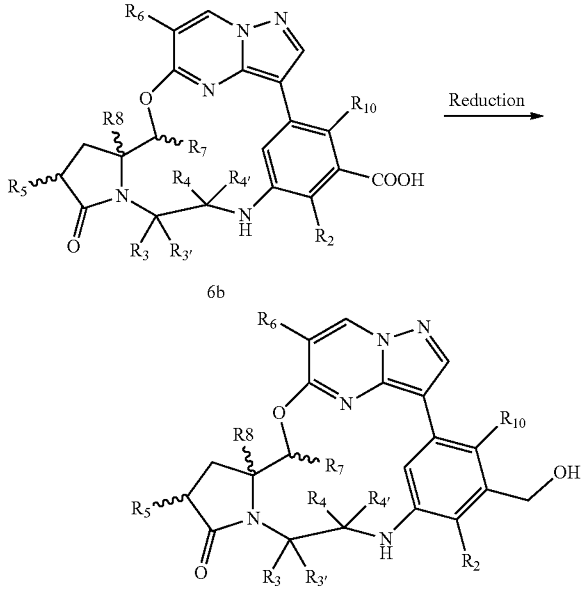

6b

7a

As shown in Scheme 8, compound 7a can undergo chlorination in presence of Thionyl chloride to give compound 8a. The final compound 8b is obtained by alkylation of alcoholates.

Scheme 8

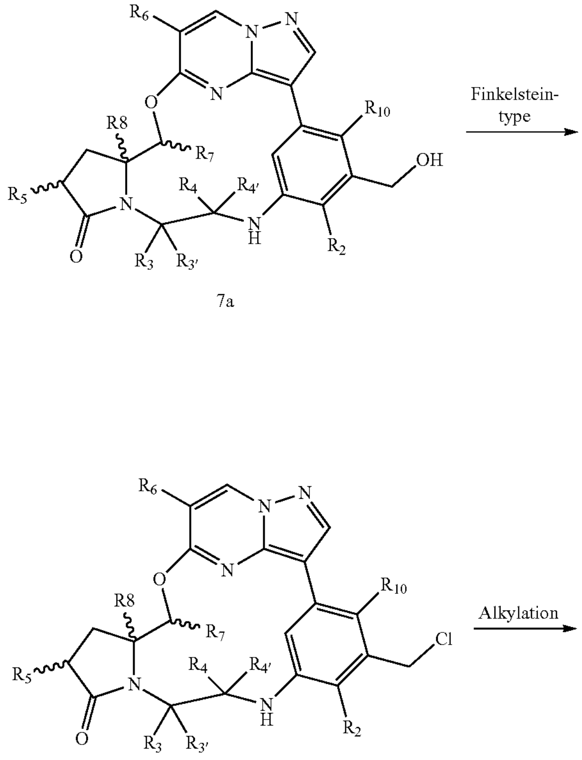

7a

8a

-continued

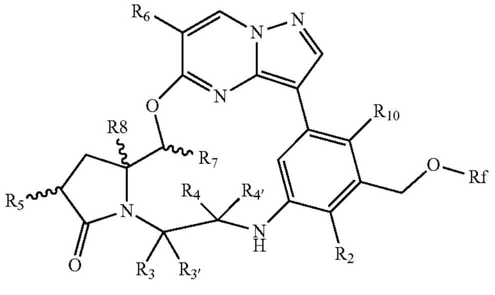

8b

-continued

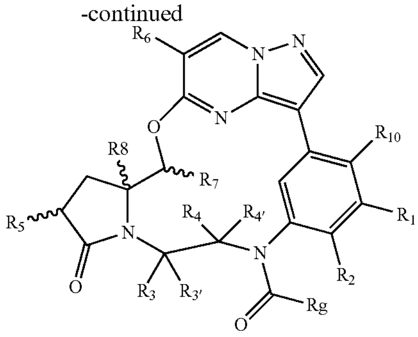

10a

As shown in Scheme 9, compound 1k, containing $R_5$=$OCH_2CH_2OBn$, can undergo hydrogenation in presence of Palladium on charcoal to afford the final compound 9a.

Scheme 9

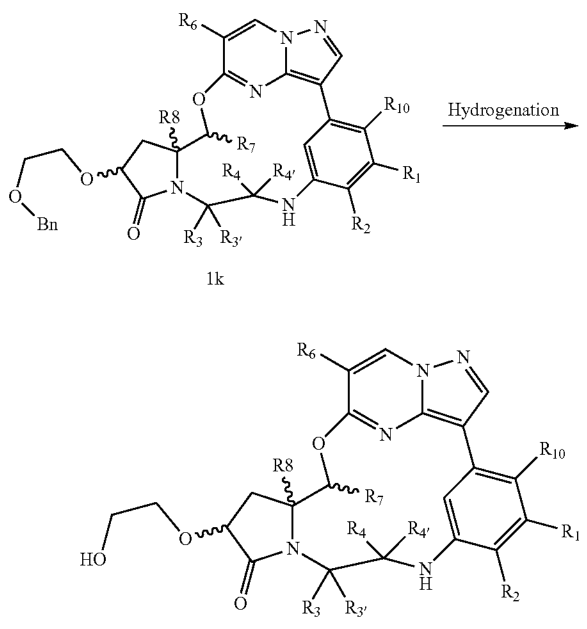

1k

9a

As shown in Scheme 10, compound 1k can undergo acylation reaction to afford the final compound 10a.

Scheme 10

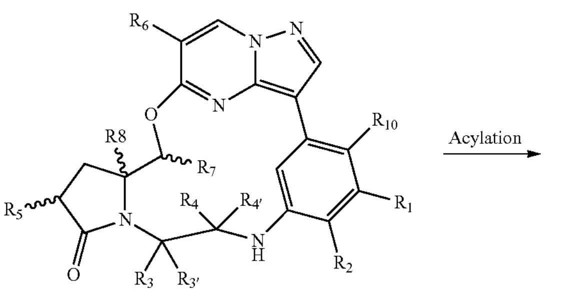

1k

As shown in Scheme 11, compound 1k can undergo alkylation reaction to afford the final compound 11a.

Scheme 11

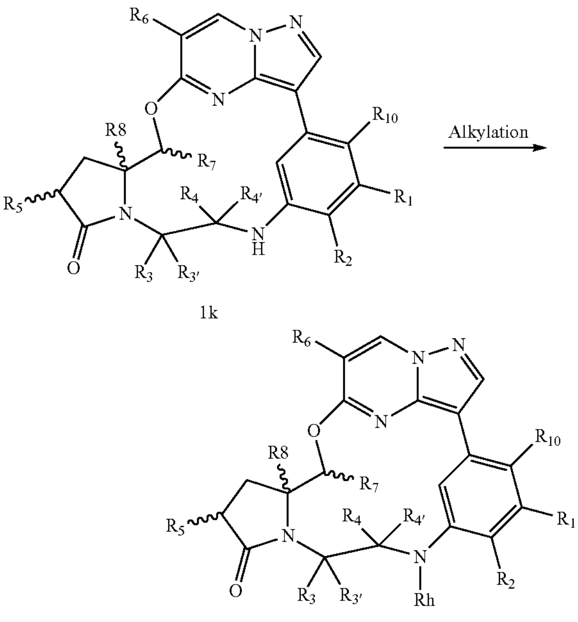

1k

11a

As shown in Scheme 12, compound 1j can be converted to compound 12a in presence of hydroxylamine. The formation of the heterocycle is achieved in presence of Triethyl orthoformate to give 12b. A deprotection of the Nosyl group afford the final compound 12c.

Scheme 12

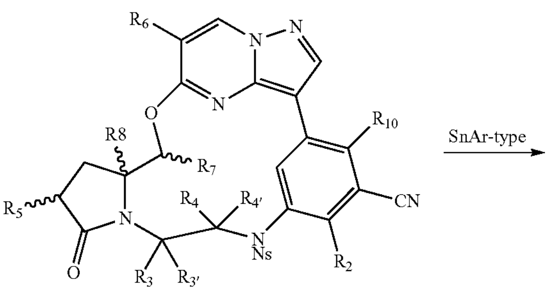

1j

-continued

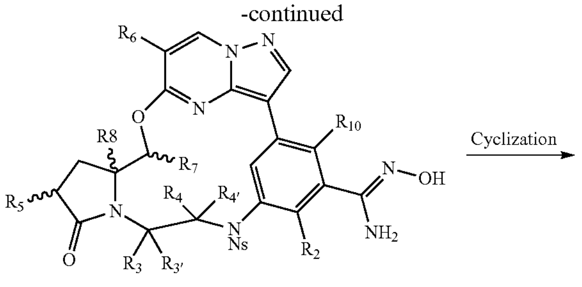

12a

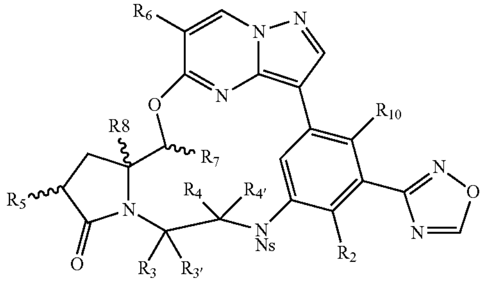

12b

Deprotection

-continued

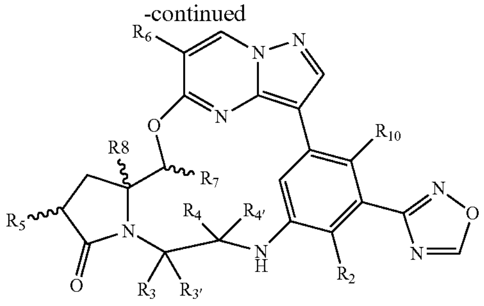

12c

As shown in Scheme 13, compound 1a can undergo aromatic nucleophilic substitution by reaction with 1b to afford 13a. The alkene 13d can be obtained by sequential deprotection of the acetal moiety, protection of the amine with Boc group and a Wittig reaction. The Boronic ester 1d can be introduced by transition metal catalyzed cross coupling to afford 13e. Sequential Nosyl protection of the aniline, its alkylation and deprotection of the Boc group led to the amine 13i. Macrocyclization was performed using Finkelstein conditions to give 13j, which followed by oxidation in presence of iodine to afford 13k. Nosyl deprotection provides final compound 13I.

Scheme 13

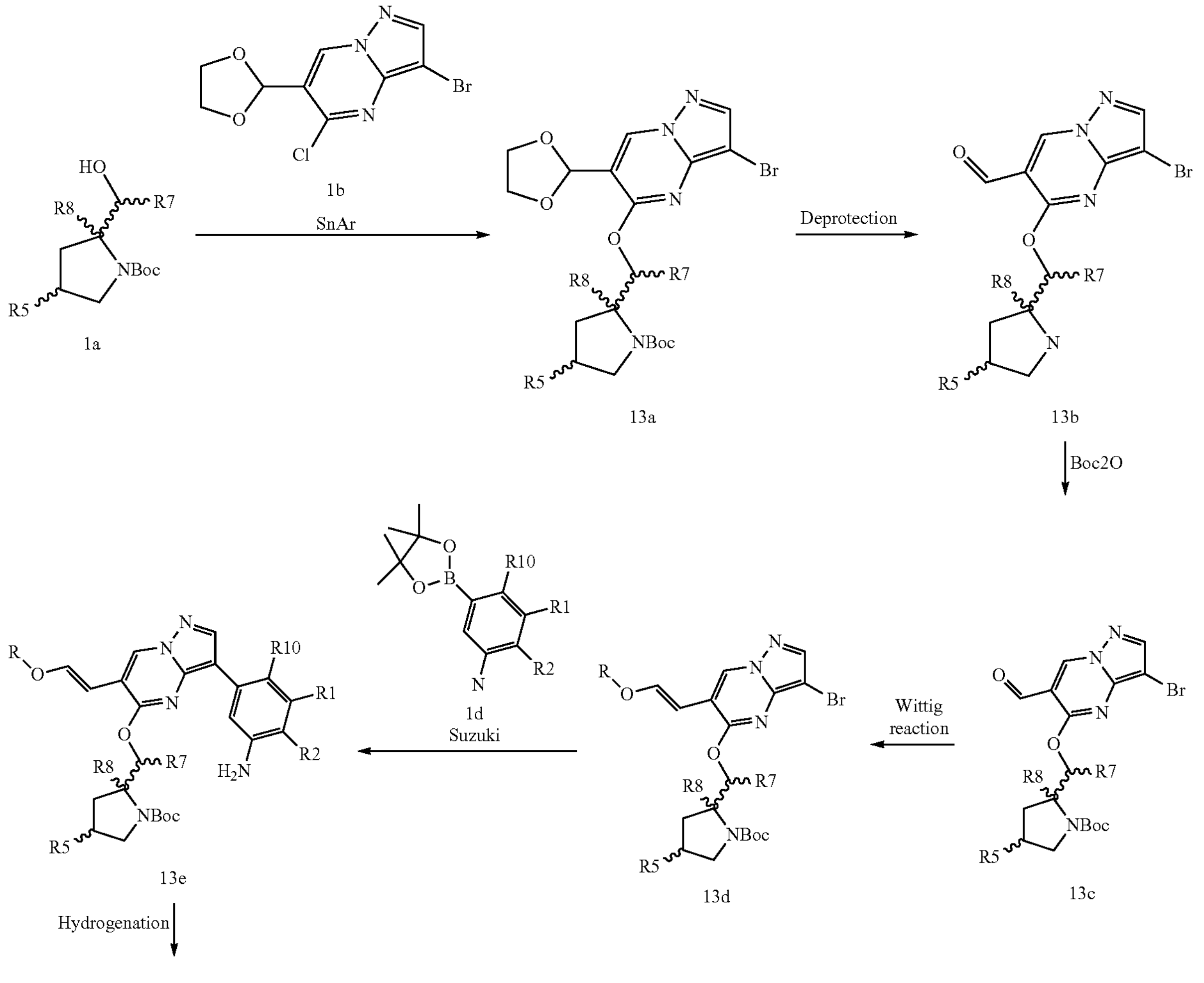

1a 13a 13b 13c 13d 13e

-continued
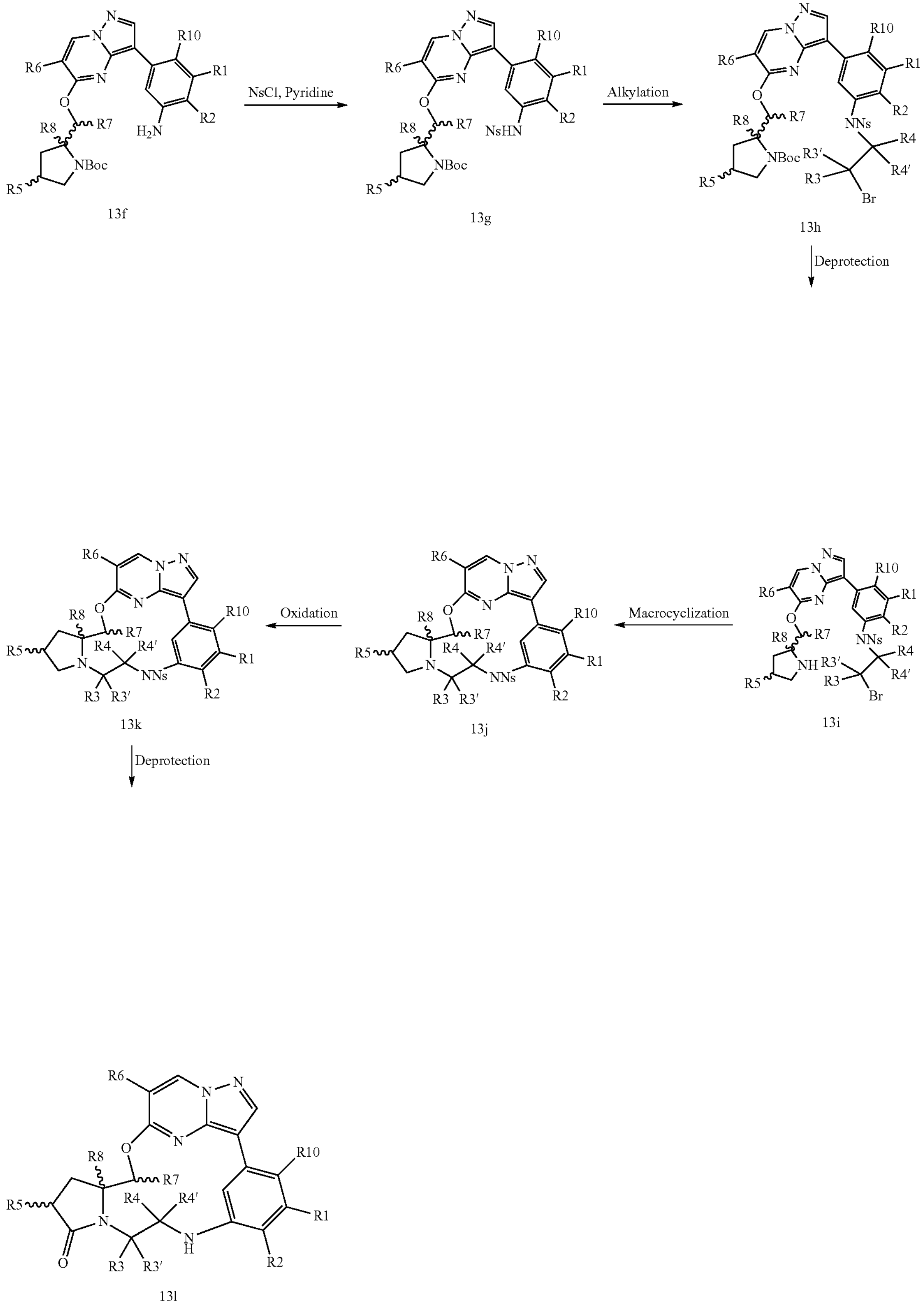
13f 13g 13h 13i 13j 13k 13l

As shown in Scheme 14, compound 1i can undergo deprotection of the Nosyl group, followed by oxidation in presence of Iodine and finally a reduction of the extra Iodine present in the structure to afford the final compound 14c.

Scheme 14

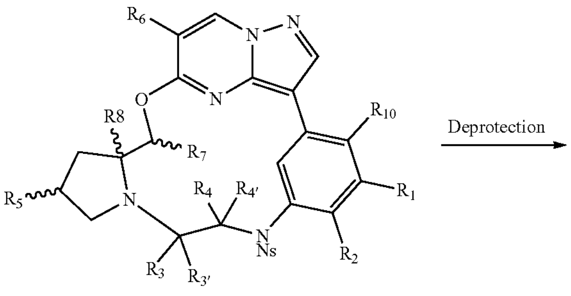

1i

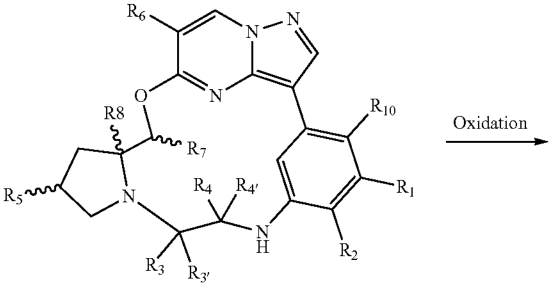

14a

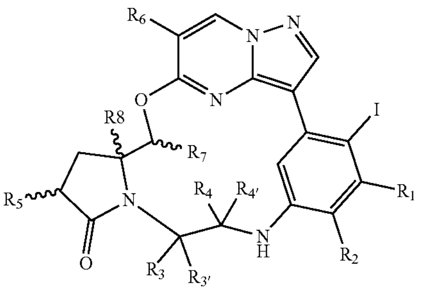

14b

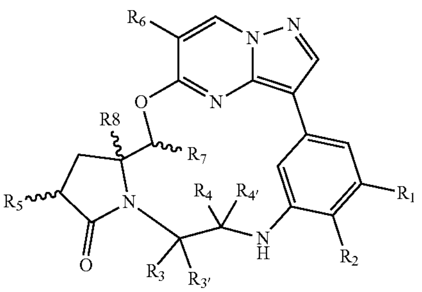

14c

As shown in Scheme 15, compound 1k can undergo a reduction of the extra Iodine (present in the structure as a consequence to oxidation in presence of Iodine) in presence of Iridium catalyst to afford the final compound 15a.

Scheme 15

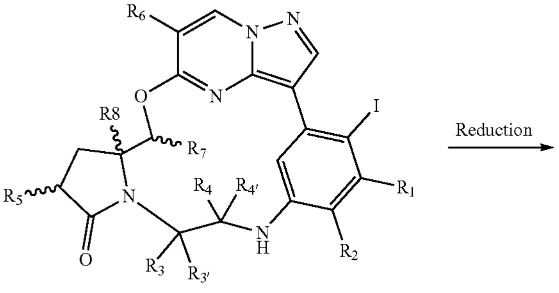

1k

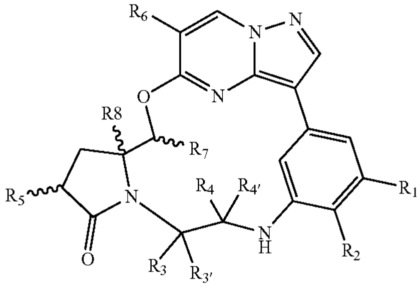

15a

As shown in Scheme 16, compound 1k can undergo a Suzuki coupling in presence of a boronic ester to afford the final compound 16a.

Scheme 16

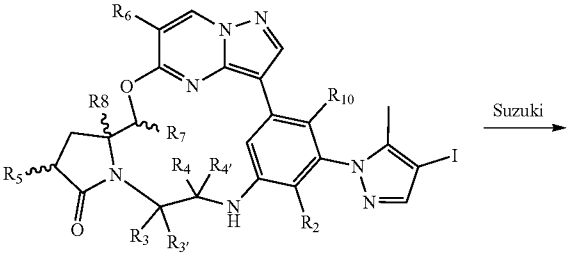

1k

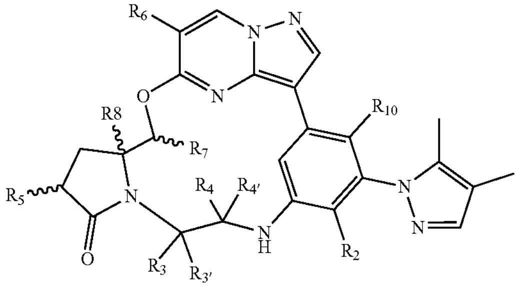

16a

As shown in Scheme 17, compound 16b can undergo alkylation in presence of an alkyl halide followed by nosyl deprotection using a sulfur derivative (for example Methylbenzenethiol) to afford the final compound 17b.

Scheme 17

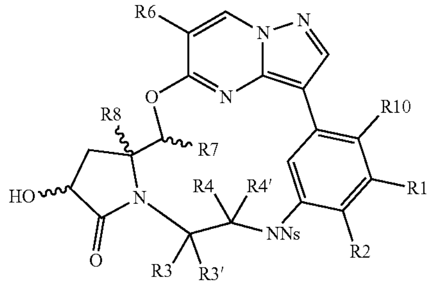

16b

Alkylation

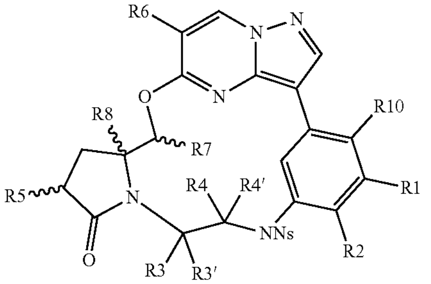

17a

Deprotection

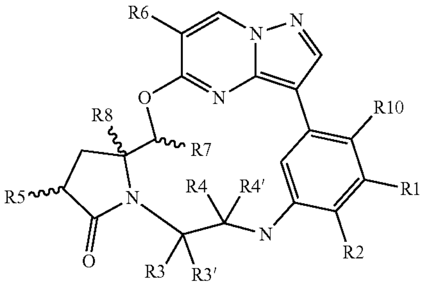

17b

Scheme 18

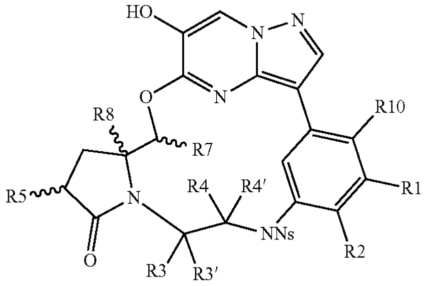

5a

Alkylation

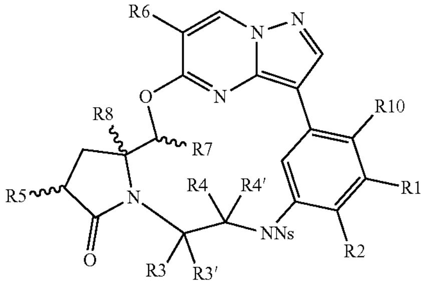

18a

Deprotection

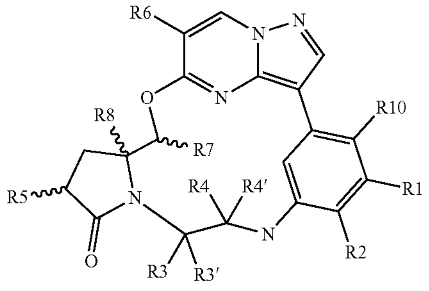

18b

As shown in Scheme 18, compound 5a can undergo alkylation in presence of an alkyl halide and a mild base (for ex. Cesium carbonate), followed by Nosyl deprotection using a sulfur derivative (for example Methylbenzenethiol) to afford the final compound 18b.

As shown in Scheme 19, compound 1k can undergo deprotection, such as silyl TBDPS removal, in presence of TBAF to afford the final compound 19a.

Scheme 19

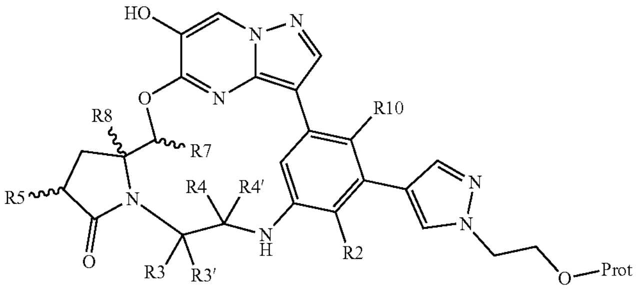

1k

Deprotection

-continued

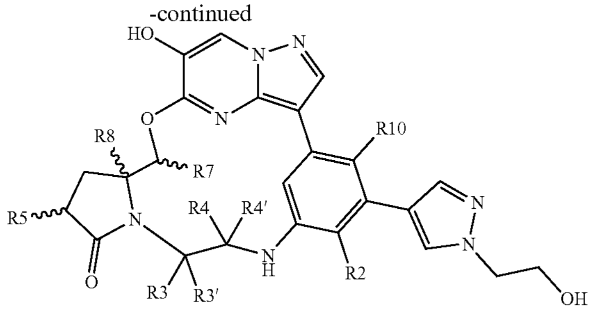

19a

As shown in Scheme 20, compound 2a can undergo Nosyl deprotection using a sulfur derivative (for example Methylbenzenethiol) to afford the final compound 20a.

Scheme 20

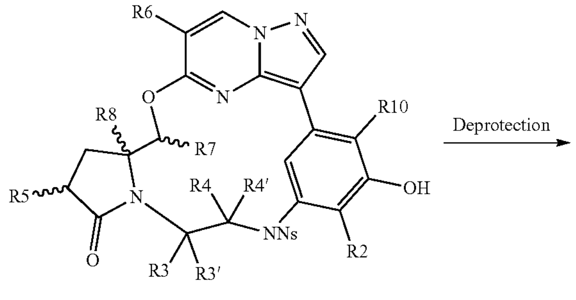

2a

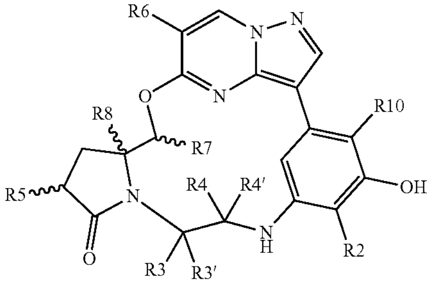

20a

As shown in Scheme 21, compound 1k can undergo dehalogenation in presence of Iridium-based catalyst to afford the final compound 21a.

Scheme 21

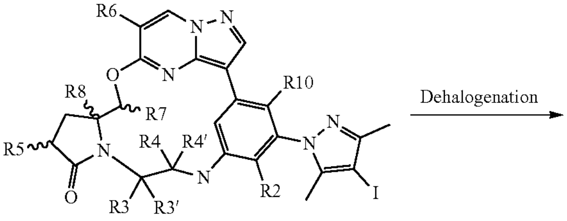

1k

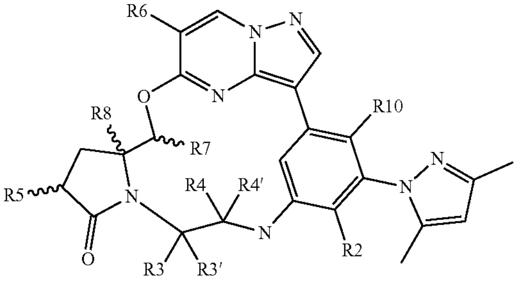

21a

As shown in Scheme 22, compound 1j can undergo hydrolysis in presence of Sodium hydroxide, followed by the imine formation using Dimethoxy-N,N-dimethylmethanamine directly followed by a cyclization in presence of Hydroxylamine to afford the intermediate 22c. The final compound 22d can be obtained by Nosyl deprotection using a sulfur derivative (for example 4-Methylbenzenethiol).

Scheme 22

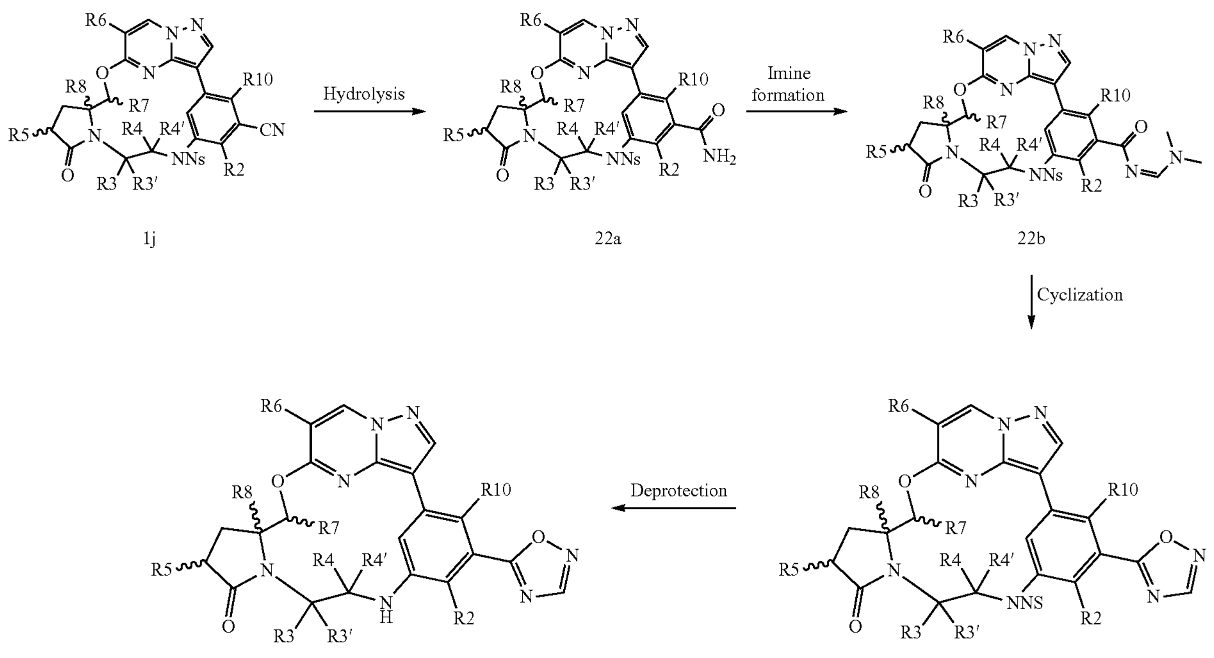

1j 22a 22b 22d 22c

As shown in Scheme 23, compound 3a can undergo Nosyl deprotection using a sulfur derivative (for example 4-Methylbenzenethiol) followed by a transition metal catalyzed cross coupling (such as a Stille coupling) to afford the final compound 23b.

Scheme 23

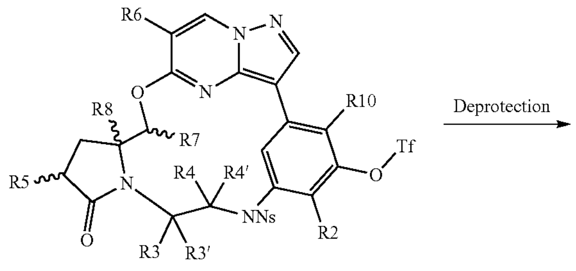

3a

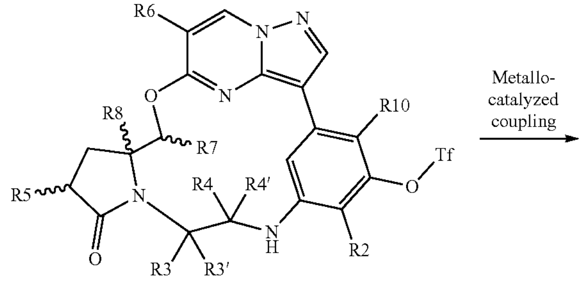

23a

-continued

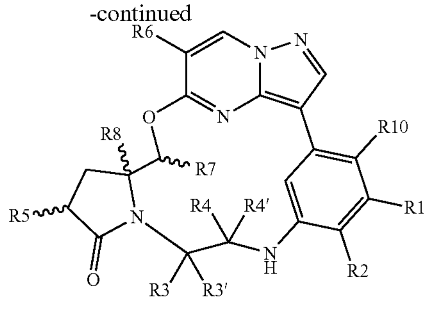

23b

As shown in Scheme 24, compound 3a can undergo silyl deprotection using a fluoride-containing reagent (for example TBAF), followed by a click reaction using an alkyl halide and Sodium azide to afford intermediate 24b. The final compound 24c could be obtained by Nosyl deprotection using a sulfur derivative (for example 4-Methylbenzenethiol).

Scheme 24

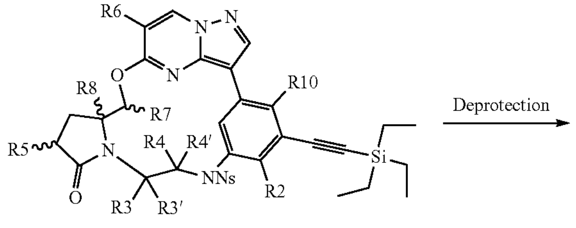

1j

-continued

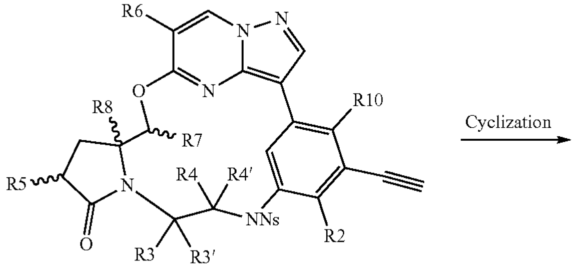

24a

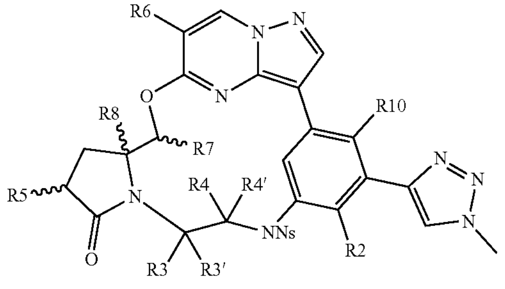

24b

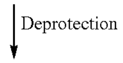

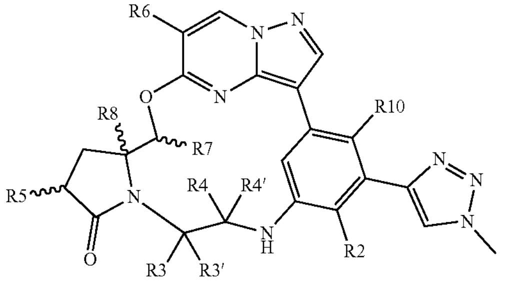

24c

As shown in Scheme 25, compound 16b can undergo ether formation by reaction with alkyl halide and TBAB to afford the final compound 25a.

Scheme 25

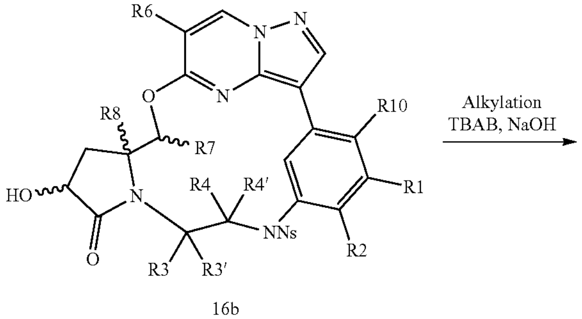

16b

-continued

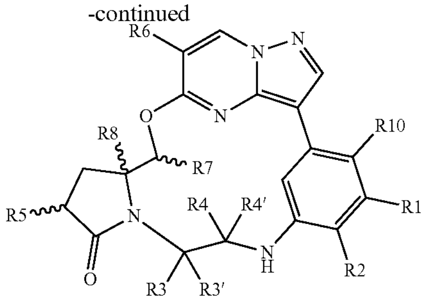

25a

As shown in Scheme 26, compound 16b can undergo a transition metal catalyzed cross coupling (such as Sonogashira coupling) followed by alkyne deprotection in presence of a mild base (such as Potassium carbonate) in alcohol to afford the final compound 26b.

Scheme 26

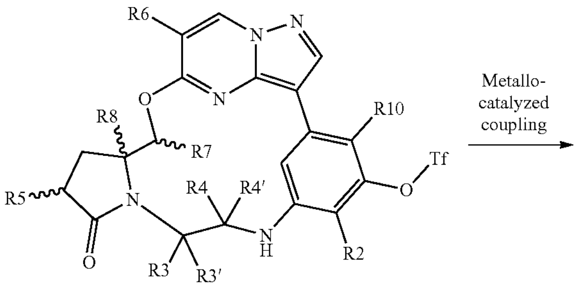

23a

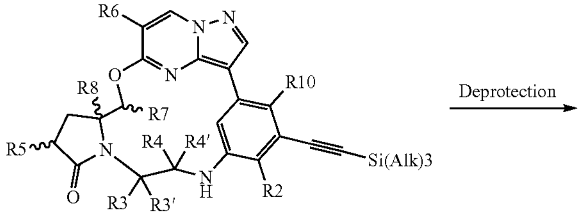

26a

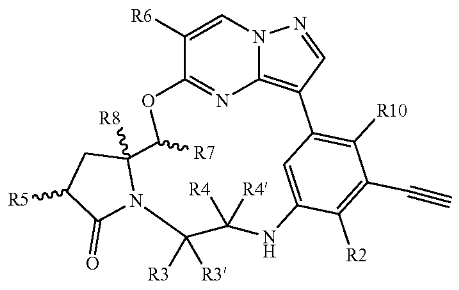

26b

As shown in Scheme 27, compound 1c can undergo amine deprotection using a strong acid (such as HCl), followed by alkylation in presence of alkyl halide to achieve intermediate 27b. The ester moiety could be reduced to primary alcohol 27c in presence of a reductive agent (such as Sodium borohydride/Calcium chloride) then a protecting group could be introduced (such as TBDMS) to obtain intermediate 27d. The compound is then engaged in a Suzuki coupling, followed by Nosyl protecting group introduction and the alcohol deprotection (using TBAF in case of silyl protecting group) to obtain 27 g. The macrocyclization could be performed by Mitsunobu reaction, followed by oxidation in presence of Iodine and Nosyl deprotection using a sulfur derivative (for example 4-Methylbenzenethiol) to afford the final compound 27j.

Scheme 27

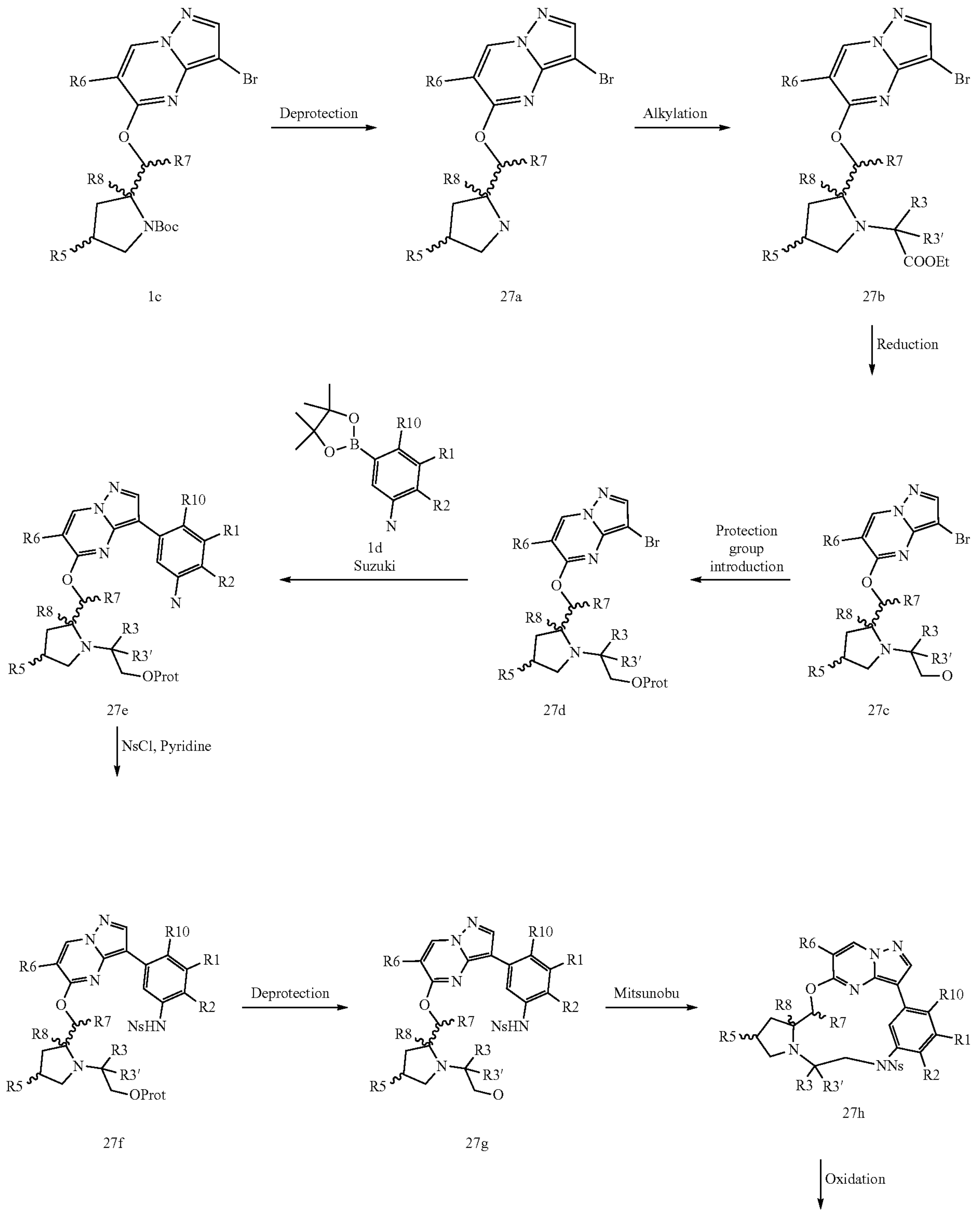

-continued

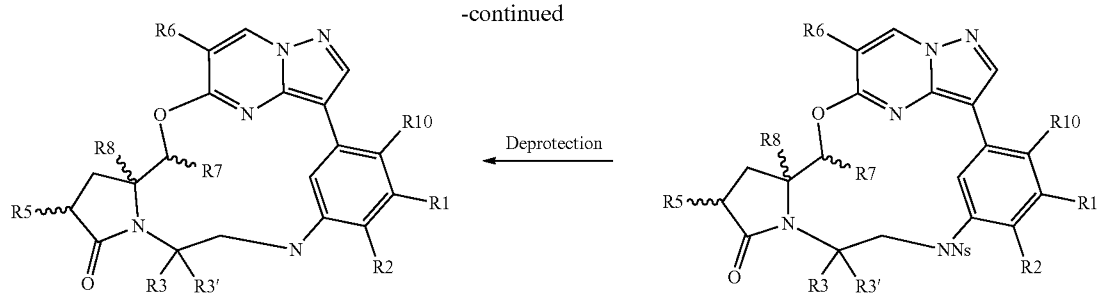

27j 27

As shown in Scheme 28, compound 5a can undergo alkylation using alkyl halide in presence of a mild base (for example Potassium carbonate) followed by nosyl deprotection using a sulfur derivative (for example 4-Methylbenzenethiol) to afford intermediate 28b. The final compound 28c could be obtained by alcohol deprotection (for example p-Toluenesulfonic acid in case of THP protecting group).

Scheme 28

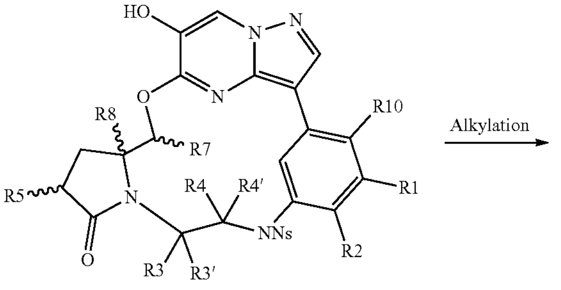

5a

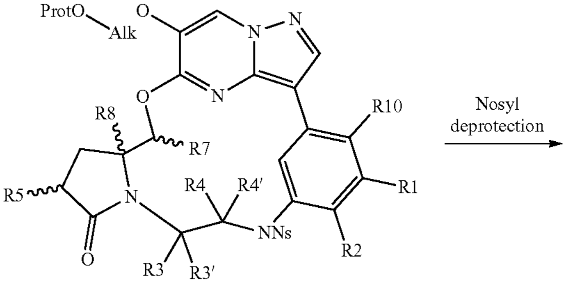

28a

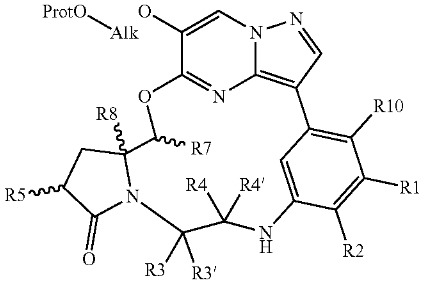

28b

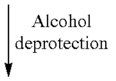

-continued

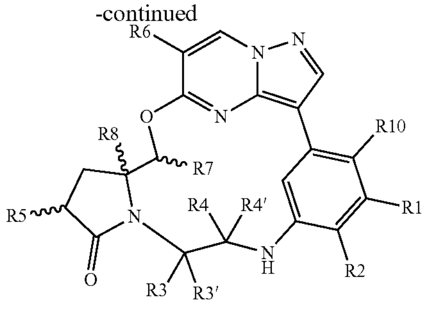

28c

A. Physicochemical Properties of the Compounds

Purification of intermediates and final products was carried out via either normal or reverse phase chromatography. Normal phase chromatography was carried out using prepacked SiO2 cartridges eluting with either gradients of hexanes and EtOAc or DCM and MeOH unless otherwise indicated. Reverse phase preparative HPLC was carried out using a Gilson semi-preparative HPLC system operated by Gilson UNIPOINT software.

Purification method PA: The purification was carried out on a Phenomenex Luna column (100 mm long×21.2 mm i.d.; 5 μm particles) at room temperature, with a constant flow rate of 20.0 mL/min. A gradient elution was performed from 32% (25 mM NH4HCO3 aqueous solution)/68% (Acetonitrile-Methanol 1:1) to 4% (25 mM NH4HCO3 aqueous solution)/96% (Acetonitrile-Methanol 1:1) in 20 minutes. The UV detector was set to 226 nm, which corresponds to the wavelength of maximum absorbance observed for the compound.

Purification method PB: The purification was carried out on a Phenomenex Gemini C18 column (100 mm long×30 mm I.D.; 5 μm particle size) at room temperature, with a flow rate of 30 mL/min. A gradient elution was performed from 70% (Water+25 mM Ammonium Bicarbonate)/5% (Acetonitrile-Methanol 50% mixture) to 27% (Water+25 mM Ammonium Bicarbonate)/73% (Acetonitrile-Methanol 50% mixture) in 20 minutes; after that, a gradient elution was performed from 27% (Water+25 mM Ammonium Bicarbonate)/73% (Acetonitrile-Methanol 50% mixture) to 0% (Water+25 mM Ammonium Bicarbonate)/100% (Acetonitrile-Methanol 50% mixture)) in 2 minutes; the resulting composition was held for 5 min; from 0% (Water+25 mM Ammonium Bicarbonate)/100% (Acetonitrile-Methanol 50% mixture) to 95% (Water+25 mM Ammonium Bicarbonate)/5% (Acetonitrile-Methanol 50% mixture) in 2 min, the resulting composition was held for 5 minutes. The standard injection volume was 8 mL. Acquisition was set to 254 nm for the UV detector.

Unless otherwise stated, analysis of final products was carried out by LCMS or reverse phase analytical HPLC.

LCMS Method A (MA)

Analytical HPLC was conducted on a X-Select CSH C18 XP column (2.5 μm 30×4.6 mm id) eluting with 0.1% formic acid in water (solvent A) and 0.1% formic acid in Acetonitrile (solvent B), using the following elution gradient 0-3 minutes: 5% to 100% B, 3-4 minutes 100% B, at a flow rate of 1.8 mL/minute at 40° C. The mass spectra (MS) were recorded on a Waters ZQ mass spectrometer (scan 200-900 uma) using electrospray positive ionisation [ES+ to give $MH^+$ molecular ions] or electrospray negative ionisation [ES− to give (M−H)− molecular ions] modes with a 20V cone voltage.

LCMS Method B (MB)

Analytical HPLC was conducted on a X-Select CSH C18 XP column (2.5 μm 30×4.6 mm id) eluting with 0.1% ammonia in water (solvent A) and 0.1% ammonia in Acetonitrile (solvent B), using the following elution gradient 0-3 minutes: 5% to 100% B, 3-4 minutes 100% B, at a flow rate of 1.8 mL/minute at 40° C. The mass spectra (MS) were recorded on a Waters ZQ mass spectrometer (scan 200-900 uma) using electrospray positive ionisation [ES+ to give $MH^+$ molecular ions] or electrospray negative ionisation [ES− to give (M−H)− molecular ions] modes with a 20V cone voltage.

LCMS Method C (MC)

Analytical HPLC was conducted on a X-Select CSH C18 XP column (2.5 μm 30×4.6 mm id) eluting with (NH4)2CO3 aq. 2 g/L in water (solvent A) and Acetonitrile (solvent B), using the following elution gradient 0-3 minutes: 5% to 100% B, 3-4 minutes 100% B, at a flow rate of 1.8 mL/minute at 40° C. The mass spectra (MS) were recorded on a Waters ZQ mass spectrometer (scan 200-900 uma) using electrospray positive ionisation [ES+ to give $MH^+$ molecular ions] or electrospray negative ionisation [ES− to give (M−H)− molecular ions] modes with a 20V cone voltage.

LCMS Method D (MD)

In addition to the general procedure LCMS: Analyses were carried out on a YMC pack ODS-AQ C18 column (50 mm long×4.6 mm i.d.; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

LCMS Method E (ME)

In addition to the general procedure LCMS: Analyses were carried out on a Phenomenex Kinetex C18 column (50 mm long×2.1 mm i.d.;, 2.6 μm particles) at 35° C., with a flow rate of 0.7 mL/min. A gradient elution was performed from 95% (50 mM ammonium acetate in water)/5% Acetonitrile to 5% (50 mM ammonium acetate in water)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

LCMS Method F (MF)

Analyses were carried out on a Phenomenex GEMINI C18 column (100 mm long×4.6 mm i.d.; 5 μm particles) at 25° C., with a flow rate of 3.014 mL/min. A gradient elution was performed as follows: 95% (65 mM ammonium acetate in water+Acetonitrile (90:10))/5% Acetonitrile for 0.30 min; from the previous composition to 100% Acetonitrile in 4.26 min; the previous composition was held for 0.60 min, and then it went to 95% (65 mM ammonium acetate in water+Acetonitrile (90:10))/5% Acetonitrile in 1.02 min; the final mobile phase composition was held for an additional 0.57 min. The standard injection volume was 3 μL. Acquisition ranges were set to 200-400 nm for the UV-PDA detector and 100-1000 m/z for the MS detector.

LCMS Method G (MG)

In addition to the general procedure LCMS: Analyses were carried out on a YMC pack ODS-AQ C18 column (50 mm long×4.6 mm I.D.; 3 μm particle size) at 35° C., with a flow rate of 2.6 mL/min. A gradient elution was performed using Agilent 1260 from 95% (Water+0.1% Formic acid)/5% Acetonitrile to 5% (Water+0.1% Formic acid)/95% Acetonitrile in 4.8 min; the resulting composition was held for 1.0 min; from 5% (Water+0.1% formic acid)/95% Acetonitrile to 95% (Water+0.1% formic acid)/5% Acetonitrile in 0.2 min. The standard injection volume was 2 μL. Acquisition ranges were set to 190-400 nm for the UV-PDA detector and 100-1000 m/z for the TOF-MS detector.

LCMS Method H (MH)

In addition to the general procedure LCMS: Analyses were carried out on a Phenomenex Kinetex C18 column (50 mm long×2.1 mm i.d.; 1.7 μm particles) at 60° C., with a flow rate of 1.5 mL/min. A gradient elution was performed from 90% (water+0.1% formic acid)/10% Acetonitrile to 10% (water+0.1% formic acid)/90% Acetonitrile in 1.50 minutes, then the final mobile phase composition was held for an additional 0.40 min. The standard injection volume was 2 μL. Acquisition ranges were set to 254 nm for the UV-PDA detector and 80-800 m/z for the MS detector.

LCMS Method I (MI)

Analyses were carried out on a Thermo Scientific Accucore C18 (50 mm long×2.1 mm I.D., 2.6 μm) at 35° C., with a flow rate of 1.50 mL/min. A gradient elution was performed from 95% (Water+0.1% Formic acid)/5% Acetonitrile to 5% (Water+0.1% Formic acid)/95% Acetonitrile in 1.30 minutes; the resulting composition was held for 0.5 min; then the final mobile phase composition; from 5% (Water+0.1% Formic acid)/95% Acetonitrile to 90% (Water+0.1% Formic acid)/10% Acetonitrile in 0.10 minutes. The injection volume was 1 μL. MS acquisition range and UV detector were set to 100-1000 m/z and 190-400 nm respectively.

LCMS Method K (MK)

Analytical HPLC was conducted on a Kinetex EVO C18 30*2.1 mm, 5 um eluting with 0.0375% TFA in water (v/v) (solvent A) and 0.01875% TFA in Acetonitrile (v/v) (solvent B), using the following elution gradient 0-1.20 minutes: 5% to 95% B, 1.2-1.55 minutes 95% to 5% B, at a flow rate of 1.5 mL/minute at 50° C. The mass spectra (MS) were recorded using ESI ionization source [ES+ to give MH+ molecular ions] modes with a 20V Qarray DC voltage.

Purification was performed using a Gilson system consisting of a binary pump (333 Model and 334 Model), ASPEC autosampler, column valve selector and UV detector. Data acquisition was performed with Trilution 3.0 software.

Scaffold S1: 3-bromo-5-chloro-6-methylpyrazolo[1,5-a]pyrimidine

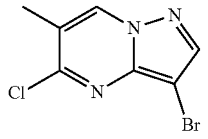

Step 1

To a solution of 1H-pyrazol-5-amine (173 g, 2.09 mol) was added EtONa (343 g, 5.04 mol, 2000 mL), followed by diethyl 2-methylpropanedioate (400 g, 2.30 mol, 392 mL). The mixture was stirred at 100° C. for 12 hours. TLC (petroleum ether/ethyl acetate=0/1, compound 4, Rf=0.3) showed that the reaction was completed. The reaction mixture was cooled down to 25° C. and filtered to get the light yellow solid. The crude was stirred in EtOH (5 L) for 12 hours, filtered to get a white solid. 7-hydroxy-6-methyl-4H-pyrazolo[1,5-a]pyrimidin-5-one, sodium salt (540 g) was obtained as a white solid.

The crude material will be used in the next step without further purification.

$^1$H NMR (ppm, 400 MHz), MeOD: 7.56 (d, J=1.8 Hz, 1H), 5.75 (d, J=2.0 Hz, 1H), 1.95 (s, 3H)

Step 2

To a solution of $POCl_3$ (3.15 kg, 20.5 mol, 1.91 L) was added 7-hydroxy-6-methyl-4H-pyrazolo[1,5-a]pyrimidin-5-one, sodium salt (366 g, 2.22 mol). The mixture was stirred at 105° C. for 40 hours. The mixture was concentrated to remove most of $POCl_3$ and the reaction mixture was diluted with ethyl acetate (5000 mL), poured into ice water (10000 mL) and adjust to pH=7-8 by addition of saturated NaHCO3 solution. Then the aqueous phases were extracted with ethyl acetate (2000 mL*3), the combined organic layer was washed with Brine (1000 mL), dried over sodium sulfate, filtered and concentrated in vacuo. The title compound, 5,7-dichloro-6-methyl-pyrazolo[1,5-a]pyrimidine, (590 g, 2.92 mol, 43.9% yield) was obtained as a black oil.

The crude material will be used in the next step without further purification.

$^1$H NMR (ppm, 400 MHz), $CDCl_3$: 8.15 (d, J=2.3 Hz, 1H), 6.69 (d, J=2.3 Hz, 1H), 2.54 (s, 3H)

Step 3

To a solution of 5,7-dichloro-6-methyl-pyrazolo[1,5-a]pyrimidine (290 g, 1.44 mol) in THE (1.5 L) were added Zn (210 g, 3.21 mol), a solution of Ammoniac (35%), (528 g, 5.27 mol, 580 mL, 3.67 eq), and a saturated NaCl solution (1.5 L). The reaction mixture was stirred at 25° C. for 2 hours. TLC (petroleum ether:ethyl acetate=3:1) showed that the reaction was completed. The mixture was filtered to remove Zn and then extracted with ethyl acetate (1000 mL*3). The combined organic layer was washed with Brine (1000 mL), dried over sodium sulfate, filtered and concentrated in vacuo to give the title compound, 5-chloro-6-methyl-pyrazolo[1,5-a]pyrimidine (420 g) obtained as a yellow solid. The crude material will be used in the next step without further purification.

$^1$H NMR (ppm, 400 MHz), $CDCl_3$: 8.49 (s, 1H), 8.05 (d, J=1.8 Hz, 1H), 6.63-6.52 (m, 1H), 2.38 (s, 3H)

Step 4

To the solution of 5-chloro-6-methyl-pyrazolo[1,5-a]pyrimidine (400 g, 2.39 mol) in Acetonitrile (2 L) was added N-Bromosuccinimide (480 g, 2.70 mol). The reaction mixture was stirred at 20° C. for 0.5 hours. LCMS showed the formation of expected compound. The mixture was poured into water (2000 mL), and the solid formed was collected by filtration. The title compound, 3-bromo-5-chloro-6-methyl-pyrazolo[1,5-a]pyrimidine (500 g, 2.03 mol, 85% yield) was obtained as yellow solid. The crude will be used in next step without further purification.

LCMS (MK) RT=0.837 min, m/z=247.9 $(M+H)^+$.

Scaffold S2: 3-bromo-5-chloro-6-methoxypyrazolo[1,5-a]pyrimidine

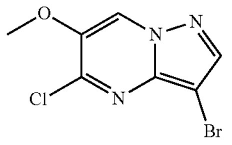

Step 1:

Dimethyl 2-methoxymalonate (100 g, 616.7 mmol) was diluted in Ethanol (200 mL) and was added to a mixture of 3-aminopyrazole (51.25 g, 616.7 mmol) and Sodium Ethanolate (370 mL) in Ethanol (1.65 L).

The mixture of the reaction was heated at 120° C. for 16 hours. Upon complete conversion, monitored by LCMS, the mixture was cooled at 0° C. The resulting violet solid was filtered off and washed with EtOH at 0° C., concentrated, co-evaporated with Acetonitrile and dried under high vacuum.

To a stirred solution of HCl 1N was added the solid portionwise at 4-5° C. The precipitate was filtered and washed with a minimum of cold water. The beige solid was concentrated in vacuum and co-evaporated with toluene (×3). The beige solid was dried high vacuum and used as such in the next step.

LCMS (MD) RT=0.405 min, m/z=182.0 $(M+H)^+$.

Step 2:

To a solution of the title compound from Step 1 (135.8 g, 7449.6 mmol) and Phosphorous oxychloride (449.8 g, 2248.9 mmol) was added N,N-diethylaniline (101.71 mL, 1049.5 mmol) slowly at 0° C. The reaction was heated at 120° C. for 4 hrs. After cooling, the excess of Phosphorous oxychloride was removed and the residue was diluted with EtOAc and washed with a saturated solution of $NaHCO_3$. The organic layer was dried overmg$SO_4$, filtered and concentrated under vacuo. The product was purified by flash chromatography using as eluents Heptane/EtOAc (100:0 to 80:20) to afford the title compound as a yellow solid (44.8 g, 27% yield).

LCMS (MH) RT=0.556 min, m/z=218.1/220.0 $(M+H)^+$.

Step 3:

The title compound from Step 2 (22.1 g, 101.36 mmol) was dissolved in Acetonitrile (304 mL) and cooled to 0° C. Then, N-Bromosuccinimide (18.04 g, 101.36 mmol) was added portionwise and the mixture was left stirring at room temperature for 30 min. Upon complete conversion, monitored by LCMS, the mixture was diluted with EtOAc and extracted with a saturated solution of $NaHCO_3$. Organic layer was dried overmg$SO_4$, filtered and concentrated. The product was purified by flash chromatography using as eluents Heptane/EtOAc (100:0 to 80:20) to afford the title compound as a yellow solid (23.7 g, 78.8%).

LCMS (MH) RT=0.769 min, m/z=295.2/299.0 $(M+H)^+$.

Step 4:

The title compound from Step 3 (20.0 g, 67.35 mmol) was suspended in EtOH (303 mL). Sodium Borohydride (3.06 g, 80.8 mmol) was added portionwise at 0° C. The reaction mixture was kept at 0° C. under continuous stirring. Upon complete conversion, monitored by LCMS, the mixture was quenched with water. EtOAc was added and extracted. The organic layer was dried overmgSO4, filtered and concentrated to dryness. The crude was purified by flash chromatography on silica gel using as eluent DCM/MeOH (100:0 to 90:10) afford the expected compound as a yellowish solid.

LCMS (MH) RT=0.655 min, m/z=260.2/262.2 $(M+H)^+$.

Scaffold S3: 3-Bromo-6-(bromomethyl)-5-chloro-pyrazolo[1,5-a]pyrimidine

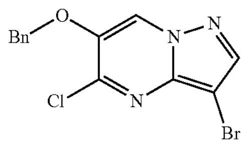 [SMILES: Clc1nc2c(Br)cnn2cc1OCc1ccccc1]

Step 1

To a solution of 2-(benzyloxy)acetic acid (166 g, 999 mmol, 143 mL, 1 eq) in MeOH (800 mL) was added dropwise Acetyl chloride (117 g, 1.50 mol, 107 mL, 1.5 eq) at 10° C. The mixture was stirred at 20° C. for 1 hr. The mixture was concentrated under vacuum. The residue was purified by column chromatography ($SiO_2$, Petroleum ether/Ethyl acetate=10/1 to 5/1) to afford the title compound (170 g, 943 mmol, 94.4% yield) as a colorless oil.

$^1H$ NMR: 400 MHz, $CDCl_3$: 7.45-7.30 (m, 5H), 4.66 (s, 2H), 4.13 (s, 2H), 3.79 (s, 3H) Step 2 To a solution of Sodium hydride (33.0 g, 824 mmol, 60% purity, 1.1 eq) in THE (675 mL) was added Ethyl formate (83.3 g, 1.12 mol, 90.4 mL, 1.5 eq). Then the title compound from Step 1 (135 g, 749 mmol, 1 eq) in THE (135 mL) was added dropwise to the mixture at 0° C. The mixture was stirred at 25° C. for 3 h. DMF (400 mL) and Ethyl Iodide (117 g, 749 mmol, 59.9 mL, 1 eq) were added dropwise to the mixture. The resulting mixture was stirred at 35° C. for 1 h. The mixture was poured into ice water (1500 mL), and extracted with Ethyl acetate (1000 mL*3). The combined organic layers were dried over $Na_2SO_4$, filtered and concentrated under reduced pressure to afford the title compound (185 g, crude) as a yellow oil which was used into next step based on the theoretical 100% yield without purification.

Step 3

To a solution of 3-aminopyrazole (41.0 g, 493 mmol, 1 eq), the title compound from Step 2 (175 g, 740 mmol, 1.5 eq) in DMF (1000 mL) was added $Cs_2CO_3$ (241 g, 740 mmol, 1.5 eq). The mixture was stirred at 110° C. for 10 hr. Upon complete conversion, monitored by LCMS, the mixture was cooled to 20° C. and poured into ice water (3000 mL), adjusted pH=5-6 by 2M HCl (700 mL), a lot of solid precipitated during this period. The mixture was filtered and the filter cake was washed with water (600 mL). The filter cake was triturated with Tert-butyl methyl ether (500 mL) to afford the title compound (65.0 g, 269 mmol, 54.6% yield) as a yellow solid.

$^1H$ NMR: DMSO-$d_6$ 400 MHz: 12.40 (s, 1H), 8.33 (s, 1H), 7.66 (d, J=2.1 Hz, 1H), 7.53-7.33 (m, 5H), 5.80 (d, J=1.7 Hz, 1H), 5.05 (s, 2H)

Step 4

To a solution of the title compound from Step 3 (80.0 g, 332 mmol, 1 eq) in Acetonitrile (600 mL) was added $POCl_3$ (127 g, 829 mmol, 77.0 mL, 2.5 eq) and N, N-Diethylaniline (495 mg, 3.32 mmol, 530 uL, 0.01 eq). Then the mixture was stirred at 100° C. for 4 hr. Upon complete conversion, monitored by LCMS, the mixture was concentrated under vacuum to remove mostly $CH_3CN$ and $POCl_3$. Then the mixture was diluted with Ethyl acetate (1000 mL) and poured into ice water (2000 mL), adjusted pH=7 by potassium carbonate, extracted with ethyl acetate (1000 mL*2). The combined organic layers were washed with Brine (1000 mL), dried over $Na_2SO_4$, filtered and concentrated under reduced pressure. The residue was purified by column chromatography ($SiO_2$, Petroleum ether/Ethyl acetate=10/1 to 5/1) to afford the title compound (66.0 g, 254 mmol, 76.6% yield) as a light-yellow solid.

$^1H$ NMR: $CDCl_3$, 400 MHz, 8.27 (s, 1H), 8.02 (d, J=2.4 Hz, 1H), 7.58-7.39 (m, 5H), 6.61 (d, J=2.4 Hz, 1H), 5.19 (s, 2H)

Step 5

To a solution of the title compound from Step 4 (69.0 g, 266 mmol, 1 eq) in Dichloromethane (650 mL) was added NBS (47.3 g, 266 mmol, 1 eq) slowly. The mixture was stirred at 25° C. for 2 hr. Upon complete conversion, monitored by LCMS, the mixture was concentrated under reduced pressure. The residue was triturated with a solution of DCM: PE=1:1(300 mL) and filtered. The filter cake was washed with water (1000 mL) to afford the expected compound (85.3 g, 252 mmol, 94.7% yield) as a light-yellow solid.

$^1H$ NMR: DMSO-$d_6$, 400 MHz, 9.23 (s, 1H), 8.31 (s, 1H), 7.59-7.17 (m, 5H), 5.27 (s, 2H)

Scaffold S4: 3-Bromo-6-(bromomethyl)-5-chloro-pyrazolo[1,5-a]pyrimidine and Scaffold S5: 3-bromo-5-chloro-6-(dibromomethyl)pyrazolo[1,5-a]pyrimidine

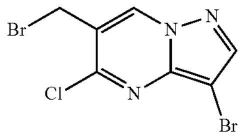

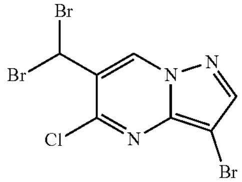

To a solution of 3-bromo-5-chloro-6-methyl-pyrazolo[1,5-a]pyrimidine (5.00 g, 20.28 mmol) in carbon tetrachloride (100 mL) was sequentially added N-Bromosuccinimide (36.10 g, 202.84 mmol) and 2,2'-azobis(2-methylpropionitrile) (333 mg, 2.028 mmol). The reaction mixture was stirred at 100° C. for 16 h.

The mixture was filtered and the remaining crude was rising with Dichloromethane. The mixture was diluted with Dichloromethane and washed with saturated aqueous sodium bicarbonate solution. The organic phase was dried over anhydrous magnesium sulfate, filtered and evaporated under reduced pressure. The residue was purified by silica gel chromatography (eluting gradient 0-5% Heptane/Dichloromethane (9:1)/ethyl acetate) to afford the title compound as a white solid (1.885 g, 28% yield).

LCMS (MH) RT=0.797 min, m/z=325.7-327.7 $(M+H)^+$.

Scaffold S5: 3-bromo-5-chloro-6-(dibromomethyl) pyrazolo[1,5-a]pyrimidine was obtained as a yellowish solid (5.045 g, 61% yield)

LCMS (MH) RT=0.966 min, m/z=403.6-405.6 $(M+H)^+$.

Scaffold S6: 3-Bromo-5-chloro-6-(methoxymethyl) pyrazolo[1,5-a]pyrimidine

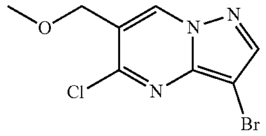

A solution of Scaffold S4 (1.885 g, 5.793 mmol) in Methanol (38 mL) was heated in a sealed tube at 100° C. for 6 h. After cooling, solvent was removed under reduced pressure and the residue was diluted in ethyl acetate. The mixture was washed with saturated aqueous sodium bicarbonate solution and Brine. The organic layer was dried over anhydrous magnesium sulfate, filtered and concentrated under reduced pressure. The residue was purified by silica gel chromatography (eluting gradient 0-20% Heptane/ethyl acetate) to afford the title compound as a white solid (1.378 g, 86% yield).

LCMS (MH) RT=0.724 min, m/z=275.9-277.9 $(M+H)^+$.

Scaffold S7: 3-Bromo-5-chloro-6-fluoro-pyrazolo[1,5-a]pyrimidine

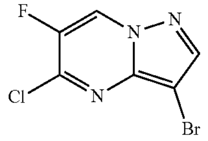 [SMILES: Fc1cn2ncc(Br)c2nc1Cl]

Step 1

To the mixture of 2-fluoro-malonic acid diethyl ester (10 g, 56.129 mmol) in ethanol (170 mL), was added 1H-pyrazol-3-ylamine (4.664 g, 56.129 mmol) and Sodium ethoxide solution (21 wt. % in ethanol) (42 mL, 112.258 mmol). The reaction mixture was heated at 120° C. for 30 h. The reaction mixture was concentrated under reduced pressure and co-evaporated with toluene. 1M HCl solution (100 mL) was added to the residue. Water was added to the reaction mixture and the precipitate was filtered. The precipitate was suspended in Acetonitrile and evaporated to dryness. The residue was suspended in toluene and evaporated to dryness under reduced pressure to afford the title compound as a light brown solid (6.85 g, 72% yield), which was used without further purifications.

LCMS (MH) RT=0.100 min, m/z=170.1 $(M+H)^+$.

Step 2

To the mixture of title compound from Step 1 (6.85 g, 40.504 mmol) and phosphorus(V) oxychloride (50 mL, 263.276 mmol) was added slowly diethyl-phenyl-amine (11 mL, 56.706 mmol) at 0° C. The reaction mixture was warmed to room temperature then heated at 120° C. for 3 h. After cooling, the reaction mixture was co-evaporated with toluene under reduced pressure. The crude residue was diluted with ethyl acetate and cooled down to 0° C. Saturated aqueous sodium bicarbonate solution was added slowly. The reaction mixture was extracted with ethyl acetate and the combined organic phases were dried over anhydrous magnesium sulfate, filtered and evaporated under reduced pressure. The residue was purified by silica gel chromatography (eluting gradient 5-20% Heptane/ethyl acetate) to afford the title compound as a white solid (5.107 g, 61% yield).

LCMS (MH) RT=0.664 min, m/z=206.0-207.9 $(M+H)^+$.

Step 3

To a mixture of the title compound from Step 2 (4.395 g, 21.334 mmol) in Acetonitrile (64 mL) at 0° C. was added portionwise N-Bromosuccinimide (3.797 g, 21.334 mmol). The reaction mixture was stirred for 30 min. A saturated aqueous sodium bicarbonate solution was added and the reaction mixture was extracted with ethyl acetate. The combined organic phases were dried over anhydrous magnesium sulfate, filtered and evaporated under reduced pressure. The residue was purified by silica gel chromatography (eluting gradient 5-20% Heptane/ethyl acetate) to afford the title compound as a yellow solid (5.796 g, 95% yield).

LCMS (MH) RT=0.859 min, m/z=283.9-285.9 $(M+H)^+$.

Step 4

The title compound from Step 3 (5.79 g, 20.344 mmol) in aqueous Ammonia (100 mL) was stirred at room temperature for 16 h. The reaction mixture was evaporated under reduced pressure. The residue was dilutes with ethyl acetate and a solution aqueous sodium carbonate solution. After separation, the aqueous phase was extracted with ethyl acetate. The combined organic layers were dried over anhydrous magnesium sulfate, filtered and evaporated under reduced pressure. The residue was purified by silica gel chromatography (eluting gradient 10-50% Heptane/ethyl acetate) to afford the title compound as yellowish solid (4.10 g, 76% yield).

LCMS (MH) RT=0.615 min, m/z=265-267 $(M+H)^+$.

Step 5

To a solution of the title compound from Step 4 (5.060 g, 19.061 mmol) in Dioxane (50 mL) was added isopentyl nitrite (5.133 mL, 38.122 mmol). The reaction mixture was heated at 110° C. for 2 h. After cooling, the reaction mixture was concentrated under reduced pressure and the crude material was washed with water. The organic layer was dried over anhydrous magnesium sulfate and concentrated under reduced pressure. The product was purified by silica gel chromatography (eluting gradient 10-20% Heptane/ethyl acetate) to afford the expected compound as a yellow solid (2.158 g, 45% yield).

LCMS (MH) RT=0.707 min, m/z=249.9-251.9 $(M+H)^+$.

Scaffold S8: 3-Bromo-5-chloro-6-(dibromomethyl) pyrazolo[1,5-a]pyrimidine

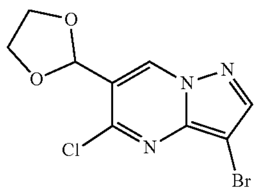 [SMILES: Clc1nc2c(Br)cnn2cc1C1OCCO1]

To a solution of Scaffold S5 (5.00 g, 12.479 mmol) in N,N-dimethylformamide (38 mL) was added ethylene glycol (15.5 mL, 249.580 mmol) at room temperature. The reaction mixture was stirred at 70° C. for 20 h. The reaction mixture was diluted with ethyl acetate and washed with saturated aqueous sodium bicarbonate solution. The organic layer was dried with anhydrous magnesium sulfate, filtered and concentrated under reduced pressure. The residue was purified by silica gel chromatography (eluting gradient 0-20% Heptane/ethyl acetate) to afford the expected compound as a beige solid (2.89 g, 76% yield).

LCMS (MH) RT=0.703 min, m/z=303.9-305.9 $(M+H)^+$.

Pyrrolidine P1: tert-butyl (2S,4R)-2-(hydroxymethyl)-4-methoxypyrrolidine-1-carboxylate

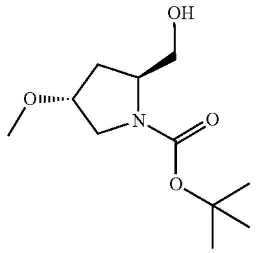 [SMILES: CO[C@@H]1C[C@@H](CO)N(C(=O)OC(C)(C)C)C1]

Step 1

To a solution of (2S,4R)-1-(tert-butoxycarbonyl)-4-hydroxypyrrolidine-2-carboxylic acid (8.3 g, 35.892 mmol) in anhydrous Acetonitrile (500 ml) was added Silver (I) Oxide (24.9 g, 107.67 mmol) followed by Iodomethane (11.2 ml, 179.4 mmol) cooled at 0° C. The resulting suspension was slowly warmed to ambient temperature and stirred vigorously for 2 days. Upon completion, monitored by LCMS, solid material was removed by filtration and the filtrate was concentrated under vacuum. The residue was purified by flash chromatography eluting with gradient of Heptane/EtOAc (from 10:0 to 5:5) to afford the title product (8.8 g, yield: 94%) as a colorless liquid.

LCMS (MH) RT=0.691 min, m/z=160.1 $(M-56)^+$.

Step 2

The title compound from Step 1 (8.8 g, 33.938 mmol) was dissolved in dry THE and cooled down to 000 under $N_2$ atmosphere. Lithium aluminium hydride (2.58 g, 67.876 mmol) was added portionwise and stirred for 2 hours. Upon completion, monitored by LCMS, $H_2O$ was added to quenched the reaction, and filtered over a pad of Celite, rinsing with EtOAc. The product was purified by flash chromatography (on silica gel) using DCM/MeOH as eluents (100: to 95:5) to afford the expected compound as a colorless oil (6.2 g, 78.99%).

LCMS (MH) RT=0.518 min, m/z=132.1 $(M-99)^+$.

Similarly, were Prepared the Following Intermediates:

| Intermediate # | Structure | Yield | NMR |
|---|---|---|---|
| P2 | | 93% yield as colorless oil | $^1$H NMR (400 MHz, DMSO) 4.69 (1H, t, J = 5.6 Hz), 4.05-4.00 (1H, m), 3.79-3.70 (1H, m), 3.41-3.32 (6H, m), 2.00- 1.99 (2H, m), 1.40 (9H, s), 1.09 (3H, t, J = 7.0 Hz). |
| P11 | 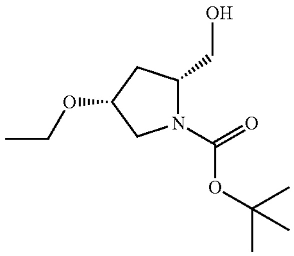 [SMILES: CCO[C@@H]1C[C@H](CO)N(C(=O)OC(C)(C)C)C1] | 49% yield as colorless oil | $^1$H NMR (400 MHz, $CDCl_3$) 4.01-3.92 (3H, m), 3.70-3.65 (2H, m), 3.56-3.42 (4H, m), 2.21-2.12 (1H, m), 1.78 (1H, s), 1.45 (9H, s), 1.18 (3H, t, J = 7.2 Hz) |
| P12 | 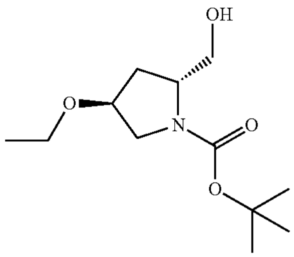 [SMILES: CCO[C@H]1C[C@H](CO)N(C(=O)OC(C)(C)C)C1] | 93% yield as colorless oil | $^1$H NMR (400 MHz, $CDCl_3$) 4.26 (1H, s), 4.05 (1H, dq, J = 2.0, 7.2 Hz), 4.00-3.95 (1H, m), 3.69 (1H, dd, J = 2.7, 11.4 Hz), 3.56 (6H, dd, J = 7.0, 11.4 Hz), 3.49-3.42 (2H, m), 3.39 (1H, dd, J = 4.6, 11.8 Hz), 2.13-2.03 (1H, m), 1.70-1.66 (1H, m), 1.46 (9H, s), 1.18 (3H, t, J = 6.6 Hz). |

-continued

| Inter-mediate # | Structure | Yield | NMR |
|---|---|---|---|
| P13 | 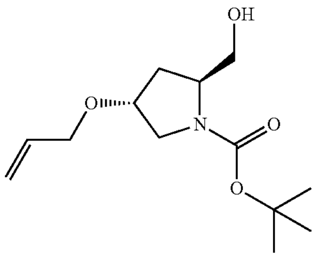 [SMILES: C=CCO[C@@H]1C[C@@H](CO)N(C(=O)OC(C)(C)C)C1] | 99% yield as colorless oil | $^1$H NMR (400 MHz, $CDCl_3$) 5.95-5.84 (1H, m), 5.31-5.17 (2H, m), 4.13-4.06 (1H, m), 4.01 (1H, s), 3.97 (2H, dd, J = 1.2, 5.3 Hz), 3.71 (1H, d, J = 12.5 Hz), 3.61 (1H, s), 3.57 (1H, dd, J = 7.0, 11.4 Hz), 3.40 (1H, dd, J = 4.7, 12.2 Hz), 2.18-2.04 (1H, m), 1.65 (1H, m), 1.47 (9H, s) |
| P14 | 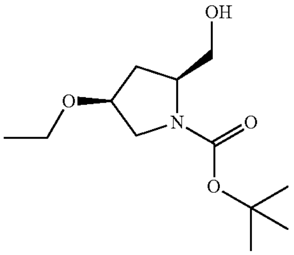 [SMILES: CCO[C@H]1C[C@@H](CO)N(C(=O)OC(C)(C)C)C1] | 100% yield as colorless oil | $^1$H NMR (400 MHz, $CDCl_3$) 4.02-3.93 (2H, m), 3.80-3.73 (2H, m), 3.56-3.42 (4H, m), 2.27-2.12 (1H, m), 1.80 (1H, s), 1.46 (9H, s), 1.19 (3H, t, J = 7.1 Hz) |

Pyrrolidine P3: tert-butyl (2S,4R)-4-(cyclobutoxy)-2-(hydroxymethyl)pyrrolidine-1-carboxylate

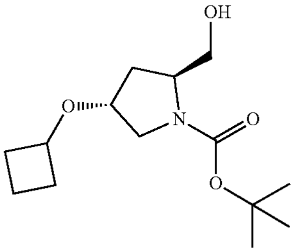 [SMILES: CC(C)(C)OC(=O)N1C[C@H](OC2CCC2)C[C@H]1CO]

Step 1

To a suspension of 01-benzyl 02-methyl (2S,4R)-4-hydroxypyrrolidine-1,2-dicarboxylate (5.0 g, 17.90 mmol) in Dichloromethane (50 mL) was added 1H-imidazole (2.438 g, 35.80 mmol) and tert-butyldimethylsilyl chloride (4.048 g, 26.85 mmol). The reaction mixture was stirred at room temperature for 8 h and 1H-imidazole (2.438 g, 35.80 mmol) and tert-butyldimethylsilyl chloride (4.048 g, 26.85 mmol) were added and the reaction mixture was stirred at room temperature for 16 h. The reaction mixture was diluted with water. The layers were separated and the aqueous layer was extracted with Dichloromethane. The combined organic layers were dried over anhydrous sodium sulfate, filtered and evaporated under reduced pressure. The residue was purified by silica gel chromatography (eluting gradient 0-20% cyclohexane/ethyl acetate) to afford 01-benzyl 02-methyl (2S,4R)-4-[tert-butyl(dimethyl)silyl]oxypyrrolidine-1,2-dicarboxylate (6.372 g, 90% yield) as colorless oil.

LCMS (MA) RT=3.36 min, m/z=394.1 $(M+H)^+$.

Step 2

To a suspension of bismuth tribromide (1.423 g, 3.17 mmol) in Acetonitrile (25 mL) under argon at 0° C. was added Triethylsilane (2.54 mL, 15.85 mmol). The reaction mixture was stirred 10 min at 0° C. and a suspension of the title compound from Step 1 (4.160 g, 10.57 mmol) and cyclobutanone (3.95 mL, 52.85 mmol) in Acetonitrile (12 mL) were added. The reaction mixture was stirred at 0° C. for 1 h then at room temperature for 1 h. The mixture was filtered and washed with ethyl acetate. The filtrate was diluted with water and ethyl acetate. The layers were separated and the aqueous layer was extracted with ethyl acetate. The combined organic layers were dried over anhydrous sodium sulfate, filtered and evaporated under reduced pressure. The residue was purified by silica gel chromatography (eluting gradient 0-20% cyclohexane/ethyl acetate) to afford the title compound as a pale yellow oil (2.03 g, 55% yield).

LCMS (MA) RT=2.70 min, m/z=334.1 $(M+H)^+$.

Step 3

To a suspension of the title compound from Step 2 (2.030 g, 6.09 mmol) in methanol (35 mL) under argon was added 10% Pd/C (200 mg). The reaction mixture was stirred under hydrogen atmosphere at room temperature for 6 h. The reaction mixture was filtered on Celite pad and washed with methanol and ethyl acetate. The filtrate was evaporated under reduced pressure to afford the title compound as colorless oil (1.205 g, 99% yield), which was used in the next step without further purification.

$^1$H NMR (400 MHz, $CDCl_3$) 4.07-3.91 (3H, m), 3.75-3.75 (3H, s), 3.15-3.10 (1H, m), 3.03-2.98 (1H, m), 2.59 (1H, s), 2.26-2.17 (3H, m), 2.05-1.85 (3H, m), 1.74-1.65 (1H, m), 1.57-1.46 (1H, m).

Step 4

To a solution of the title compound from Step 3 (1.205 g, 6.05 mmol) in tetrahydrofuran (90 mL) was added Triethylamine (2.53 mL, 18.15 mmol), DMAP (74 mg, 0.61 mmol) and $Boc_2O$ (3.961 g, 18.15 mmol). The reaction mixture was stirred at 70° C. for 16 h. The reaction mixture was cooled down to room temperature and the solvent was evaporated under reduced pressure. The residue was purified by silica gel chromatography (eluting gradient 0-20% cyclohexane/ethyl acetate) to afford the title compound as a light yellow oil (1.460 g, 81%).

$^1$H NMR (400 MHz, $CDCl_3$) 4.44-4.32 (1H, m), 4.11-4.05 (1H, m), 4.00-3.91 (1H, m), 3.75 (3H, m), 3.63-3.41 (2H, m), 2.32-2.18 (3H, m), 2.09-1.92 (3H, m), 1.74-1.66 (1H, m), 1.56-1.51 (1H, m), 1.48-1.41 (9H, m).

Step 5

To a suspension of the title compound from Step 4 (1.460 g, 4.88 mmol) in a mixture of EtOH/THF 1:1 (44 mL) cooled at 0° C. were added sodium borohydride (369 mg, 9.76 mmol) and calcium chloride (542 mg, 4.88 mmol). The solution was warmed up to room temperature and stirred for 2 h at RT. The reaction mixture was quenched by addition of water and aqueous HCl 1M until pH=4. EtOAc was added. The layers were separated. The aqueous layer was extracted with EtOAc (3×40 mL). The combined organic layers were dried over sodium sulfate and concentrated in vacuo. The residue was purified by silica gel chromatography using Cyclohexane/EtOAc 100:0 to 50:50 as eluent.

The expected fractions were collected and evaporated under reduced pressure to afford the expected compound as a colorless oil (1.242 g, 4.58 mmol, 94%).

$^1$H NMR (400 MHz, $CDCl_3$), 4.14-4.06 (1H, m), 4.00-3.90 (2H, m), 3.72 (1H, dd, J=2.4, 11.5 Hz), 3.59-3.54 (2H, m), 3.38 (1H, dd, J=4.6, 12.0 Hz), 2.27-2.19 (2H, m), 2.13-1.89 (3H, m), 1.75-1.64 (2H, m), 1.55-1.51 (1H, m), 1.49 (9H, m).

Similarly, were prepared the following intermediates:

Pyrrolidine P6: tert-butyl (2S,4R)-2-(hydroxymethyl)-4-(trideuteriomethyl)pyrrolidine-1-carboxylate

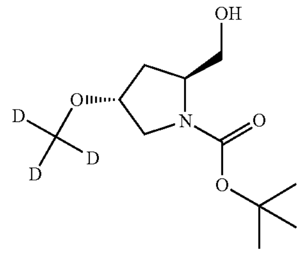

Step 1

To a solution of 1-(tert-butyl) 2-methyl (2S,4R)-4-hydroxypyrrolidine-1,2-dicarboxylate (3.2 g, 13.046 mmol) was dissolved in dry tetrahydrofuran (65 mL) at 0° C. was added sodium hydride (60% dispersion in mineral oil) (1.044 g, 26.092 mmol). The reaction mixture was stirred for 45 min. Iodomethane-d3 (1.624 g, 26.092 mmol) was added and the reaction mixture was stirred for 30 min. The reaction mixture was quenched at 0° C. with water and extracted with ethyl acetate. The combined organic phases were dried over anhydrous magnesium sulfate, filtered and concentrated under reduced pressure. The residue was purified by silica gel chromatography (eluting gradient 0-50% Heptane/ethyl acetate) to afford the title compound as a white solid (2.6 g, 39% yield).

LCMS (MH) RT=0.736 min, m/z=163.1 $(M+H)^+$-Boc.

Step 2

To the title compound from Step 1 (2.6 g, 10.471 mmol) was added borane dimethyl sulfide complex solution (2.0 M/THF) (15 mL), dropwise at 0° C. The mixture was stirred at room temperature for 16 h. The reaction mixture was carefully quenched with methanol at 0° C. The solvent was removed under reduced pressure. The residue was purified by silica gel chromatography (eluting gradient 0-40% Heptane/ethyl acetate) to afford the expected compound as a colorless oil (2.2 g, 90% yield).

LCMS (MH) RT=0.534 min, m/z=135.1 $(M+H)^+$-Boc.

| Intermediate # | Structure | Yield | 1H NMR |
|---|---|---|---|
| P4 | 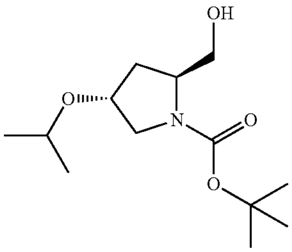 [SMILES: CC(C)O[C@@H]1C[C@@H](CO)N(C(=O)OC(C)(C)C)C1] | 97% yield as colorless oil | $^1$H NMR (400 MHz, $CDCl_3$) 4.13-4.05 (2H, m), 3.74-3.50 (4H, m), 3.42 (1H, dd, J = 4.7, 12.0 Hz), 2.10-2.06 (2H, m), 1.69-1.64 (1H, m), 1.48 (9H, s), 1.16 (6H, t, J = 6.1 Hz). |
| P5 | 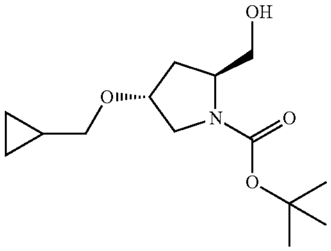 [SMILES: CC(C)(C)OC(=O)N1C[C@H](OCC2CC2)C[C@H]1CO] | 95% yield as colorless oil | $^1$H NMR (400 MHz, DMSO), 4.70-4.67 (1H, m), 4.06-4.01 (1H, m), 3.79-3.70 (1H, m), 3.44-3.31 (3H, m), 3.28-3.20 (2H, m), 3.17-3.12 (1H, m), 2.07-1.86 (2H, m), 1.40 (9H, s), 1.02-0.89 (1H, m), 0.44 (2H, d, J = 8.0 Hz), 0.17-0.12 (2H, m). |

Similarly, were Prepared the Following Intermediates:

| Intermediate # | Structure | Yield | LCMS |
|---|---|---|---|
| P7 | 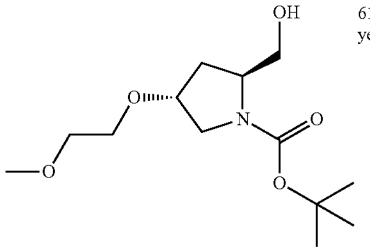 | 61% yield as yellowish oil | LCMS (MH) RT = 0.545 min, m/z = 220.1 $(M + H)^+ - 55$. |
| P8 | 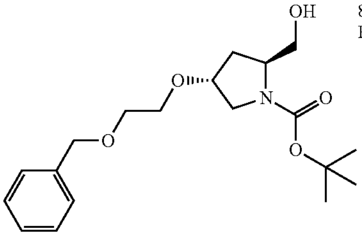 | 83% yield as Pinkish oil | LCMS (MH) RT = 0.876 min, m/z = 296.1 $(M + H)^+ - 55$. |

Pyrrolidine P9: tert-butyl (2S,4R)-4-cyclopropoxy-2-(hydroxymethyl)pyrrolidine-1-carboxylate

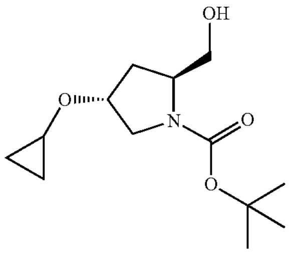 [SMILES: CC(C)(C)OC(=O)N1C[C@H](OC2CC2)C[C@H]1CO]

Step 1

To a suspension Benzyl chloroformate (23.4 mL, 166.8 mmol) in THF/Water (100 mL/50 mL) under vigorous stirring was added Potassium carbonate (46.11 g, 333.6 mmol) then Methyl (2S,4R)-4-hydroxypyrrolidine-2-carboxylate hydrochloride (16.15 g, 111.2 mmol) carefully. The reaction mixture was stirred at room temperature for 2 h. Upon complete conversion, monitored by LCMS, the mixture was acidified with aqueous HCl 1M until pH=1. The layers were separated. The aqueous layer was extracted with EtOAc (3×100 mL) and the combined organic layer was washed with Brine, dried over anhydrous Sodium sulfate, filtered and evaporated under reduced pressure. The residue was purified on silica gel column using Cyclohexane/EtOAc (100:0 to 0:100) as eluent to afford the title compound as yellow oil (20.58 g, 66% yield).

LCMS (MA) RT=1.93 min, m/z=280.1 (M+H)+

Step 2

Palladium (II) acetate (787 mg, 3.50 mmol) and 1,10-Phenanthroline (695 mg, 3.85 mmol) were dissolved in dry Dichloromethane (40 mL) under Argon and the resulting solution was stirred min at room temperature. Then was added Ethyl vinyl ether (140 mL). The solution was degassed by bubbling argon 10 min. The reaction mixture was stirred for 15 min at room temperature and an Argon-atmosphere solution of the title compound from Step 1 (9.79 g, 35.05 mmol) in dry Dichloromethane (110 mL) was added. The reaction mixture was stirred at reflux overnight. Upon complete conversion, monitored by TLC plate, the reaction mixture was cooled down to room temperature and diluted with water (100 mL). The aqueous layer was extracted with DCM (3×60 mL). The combined organic layer was dried over Sodium sulfate and concentrated in vacuo. The residue was purified by silica gel chromatography using Cyclohexane/EtOAc (100:0 to 50:50) as eluent to afford the title compound as an pale yellow oil (6.796 g, 64%).

LCMS (MA) RT=2.56 min, m/z=306.1 $(M+H)^+$

Step 3

Under argon atmosphere, to a suspension of Diethylzinc in Hexane 1 M (86.0 mL, 85.53 mmol) in DCM (300 mL) cooled at 0° C. was added dropwise Diiodomethane (6.94 mL, 85.53 mmol) in DCM (60 mL). The reaction mixture was stirred at 0° C. for 30 min. Then the title compound from Step 2 (8.70 g, 28.51 mmol) in DCM (100 mL) was added dropwise at 0° C. The mixture was warmed to room temperature and stirred overnight at rt. LCMS monitoring highlighted partial conversion and the mixture was further stirred at rt for 10 h. The reaction mixture was quenched by addition of saturated aqueous Ammonium chloride solution (150 mL). The layers were separated and the aqueous layer was extracted with DCM (3×100 mL). The combined organic layer was dried over Sodium sulfate and concentrated in vacuo to afford the title compound as a colorless oil (6.69 g, 74% yield). The crude was directly engaged in the next step without further purification.

LCMS (MA) RT=2.55 min, m/z=320.1 $(M+H)^+$

Step 4

Under argon, to a suspension of the title compound from Step 3 (2.83 g, 8.88 mmol) in Methanol (50 mL) was added Palladium on charcoal 10% (275 mg). The reaction mixture was stirred under hydrogen atmosphere at room temperature for 4 h. Upon complete conversion, monitored by TLC plate, the mixture was filtered on Celite and washed with MeOH and EtOAc. The filtrate was evaporated under reduced pressure to afford the title compound as colorless oil (1.54 g, 94% yield). The crude was directly engaged in the next step without further purification.

$^1$H NMR (400 MHz, DMSO) δ 4.11-4.06 (1H, m), 3.75 (1H, t, J=7.8 Hz), 3.62 (3H, s), 3.28-3.23 (1H, m), 2.95 (1H, dd, J=4.7, 11.5 Hz), 2.84 (1H, qd, J=1.3, 11.6 Hz), 2.67 (1H, s), 2.08-2.01 (1H, m), 1.90-1.83 (1H, m), 0.48-0.41 (4H, m);

Step 5

To a solution of the title compound from Step 4 (1.54 g, 8.31 mmol) in THE (125 mL) were added Et3N (3.48 mL, 24.94 mmol), DMAP (101 mg, 0.83 mmol) and then $Boc_2O$ (5.44 g, 24.94 mmol).

The reaction mixture was stirred at 70° C. overnight. After cooling down to room temperature, the solvent was evaporated under reduced pressure. The residue was purified by silica gel chromatography using Cyclohexane/EtOAc (100:0 to 50:50) as eluent to afford the title compound as a light-yellow oil (1.52 g, 64% yield).

$^1$H NMR (400 MHz, DMSO) δ 4.18-4.13 (2H, m), 3.67 (3H, s), 3.45 (2H, dd, J=4.5, 7.5 Hz), 3.33-3.29 (1H, m), 2.39-2.28 (1H, m), 2.03-1.92 (1H, m), 1.34 (9H, s), 0.50-0.43 (4H, m);

Step 6

To a suspension of the title compound from Step 5 (1.52 g, 5.34 mmol) in a mixture of EtOH/THF 1:1 (50 mL) cooled at 0° C. were added Sodium borohydride (404 mg, 10.68 mmol) and Calcium chloride (593 mg, 5.34 mmol). The solution was warmed to room temperature and stirred for 1 h at rt. The reaction mixture was quenched by addition of Water and aqueous HCl 1M until pH=4. EtOAc was added. The layers were separated and the aqueous layer was extracted with EtOAc (3×40 mL). The combined organic layer was dried over Sodium sulfate and concentrated in vacuo. The residue was purified by silica gel chromatography using Cyclohexane/EtOAc (100:0 to 50:50) as eluent to afford the expected compound as a colorless oil (1.30 g, 95% yield).

$^1$H NMR (400 MHz, DMSO) δ 4.71 (1H, t, J=5.7 Hz), 4.15-4.10 (1H, m), 3.73 (1H, s), 3.47-3.43 (3H, m), 3.28-3.23 (2H, m), 2.08-1.92 (2H, m), 1.40 (9H, s), 0.48-0.42 (4H, m).

Pyrrolidine P10: tert-butyl (2S)-2-(hydroxymethyl)-4-(methoxymethyl)pyrrolidine-1-carboxylate

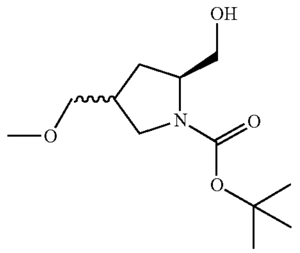 [SMILES: COCC1C[C@@H](CO)N(C(=O)OC(C)(C)C)C1]

Step 1

To (2S,4R)-1-(tert-butoxycarbonyl)-4-hydroxypyrrolidine-2-carboxylic acid (10 g, 43.243 mmol) was added Borane-methyl sulfide complex (30 mL) at 0° C. under nitrogen atmosphere. The mixture spontaneously started to heat with effervescence. The mixture was kept stirring for 16 h at room temperature. Methanol was added slowly and dropwise at 0° C. until the bubbling was stopped and the mixture was concentrated under vacuum to afford the title compound as a colorless oil (9.3 g, yield: 99%). The crude was used as such in the next step.

LCMS (MH) RT=0.340 min, m/z=162.1 (M-56)/118.2 (M-100)

Step 2

To a solution of the title compound from Step 1 (9.17 g, 42.206 mmol) in DMF (130 mL) was added Imidazole (5.75 g, 84.41 mmol) followed by tert-Butylchlorodiphenylsilane (11.93 mL, 46.427 mmol) at 0° C. and stirred for 16 h. Upon complete conversion, monitored by LCMS, a solution of saturated $NaHCO_3$ (200 mL) was added and the mixture was extracted with EtOAc (4×100 mL). The combined organic layers were dried overmgSO4, filtered and concentrated under vacuum. The crude was purified on column of silica gel using Heptane/EtOAc (from 100.0 to 40:60) as eluent to afford the expected compound as yellowish gum (3.75 g, yield: 19.5%).

LCMS (MH) RT=1.396 min, m/z=356.1 (M-100)

Step 3

To a solution of the title compound from Step 2 (3.75 g, 8.23 mmol) in DCM (40 mL) was added Dess-Martin periodinane (6.981 g, 16.458 mmol) portionwise at room temperature and keep stirring for 16 h.

A solution of saturate aqueous solution of $NaHCO_3$ (100 mL) was added and the mixture was extracted with DCM. The combined organic layers were dried overmg$SO_4$, filtered and concentrated under vacuum. The product was purified on column of silica gel using as eluent Heptane/EtOAc (80:20) to afford the expected compound (3.6 g, yield: 96%) as a colorless gum.

LCMS (MH) RT=1.478 min, m/z=354.1 (M-100)/320.0 (M-259)

Step 4

To Methoxymethyl)triphenylphosphonium chloride (5.78 g, 16.88 mmol) in dry THE (25 ml) was added Potassium bis(trimethylsilyl)amide solution 1M in THE (17 ml, 16.884 mmol) portionwise at −78° C. and kept stirring for 30 min. To the mixture was added the title compound from Step 3 (3.83 g, 8.442 mmol) in dry THE (15 ml). The resulting mixture was stirred for 1 h at the same temperature. Upon complete conversion, monitored by LCMS, a saturated aqueous solution of $NaHCO_3$ (100 mL) was added and extracted with EtOAc (4×50 mL). The combined organic layer was dried overmg$SO_4$, filtered and concentrated under vacuum. The product was purified on column of silica gel using Heptane/EtOAc (93:7) as eluent to afford the expected compound as yellowish viscous oil (3.06 g, yield: 75%).

LCMS (MH) RT=1.650 min, m/z=382.1 (M-100)

Step 5

To a solution of the title compound from Step 4 (3.03 g 6.298 mmol) in Ethyl acetate (20 mL) was added Palladium on activated carbon wet 10% (0.5 g) and purged with hydrogen atmosphere (balloon) and stirred at room temperature for 16 h. Upon complete conversion, monitored by LCMS, the mixture was filtered over a pad of Celite rinsing with EtOAc. Solvent was removed on the rotavapor. The crude was dried under high vacuum to afford the expected compound as yellow gum (2.95 g, yield: 96.83%), which was used as such in the next step.

LCMS (MH) RT=1.645 min, m/z=384.1 (M-100)

Step 6

To the title compound from Step 5 (2.95 g, 6.098 mmol) in THE (40 ml) was added Tetrabutylammonium fluoride, 1M in THE (18.3 mL) at room temperature and stirred for 16 h. The mixture was diluted with EtOAc (100 mL) and washed twice with a saturated aqueous solution of $NaHCO_3$ (50 mL). The organic layer was dried overmg$SO_4$, filtered and concentrated under vacuum. The crude was purified on column of silica gel using Heptane/EtOAc (80:20) as eluent to afford the expected product as a colorless oil (1.29 g, yield: 86%).

LCMS (MH) RT=0.595 min, m/z=190.1 (M-56)/146.1 (M-100)

Pyrrolidine P15: tert-butyl (4R)-2-(hydroxymethyl)-4-methoxy-2-methylpyrrolidine-1-carboxylate

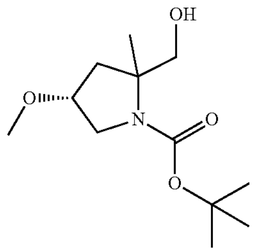 [SMILES: CO[C@H]1CN(C(=O)OC(C)(C)C)C(C)(CO)C1]

Step 1

To a solution of (2S,4R)-1-(tert-butoxycarbonyl)-4-hydroxypyrrolidine-2-carboxylic acid (8.3 g, 35.892 mmol) in anhydrous Acetonitrile (500 ml) was added Silver (I) Oxide (24.9 g, 107.67 mmol) followed by Iodomethane (11.2 ml, 179.4 mmol) cooled at 0° C. The resulting suspension was slowly warmed to ambient temperature and stirred vigorously for 2 days. Upon completion, monitored by LCMS, solid material was removed by filtration and the filtrate was concentrated under vacuum. The residue was purified by flash chromatography eluting with gradient of Heptane/EtOAc (from 10:0 to 5:5) to afford the title product (8.8 g, yield: 94%) as a colorless liquid.

LCMS (MH) RT=0.691 min, m/z=160.1 $(M-56)^+$.

Step 2 n-butyllithium 2.5 M in n-hexane (6.94 mL, 17.35 mmol) was added dropwise at 5° C. to a solution of Diisopropylamine (2.44 mL, 17.35 mmol) in THE (100 mL) and stirred for 10 min. Then the mixture was cooled to −35° C. and combined with a solution of the title compound from Step 1 (3.00 g, 11.57 mmol) in THE (100 mL). The mixture was stirred at 0° C. for 1 h and then cooled to −78° C. Methyliodide (1.080 mL, 17.35 mmol) was added dropwise and the mixture was stirred for 4hat −78° C. Then 10 mL sat. ammonium chloride solution was added dropwise and the mixture was heated to rt. Then it was mixed with water and extracted three times with ethyl acetate. The combined organic phase was dried on sodium sulfate, filtered and evaporated under vacuum. The residue was purified by column chromatography using Cyclohexane/EtOAc (80/20) as eluent to afford the title compound as a yellow oil (1.548 g, 5.66 mmol, 49% yield).

Step 3

To a suspension of the title compound from Step 2 (1.55 g, 5.66 mmol) in a mixture of EtOH/THF (30 mL/30 mL) cooled at 0° C. were added Sodium borohydride (0.428 g, 11.33 mmol) and Calcium chloride (0.629 g, 5.66 mmol). The solution was warmed up to room temperature and stirred for 1 h at rt. The reaction mixture was quenched by addition of water and aqueous HCl 1 M until pH=4. EtOAc was added and the layers were separated. The aqueous layer was extracted with EtOAc (3×60 mL). The combined organic layers were dried over sodium sulfate, filtered and concentrated in vacuo. The residue was purified by silica gel chromatography using Cyclohexane/EtOAc (100/0 to 60/40) as eluent to afford the expected product as colorless oil (0.782 g, 3.19 mmol, 56% yield) as a colorless oil.

$^1H$ NMR (400 MHz, DMSO) 4.77-4.68 (1H, m), 3.85-3.79 (1H, m), 3.72-3.36 (3H, m), 3.31-3.23 (1H, m), 3.22-3.20 (3H, m), 2.33-2.13 (1H, m), 1.77-1.65 (1H, m), 1.39 (9H, d, J=3.8 Hz), 1.28-1.22 (3H, m).

Pyrrolidine P16: tert-butyl (4R)-2-(1-hydroxyethyl)-4-methoxypyrrolidine-1-carboxylate

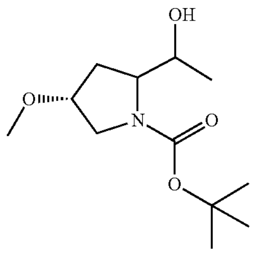 [SMILES: CO[C@@H]1CC(C(C)O)N(C(=O)OC(C)(C)C)C1]

Step 1

To a stirred solution of 2M Oxalyl chloride solution in DCM (10 mL, 20 mmol) in Dichloromethane (100 mL) at −78° C. was added Dimethyl sulfoxide (2.84 mL, 40 mmol) dropwise via syringe. The mixture was stirred at −78° C. for 10 min and a solution of Pyrrolidine P1 (2.31 g, 10 mmol) in Dichloromethane (25 mL) was added. The mixture was stirred at −78° C. for 15 minutes, and Triethylamine (4.30 mL, 40 mmol) was added. After 15 minutes, the reaction mixture was allowed to warm to 0° C. and stirred at that temperature for 30 minutes. The mixture was washed with water and Brine, dried with sodium sulfate, filtered, and concentrated in vacuo. The crude was purified by column chromatography on silica gel using a Cyclohexane/EtOAc (0-50%) to afford the title compound (Diastereomer mixture) as a colorless oil (2.44 g).

Dia1: $^1H$ NMR (400 MHz, $CDCl_3$) 9.45 (1H, d, J=3.8 Hz), 4.23-4.17 (1H, m), 3.98-3.93 (1H, m), 3.75 (1H, d, J=12.0 Hz), 3.57-3.49 (1H, m), 3.35 (3H, s), 2.29-2.19 (1H, m), 2.00-1.89 (1H, m), 1.45 (9H, s).

Dia2: $^1H$ NMR (400 MHz, $CDCl_3$) 9.57 (1H, d, J=2.7 Hz), 4.32 (1H, t, J=8.1 Hz), 3.98-3.93 (1H, m), 3.57-3.49 (2H, m), 3.35 (3H, s), 2.29-2.19 (1H, m), 2.00-1.89 (1H, m), 1.49 (9H, s).

Step 2

To a solution of the title compound from Step 1 (1.63 g, 7.10 mmol) in anhydrous Diethyl ether (105 mL) under nitrogen atmosphere cooled to 0° C. was added via syringe Methylmagnesium bromide (3M in Diethyl ether; 5.92 mL, 17.77 mmol) and the resulting solution stirred for two hours at 0° C. The reaction was quenched with saturated solution of Ammonium chloride and extracted with Diethyl ether. The organic layer was dried over anhydrous sodium sulfate, filtered and evaporated under reduced pressure. The residue was purified by silica gel column chromatography using Cyclohexane/EtOAc (100/0-50/50) to afford the expected compound (diastereomer mixture) as a colorless oil (150 mg, 0.611 mmol).

Dia1: $^1H$ NMR (400 MHz, $CDCl_3$), 4.06-3.68 (4H, m), 3.32-3.31 (4H, m), 2.17-2.09 (1H, m), 1.82-1.68 (1H, m), 1.50 (9H, s), 1.15 (3H, d, J=6.6 Hz).

Dia2: $^1$H NMR (400 MHz, $CDCl_3$), 4.06-3.68 (4H, m), 3.32-3.31 (4H, m), 2.17-2.09 (1H, m), 1.82-1.68 (1H, m), 1.50 (9H, s), 1.09 (3H, d, J=6.7 Hz).

Intermediate I1: 1-(3-bromo-5-nitrophenyl)-5-methyl-1H-pyrazole

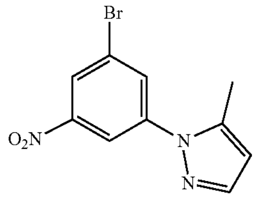 [SMILES: Cc1ccnn1-c1cc(Br)cc([N+](=O)[O-])c1]

Step 1

In a sealed tube 1-bromo-3-iodo-5-nitrobenzene (3.0 g, 9.149 mmol) was dissolved in DMSO (9 mL). Tert-butyl carbazate (1.451 g, 10.979 mmol), cesium carbonate (4.471 g, 13.723 mmol) and copper(I) iodide (174 mg, 0.915 mmol) were added and the reaction mixture was stirred at 50° C. for 4 h. Water was added and the mixture was extracted with ethyl acetate. The combined organic layers were dried over anhydrous magnesium sulfate, filtered and concentrated under reduced pressure. The residue was purified by silica gel chromatography (eluting gradient 0-15% Heptane/ethyl acetate) to afford tert-butyl 1-(3-bromo-5-nitrophenyl)hydrazine-1-carboxylate (1.045 g, 34% yield) as a brown sticky solid.

LCMS (MH) RT=1.044 min, m/z=275.9-277.9 $(M+H)^+$.

Step 2

The title compound from Step 1 (1.040 g, 3.131 mmol) was dissolved in HCl (4M/Dioxane) (10 mL). The reaction mixture was stirred at room temperature for 16 h. The solvent was removed under reduced pressure to afford the crude (3-bromo-5-nitrophenyl)hydrazine dihydrochloride (950 mg, 100% yield) as a brown solid which was used without further purifications.

LCMS (MH) RT=0.518 min, m/z=231.9-233.9 $(M+H)^+$.

Step 3

To a solution of the title compound from Step 2 (950 mg, 3.131 mmol) in ethanol (12 mL) was added Triethylamine (1.306 mL, 9.39 mmol) followed by ethyl 2-((dimethylamino)methylene)-3-oxobutanoate (696 mg, 3.757 mmol) at room temperature. The reaction mixture was heated at 100° C. for 2 h. After cooling, a saturated aqueous sodium bicarbonate solution was added and the mixture was extracted with ethyl acetate. The combined organic layers were dried over anhydrous magnesium sulfate, filtered and evaporated under reduced pressure. The residue was purified by silica gel chromatography (eluting solvent 80/20% Heptane/ethyl acetate) to afford ethyl 1-(3-bromo-5-nitrophenyl)-5-methyl-1H-pyrazole-4-carboxylate (780 mg, 75% yield) as an orange solid.

LCMS (MH) RT=1.026 min, m/z=353.9-356.0 $(M+H)^+$.

Step 4

In a pressure flask, to the title compound from Step 3 (780 mg, 2.202 mmol) was added acetic acid/HBr (3:1) (7 mL) and the mixture was heated at 150° C. for 5 days. After cooling, solvent was removed under reduced pressure and the crude residue was diluted with ethyl acetate and washed with a saturated aqueous sodium bicarbonate solution and Brine. The organic layer was dried over anhydrous magnesium sulfate, filtered and evaporated under reduced pressure. The residue was purified by silica gel chromatography (eluting eluent 90/10% Heptane/ethyl acetate) to afford the expected compound (300 mg, 48% yield) as a brown solid.

LCMS (MH) RT=0.896 min, m/z=281.9-283.9 $(M+H)^+$.

Intermediate I2: 1-bromo-3-nitro-5-(propan-2-yloxy)benzene

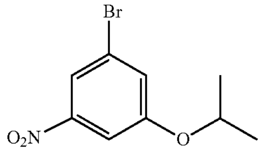

To a solution of 3-bromo-5-nitro-phenol (5.0 g, 22.9 mmol) in acetone (100 mL was added portionwise potassium carbonate (4.75 g, 34.4 mmol). The reaction mixture was stirred at room temperature for 10 min. Then 2-iodopropane (4.0 mL, 68.70 mmol) was added and the reaction mixture was heated at 70° C. for 5 h. The reaction mixture was cooled to room temperature. The insoluble material was filtered off and washed with acetone. The filtrate was concentrated under reduced pressure to afford the expected compound (6.0 g, 100% yield) as yellow liquid.

LCMS (MA) RT=3.12 min, m/z=260.1 $(M+H)^+$.

Intermediate I3: 1-(benzyloxy)-3-bromo-5-nitrobenzene

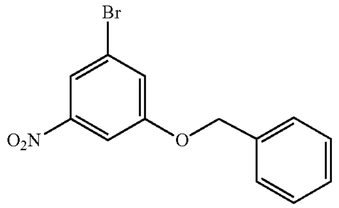 [SMILES: O=[N+]([O-])c1cc(Br)cc(OCc2ccccc2)c1]

To a solution of 3-bromo-5-nitro-phenol (20 g, 91.74 mmol) in acetone (200 mL) was added portionwise potassium carbonate (19.02 g, 137.61 mmol). The reaction mixture was stirred at room temperature for 10 min. Then Bromomethylbenzene (11.46 mL, 96.33 mmol) was added and the reaction mixture was heated at 70° C. for 2 h. The reaction mixture was cooled to room temperature. The insoluble material was filtered off and washed with acetone. The filtrate was concentrated under reduced pressure to afford the expected compound (28.3 g, 100% yield) as a cream solid.

$^1$H NMR (400 MHz, $CDCl_3$) 8.01-7.99 (1H, m), 7.79-7.78 (1H, m), 7.48-7.44 (6H, m), 5.16 (2H, s).

Intermediate I4: Mixture of 1-(3-bromo-5-nitrophenyl)-1H-pyrazole and 1-(3-iodo-5-nitrophenyl)-1H-pyrazole

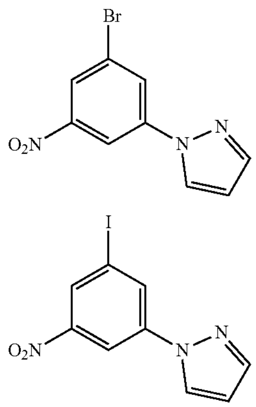

To a stirred solution of 3-bromo-5-iodo-benzoic acid (30 g, 91.77 mmol) in dry tert-butanol (150 mL) and Triethylamine (16.6 mL, 119.30 mmol) under argon was added Diphenylphosphorylazide (21.7 mL, 100.95 mmol). The reaction mixture was refluxed at 80° C. under argon for 16 h. The reaction mixture was cooled to room temperature and the solvent were evaporated under reduced pressure. The residue was dissolved in ethyl acetate and successively washed with a 10% Sodium hydroxide solution, water and Brine. The organic layer was dried over anhydrous sodium sulfate, filtered and evaporated under reduced pressure. The residue was purified by silica gel chromatography (eluting eluent 90/10% cyclohexane/ethyl acetate) to afford the expected compound (32.2 g, 88% yield) as yellowish amorphous solid.

$^1$H NMR (400 MHz, DMSO) 9.66 (1H, s), 7.86 (1H, t, J=1.6 Hz), 7.70 (1H, t, J=1.8 Hz), 7.50 (1H, t, J=1.6 Hz), 1.48-1.47 (9H, m).

Similarly Prepared:

| Int. no | structure | name | Intermediate | Analytical data |
|---|---|---|---|---|
| I6 | 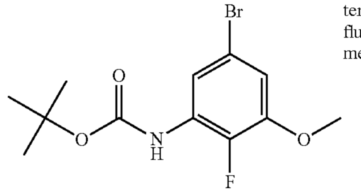 | tert-butyl N-(5-bromo-2-fluoro-3-methoxyphenyl)carbamate | From 5-bromo-2-fluoro-3-methoxy-benzoic acid 82% yield as a white solid | LCMS (MA) RT = 3.01 min, m/z = 320-322 $(M + H)^+$. |

In a pressure flask, 3-bromo-5-iodonitrobenzene (7.2 g, 21.958 mmol), Pyrazole (1.495 g, 21.958 mmol), copper(I) iodide (836 mg, 4.392 mmol), trans-N,N'-dimethylcyclohexane-1,2-diamine (1.249 mL, 21.958 mmol) and cesium carbonate (21.67 g, 65.67 mmol) in DMF (45 mL).

The reaction mixture was bubbled with a nitrogen stream for 5 min and the mixture was stirred at 50° C. for 12 h. The reaction mixture was filtered over a pad of Celite and rinsing with ethyl acetate. The filtrate was concentrated under reduced pressure. The residue was purified by silica gel chromatography (eluting gradient 0-20% Heptane/ethyl acetate) to afford to afford a mixture of the expected compound and 1-(3-iodo-5-nitrophenyl)-1H-pyrazole (3.3 g, 25% yield) as a brown solid.

LCMS (MH) RT=0.902 min, m/z=267.9-269.9 $(M+H)^+$ and RT=0.942 min, m/z=315.9 $(M+H)^+$.

Intermediate I5: tert-butyl N-(3-bromo-5-iodophenyl)carbamate

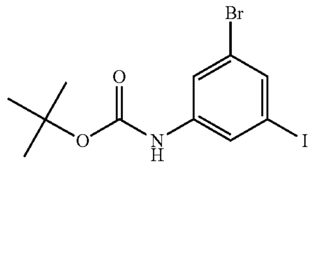 [SMILES: CC(C)(C)OC(=O)Nc1cc(Br)cc(I)c1]

Intermediate I7: tert-butyl N-{3-bromo-5-[2-(triethylsilyl)ethynyl]phenyl}carbamate

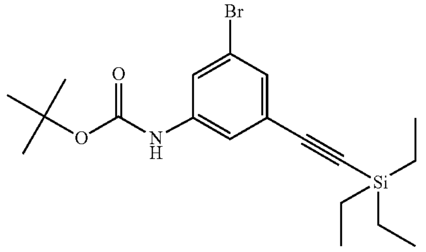 [SMILES: CC[Si](C#Cc1cc(Br)cc(NC(=O)OC(C)(C)C)c1)(CC)CC]

To a solution of Intermediate I5 (32.2 g, 80.9 mmol) in dry tetrahydrofuran (250 mL) under Argon was added (triethylsilyl)acetylene (21.74 mL, 121.35 mmol), Bis(triphenylphosphine) palladium(II) dichloride (2.84 g, 4.045 mmol), copper iodide (770 mg, 4.045 mmol) and Triethylamine (33.83 mL, 242.7 mmol. The reaction mixture was stirred at room temperature for 2 h. The reaction mixture was diluted with water and extracted with ethyl acetate. The combined organic layers were washed with Brine and dried over anhydrous sodium sulfate, filtered and evaporated under reduced pressure. The residue was purified by silica gel chromatography (eluting eluent 90/10% cyclohexane/ethyl acetate) to afford the expected compound (27.1 g, 82% yield) as a brown oil.

$^1H$ NMR (400 MHz, $CDCl_3$) 7.63 (1H, m), 7.45-7.37 (1H, m), 7.30-7.27 (1H, m), 6.47-6.43 (1H, m), 1.54-1.53 (9H, m), 1.08-1.03 (9H, m), 0.71-0.65 (6H, m).

Intermediate I8: 3-bromo-5-(propan-2-yloxy)aniline

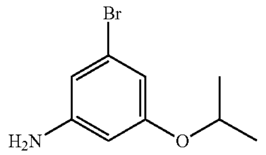

To a solution of Intermediate I2 (6.0 g, 22.9 mmol) in ethanol (140 mL) was added portionwise tin (II) chloride dihydrate (20.7 g, 91.6 mmol). The reaction mixture was heated under reflux for 2 h. The reaction mixture was poured into water. The aqueous phase was basified with 33% NaOH solution and stirred at room temperature for 10 min. After extraction with ethyl acetate, the organic phase was dried over anhydrous sodium sulfate, filtered and evaporated under reduced pressure. The residue was purified by silica gel chromatography (eluting gradient 10-40% cyclohexane/ethyl acetate) to afford the expected compound (5.30 g, 100% yield) as a yellowish liquid.

LCMS (MA) RT=2.51 min, m/z=232.1 $(M+H)^+$.

Intermediate I9: 3-(benzyloxy)-5-bromoaniline

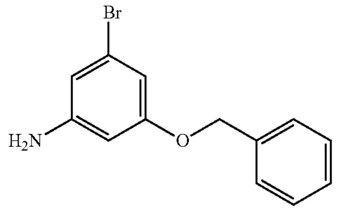 [SMILES: Nc1cc(Br)cc(OCc2ccccc2)c1]

To a solution of Intermediate I3 (13 g, 42.19 mmol) in ethanol (250 mL) was added portionwise tin (II) chloride dihydrate (38.08 g, 168.76 mmol) and the reaction mixture was heated under reflux for 1 h. The reaction mixture was poured into water. The aqueous phase was basified with 33% NaOH solution and stirred at room temperature for 10 min. After extraction with ethyl acetate, the organic phase was dried over anhydrous sodium sulfate, filtered and evaporated under reduced pressure. The residue was purified by silica gel chromatography (eluting gradient 10-40% cyclohexane/ethyl acetate) to afford the expected compound (11.35 g, 96% yield) as a pale yellow oil.

LCMS (MA) RT=2.93 min, m/z=280.0 $(M+H)^+$.

Intermediate I10: 3-bromo-5-[2-(triethylsilyl)ethynyl]aniline

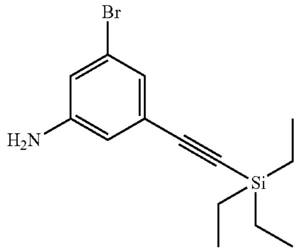 [SMILES: CC[Si](C#Cc1cc(N)cc(Br)c1)(CC)CC]

To a solution of Intermediate I7 (27.10 g, 66.03 mmol postulated) in Dichloromethane (300 mL) was added trifluoroacetic acid (50 mL) at room temperature. The reaction mixture was stirred for 2 h at room temperature. Solvent was evaporated under reduced pressure. The residue was purified by silica gel chromatography (eluting solvent 90/10% cyclohexane/ethyl acetate) to afford the expected compound (18.90 g, 92% yield) as a brown solid.

LCMS (MA) RT=3.65 min, m/z=351-353 $(M+H)^+$.

Intermediate I11: 5-bromo-2-fluoro-3-methoxyaniline

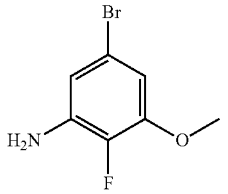

To a solution of Intermediate I6 (1.05 g, 3.27 mmol) in Dichloromethane (10 mL) was added trifluoroacetic acid (2 mL, 26.11 mmol) and the reaction mixture was stirred at room temperature for 16 h. The solvent was evaporated under reduced pressure. The residue was diluted with ethyl acetate and washed with saturated aqueous sodium bicarbonate solution and Brine. The organic layer was dried over anhydrous sodium sulfate, filtered and evaporated under reduced pressure to afford the expected compound (700 mg, 97% yield) as a brown solid.

LCMS (MA) RT=2.27 min, m/z=220-222 $(M+H)^+$.

Intermediate I12: 3-bromo-5-(3,5-dimethyl-1H-pyrazol-1-yl)aniline

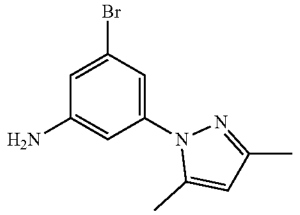

In a pressure flask, 3-bromo-5-iodoaniline hydrochloride (1.2 g, 3.589 mmol), 3,5-dimethylpyrazole (345 mg, 3.589 mmol), copper(I) iodide (410 mg, 2.153 mmol), DL-Proline (165 mg, 1.436 mmol), and cesium carbonate (3.508 g, 10.767 mmol) in DMSO (12 mL) were bubbled with a nitrogen stream for 1 min and the mixture was stirred at 150° C. for 16 h. A saturated aqueous sodium bicarbonate solution was added and the mixture was extracted with ethyl acetate. The combined organic layers were dried over anhydrous magnesium sulfate, filtered and concentrated under reduced pressure. The residue was purified by silica gel chromatography (eluting gradient 0-1.5% Dichloromethane/methanol) to afford the expected compound (220 mg. 23% yield) as a brown solid.

LCMS (MH) RT=0.744 min, m/z=266-268 $(M+H)^+$.

Intermediate I13: Mixture of 3-bromo-5-(1H-pyrazol-1-yl)aniline and 3-iodo-5-(1H-pyrazol-1-yl)aniline

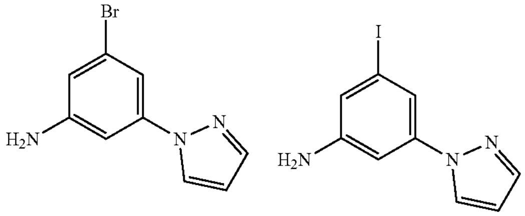

To a mixture of Intermediate I4 (3.3 g, 5.659 mmol) and ammonium chloride (1.311 g, 24.5 mmol) were dissolved in of ethanol/water (4:1) (30 mL). Iron powder (3.4 g, 28.295 mmol) was added and the reaction mixture was stirred at 50° C. for 88 h. The reaction mixture was diluted with ethyl acetate and filtered through a Celite pad. The filtrate was washed with a saturated aqueous sodium bicarbonate solution and extracted with ethyl acetate. The combined organic layers were dried over anhydrous magnesium sulfate, filtered, concentrated under reduced pressure. The residue was purified by silica gel chromatography (eluting gradient 0-50% Heptane/ethyl acetate) to afford the mixture of the expected compound and 3-iodo-5-(1H-pyrazol-1-yl)aniline (1.8 g, 61% yield) as a brown sticky solid.

LCMS (MH) RT=0.647 min, m/z=237.9-239.9 $(M+H)^+$ and RT=0.688 min, m/z=286.0 $(M+H)^+$.

Intermediate I14: 3-bromo-5-(5-methyl-1H-pyrazol-1-yl)aniline

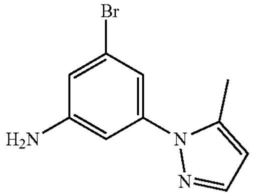

To a stirred solution of Intermediate I1 (300 mg, 1.063 mmol) in ethanol/water (5:1) (11 mL) was added ammonium chloride (398 mg, 7.441 mmol) and Iron powder (297 mg, 5.315 mmol). The reaction mixture was stirred at 50° C. for 4 h. The reaction mixture was filtered over a Celite pad and rinsing with ethyl acetate. The filtrate was concentrated under reduced pressure. Water was added and the mixture was extracted with ethyl acetate. The combined organic layers were dried over anhydrous magnesium sulfate, filtered and concentrated under reduced pressure. The residue was purified by silica gel chromatography (eluting gradient 0-25% Heptane/ethyl acetate) to afford the expected compound (200 mg, 75% yield) as a brown solid.

LCMS (MH) RT=0.669 min, m/z=252.0-253.9 $(M+H)^+$.

Intermediate I15: methyl 3-amino-5-bromobenzoate

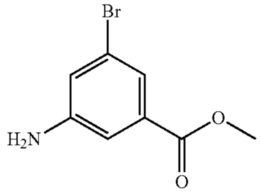

To a solution of 3-amino-5-bromobenzoic acid (5.00 g, 23.144 mmol) in methanol (93 mL) under nitrogen atmosphere, was added dropwise thionyl chloride (25.184 mL, 347.16 mmol) at 0° C. The reaction mixture was warmed to room temperature then stirred at 70° C. for 4 h. The solvent was evaporated under reduced pressure then co-evaporated with Heptane. The residue was dried under reduced pressure to afford Methyl 3-amino-5-bromobenzoate (7.85 g, 100% yield) as beige solid which was used without further purifications.

LCMS (MH) RT=0.692 min, m/z=230-232 $(M+H)^+$.

Intermediate I16: 3-bromo-5-(1-{2-[(tert-butyldiphenylsilyl)oxy]ethyl}-1H-pyrazol-4-yl)aniline

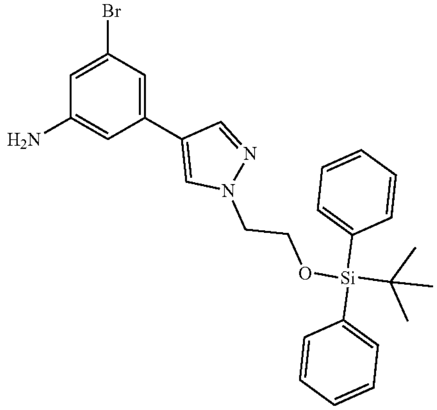 [SMILES: CC(C)(C)[Si](OCCn1cc(-c2cc(N)cc(Br)c2)cn1)(c1ccccc1)c1ccccc1]

Step 1

To a suspension of Intermediate I5 (1.50 g, 3.77 mmol) in Dioxane/Water (48/12 mL) were added 2-[4-(4,4,5,5-tetramethyl-1,3,2-dioxaborolan-2-yl)pyrazol-1-yl]ethanol (1.08 g, 4.52 mmol), Tetrakis(triphenylphosphine)palladium(0) (87 mg, 0.07 mmol), Xphos (72 mg, 0.15 mmol) and Potassium phosphate tribasic (2.40 g, 11.31 mmol). The reaction mixture was degassed by bubbling under argon for 10 min and stirred at 100° C. for 1 h. The resulting mixture was allowed to cooled to room temperature. Solvent was evaporated under reduced pressure. The residue was purified by flash chromatography using Cyclohexane/EtOAc (100:0 to 0:100) as eluent. The expected fractions were combined and evaporated under reduced pressure to afford the title compound as a yellow oil (1.63 g, quant.).

LCMS (MA) RT=2.46 min, m/z=382.1/384.1 $(M+H)^+$.

Step 2

To a solution of the title compound from Step 1 (1.53 g, 4.00 mmol) in THE (15 mL) were added Imidazole (544 mg, 8.00 mmol) and tert-Butyldiphenylchlorosilane (1.56 mL, 6.00 mmol). The mixture was stirred at room temperature for 1 h. Upon complete conversion, monitored by LCMS, water and EtOAc were added and the layers were separated. The aqueous layer was extracted with EtOAc (2×20 mL) and the combined organic layers were dried over anhydrous sodium sulfate, filtered and evaporated under reduced pressure. The residue was purified by silica gel column chromatography using Cyclohexane/EtOAc (100:0 to 50:50) as eluent to afford the title compound as a pale yellow foam (1.91 g, 77%).

LCMS (MA) RT=3.83 min, m/z=620.2/622.2 $(M+H)^+$.

Step 3

To a solution of the title compound from Step 2 (1.91 g, 3.07 mmol) in DCM (45 mL) was added HCl 4 M in 1,4-Dioxane (2.30 mL, 9.22 mmol). The mixture was stirred at room temperature for 5 h. LCMS monitoring showed partial conversion, therefore additional HCl 4 M in 1,4-Dioxane (1.50 mL, 6.14 mmol, 2 eq) was added and the mixture was stirred at room temperature overnight. Upon complete conversion, monitored by LCMS, the mixture was carefully quenched with a saturated solution of $NaHCO_3$. The layers were separated. The aqueous layer was extracted with DCM (2×20 mL) and the combined organic layers were dried over anhydrous sodium sulfate, filtered and evaporated under reduced pressure. The residue was purified on silica gel column using Cyclohexane/EtOAc (100:0 to 60:40) as eluent to afford the title compound as an orange oil (1.39 g, 88% yield).

LCMS (MA) RT=3.44 min, m/z=520.2/522.2 $(M+H)^+$.

Aniline A1: 3-Fluoro-5-(tetramethyl-1,3,2-dioxaborolan-2-yl)aniline

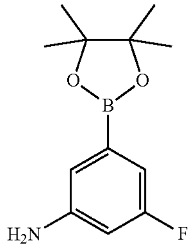 [SMILES: CC1(C)OB(c2cc(N)cc(F)c2)OC1(C)C]

A mixture of 3-bromo-5-fluoroaniline (21.2 g, 111.61 mmol), bis(pinacolato)diboron (28.34 g, 111.61 mmol), potassium acetate (32.86 g, 334.83 mmol) and [1,1'-bis (diphenylphosphino) ferrocene]dichloropalladium(II) (2.45 g, 3.90 mmol) in 1,4-Dioxane (120 mL) was purged with argon and then heated at 90° C. for 16 h. The hot reaction mixture was filtered through a Whatmann paper filter. The filtrate was diluted in ethyl acetate and washed with water and Brine. The organic layer was dried over anhydrous sodium sulfate then filtered and evaporated under reduced pressure. The residue was purified by silica gel chromatography (eluting gradient 0-20% pentane/ethyl acetate). The residue was triturated in n-Heptane, then filtered and dried to afford the expected compound (11.73 g, 44% yield) as a beige solid.

LCMS (MA) RT=2.53 min, m/z=238.2 $(M+H)^+$.

Similarly Prepared:

| Int. no | Structure | Name | From intermediates | Analytical data |
|---|---|---|---|---|
| A2 | 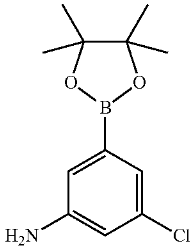 [SMILES: CC1(C)OB(c2cc(N)cc(Cl)c2)OC1(C)C] | 3-chloro-5-(4,4,5,5-tetramethyl-1,3,2-dioxaborolan-2-yl) aniline | From 3-bromo-5-chloroaniline 79% yield as a beige solid | LCMS (MA) RT = 2.74 min, m/z = 254.1 $(M + H)^+$. |
| A3 | 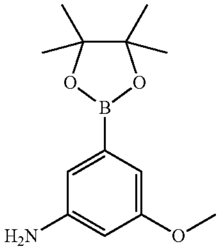 [SMILES: COc1cc(N)cc(B2OC(C)(C)C(C)(C)O2)c1] | 3-methoxy-5-(4,4,5,5-tetramethyl-1,3,2-dioxaborolan-2-yl) aniline | From 3-bromo-5-methoxyaniline 90% yield as a red oil | LCMS (MA) RT = 1.99 min, m/z = 250 $(M + H)^+$. |

-continued

| Int. no | Structure | Name | From intermediates | Analytical data |
|---|---|---|---|---|
| A4 | 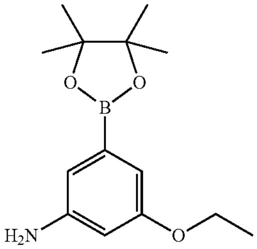 [SMILES: CCOc1cc(N)cc(B2OC(C)(C)C(C)(C)O2)c1] | 3-ethoxy-5-(4,4,5,5-tetramethyl-1,3,2-dioxaborolan-2-yl) aniline | From 3-bromo-5-ethoxy-aniline 71% yield as cream crystals | LCMS (MA) RT = 2.30 min, m/z = 264.2 $(M + H)^+$. |
| A5 | 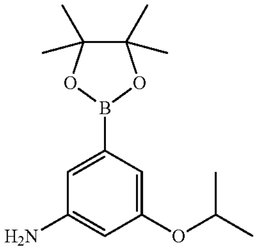 [SMILES: CC(C)Oc1cc(N)cc(B2OC(C)(C)C(C)(C)O2)c1] | 3-isopropoxy-5-(4,4,5,5-tetramethyl-1,3,2-dioxaborolan-2-yl)aniline | From Intermediate I8 82% yield as a red oil | LCMS (MA) RT = 2.37 min, m/z = 278.2 $(M + H)^+$. |
| A6 | 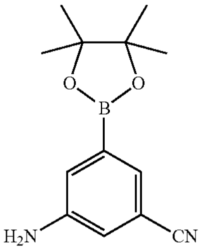 [SMILES: CC1(C)OB(c2cc(N)cc(C#N)c2)OC1(C)C] | 3-amino-5-(4,4,5,5-tetramethyl-1,3,2-dioxaborolan-2-yl) benzonitrile | From 3-amino-5-bromo-benzonitrile 84% yield as white solid | LCMS (MA) RT = 2.53 min, m/z = 245.2 $(M + H)^+$. |
| A7 | 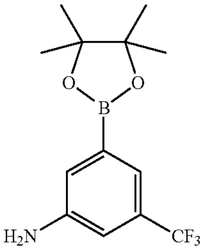 [SMILES: CC1(C)OB(c2cc(N)cc(C(F)(F)F)c2)OC1(C)C] | 3-(4,4,5,5-tetramethyl-1,3,2-dioxaborolan-2-yl)-5-(trifluoromethyl) aniline | From 3-amino-5-bromobenzo-trifluoride 99% yield as brown oil | LCMS (MA) RT = 2.89 min, m/z = 288.1 $(M + H)^+$. |
| A8 | 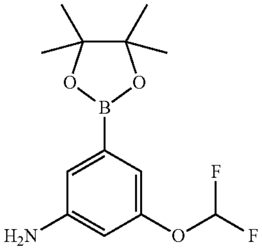 [SMILES: CC1(C)OB(c2cc(N)cc(OC(F)F)c2)OC1(C)C] | 3-(difluoromethoxy)-5-(4,4,5,5-tetramethyl-1,3,2-dioxaborolan-2-yl)aniline | From 3-bromo-5-(difluoromethoxy) aniline 64% yield as light orange oil | LCMS (MA) RT = 2.64 min, m/z = 286.1 $(M + H)^+$. |
| A9 | 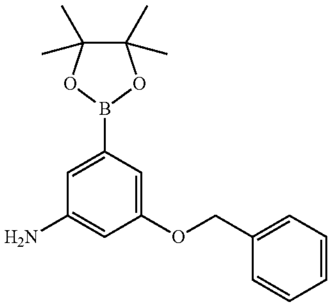 [SMILES: CC1(C)OB(c2cc(N)cc(OCc3ccccc3)c2)OC1(C)C] | 3-benzyloxy-5-(4,4,5,5-tetramethyl-1,3,2-dioxaborolan-2-yl)aniline | From Intermediate I9 71% yield as a cream solid | LCMS (MA) RT = 2.70 min, m/z = 326.1 $(M + H)^+$. |

-continued

| Int. no | Structure | Name | From intermediates | Analytical data |
|---|---|---|---|---|
| A10 | 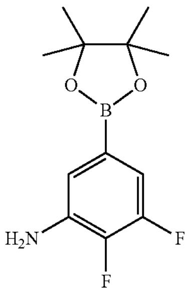 [SMILES: CC1(C)OB(c2cc(N)c(F)c(F)c2)OC1(C)C] | 3,4-difluoro-5-(4,4,5,5-tetramethyl-1,3,2-dioxaborolan-2-yl) aniline | From 3-bromo-4,5-difluoro-aniline 69% yield as a yellow oil | $^1$H NMR (400 MHz, DMSO) 6.65-6.57 (2H, m), 5.24 (2H, bs), 1.29-1.28 (12H, m). |
| A11 | 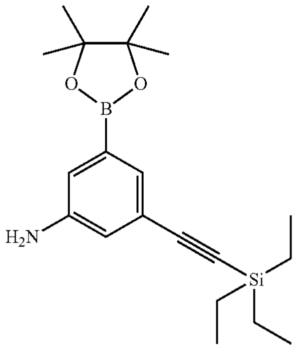 [SMILES: CC[Si](C#Cc1cc(N)cc(B2OC(C)(C)C(C)(C)O2)c1)(CC)CC] | 3-(4,4,5,5-tetramethyl-1,3,2-dioxaborolan-2-yl)-5(2-triethylsilyl ethynyl)aniline | From Intermediate I10 67% yield as a brown oil | LCMS (MA) RT = 3.67 min, m/z = 358 $(M + H)^+$. |
| A12 | 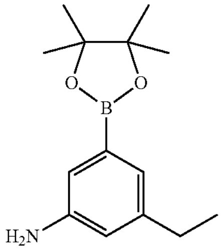 | 3-ethyl-5-(4,4,5,5-tetramethyl-1,3,2-dioxaborolan-2-yl) aniline | From 3-bromo-5-ethyl-aniline 44% yield as a yellow solid | LCMS (MA) RT = 2.12 min, m/z = 248.2 $(M + H)^+$ |
| A13 | 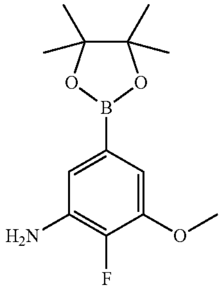 [SMILES: COc1cc(B2OC(C)(C)C(C)(C)O2)cc(N)c1F] | 2-fluoro-3-methoxy-5-(4,4,5,5-tetramethyl-1,3,2-dioxaborolan-2-yl)aniline | From Intermediate I11 58% yield as a white solid | LCMS (MA) RT = 2.50 min, m/z = 268.2 $(M + H)^+$. |
| A14 | 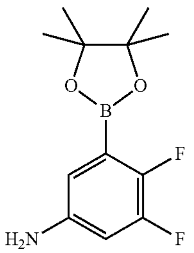 [SMILES: CC1(C)OB(c2cc(N)cc(F)c2F)OC1(C)C] | 2,3-difluoro-5-(4,4,5,5-tetramethyl-1,3,2-dioxaborolan-2-yl) aniline | From 5-bromo-2,3-difluoro-aniline 40% yield as a white solid | LCMS (MA) RT = 2.85 min, m/z = 256 $(M + H)^+$. |

-continued

| Int. no | Structure | Name | From intermediates | Analytical data |
|---|---|---|---|---|
| A15 | 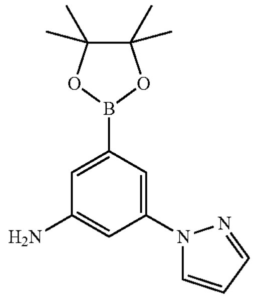 [SMILES: CC1(C)OB(c2cc(N)cc(-n3cccn3)c2)OC1(C)C] | 3-pyrazol-1-yl-5-(4,4,5,5-tetramethyl-1,3,2-dioxaborolan-2-yl)aniline | From Intermediate I13 90% yield as a brown solid | LCMS (MH) RT = 0.803 min, m/z = 286.1 $(M + H)^+$. |
| A16 | 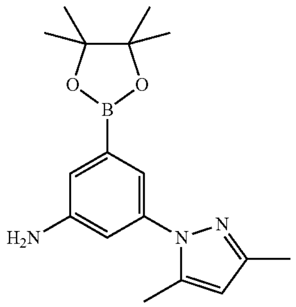 [SMILES: Cc1cc(C)n(-c2cc(N)cc(B3OC(C)(C)C(C)(C)O3)c2)n1] | 3-(3,5-dimethylpyrazol-1-yl)-5-(4,4,5,5-tetramethyl-1,3,2-dioxaborolan-2-yl) aniline | From Intermediate I12 34% yield as a brown sticky solid | LCMS (MI) RT = 0.866 min, m/z = 314.1 $(M + H)^+$. |
| A17 | 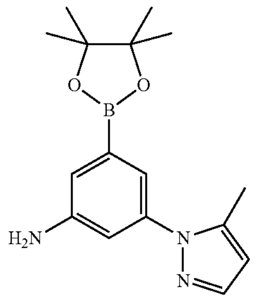 [SMILES: Cc1ccnn1-c1cc(N)cc(B2OC(C)(C)C(C)(C)O2)c1] | 3-(5-methylpyrazol-1-yl)-5-(4,4,5,5-tetramethyl-1,3,2-dioxaborolan-2-yl)aniline | From Intermediate I14 100% yield as black solid | LCMS (MH) RT = 0.819 min, m/z = 300.1 $(M + H)^+$. |
| A18 | 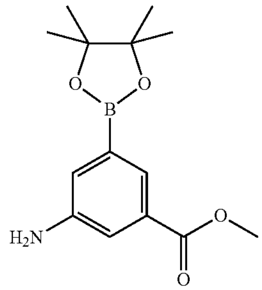 [SMILES: COC(=O)c1cc(N)cc(B2OC(C)(C)C(C)(C)O2)c1] | methyl 3-amino-5-(4,4,5,5-tetramethyl-1,3,2-dioxaborolan-2-yl) benzoate | From Intermediate I15 92% yield as beige solid | LCMS (MH) RT = 0.801 min, m/z = 278.1 $(M + H)^+$. |

-continued

| Int. no | Structure | Name | From intermediates | Analytical data |
|---|---|---|---|---|
| A19 | 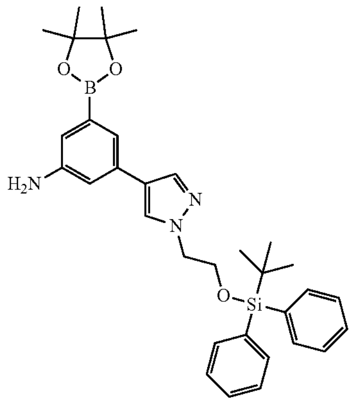 [SMILES: CC1(C)OB(c2cc(N)cc(-c3cnn(CCO[Si](c4ccccc4)(c4ccccc4)C(C)(C)C)c3)c2)OC1(C)C] | 3-[1-[2-[tert-butyl(diphenyl)silyl]oxyethyl]pyrazol-4-yl]-5-(4,4,5,5-tetramethyl-1,3,2-dioxaborolan-2-yl)aniline | From Intermediate I16 76% yield as brown oil | LCMS (MA) RT = 3.45 min, m/z = 568.3 $(M + H)^+$. |

Aniline A20: 3-cyclopropyl-5-(4,4,5,5-tetramethyl-1,3,2-dioxaborolan-2-yl)aniline

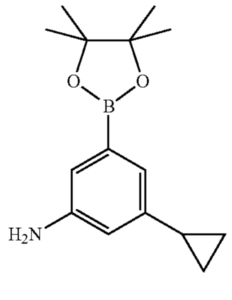 [SMILES: CC1(C)OB(c2cc(N)cc(C3CC3)c2)OC1(C)C]

Step 1

To a stirred solution of 3-Bromo-5-iodo-benzoic acid (20.0 g, 61.18 mmol) in dry tert-Butanol (100 mL) and Triethylamine (11.0 mL, 79.53 mmol) under Argon was added Diphenyl phosphoryl-azide (14.5 mL, 67.30 mmol). The reaction mixture was refluxed (80° C.) under Argon overnight. The reaction mixture was cooled down to room temperature and the solvent were evaporated in vacuo. The residue was dissolved in ethyl acetate (50 mL) and washed successively with a 10% NaOH solution (30 mL), water (2×50 mL) and Brine. The organic layer was dried over sodium sulfate, filtered and evaporated in vacuo. The crude residue was purified by silica gel chromatography using Cyclohexane/EtOAc (90:10) as eluent to afford the title compound as yellow amorphous solid (16.2 g, 67% yield).

LCMS (MA) RT=3.38 min, m/z=341.8/343.8 $(M+H)^+$.

Step 2

To a suspension of the title compound from Step 1 (3.0 g, 7.54 mmol) in Toluene/Water (36/6 mL) were added Cyclopropylboronic acid (842 mg, 9.80 mmol), Palladium(II) acetate (85 mg, 0.38 mmol), Tricyclohexylphosphine (211 mg, 0.75 mmol) and Potassium phosphate tribasic (4.801 g, 22.62 mmol). The reaction mixture was degassed by bubbling under argon for 10 min and stirred at 110° C. for 39 h. Upon 95% conversion, monitored by LCMS, the mixture was cooled to room temperature and the solvent was evaporated under reduced pressure. The residue was purified on silica gel column using Cyclohexane/EtOAc (100:0 to 85:15) as eluent. A second purification on silica gel column was performed using Cyclohexane/EtOAc (100:0 to 90:10) as eluent to afford the title compound as orange oil (1.26 g, 53% yield).

LCMS (MA) RT=3.16-3.22 min, m/z=312.2/314.1 $(M+H)^+$.

Step 3

To a solution of title compound from Step 2 (1.26 g, 4.03 mmol) in DCM (60 mL) was added HCl 4 M in 1,4-Dioxane (5.04 mL, 20.15 mmol). The mixture was stirred at room temperature for 8 h. Upon complete conversion, monitored by LCMS, the mixture was carefully quenched with a saturated solution of $NaHCO_3$. The layers were separated and the aqueous layer was extracted with DCM (2×20 mL). The combined organic layer was dried over anhydrous Sodium sulfate, filtered and evaporated under reduced pressure. The residue was purified on silica gel column using Cyclohexane/EtOAc (100:0 to 90:10) as eluent to afford the title compound as orange oil (660 mg, 3.11 mmol, 77%).

LCMS (MA) RT=2.45 min, m/z=212.0/214.0 $(M+H)^+$.

Step 4

The title compound from Step 3 was further purified by column chromatography using Cyclohexane/EtOAc (100:0 to 85:15) as eluent to afford 483 mg of an orange oil.

Under argon atmosphere, to a solution of 3-bromo-5-cyclopropyl-aniline (433 mg, 2.04 mmol) in dry 1,4-Dioxane (12 mL) were added Bis(pinacolato)diboron (544 mg, 2.14 mmol), KOAc (600 mg, 6.12 mmol) and [1,1'-Bis(diphenylphosphino)ferrocene]dichloropalladium(II) complex with DCM (42 mg, 0.05 mmol). The reaction mixture was heated at 90° C. for 3 h. LCMS monitoring showed 50% conversion. Additional Bis(pinacolato)diboron (272 mg, 1.07 mmol), KOAc (300 mg, 3.06 mmol) and [1,1'-Bis(diphenylphosphino)ferrocene]dichloropalladium(II) complex with DCM (42 mg, 0.05 mmol) were added and the reaction was stirred at 90° C. for 5 h. Upon complete conversion, monitored by LCMS, the mixture was cooled to rt and the solvent was evaporated under reduced pressure. The residue was diluted with a saturated solution of NaCl and EtOAc and the layers were separated. The aqueous layer was extracted with EtOAc (2×20 mL) and the combined organic layer was dried over anhydrous sodium sulfate, filtered and evaporated under reduced pressure. The residue was purified on silica gel column using Cyclohexane/EtOAc (100:0 to 85:15) as eluent to afford the expected compound as a pale brown foam (251 mg, 48% yield).

LCMS (MA) RT=2.11 min, m/z=260.2 $(M+H)^+$.

Example 1: (12R,14S)-4-fluoro-12,18-dimethoxy-16-oxa-7,10,20,21,24-pentaazapentacyclo$[15.5.2.1^{2},6.0^{10},^{14}.0^{20},^{23}]$pentacosa-1(23),2(25),3,5,17(24),18,21-heptaen-11-one

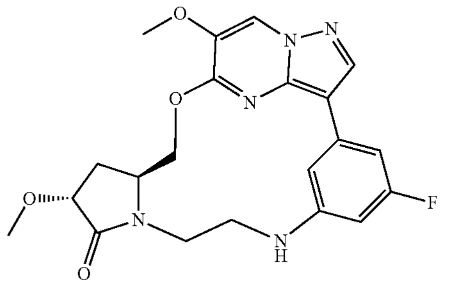 [SMILES: COc1cn2ncc3c2nc1OC[C@@H]1C[C@@H](OC)C(=O)N1CCNc1cc(F)cc-3c1]

2

Step 1

To a solution of Pyrrolidine P1 (2.7 g, 10.29 mmol) in dry DMF (50 mL) was added Sodium hydride, 60% in mineral oil (0.823 g, 20.57 mmol) at 0° C. After 30 min, Scaffold S2 (2.617 g, 11.31 mmol) was added and the mixture was stirred at 4-5° C. for 15 min. Monitoring by LCMS showed complete conversion. Water was added dropwise carefully at 4-5° C. and the mixture was extracted with EtOAc (4×20 mL). The combined organic layers were washed with Brine then dried over $Na_2SO_4$, filtered and concentrated under vacuum. The product was purified on column of silica gel using Cyclohexane/EtOAc (100-0 to 50-50) as eluent to afford the expected compound (3.498 g, 7.65 mmol, 74%) as a light brown oil.

LCMS (MA) RT=2.76 min, m/z=459 $(M+H)^+$.

Step 2

A solution of $K_3PO_4$ (21.01 mmol, 4.46 g) in water (9 mL) was added to a solution of the title compound from Step 1 (7 mmol, 3.203 g), Aniline A1 (9.11 mmol, 2.159 g) and Xphos (0.28 mmol, 229 mg) in Dioxane (26 mL). The reaction mixture was degassed with argon during 15 min. To the reaction mixture was added $Pd(PPh_3)_4$ (0.14 mmol, 162 mg) and the reaction was heated at 100° C. for 3 h. Monitoring by LC/MS showed reaction was complete. The reaction mixture was filtered over Celite then solvent was removed under reduced pressure. The compound was purified by Flash chromatography using a 120 g SiO2 column eluted with Cyclohexane/EtOAc 100/0 to 50/50 to afford the expected compound (3.395 g, 6.96 mmol, 99%) as a brown oil.

LCMS (MA) RT=2.61 min, m/z=488.2 $(M+H)^+$.

Step 3

To a solution of the title compound from Step 2 (3.524 g, 7.23 mmol) in CH3CN (36 mL) were added Pyridine (0.877 mL, 10.84 mmol) and 2-Nitrobenzenesulfonyl chloride (2.083 g, 9.40 mmol). The reaction mixture was heated at 70° C. for overnight. Monitoring reaction by LCMS showed complete reaction. The reaction mixture was poured into water. After extraction with EtOAc, the organic phase was dried ($Na_2SO_4$), filtered and concentrated under reduced pressure. The crude was triturated in Diisopropyl ether to the title compound (4.064 g, 6.04 mmol, 84%) as a brown oil.

LCMS (MA) RT=2.95 min, m/z=673.2 $(M+H)^+$.

Step 4

To a solution of the title compound from Step 3 (0.500 g, 0.74 mmol) in Acetonitrile (5 mL) was added Cesium carbonate (0.727 g, 2.23 mmol) and 1,2-Dibromoethane (0.961 mL, 11.15 mmol). The reaction mixture was heated to reflux for 4 h. Monitoring of the reaction mixture by LCMS showed the reaction was completed. The solvent was removed, the residue was taken in EtOAc (50 mL) extracted with water (50 mL) then Brine (2×40 mL), the organic layer was dried over anhydrous $Na_2SO_4$, filtered and dried under vacuum to afford the expected compound (0.598 g, 0.74 mmol postulated, quantitative yield) as a yellow/orange solid.

LCMS (MA) RT=3.13 min, m/z=780 $(M+H)^+$.

Step 5

To a suspension of the title compound from Step 4 (0.598 g, 0.77 mmol) in DCM (5 mL) was added Hydrogen Chloride solution 4M in 1,4-Dioxane (1.918 mL, 7.67 mmol). The reaction mixture was left stirring overnight. LCMS showed complete reaction. The solvent was removed under reduced pressure to afford the expected compound (0.622 g, 0.77 mmol postulated, quantitative yield) as a brown solid.

LCMS (MA) RT=1.97 min, m/z=679 $(M+H)^+$.

Step 6

To a solution of the title compound from Step 5 (0.622 g, 0.87 mmol) in CH3CN (62 mL) was added Sodium hydrogenocarbonate (0.365 g, 4.34 mmol), cesium carbonate (0.849 g, 2.61 mmol) then Potassium iodide (0.433 g, 2.61 mmol). The resulting mixture was heated at 90° C. for 4 h. Monitoring by LC/MS showed reaction was complete. The reaction mixture was filtered then the solid was purified on silica gel column using DCM/MeOH 100/0 to 98/2 as eluent to afford the expected compound (0.106 g, 0.18 mmol, 20% yield) as a white solid.

LCMS (MA) RT=2.29 min, m/z=599 $(M+H)^+$.

Step 7

To a mixture of the title compound from Step 6 (0.106 g, 0.18 mmol) in THF/$H_2O$ (9 mL/3.9 mL) was added Sodium bicarbonate (0.298 g, 3.54 mmol). The reaction mixture was stirred 10 min at room temperature then Iodine (0.674 g, 2.66 mmol) was added. The reaction mixture was stirred at 60° C. for 2 h. Monitoring by LC/MS showed reaction was complete. The reaction mixture was quenched by saturated sodium thiosulfate solution then extracted by ethyl acetate. The organic layer was dried over anhydrous sodium sulfate, filtered and evaporated under reduced pressure to afford the expected compound (0.118 g, 0.18 mmol postulated, quantitative yield) as a yellow solid.

LCMS (MA) RT=2.49 min, m/z=613 $(M+H)^+$.

Step 8

The title compound from Step 7 (0.118 g, 0.19 mmol) and Cesium carbonate (0.126 g, 0.39 mmol) were dissolved in DMF (2 mL). 4-Methylbenzenethiol (0.029 g, 0.23 mmol) was added and the mixture was stirred at room temperature overnight. Monitoring of the reaction mixture by LCMS showed the reaction was completed. The reaction mixture was filtered to remove cesium carbonate. Solvent was evaporated and the residue was purified by flash column chromatography using (DCM/MeOH 100/0 to 95/5) as eluent. The product fractions were collected and the solvent was evaporated. The residue was purified by flash column chromatography using Cyclohexane/EtOAc (100/0 to 0/100) as eluent to afford the expected product (0.008 g, 10% Yield) as a pale yellow powder.

LCMS (MA) RT=2.15 min, m/z=428 $(M+H)^+$.

LCMS (MB) RT=2.22 min, m/z=428 $(M+H)^+$.

$^1H$ NMR (400 MHz, DMSO) 8.79 (1H, s), 8.40 (1H, s), 7.63 (1H, s), 6.73 (1H, dd, J=1.2, 9.2 Hz), 6.33 (1H, t, J=5.8 Hz), 6.22-6.17 (1H, m), 4.96 (1H, d, J=10.4 Hz), 4.49-4.46 (1H, m), 4.36-4.31 (1H, m), 4.07-4.00 (1H, m), 3.90-3.89 (3H, m), 3.62-3.51 (1H, m), 3.42-3.35 (1H, m), 3.33 (3H, s), 3.25-3.19 (2H, m), 2.50-2.40 (1H, m), 2.00-1.91 (1H, m).

Similarly Prepared:

| Ex no | Structure/Name | From intermediates | Analytical data |
| --- | --- | --- | --- |
| 2 | 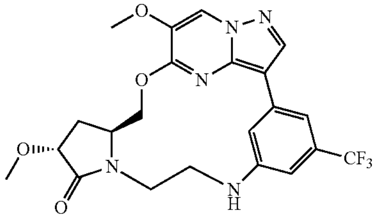 [SMILES: COc1cn2ncc3c2nc1OC[C@@H]1C[C@@H](OC)C(=O)N1CCNc1cc-3cc(C(F)(F)F)c1] (12R,14S)-12,18-dimethoxy-4-(trifluoromethyl)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S2 Pyrrolidine P1 Aniline A7 27% yield as a pale yellow solid | LCMS (MA) RT = 2.46 min, m/z = 478 $(M + H)^+$ LCMS (MC) RT = 2.40 min, m/z = 478 $(M + H)^+$. $^1$H NMR (400 MHz, DMSO) 8.81 (1H, s), 8.51 (1H, s), 7.99-7.96 (1H, m), 7.17 (1H, s), 6.73 (1H, s), 6.54 (1H, t, J = 6.0 Hz), 4.98-4.95 (1H, m), 4.60-4.40 (1H, m), 4.37-4.31 (1H, m), 4.08-4.01 (1H, m), 3.90 (3H, s), 3.54 (1H, dd, J = 10.3, 13.8 Hz), 3.45 (3H, s), 3.30-3.20 (2H, m), 2.45-2.35 (1H, m), 1.99-1.91 (1H, m), 1.16-1.15 (1H, m). |
| 3 | 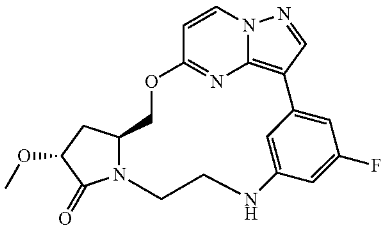 [SMILES: CO[C@@H]1C[C@H]2COc3ccn4ncc(c4n3)-c3cc(F)cc(c3)NCCN2C1=O] (12R,14S)-4-fluoro-12-methoxy-16-oxa-7,10,20,21,24-pentaazapentacyclo[15.5.2.1$^{2}$,6.0$^{10}$,$^{1}$4.0$^{20}$,$^{23}$] pentacosa-1(23),2(25),3,5,17(24),18,21-heptaen-11-one | Scaffold 3-bromo-5-chloro-pyrazolo[1,5-a]pyrimidine Pyrrolidine P1 Aniline A1 58% yield as an off-white crystal | LCMS (MA) RT = 2.21 min, m/z = 398.1 $(M + H)^+$. LCMS (MB) RT = 2.21 min, m/z = 398.2 $(M + H)^+$. $^1$H NMR (400 MHz, DMSO) 8.99 (1H, d, J = 7.6 Hz), 8.54-8.54 (1H, m), 7.68 (1H, s), 6.77-6.73 (1H, m), 6.67 (1H, d, J = 7.4 Hz), 6.34 (1H, t, J = 5.9 Hz), 6.24-6.19 (1H, m), 4.94 (1H, d, J = 11.0 Hz), 4.48-4.45 (1H, m), 4.37-4.31 (1H, m), 3.95 (1H, t, J = 10.7 Hz), 3.63-3.50 (1H, m), 3.46 (3H, s), 3.39 (1H, s), 3.27-3.19 (2H, m), 2.44 (1H, s), 2.01-1.92 (1H, m). |
| 4 | 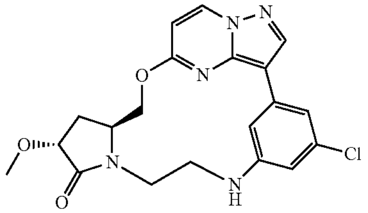 [SMILES: CO[C@@H]1C[C@H]2COc3ccn4ncc(c4n3)-c3cc(Cl)cc(c3)NCCN2C1=O] (12R,14S)-4-chloro-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P1 Aniline A2 17% Yield as a yellow solid | LCMS (MA) RT = 2.38 min, m/z = 414 $(M + H)^+$. LCMS (MC) RT = 2.36 min, m/z = 414 $(M + H)^+$. $^1$H NMR (400 MHz, DMSO): 9.00 (1H, d, J = 7.4 Hz), 8.58-8.56 (1H, m), 7.78-7.78 (1H, m), 6.97 (1H, s), 6.67 (1H, d, J = 7.4 Hz), 6.48 (1H, t, J = 1.7 Hz), 6.38-6.34 (1H, m), 4.94 (1H, dd, J = 0.9, 10.5 Hz), 4.48-4.46 (1H, m), 4.34 (1H, t, J = 8.9 Hz), 3.98-3.92 (1H, m), 3.65-3.50 (1H, m), 3.39-3.35 (1H, m), 3.33 (3H, s), 3.27-3.19 (2H, m), 2.45-2.30 (1H, m), 2.00-1.92 (1H, m). |
| 5 | 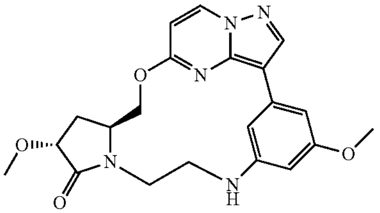 (12R,14S)-4,12-d i meth oxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P1 Aniline A3 38% yield as a white solid | LCMS (MA) RT = 2.09 min, m/z = 410 $(M + H)^+$. LCMS (MC) RT = 2.06 min, m/z = 410 $(M + H)^+$. $^1$H NMR (400 MHz, DMSO) 8.98-8.96 (1H, m), 8.51 (1H, s), 7.49-7.46 (1H, m), 6.65-6.63 (1H, m), 6.55 (1H, s), 6.06-6.02 (2H, m), 4.93 (1H, d, J = 10.4 Hz), 4.49-4.46 (1H, m), 4.33 (1H, t, J = 8.8 Hz), 4.05-3.91 (1H, m), 3.73-3.72 (3H, m), 3.60-3.45 (1H, m), 3.35-3.25 (3H), 3.24-3.17 (2H, m), 2.45-2.35 (1H, m), 2.01-1.94 (1H, m), 1.25-1.16 (1H, m). |

-continued

| Ex no | Structure/Name | From intermediates | Analytical data |
|---|---|---|---|
| 6 | 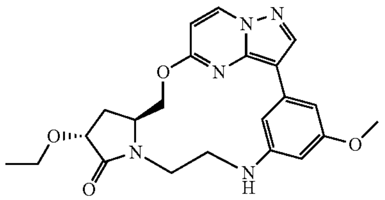 [SMILES: CCO[C@@H]1C[C@H]2COc3ccn4ncc(c4n3)-c3cc(cc(OC)c3)NCCN2C1=O] (12R,14S)-12-ethoxy-4-methoxy-16-oxa-7,10,20,21,24-pentaazapentacyclo[15.5.2.1$^2$,6.0$^{10}$,$^1$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P2 Aniline A3 50% yield as a cream solid | LCMS (MA) RT = 2.22 min, m/z = 424.2 $(M + H)^+$. LCMS (MB) RT = 2.28 min, m/z = 424.3 $(M + H)^+$. $^1$H NMR (400 MHz, DMSO) 8.98-8.95 (1H, m), 8.50 (1H, s), 7.46 (1H, s), 6.65-6.62 (1H, m), 6.54 (1H, d, J = 1.1 Hz), 6.05-6.02 (2H, m), 4.92 (1H, d, J = 10.8 Hz), 4.46-4.38 (2H, m), 3.98-3.82 (2H, m), 3.73 (3H, s), 3.55 (2H, s), 3.59-3.32 (1H, m), 3.20 (2H, s), 2.46-2.39 (1H, m), 2.01-1.92 (1H, m), 1.15 (3H, t, J = 7.0 Hz). |
| 7 | 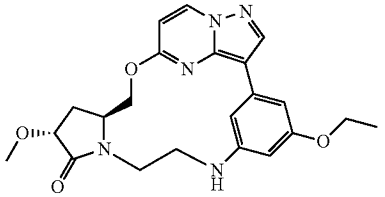 [SMILES: CCOc1cc2cc(c1)-c1cnn3ccc(nc13)OC[C@@H]1C[C@@H](OC)C(=O)N1CCN2] (12R,14S)-4-ethoxy-12-methoxy-16-oxa-7,10,20,21,24-pentaazapentacyclo[15.5.2.1$^2$,6.0$^{10}$,$^1$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P1 Aniline A4 11% yield as a yellow solid | LCMS (MA) RT = 2.23 min, m/z = 424 $(M + H)^+$. LCMS (MC) RT = 2.22 min, m/z = 424 $(M + H)^+$. $^1$H NMR (400 MHz, DMSO): 8.98-8.95 (1H, m), 8.50 (1H, s), 7.46 (1H, s), 6.65-6.62 (1H, m), 6.54 (1H, dd, J = 1.2, 1.8 Hz), 6.03-6.01 (2H, m), 4.94-4.91 (1H, m), 4.46 (1H, s), 4.36-4.30 (1H, m), 4.02-3.90 (3H, m), 3.45-3.45 (4H, m), 3.44-3.37 (1H, m), 3.24-3.15 (2H, m), 2.35-2.27 (1H, m), 2.01-1.91 (1H, m), 1.35-1.30 (3H, m). |
| 8 | 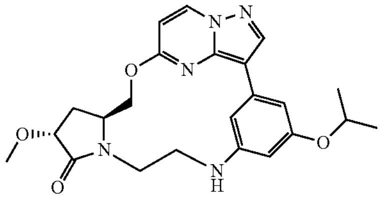 [SMILES: CO[C@@H]1C[C@H]2COc3ccn4ncc(c4n3)-c3cc(cc(OC(C)C)c3)NCCN2C1=O] (12R,14S)-12-methoxy-4-(propan-2-yloxy)-16-oxa-7,10,20,21,24-pentaazapentacyclo[15.5.2.1$^2$,6.0$^{10}$,$^1$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A5 21% yield as a white solid | LCMS (MA) RT = 2.32 min, m/z = 438.2 $(M + H)^+$. LCMS (MC) RT = 2.33 min, m/z = 438.3 $(M + H)^+$. $^1$H NMR (400 MHz, $CDCl_3$): 8.53-8.51 (1H, m), 8.30-8.30 (1H, m), 7.58 (1H, s), 6.67 (1H, s), 6.43-6.41 (1H, m), 6.23-6.21 (1H, m), 5.08-5.05 (2H, m), 4.62-4.55 (4H, m), 4.26-4.21 (2H, m), 3.92-3.86 (2H, m), 3.63-3.62 (3H, m), 3.37 (3H, s), 2.63 (2H, dd, J = 8.2, 12.9 Hz), 2.22-2.14 (3H, m). |
| 9 | 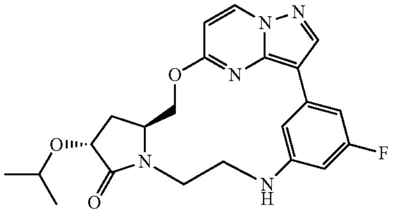 [SMILES: CC(C)O[C@@H]1C[C@H]2COc3ccn4ncc(c4n3)-c3cc(F)cc(c3)NCCN2C1=O] (12R,14S)-4-fluoro-12-(propan-2-yloxy)-16-oxa-7,10,20,21,24-pentaazapentacyclo[15.5.2.1$^2$,6.0$^{10}$,$^1$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P4 Aniline A1 52% yield as a white solid | LCMS (MA) RT = 2.45 min m/z = 426.2 $(M + H)^+$. LCMS (MC) RT = 2.45 min m/z = 426.2 $(M + H)^+$. $^1$H NMR (400 MHz, DMSO) 8.99 (1H, d, J = 7.4 Hz), 8.54 (1H, s), 7.68 (1H, s), 6.77-6.73 (1H, m), 6.66 (1H, d, J = 7.4 Hz), 6.34 (1H, t, J = 5.9 Hz), 6.24-6.19 (1H, m), 4.95-4.90 (1H, m), 4.52 (1H, t, J = 8.6 Hz), 4.43-4.47 (1H, m), 4.04-3.95 (2H, m), 3.59-3.51 (1H, m), 3.42-3.37 (1H, m), 3.26-3.21 (2H, m), 2.44-2.39 (1H, m), 1.97-1.89 (1H, m), 1.14 (6H, dd, J = 6.2, 8.4 Hz) |

-continued

| Ex no | Structure/Name | From intermediates | Analytical data |
|---|---|---|---|
| 10 | 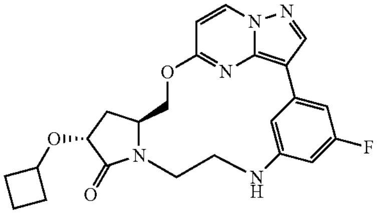 [SMILES: O=C1[C@H](OC2CCC2)C[C@H]2COc3ccn4ncc(c4n3)-c3cc(F)cc(c3)NCCN12] (12R,14S)-12-cyclobutoxy-4-fluoro-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P3 Aniline A1 36% yield as a white solid | LCMS (MA) RT = 2.55 min, m/z = 438.2 $(M + H)^+$. LCMS (MC) RT = 2.55 min, m/z = 438.2 $(M + H)^+$. $^1$H NMR (400 MHz, DMSO) 8.99 (1H, d, J = 7.4 Hz), 8.54 (1H, s), 7.67 (1H, s), 6.77-6.74 (1H, m), 6.67 (1H, d, J = 7.6 Hz), 6.34 (1H, t, J = 5.7 Hz), 6.23-6.19 (1H, m), 4.94-4.90 (1H, m), 4.50-4.36 (2H, m), 4.29-4.22 (1H, m), 3.97 (1H, t, J = 10.8 Hz), 3.56-3.50 (1H, m), 3.42-3.36 (1H, m), 3.26-3.19 (2H, m), 2.43-2.38 (1H, m), 2.23-2.15 (2H, m), 2.00-1.81 (3H, m), 1.67-1.59 (1H, m), 1.49-1.41 (1H, m). |
| 11 | 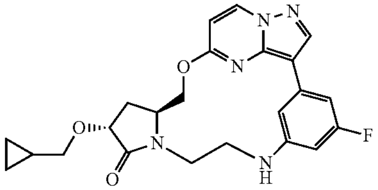 [SMILES: O=C1[C@H](OCC2CC2)C[C@H]2COc3ccn4ncc(c4n3)-c3cc(F)cc(c3)NCCN12] (12R,14S)-12-(cyclopropylmethoxy)-4-fluoro-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P5 Aniline A1 26% yield as a yellow solid | LCMS (MA) RT = 2.50 min, m/z = 438 $(M + H)^+$. LCMS (MC) RT = 2.50 min, m/z = 438 $(M + H)^+$. $^1$H NMR (400 MHz, DMSO): 8.99 (1H, d, J = 7.4 Hz), 8.55-8.54 (1H, m), 7.68-7.66 (1H, m), 6.77-6.73 (1H, m), 6.67 (1H, d, J = 7.4 Hz), 6.36-6.31 (1H, m), 6.24-6.19 (1H, m), 4.94 (1H, d, J = 10.8 Hz), 4.47-4.41 (2H, m), 4.06-3.92 (1H, m), 3.67-3.52 (2H, m), 3.45-3.35 (2H, m), 3.27-3.18 (2H, m), 2.45-2.35 (1H, m), 2.00-1.99 (1H, m), 1.08-0.99 (1H, m), 0.50-0.46 (2H, m), 0.22-0.18 (2H, m). |
| 12 | 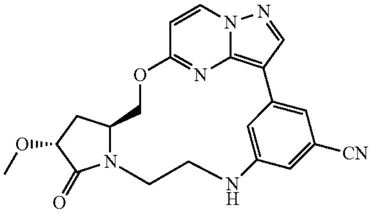 [SMILES: CO[C@@H]1C[C@H]2COc3ccn4ncc(c4n3)-c3cc(C#N)cc(c3)NCCN2C1=O] (12R,14S)-12-methoxy-11-oxo-16-oxa-7,10,20,21,24-pentaazapentacyclo[15.5.2.1$^{2}$,6.0$^{10}$,$^{1}$4.0$^{20}$,23]pentacosa-1(23),2,4,6(25),17(24),18,21-heptaene-4-carbonitrile | Scaffold 3-bromo-5-chloro-pyrazolo[1,5-a]pyrimidine Pyrrolidine P1 Aniline A6 22% yield as a beige solid | LCMS (MA) RT = 2.16 min, m/z = 405.1 $(M + H)^+$. LCMS (MC) RT = 2.15 min, m/z = 405.2 $(M + H)^+$. $^1$H NMR (400 MHz, DMSO) 9.03-9.00 (1H, m), 8.63-8.62 (1H, m), 8.09 (1H, s), 7.35 (1H, s), 6.78 (1H, dd, J = 1.4, 2.2 Hz), 6.69 (1H, d, J = 7.4 Hz), 6.56 (1H, t, J = 5.7 Hz), 4.94 (1H, d, J = 10.6 Hz), 4.48 (1H, d, J = 7.8 Hz), 4.37-4.31 (1H, m), 3.96 (1H, t, J = 10.8 Hz), 3.63-3.52 (1H, m), 3.45 (3H, s), 3.33-3.32 (3H, m), 2.48-2.40 (1H, m), 2.00-1.91 (1H, m). |
| 13 | 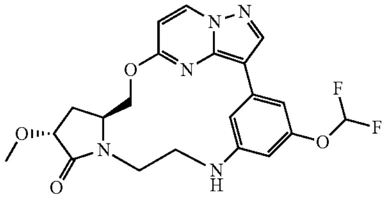 [SMILES: CO[C@@H]1C[C@H]2COc3ccn4ncc(c4n3)-c3cc(cc(OC(F)F)c3)NCCN2C1=O] (12R,14S)-4-(difluoromethoxy)-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A8 31% yield as a salmon solid | LCMS (MA) RT = 2.32 min, m/z = 446.1 $(M + H)^+$. LCMS (MC) RT = 2.31 min, m/z = 446.1 $(M + H)^+$. 1H NMR (400 MHz, DMSO) 9.01-8.97 (1H, m), 8.54-8.52 (1H, m), 7.70 (1H, s), 6.74 (1H, s), 6.68-6.65 (1H, m), 6.38-6.32 (1H, m), 6.23 (1H, s), 4.93 (1H, d, J = 11.0 Hz), 4.48-4.45 (1H, m), 4.34 (1H, t, J = 8.7 Hz), 3.95 (1H, t, J = 10.8 Hz), 3.58-3.49 (1H, m), 3.43 (3H, s), 3.42-3.35 (1H, m), 3.27-3.21 (2H, m), 2.46-2.40 (1H, m), 2.01-1.93 (1H, m). |

-continued

| Ex no | Structure/Name | From intermediates | Analytical data |
|---|---|---|---|
| 14 | 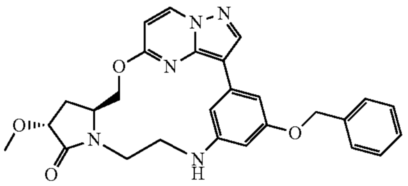 [SMILES: CO[C@@H]1C[C@H]2COc3ccn4ncc(c4n3)-c3cc(cc(OCc4ccccc4)c3)NCCN2C1=O] (12R, 14S)-4-(benzyloxy)-12-methoxy-16-oxa-7,10,20,21,24-pentaazapentacyclo[15.5.2.1$^{2}$,6.0$^{10}$,14.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A9 69% yield as a white crystals | LCMS (MA) RT = 2.56 min, m/z = 486.2 (M + H)$^{+}$. LCMS (MC) RT = 2.55 min, m/z = 486.2 (M + H)$^{+}$. $^{1}$H NMR (400 MHz, DMSO): 8.97 (1H, d, J = 7.6 Hz), 8.51 (1H, s), 7.49-7.46 (3H, m), 7.43-7.38 (2H, m), 7.35-7.31 (1H, m), 6.65-6.63 (2H, m), 6.12-6.10 (1H, m), 6.05 (1H, t, J = 5.6 Hz), 5.09-5.07 (2H, s), 4.92 (1H, d, J = 10.6 Hz), 4.49-4.44 (1H, m), 4.33 (1H, t, J = 8.9 Hz), 3.97-3.90 (1H, m), 3.57-3.49 (1H, m), 3.44 (3H, s), 3.44-3.37 (1H, m), 3.27-3.17 (2H, m), 2.46-2.4 (1H, m), 2.01-1.93 (1H, m). |
| 15 | 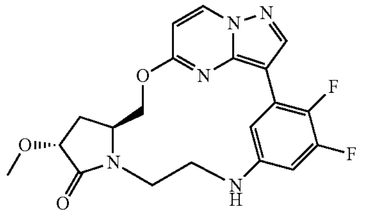 [SMILES: CO[C@@H]1C[C@H]2COc3ccn4ncc(c4n3)-c3cc(cc(F)c3F)NCCN2C1=O] (12R,14S)-3,4-difluoro-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A14 17% yield as a white solid | LCMS (MA) RT = 2.32 min, m/z = 416.2 (M + H)$^{+}$. LCMS (MC) RT = 2.31 min, m/z = 416.2 (M + H)$^{+}$. $^{1}$H NMR (400 MHz, DMSO) 9.06 (1H, d, J = 7.6 Hz), 8.41 (1H, d, J = 3.6 Hz), 7.57-7.55 (1H, m), 6.74 (1H, d, J = 7.6 Hz), 6.45-6.39 (1H, m), 6.22 (1H, t, J = 6.1 Hz), 4.95 (1H, d, J = 11.0 Hz), 4.48-4.39 (1H, m), 4.37-4.30 (1H, m), 4.00-3.90 (1H, m), 3.57-3.46 (1H, m), 3.44 (3H, s), 3.35-3.28 (1H, m), 3.24-3.18 (2H, m), 2.47-2.37 (1H, m), 1.98-1.88 (1H, m). |
| 16 | 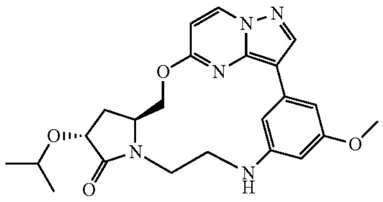 [SMILES: COc1cc2cc(c1)-c1cnn3ccc(nc13)OC[C@@H]1C[C@@H](OC(C)C)C(=O)N1CCN2] (12R,14S)-4-methoxy-12-(propan-2-yloxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P4 Aniline A3 20% yield as a beige solid | LCMS (MA) RT = 2.33 min, m/z = 438.2 (M + H)$^{+}$. LCMS (MC) RT = 2.33 min, m/z = 438.3 (M + H)$^{+}$. $^{1}$H NMR (400 MHz, DMSO) 8.96 (1H, d, J = 7.6 Hz), 8.51 (1H, s), 7.47 (1H, s), 6.63 (1H, d, J = 7.5 Hz), 6.56-6.54 (1H, m), 6.06-6.02 (2H, m), 4.93-4.88 (1H, m), 4.53-4.42 (2H, m), 4.03-3.94 (2H, m), 3.73 (3H, s), 3.64-3.48 (1H, m), 3.43-3.36 (1H, m), 3.23-3.16 (2H, m), 2.43-2.38 (1H, m), 1.97-1.88 (1H, m), 1.14 (6H, dd, J = 6.1, 8.4 Hz). |
| 17 | 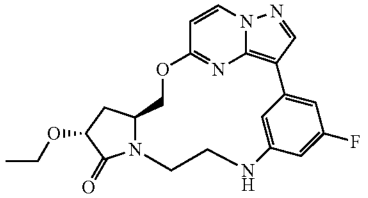 [SMILES: CCO[C@@H]1C[C@H]2COc3ccn4ncc(c4n3)-c3cc(F)cc(c3)NCCN2C1=O] (12R,14S)-12-ethoxy-4-fluoro-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P2 Aniline A1 10% yield as a beige solid | LCMS (MA) RT = 2.35 min, m/z = 412.2 (M + H)$^{+}$. LCMS (MC) RT = 2.34 min, m/z = 412.2 (M + H)$^{+}$. $^{1}$H NMR (400 MHz, DMSO) 9.00 (1H, d, J = 7.6 Hz), 8.55 (1H, s), 7.68-7.67 (1H, m), 6.77-6.74 (1H, m), 6.67 (1H, d, J = 7.4 Hz), 6.34 (1H, t, J = 5.3 Hz), 6.24-6.19 (1H, m), 4.93 (1H, dd, J = 1.6, 8.8 Hz), 4.49-4.39 (2H, m), 3.99-3.83 (2H, m), 3.60-3.51 (2H, m), 3.42-3.34 (1H, m), 3.26-3.16 (2H, m), 2.48-2.38 (1H, m), 2.00-1.92 (1H, m), 1.15 (3H, t, J = 7.0 Hz). |

-continued

| Ex no | Structure/Name | From intermediates | Analytical data |
| --- | --- | --- | --- |
| 18 | 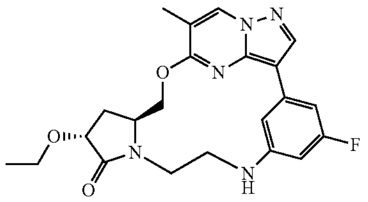 [SMILES: CCO[C@@H]1C[C@H]2COc3nc4c(cnn4cc3C)-c3cc(F)cc(c3)NCCN2C1=O] (12R,14S)-12-ethoxy-4-fluoro-18-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold S1 Pyrrolidine P2 Aniline A1 45% yield as a white solid | LCMS (MA) RT = 2.50 min, m/z = 426.2 (M + H)$^{+}$. LCMS (MC) RT= 2.49 min, m/z = 426.2 (M + H)$^{+}$. $^{1}$H NMR (400 MHz, $CDCl_3$) 8.38 (1H, d, J = 1.1 Hz), 8.22 (1H, s), 7.73-7.70 (1H, m), 6.72-6.68 (1H, m), 6.24-6.19 (1H, m), 5.14 (1H, d, J = 11.2 Hz), 4.55-4.50 (1H, m), 4.33 (1H, dd, J = 8.2, 9.5 Hz), 4.07-3.99 (1H, m), 3.92-3.56 (6H, m), 3.31-3.24 (1H, m), 2.66 (1H, dd, J = 8.0, 12.9 Hz), 2.26 (3H, s), 2.20-2.10 (1H, m), 1.33-1.26 (3H, m). |
| 19 | 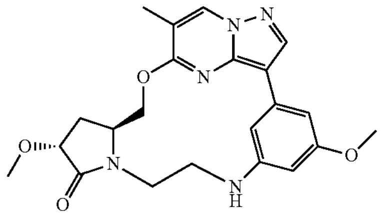 (12R,14S)-4,12-dimethoxy-18-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S1 Pyrrolidine P1 Aniline A3 3% yield as a white solid | LCMS (MA) RT = 2.23 min, m/z = 424 (M + H)$^{+}$. LCMS (MC) RT = 2.22 min, m/z = 424 (M + H)$^{+}$. $^{1}$H NMR (400 MHz, DMSO) 8.88 (1H, d, J = 1.1 Hz), 8.41 (1H, s), 7.66-7.54 (1H, m), 7.46-7.45 (1H, m), 6.53 (1H, dd, J = 1.2, 2.2 Hz), 6.04-6.01 (2H, m), 4.94 (1H, s), 4.35 (1H, dd, J = 8.2, 9.3 Hz), 3.99 (1H, t, J = 10.8 Hz), 3.72 (3H, s), 3.56-3.50 (1H, m), 3.45-3.44 (3H, m), 3.24-3.19 (2H, m), 2.18 (3H, d, J = 1.3 Hz), 2.00-1.92 (1H, m), 1.18 (2H, s). |
| 20 | 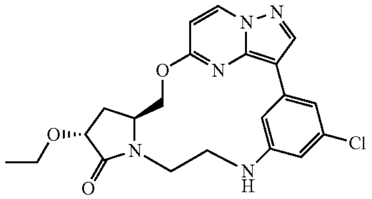 [SMILES: CCO[C@@H]1C[C@H]2COc3ccn4ncc(c4n3)-c3cc(Cl)cc(c3)NCCN2C1=O] (12R,14S)-4-chloro-12-ethoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P2 Aniline A2 48% yield as a pale yellow solid | LCMS (MA) RT = 2.50 min, m/z = 428 (M + H)$^{+}$. LCMS (MC) RT = 2.49 min, m/z = 428 (M + H)$^{+}$. $^{1}$H NMR (400 MHz, DMSO) 9.00 (1H, d, J = 7.6 Hz), 8.57 (1H, s), 7.78 (1H, s), 6.98-6.96 (1H, m), 6.67 (1H, d, J = 7.4 Hz), 6.49-6.47 (1H, m), 6.38-6.33 (1H, m), 4.94-4.90 (1H, m), 4.47-4.39 (2H, m), 4.05-3.82 (2H, m), 3.61-3.50 (2H, m), 3.41-3.36 (1H, m), 3.25-3.20 (2H, m), 2.46-2.41 (1H, m), 2.00-1.92 (1H, m), 1.15 (3H, t, J = 7.2 Hz). |
| 21 | 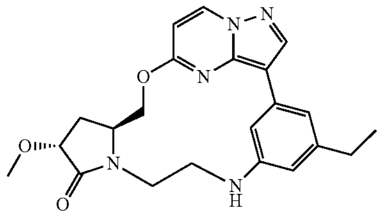 [SMILES: CCc1cc2cc(c1)-c1cnn3ccc(nc13)OC[C@@H]1C[C@@H](OC)C(=O)N1CCN2] (12R,14S)-4-ethyl-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A12 31% yield as a light yellow solid | LCMS (MA) RT = 2.37 min, m/z = 408.2 (M + H)$^{+}$. LCMS (MC) RT = 2.37 min, m/z = 408.2 (M + H)$^{+}$. $^{1}$H NMR (400 MHz, DMSO) 8.98-8.95 (1H, m), 8.47 (1H, s), 7.66-7.63 (1H, m), 6.78 (1H, s), 6.64-6.62 (1H, m), 6.31 (1H, s), 5.96 (1H, t, J = 5.9 Hz), 4.94-4.90 (1H, m), 4.47-4.44 (1H, m), 4.36-4.30 (1H, m), 3.96-3.91 (1H, m), 3.55-3.47 (1H, m), 3.45 ( 3H, s), 3.44-3.36 (1H, m), 3.24-3.15 (2H, m), 2.57-2.37 (3H, m), 2.01-1.93 (1H, m), 1.22-1.17 (3H, m). |

-continued

| Ex no | Structure/Name | From intermediates | Analytical data |
|---|---|---|---|
| 22 | 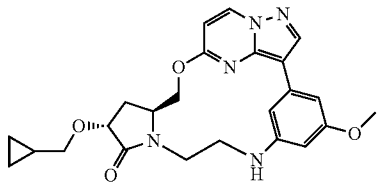 [SMILES: COc1cc2cc(c1)-c1cnn3ccc(nc13)OC[C@@H]1C[C@@H](OCC3CC3)C(=O)N1CCN2]<br>(12R,14S)-12-(cyclopropylmethoxy)-4-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine<br>Pyrrolidine P5<br>Aniline A3<br>46% yield<br>as a yellow solid | LCMS (MA) RT = 2.37 min, m/z = 450 (M + H)$^{+}$.<br>LCMS (MC) RT = 2.37 min, m/z = 450 (M + H)$^{+}$.<br>$^{1}$H NMR (400 MHz, DMSO) 8.98-8.95 (1H, m), 8.51 (1H, s), 7.47-7.47 (1H, m), 6.65-6.62 (1H, m), 6.55 (1H, dd, J = 1.2, 2.2 Hz), 6.06-6.02 (2H, m), 4.92 (1H, d, J = 10.8 Hz), 4.46-4.40 (2H, m), 3.94 (1H, t, J = 10.6 Hz), 3.73 (3H, s), 3.64 (1H, dd, J = 6.9, 10.2 Hz), 3.33-3.32 (3H, m), 3.26-3.17 (2H, m), 2.45-2.30 (1H, m), 2.03-1.94 (1H, m), 1.07-0.99 (1H, m), 0.50-0.46 (2H, m), 0.22-0.18 (2H, m). |
| 23 | 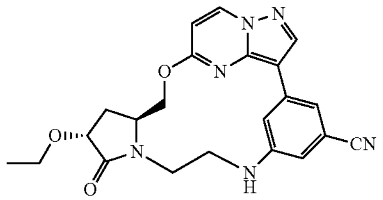 [SMILES: CCO[C@@H]1C[C@H]2COc3ccn4ncc(c4n3)-c3cc(C#N)cc(c3)NCCN2C1=O]<br>(12R,14S)-12-ethoxy-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carbonitrile | Scaffold 3-bromo-5-chloro-pyrazolo[1,5-a]pyrimidine<br>Pyrrolidine P2<br>Aniline A6<br>21% yield<br>as a white solid | LCMS (MA) RT = 2.28 min, m/z = 419.2 (M + H)$^{+}$.<br>LCMS (MC) RT = 2.28 min, m/z = 419.2 (M + H)$^{+}$.<br>$^{1}$H NMR (400 MHz, DMSO) 9.01 (1H, d, J = 7.4 Hz), 8.63 (1H, s), 8.09 (1H, s), 7.35 (1H, s), 6.78 (1H, dd, J = 1.3, 2.3 Hz), 6.69 (1H, d, J = 7.4 Hz), 6.58-6.54 (1H, m), 4.93 (1H, d, J = 10.6 Hz), 4.49-4.39 (2H, m), 4.00-3.83 (2H, m), 3.61-3.52 (2H, m), 3.30-3.19 (2H, m), 2.48-2.38 (1H, m), 2.00-1.91 (1H, m), 1.25-1.23 (1H, m), 1.17-1.12 (3H, m). |
| 24 | 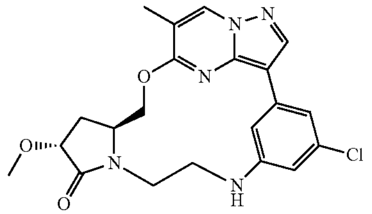 [SMILES: CO[C@@H]1C[C@H]2COc3nc4c(cnn4cc3C)-c3cc(Cl)cc(c3)NCCN2C1=O]<br>(12R,14S)-4-chloro-12-methoxy-18-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S1<br>Pyrrolidine P1<br>Aniline A2<br>47% yield<br>as a white solid | LCMS (MA) RT = 2.50 min, m/z = 428 (M + H)$^{+}$.<br>LCMS (MC) RT = 2.51 min, m/z = 428 (M + H)$^{+}$.<br>$^{1}$H NMR (400 MHz, DMSO) 8.90 (1H, d, J = 1.1 Hz), 8.47 (1H, s), 7.77-7.75 (1H, m), 6.95 (1H, t, J = 1.5 Hz), 6.47 (1H, t, J = 2.1 Hz), 6.34 (1H, t, J = 5.9 Hz), 4.95 (1H, d, J = 10.4 Hz), 4.47-4.45 (1H, m), 4.36 (1H, dd, J = 8.4, 9.5 Hz), 4.12-3.96 (1H, m), 3.65-3.50 (1H, m), 3.45 (3H, s), 3.40-3.30 (1H, m), 3.25-3.10 (2H, m), 2.45-2.40 (1H, m), 2.18 (3H, d, J = 1.1 Hz), 2.00-1.91 (1H, m). |
| 25 | 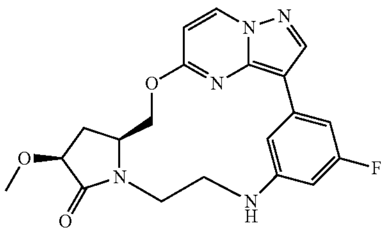 [SMILES: CO[C@H]1C[C@H]2COc3ccn4ncc(c4n3)-c3cc(F)cc(c3)NCCN2C1=O]<br>(12S,14S)-4-fluoro-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine<br>Pyrrolidine 215918-39-1<br>Aniline A1<br>21% yield<br>as a yellow solid | LCMS (MA) RT = 2.31 min, m/z = 398 (M + H)$^{+}$.<br>LCMS (MC) RT = 2.30 min, m/z = 398 (M + H)$^{+}$.<br>$^{1}$H NMR (400 MHz, DMSO) 9.00 (1H, d, J = 7.6 Hz), 8.55 (1H, s), 7.69-7.68 (1H, m), 6.78-6.67 (2H, m), 6.33 (1H, t, J = 5.9 Hz), 6.24-6.19 (1H, m), 5.10 (1H, d, J = 10.8 Hz), 4.47 (1H, t, J = 8.0 Hz), 3.88 (1H, t, J = 10.4 Hz), 3.79 (1H, d, J = 6.1 Hz), 3.64-3.55 (1H, m), 3.32 (3H, s), 3.30-3.22 (1H, m), 3.19-3.16 (2H, m), 2.41-2.33 (1H, m), 1.96 (1H, d, J = 14.4 Hz). |

-continued

| Ex no | Structure/Name | From intermediates | Analytical data |
|---|---|---|---|
| 26 | 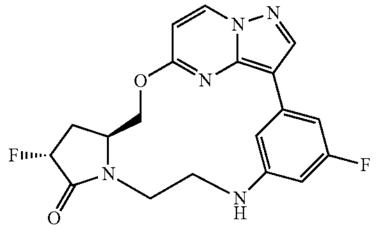 [SMILES: O=C1[C@H](F)C[C@H]2COc3ccn4ncc(c4n3)-c3cc(F)cc(c3)NCCN12] (12R,14S)-4,12-difluoro-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine 1138324-48-7 Aniline A1 40% yield as a beige solid | LCMS (MA) RT = 2.27 min m/z = 386.3 (M + H)$^+$ LCMS (MC) RT = 2.26 min, m/z = 386.2 (M + H)$^+$. $^1$H NMR (400 MHz, DMSO) 9.01-8.99 (1H, m), 8.56-8.55 (1H, m), 7.68-7.66 (1H, m), 6.78-6.74 (1H, m), 6.68 (1H, d, J = 7.6 Hz), 6.35 (1H, t, J = 5.9 Hz), 6.25-6.20 (1H, m), 4.98 (1H, d, J = 10.8 Hz), 4.60 (1H, s), 4.05-3.94 (1H, m), 3.61-3.39 (2H, m), 3.30-3.24 (2H, m), 2.68-2.58 (1H, m), 2.34-2.22 (1H, m), 1.42-1.41 (1H, m). |
| 27 | 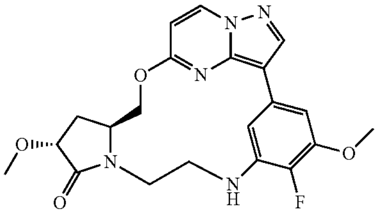 (12R,14S)-5-fluoro-4,12-dimethoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A13 32% yield as a yellow solid | LCMS (MA) RT = 2.16 min, m/z = 428.1 (M + H)$^+$. LCMS (MC) RT = 2.17 min, m/z = 428.2 (M + H)$^+$. $^1$H NMR (400 MHz, DMSO) 8.98-8.95 (1H, m), 8.55 (1H, s), 7.63 (1H, d, J = 5.1 Hz), 6.76 (1H, dd, J = 1.6, 6.9 Hz), 6.65-6.63 (1H, m), 5.99-5.95 (1H, m), 4.92 (1H, d, J = 10.6 Hz), 4.50-4.47 (1H, m), 4.36-4.30 (1H, m), 3.96-3.90 (1H, m), 3.86 (3H, s), 3.62-3.52 (1H, m), 3.45 (3H, s), 3.37-3.25 (2H, m), 3.21-3.14 (1H, m), 2.47-2.41 (1H, m), 2.01-1.93 (1H, m). |
| 28 | 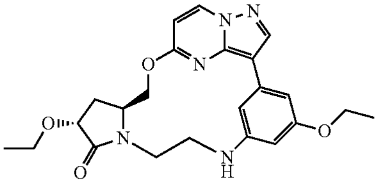 [SMILES: CCOc1cc2cc(c1)-c1cnn3ccc(nc13)OC[C@@H]1C[C@@H](OCC)C(=O)N1CCN2] (12R,14S)-4,12-diethoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P2 Aniline A4 39% yield as a yellow solid | LCMS (MA) RT = 2.32 min, m/z = 438 (M + H)$^+$. LCMS (MC) RT = 2.33 min, m/z = 438 (M + H)$^+$. $^1$H NMR (400 MHz, DMSO) 8.97-8.95 (1H, m), 8.50 (1H, s), 7.45 (1H, s), 6.65-6.62 (1H, m), 6.54 (1H, s), 6.04-6.01 (2H, m), 4.92 (1H, d, J = 11.0 Hz), 4.46-4.38 (2H, m), 4.12-3.84 (4H, m), 3.60-3.50 (2H, m), 3.19-3.16 (4H, m), 2.00-1.95 (1H, m), 1.33 (3H, t, J = 7.0 Hz), 1.15 (3H, t, J = 7.0 Hz). |
| 29 | 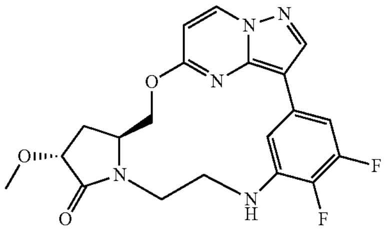 [SMILES: CO[C@@H]1C[C@H]2COc3ccn4ncc(c4n3)-c3cc(F)c(F)c(c3)NCCN2C1=O] (12R,14S)-4,5-difluoro-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P1 Aniline A10 39% yield as yellow solid | LCMS (MA) RT = 2.40 min, m/z = 416 (M + H)$^+$. LCMS (MC) RT = 2.40 min, m/z = 416 (M + H)$^+$. $^1$H NMR (400 MHz, $CDCl_3$) 8.51-8.48 (1H, m), 8.21-8.20 (1H, m), 7.78-7.64 (1H, m), 6.74-6.67 (1H, m), 6.43-6.40 (1H, m), 5.09-5.03 (1H, m), 4.56-4.43 (2H, m), 4.21 (1H, dd, J = 8.2, 9.3 Hz), 3.95-3.83 (1H, m), 3.62-3.61 (4H, m), 2.96-2.95 (2H, m), 2.88-2.88 (2H, m), 2.64 (1H, dd, J = 8.0, 13.1 Hz). |

-continued

| Ex no | Structure/Name | From intermediates | Analytical data |
|---|---|---|---|
| 30 | 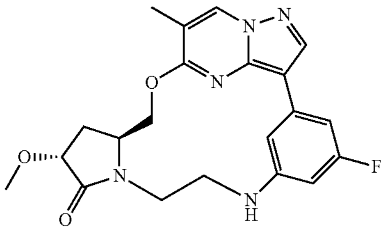 [SMILES: CO[C@@H]1C[C@H]2COc3nc4c(cnn4cc3C)-c3cc(F)cc(c3)NCCN2C1=O] (12R,14S)-4-fluoro-12-methoxy-18-methyl-16-oxa-7,10,20,21,24-pentaazapentacyclo[15.5.2.1²,6.0¹⁰,¹4.0²⁰,²³]pentacosa-1(23),2(25),3,5,17(24),18,21-heptaen-11-one | Scaffold S1 Pyrrolidine P1 Aniline A1 89% yield as white solid | LCMS (MD) RT = 3.134 min, m/z = 412.1 $(M + H)^+$. LCMS (ME) RT = 3.502 min, m/z = 412.1 $(M + H)^+$. $^1$H NMR (400 MHz, DMSO) d 8.90 (d, J = 1.2 Hz, 1H), 8.44 (s, 1H), 7.66 (s, 1H), 6.73 (d, J = 9.4 Hz, 1H), 6.32 (t, J = 5.8 Hz, 1H), 6.20 (dt, J = 11.8, 2.1 Hz, 1H), 4.96 (d, J = 10.7 Hz, 1H), 4.47 (s, 1H), 4.36 (t, J = 8.9 Hz, 1H), 4.00 (t, J = 10.7 Hz, 1H), 3.55 (dd, J = 12.4, 8.4 Hz, 1H), 3.45 (s, 3H), 3.39 (d, J = 10.3 Hz, 1H), 3.28-3.15 (m, 2H), 2.48-2.40 (m, 1H), 2.18 (d, J = 0.9 Hz, 3H), 2.02-1.89 (m, 1H). |
| 31 | 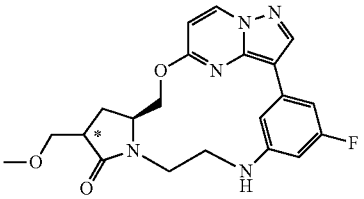 [SMILES: COCC1C[C@H]2COc3ccn4ncc(c4n3)-c3cc(F)cc(c3)NCCN2C1=O] E1-(12R,14S)-4-fluoro-12-(methoxymethyl)-16-oxa-7,10,20,21,24-pentaazapentacyclo[15.5.2.1²,6.0¹⁰,¹4.0²⁰,²³]pentacosa-1(23),2(25),3,5,17(24),18,21-heptaen-11-one | Scaffold 3-bromo-5-chloro-pyrazolo[1,5-a]pyrimidine Pyrrolidine P10 Aniline A1 71% yield as a white solid | LCMS (MD) RT = 3.115 min, m/z = 412.1 $(M + H)^+$. LCMS (ME) RT = 3.500 min, m/z = 412.1 $(M + H)^+$. 1H NMR (400 MHz, DMSO) d 8.91 (d, J = 1.2 Hz, 1H), 8.54 (s, 1H), 8.45 (s, 1H), 7.78 (s, 1H), 7.72-7.69 (m, 1H), 7.34 (s, 1H), 6.96 (t, J = 2.0 Hz, 1H), 6.53 (dd, J = 2.4, 1.8 Hz, 1H), 6.35 (t, J = 5.8 Hz, 1H), 4.98 (d, J = 11.1 Hz, 1H), 4.51 (brs, 1H), 4.37 (t, J = 8.9 Hz, 1H), 4.01 (t, J = 10.8 Hz, 1H), 3.59 (dd, J = 23.1, 9.4 Hz, 1H), 3.46 (s, 3H), 3.41 (d, J = 13.3 Hz, 1H), 3.27 (dd, J = 11.6, 4.9 Hz, 2H), 2.47 (d, J = 8.1 Hz, 1H), 2.19 (s, 3H), 1.97 (dt, J = 11.7, 8.7 Hz, 1H). |
| 32 | 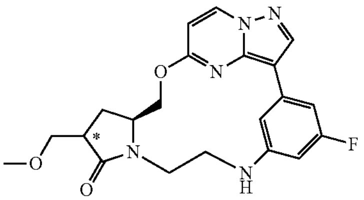 [SMILES: COCC1C[C@H]2COc3ccn4ncc(c4n3)-c3cc(F)cc(c3)NCCN2C1=O] E2-(12S,14S)-4-fluoro-12-(methoxymethyl)-16-oxa-7,10,20,21,24-pentaazapentacyclo[15.5.2.1²,6.0¹⁰,¹4.0²⁰,²³]pentacosa-1(23),2(25),3,5,17(24),18,21-heptaen-11-one | Scaffold 3-bromo-5-chloro-pyrazolo[1,5-a]pyrimidine Pyrrolidine P10 Aniline A1 68% yield as a white solid | LCMS (MD) RT = 3.019 min, m/z = 412.1 $(M + H)^+$. LCMS (ME) RT = 3.416 min, m/z = 412.1 $(M + H)^+$. 1H NMR (400 MHz, DMSO) d 8.99 (d, J = 7.5 Hz, 1H), 8.54 (s, 1H), 7.71 (s, 1H), 6.75 (d, J = 10.2 Hz, 1H), 6.67 (d, J = 7.5 Hz, 1H), 6.32 (t, J = 5.9 Hz, 1H), 6.21 (dt, J = 11.8, 2.1 Hz, 1H), 4.94 (d, J = 10.9 Hz, 1H), 4.41 (s, 1H), 3.99 (t, J = 10.6 Hz, 1H), 3.60 (dd, J = 11.4, 8.9 Hz, 1H), 3.55 (dd, J = 9.5, 3.8 Hz, 1H), 3.49 (dd, J = 9.5, 5.8 Hz, 1H), 3.40 (dt, 1H), 3.25 (s, 3H), 3.18 (dd, J = 14.2, 9.0 Hz, 2H), 2.91 (tdd, J = 9.7, 5.5, 4.0 Hz, 1H), 2.10 (t, J = 10.6 Hz, 2H). |
| 33 | 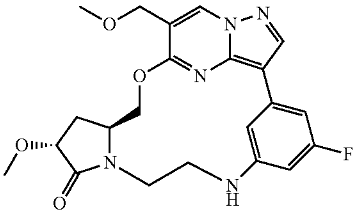 [SMILES: COCc1cn2ncc3c2nc1OC[C@@H]1C[C@@H](OC)C(=O)N1CCNc1cc(F)cc-3c1] (12R,14S)-4-fluoro-12-methoxy-18-(methoxymethyl)-16-oxa-7,10,20,21,24-pentaazapentacyclo[15.5.2.1²,6.0¹⁰,¹4.0²⁰,²³]pentacosa-1(23),2(25),3,5,17(24),18,21-heptaen-11-one | Scaffold S6 Pyrrolidine P1 Aniline A1 66% yield as a white solid | LCMS (MD) RT = 3.005 min, m/z = 442.1 $(M + H)^+$. LCMS (ME) RT = 3.401 min, m/z = 442.1 $(M + H)^+$. 1H NMR (400 MHz, DMSO) d 8.95 (s, 1H), 8.53 (s, 1H), 7.65 (s, 1H), 6.75 (d, J = 9.3 Hz, 1H), 6.33 (t, J = 5.8 Hz, 1H), 6.21 (dt, J = 11.8, 2.1 Hz, 1H), 4.97 (d, J = 10.7 Hz, 1H), 4.49 (t, J = 7.5 Hz, 1H), 4.45 (d, J = 12.4 Hz, 1H), 4.41 (d, J = 13.0 Hz, 1H), 4.36 (dd, J = 9.4, 8.4 Hz, 1H), 4.00 (t, J = 10.7 Hz, 1H), 3.62-3.51 (m, 1H), 3.45 (s, 3H), 3.40 (d, J = 3.9 Hz, 1H), 3.37 (s, 3H), 3.27-3.13 (m, 2H), 2.45 (dd, J = 12.7, 8.1 Hz, 1H), 1.95 (dt, J = 11.6, 8.8 Hz, 1H). |

-continued

| Ex no | Structure/Name | From intermediates | Analytical data |
|---|---|---|---|
| 34 | 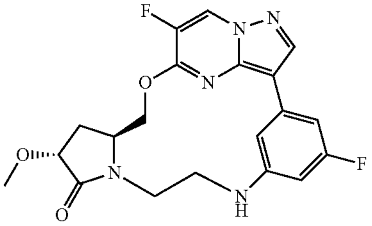 [SMILES: CO[C@@H]1C[C@H]2COc3nc4c(cnn4cc3F)-c3cc(F)cc(c3)NCCN2C1=O]<br>(12R,14S)-4,18-difluoro-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S7<br>Pyrrolidine P1<br>Aniline A1<br>13% yield<br>as a white solid | LCMS (MD) RT = 3.016 min, m/z = 416.1(M + H)$^{+}$. LCMS (MF) RT = 4.828 min, m/z = 416.2 (M + H)$^{+}$. 1H NMR (400 MHz, DMSO) d 9.51 (d, J = 5.9 Hz, 1H), 8.55 (s, 1H), 7.61 (s, 1H), 6.76 (d, J = 10.1 Hz, 1H), 6.36 (t, J = 5.8 Hz, 1H), 6.23 (dt, J = 11.8, 2.1 Hz, 1H), 4.98 (d, J = 11.1 Hz, 1H), 4.50 (t, J = 8.8 Hz, 1H), 4.35 (t, J = 8.8 Hz, 1H), 4.13 (t, J = 10.7 Hz, 1H), 3.56 (dt, J = 11.8, 7.3 Hz, 1H), 3.45 (s, 3H), 3.39 (d, J = 10.6 Hz, 1H), 3.28-3.15 (m, 2H), 2.47 (dd, J = 12.0, 8.0 Hz, 1H), 2.03-1.90 (m, 1H). |
| 35 | 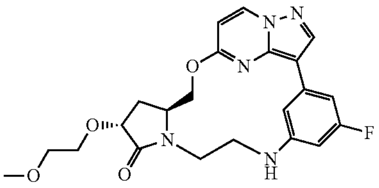 [SMILES: COCCO[C@@H]1C[C@H]2COc3ccn4ncc(c4n3)-c3cc(F)cc(c3)NCCN2C1=O]<br>(12R,14S)-4-fluoro-12-(2-methoxyethoxy)-16-oxa-7,10,20,21,24-pentaazapentacyclo[15.5.2.1$^{2}$,6.01$^{0}$,$^{1}$4.0$^{20}$,23]pentacosa-1(23),2,4,6(25),17(24),18,21-heptaen-11-one | Scaffold 3-bromo-5-chloro-pyrazolo[1,5-a]pyrimidine<br>Pyrrolidine P7<br>Aniline A1<br>70% yield<br>as a beige solid | LCMS (MD) RT = 2.026 min, m/z = 442.2(M + H)$^{+}$. LCMS (ME) RT = 3.406 min, m/z = 442.1 (M + H)$^{+}$. 1H NMR (400 MHz, DMSO) d 8.99 (d, J = 7.5 Hz, 1H), 8.54 (s, 1H), 7.67 (s, 1H), 6.75 (d, J = 9.3 Hz, 1H), 6.67 (d, J = 7.5 Hz, 1H), 6.34 (t, J = 5.8 Hz, 1H), 6.21 (dt, J = 11.8, 2.1 Hz, 1H), 4.94 (d, J = 10.7 Hz, 1H), 4.45 (d, J = 6.0 Hz, 1H), 3.97 (dd, J = 10.7, 9.4 Hz, 1H), 3.95 (t, J = 11.4 Hz, 1H), 3.69-3.62 (m, 1H), 3.60-3.50 (m, 1H), 3.48 (t, J = 4.8 Hz, 2H), 3.44-3.35 (m, 1H), 3.26 (s, 3H), 3.25-3.14 (m, 2H), 2.44 (dd, J = 12.7, 8.2 Hz, 2H), 1.98 (dt, J = 12.0, 8.8 Hz, 1H). |
| 36 | 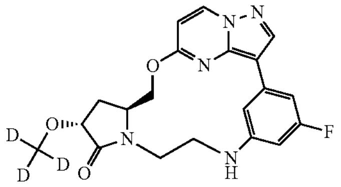 [SMILES: [2H]C([2H])([2H])O[C@@H]1C[C@H]2COc3ccn4ncc(c4n3)-c3cc(F)cc(c3)NCCN2C1=O]<br>(12R,14S)-4-fluoro-12-($^{2}$H3)methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine<br>Pyrrolidine P6<br>Aniline A1<br>49% yield<br>as a white solid | LCMS (MD) RT = 2.887 min, m/z = 401.1 (M + H)$^{+}$. LCMS (ME) RT = 3.251 min, m/z = 401.2 (M + H)$^{+}$. 1H NMR (400 MHz, DMSO) d 8.99 (d, J = 7.5 Hz, 1H), 8.54 (s, 1H), 7.67 (s, 1H), 6.81-6.70 (m, 1H), 6.67 (d, J = 7.5 Hz, 1H), 6.34 (t, J = 5.8 Hz, 1H), 6.21 (dt, J = 11.8, 2.1 Hz, 1H), 4.94 (d, J = 10.9 Hz, 1H), 4.48 (t, J = 8.0 Hz, 1H), 4.33 (t, J = 8.8 Hz, 1H), 3.95 (t, J = 10.8 Hz, 1H), 3.55 (dt, J = 11.4, 9.0 Hz, 1H), 3.38 (dd, J = 16.4, 6.9 Hz, 1H), 3.30-3.12 (m, 2H), 2.44 (dd, J = 12.7, 8.2 Hz, 1H), 1.96 (dt, J = 11.9, 8.8 Hz, 1H). |
| 37 | 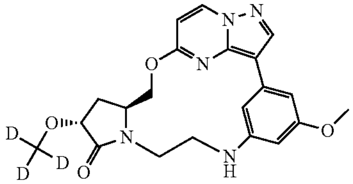 [SMILES: [2H]C([2H])([2H])O[C@@H]1C[C@H]2COc3ccn4ncc(c4n3)-c3cc(cc(OC)c3)NCCN2C1=O]<br>(12R,14S)-12-(2H3)methoxy-4-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine<br>Pyrrolidine P6<br>Aniline A3<br>12% yield<br>as a beige solid | LCMS (MD) RT = 2.668 min, m/z = 413.1 (M + H)$^{+}$. LCMS (ME) RT = 3.092 min, m/z = 413.2 (M + H)$^{+}$. 1H NMR (400 MHz, DMSO) d 8.92 (d, J = 7.5 Hz, 1H), 8.46 (s, 1H), 7.43 (s, 1H), 6.60 (d, J = 7.5 Hz, 1H), 6.50 (d, J = 0.7 Hz, 1H), 6.01 (d, J = 5.8 Hz, 1H), 5.99 (t, J = 2.1 Hz, 1H), 4.88 (d, J = 10.8 Hz, 1H), 4.41 (t, J = 9.1 Hz, 1H), 4.29 (t, J = 8.9 Hz, 1H), 3.89 (t, J = 10.7 Hz, 1H), 3.69 (s, 3H), 3.55-3.44 (m, 1H), 3.42-3.31 (m, 1H), 3.20-3.05 (m, 2H), 2.39 (dd, J = 12.7, 8.2 Hz, 1H), 1.93 (dt, J = 11.8, 8.8 Hz, 1H). |

-continued

| Ex no | Structure/Name | From intermediates | Analytical data |
|---|---|---|---|
| 38 | 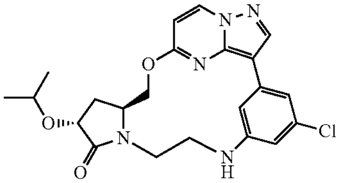 [SMILES: CC(C)O[C@@H]1C[C@H]2COc3ccn4ncc(c4n3)-c3cc(Cl)cc(c3)NCCN2C1=O] (12R,14S)-4-chloro-12-(propan-2-yloxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P4 Aniline A2 40% yield as a beige solid | LCMS (MA) RT = 2.58 min/ MH+ = 442.0 LCMS (MB) RT = 2.60 min/ MH+ = 442.1 $^{1}$H NMR (400 MHz, DMSO) 9.00 (1H, d, J = 7.6 Hz), 8.57 (1H, s), 7.78 (1H, s), 6.97 (1H, t, J = 1.4 Hz), 6.67 (1H, d, J = 7.4 Hz), 6.48 (1H, t, J = 2.0 Hz), 6.36 (1H, t, J = 6.2 Hz), 4.94-4.89 (1H, m), 4.54-4.44 (2H, m), 4.04-3.94 (2H, m), 3.63-3.50 (1H, m), 3.40-3.36 (1H, m), 3.25-3.19 (2H, m), 2.43-2.38 (1H, m), 1.96-1.88 (1H, m), 1.14 (6H, dd, J = 6.1,8.4 Hz). |
| 39 | 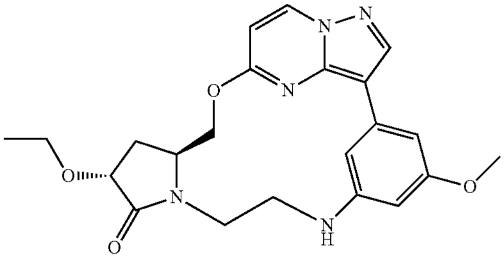 (2$^{3}$Z,2$^{4}$E,5$^{2}$S,5$^{4}$R)-5$^{4}$-ethoxy-1$^{5}$-methoxy-2$^{6}$-methyl-3-oxa-8-aza-2(3,5)-pyrazolo[1,5-a]96yrimidine-5(2,1)-pyrrolidina-1(1,3)-benzenacyclooctaphan-5$^{5}$-one | Scaffold S1 Pyrrolidine P2 Aniline A3 42% yield as a beige solid | LCMS (MA) RT = 2.43 min/ MH+ = 438.2 LCMS (MB) RT = 2.45 min/ MH+ = 438.3 $^{1}$H NMR (400 MHz, DMSO) 8.87 (1H, d, J = 1.1 Hz), 8.41 (1H, s), 7.46 (1H, s), 6.53 (1H, dd, J = 1.1, 2.1 Hz), 6.04-6.01 (2H, m), 4.94 (1H, d, J = 11.0 Hz), 4.47-4.41 (2H, m), 3.99 (1H, t, J = 10.7 Hz), 3.84 (1H, ddd, J = 5.9, 8.2, 15.2 Hz), 3.72 (3H, s), 3.60-3.52 (2H, m), 3.45-3.35 ( 1H, m), 3.24-3.15 (2H, m), 2.49-2.43 ( 1H, m), 2.18-2.17 (3H, m), 2.00-1.92 (1H, m), 1.15 (3H,t, J = 7.0 Hz) |
| 40 | 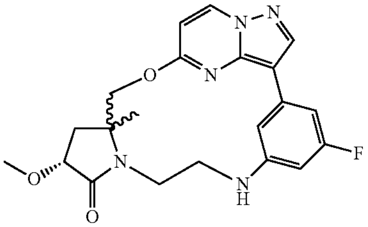 (12R,14S)-12-ethoxy-4-methoxy-18-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P12 Aniline A1 24% yield, as white solid | LCMS (MA) RT = 3.200 min, m/z = 412.1 (M + H)$^{+}$. LCMS (MD): RT = 3.07 min. m/z = 412.1 (M + H)$^{+}$. 1H NMR (400 MHz, $CDCl_3$) d 8.49 (d, J = 7.5 Hz, 1H), 8.29 (s, 1H), 8.12 (brs, 1H), 6.67 (d, J = 9.8 Hz, 1H), 6.42 (d, J = 7.5 Hz, 1H), 6.19 (dd, J = 9.1, 2.0 Hz, 1H), 5.70 (d, J = 11.9 Hz, 1H), 4.20 (d, J = 11.9 Hz, 1H), 3.85 (t, J = 7.4 Hz, 1H), 3.82-3.61 (m, 3H), 3.56 (s, 3H), 3.51-3.36 (m, 1H), 2.37 (d, J = 14.0 Hz, 1H), 2.00 (dd, J = 13.8, 7.2 Hz, 1H), 1.33 (s, 3H), 0.92-0.75 (m, 1H). |
| 41 | 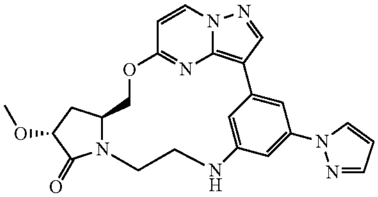 [SMILES: CO[C@@H]1C[C@H]2COc3ccn4ncc(c4n3)-c3cc(cc(-n4cccn4)c3)NCCN2C1=O] (12R,14S)-12-methoxy-4-(1H-pyrazol-1-yl)-16-oxa-7,10,20,21,24-pentaazapentacyclo[15.5.2.1$^{2}$,6.0$^{10}$,$^{1}$4.0$^{20}$,$^{23}$]pentacosa- | Scaffold 3-bromo-5-chloro-pyrazolo[1,5-a]pyrimidine Pyrrolidine P1 Aniline A15 35 mg, 88% yield as white solid | LCMS (MD) RT = 2.766 min, m/z = 446.1 (M + H)$^{+}$. LCMS (ME) RT = 3.281 min, m/z = 446.2 (M + H)$^{+}$. $^{1}$H NMR (400 MHz, DMSO) d 9.00 (d, J = 7.5 Hz, 1H), 8.63 (s, 1H), 8.45 (d, J = 2.2 Hz, 1H), 7.79 (s, 1H), 7.71 (d, J = 1.5 Hz, 1H), 7.36 (s, 1H), 6.98 (t, J = 2.0 Hz, 1H), 6.68 (d, J = 7.5 Hz, 1H), 6.53 (dd, J = 2.3, 1.9 Hz, 1H), 6.36 (t, J = 5.8 Hz, 1H), 4.96 (d, J = 10.8 Hz, 1H), 4.51 (s, 1H), 4.35 (t, J = 8.9 Hz, 1H), 3.97 (t, J = 10.8 Hz, 1H), 3.66-3.51 (m, 1H), 3.46 (s, 3H), |

-continued

| Ex no | Structure/Name | From intermediates | Analytical data |
|---|---|---|---|
| | 1(23),2(25),3,5,17(24),18,<br>21-heptaen-11-one | | 3.44-3.38 (m, 1H), 3.31-3.18 (m, 2H), 2.45 (dd, J = 12.7, 8.2 Hz, 1H), 1.98 (dt, J = 11.8, 8.8 Hz, 1H). |
| 42 | 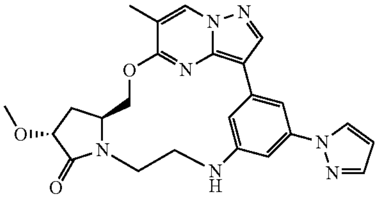 [SMILES: CO[C@@H]1C[C@H]2COc3nc4c(cnn4cc3C)-c3cc(cc(-n4cccn4)c3)NCCN2C1=O]<br>(12R,14S)-12-methoxy-18-methyl-4-(1H-pyrazol-1-yl)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S1<br>Pyrrolidine P1<br>Aniline A15<br>185 mg, 81% yield as white solid | LCMS (MD) RT = 2.981 min, m/z = 460.3 $(M + H)^+$.<br>LCMS (ME) RT = 4.675 min, m/z = 460.2 $(M + H)^+$.<br>$^1$H NMR (400 MHz, DMSO) d 8.91 (d, J = 1.2 Hz, 1H), 8.54 (s, 1H), 8.45 (s, 1H), 7.78 (s, 1H), 7.72-7.69 (m, 1H), 7.34 (s, 1H), 6.96 (t, J = 2.0 Hz, 1H), 6.53 (dd, J = 2.4, 1.8 Hz, 1H), 6.35 (t, J = 5.8 Hz, 1H), 4.98 (d, J = 11.1 Hz, 1H), 4.51 (brs, 1H), 4.37 (t, J = 8.9 Hz, 1H), 4.01 (t, J = 10.8 Hz, 1H), 3.59 (dd, J = 23.1, 9.4 Hz, 1H), 3.46 (s, 3H), 3.41 (d, J = 13.3 Hz, 1H), 3.27 (dd, J = 11.6, 4.9 Hz, 2H), 2.47 (d, J = 8.1 Hz, 1H), 2.19 (s, 3H), 1.97 (dt, J = 11.7, 8.7 Hz, 1H). |
| 43 | 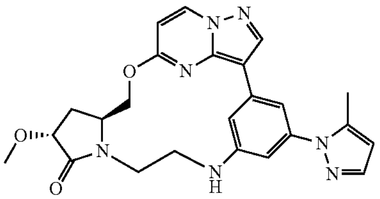 [SMILES: CO[C@@H]1C[C@H]2COc3ccn4ncc(c4n3)-c3cc(cc(-n4nccc4C)c3)NCCN2C1=O]<br>(12R,14S)-12-methoxy-4-(5-methyl-1H-pyrazol-1-yl)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine<br>Pyrrolidine P1<br>Aniline A17<br>29 mg, 9% over 3 steps | LCMS (MH) RT = 2.780 min, m/z = 460.2 $(M + H)^+$.<br>LCMS (ME) RT = 3.291 min, m/z = 460.2 $(M + H)^+$.<br>1H NMR (400 MHz, DMSO) d 9.00 (d, J = 7.5 Hz, 1H), 8.59 (s, 1H), 7.87 (s, 1H), 7.52 (d, J = 1.6 Hz, 1H), 7.02 (s, 1H), 6.68 (d, J = 7.5 Hz, 1H), 6.56 (t, J = 1.9 Hz, 1H), 6.35 (t, J = 5.8 Hz, 1H), 6.25 (s, 1H), 4.98 (d, J = 10.8 Hz, 1H), 4.52 (s, 1H), 4.35 (t, J = 8.8 Hz, 1H), 3.97 (t, J = 10.8 Hz, 1H), 3.57 (dd, J = 16.3, 5.8 Hz, 1H), 3.46 (s, 3H), 3.45-3.36 (m, 1H), 3.27 (dd, J = 14.3, 8.7 Hz, 2H), 2.46 (dd, J = 12.7, 8.2 Hz, 1H), 2.36 (s, 3H), 1.99 (dt, J = 11.8, 8.8 Hz, 1H). |
| I17 | 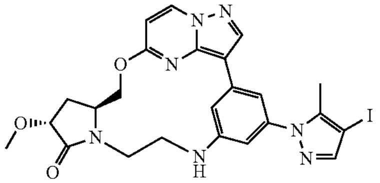 [SMILES: CO[C@@H]1C[C@H]2COc3ccn4ncc(c4n3)-c3cc(cc(-n4ncc(I)c4C)c3)NCCN2C1=O]<br>(12R,14S)-4-(4-iodo-5-methyl-1H-pyrazol-1-yl)-12-methoxy-16-oxa-7,10,20,21,24-pentaazapentacyclo[15.5.2.12,6.010,14.020,23]pentacosa-1(23),2,4,6(25),17(24),18,21-heptaen-11-one | Scaffold 3-bromo-5-chloro-pyrazolo[1,5-a]pyrimidine<br>Pyrrolidine P1<br>Aniline A17<br>180 mg, 43% over 3 steps | LCMS (MH) RT = 0.973 min, m/z = 586.2 $(M + H)^+$. |
| 85 | 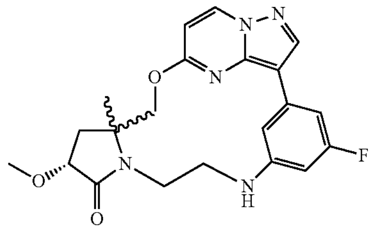<br>E1-(12R,14S)-4-fluoro-12-methoxy-14-methyl-16- | Scaffold 3-bromo-5-chloro-pyrazolo[1,5-a]pyrimidine<br>Pyrrolidine P15<br>Aniline A1<br>6 mg obtained after SFC separation as white solid | LCMS (MD) RT = 3.20 min, m/z = 412.1 $(M + H)^+$.<br>LCMS(basic) RT = 3.55 min, m/z = 412.1 $(M + H)^+$.<br>OR (c:0.1333, DMSO): +1.320<br>1H NMR (400 MHz, $CDCl_3$) δ 8.49 (d, J = 7.5 Hz, 1H), 8.29 (s, 1H), 8.12 (brs, 1H), 6.67 (d, J = 9.8 Hz, 1H), 6.42 (d, J = 7.5 Hz, 1H), 6.19 (dd, J = 9.1,2.0 Hz, 1H), 5.70 (d, J = 11.9 Hz, 1H), 4.20 (d, J = 11.9 Hz, 1H), 3.85 (t, J = 7.4 Hz, 1H), 3.82-3.61 (m, 3H), 3.56 (s, 3H), |

-continued

| Ex no | Structure/Name | From intermediates | Analytical data |
|---|---|---|---|
| | oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | | 3.51-3.36 (m, 1H), 2.37 (d, J = 14.0Hz, 1H), 2.00 (dd, J = 13.8, 7.2 Hz, 1H), 1.33 (s, 3H), 0.92 ¿ 0.75 (m, 1H). |
| 86 | 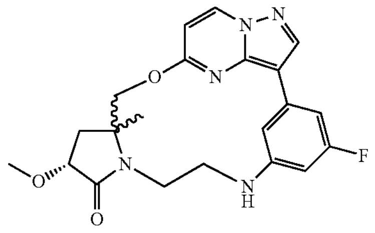 E2-(12R,14R)-4-fluoro-12-methoxy-14-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P15 Aniline A1 6 mg obtained after SFC separation as white solid | LCMS (MD) RT = 3.07 min, m/z = 412.2 $(M + H)^+$. LCMS(basic) RT = 3.45 min, m/z = 412.1 $(M + H)^+$. OR (c:0.1333, DMSO): +33.90 1H NMR (400 MHz, $CDCl_3$) d 8.50 (d, J = 7.5 Hz, 1H), 8.30 (s, 1H), 8.06 (brs, 1H), 6.68 (d, J = 9.7 Hz, 1H), 6.43 (d, J = 7.5 Hz, 1H), 6.20 (d, J = 10.9 Hz, 1H), 5.65 (d, J = 10.4 Hz, 1H), 4.13 (t, J = 8.1 Hz, 1H), 3.83 (d, J = 11.7 Hz, 1H), 3.65 (dd, J = 14.3, 6.4 Hz, 1H), 3.61 (s, 3H), 3.42 (d, J = 5.5 Hz, 1H), 2.77 (dd, J = 12.5, 8.0 Hz, 1H), 1.79 (dd, J = 12.2, 8.9 Hz, 2H), 1.40 (s, 3H), 0.90-0.74 (m, 2H). |
| 87 | 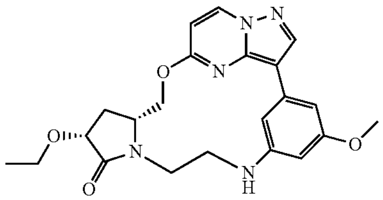 [SMILES: CCO[C@@H]1C[C@@H]2COc3ccn4ncc(c4n3)-c3cc(cc(OC)c3)NCCN2C1=O] (12R,14R)-12-ethoxy-4-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P11 Aniline A3 75% yield as light salmon solid | LCMS (MA) RT = 2.32 min, m/z = 424.2 $(M + H)^+$. LCMS(MC) RT = 2.20 min, m/z = 424.4 $(M + H)^+$. $^{1}$H NMR (400 MHz, DMSO) 8.97-8.95 (1H, m), 8.50 (1H, s), 7.48-7.44 (1H, m), 6.65-6.62 (1H, m), 6.55 (1H, d, J = 0.8 Hz), 6.04-6.02 (2H, m), 5.07 (1H, d, J = 10.6 Hz), 4.44 (1H, t, J = 8.2 Hz), 3.95-3.87 (2H, m), 3.77-3.69 (4H, m), 3.65-3.53 (2H, m), 3.48-3.40 (1H, m), 3.34-3.09 (2H, m), 2.40-2.31 (1H, m), 1.95 (1H, d, J = 14.0 Hz), 1.15 (3H,t, J = 7.0 Hz) |
| I29 | 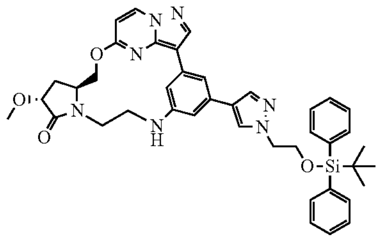 (12R,14S)-4-(1-{2-[(tert-butyldiphenylsilyl)oxy]ethyl}-1H-pyrazol-4-yl)-12-methoxy-16-oxa-7,10,20,21,24-pentaazapentacyclo[15.5.2.12,6.010,14.020,23]pentacosa-1(23),2,4,6(25),17(24),18,21-heptaen-11-one | Scaffold 3-bromo-5-chloro-pyrazolo[1,5-a]pyrimidine Pyrrolidine P1 Aniline A19 99% yield as orange foam | LCMS (MA) RT = 2.32 min, m/z = 424.2 $(M + H)^+$. |
| 103 | 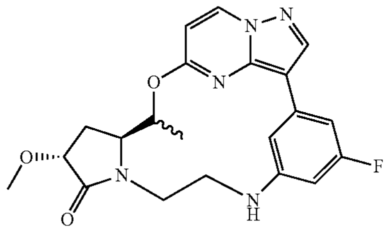 [SMILES: CO[C@@H]1C[C@H]2C(C)Oc3ccn4ncc(c4n3)-c3cc(F)cc(c3)NCCN2C1=O] | Scaffold 3-bromo-5-chloro-pyrazolo[1,5-a]pyrimidine Pyrrolidine P16 Aniline A1 37% yield as green solid | LCMS (MA) RT = 2.22 min, m/z = 412.3 $(M + H)^+$. LCMS(MC) RT = 2.21 min, m/z = 412.3 $(M + H)^+$. $^{1}$H NMR (400 MHz, $CDCl_3$) 8.52 (1H, d, J = 7.5 Hz), 8.28 (1H, s), 7.70 (1H, s), 6.71-6.67 (1H, m), 6.41 (1H, d, J = 7.6 Hz), 6.23 (1H, dt, J = 11.0, J = 2.2 Hz), 5.62-5.55 (1H, m), 4.71-4.68 (1H, m), 4.18 |

-continued

| Ex no | Structure/Name | From intermediates | Analytical data |
|---|---|---|---|
| | E1-(12R,14S,15R*)-4-fluoro-12-methoxy-15-methyl-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | | (1H, t, J = 8.8 Hz), 3.88-3.80 (1H, m), 3.70-3.65 (1H, m), 3.64 (3H, s), 3.62-3.56 (2H, m), 3.27-3.20 (1H, m), 2.66-2.59 (1H, m), 2.09-2.00 (1H, m), 1.31 (3H, d, J = 6.7 Hz). |
| 108 | 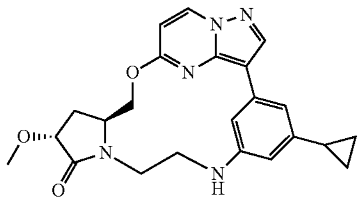 [SMILES: CO[C@@H]1C[C@H]2COc3ccn4ncc(c4n3)-c3cc(cc(C4CC4)c3)NCCN2C1=O] (12R,14S)-4-cyclopropyl-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A20 27% yield as pale yellow solid | LCMS (MA) RT = 2.28 min, m/z = 420.4 $(M + H)^+$ LCMS (MC) RT = 2.27 min, m/z = 420.4 $(M + H)^+$ $^{1}$H NMR (400 MHz, DMSO) 8.96 (1H, d, J = 7.4 Hz), 8.49 (1H, s), 7.60 (1H,s), 6.67-6.65 (1H, m), 6.63 (1H, d, J = 7.4 Hz), 6.18-6.16 (1H, m), 5.93 (1H,t, J = 5.8 Hz), 4.91 (1H,d, J = 10.4 Hz), 4.49-4.42 (1H, m),4.33 (1H,t, J = 8.7 Hz), 3.93 (1H, t, J = 10.7 Hz), 3.55-3.47 (1H, m), 3.45 (3H, s), 3.42-3.36 (1H, m), 3.23-3.15 (2H, m), 2.46-2.41 (1H, m), 2.01-1.93 (1H, m), 1.85-1.78 (1H, m), 0.92-0.87 (2H, m), 0.72-0.59 (2H, m). |
| 111 | 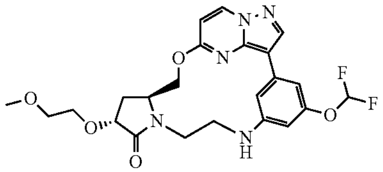 [SMILES: COCCO[C@@H]1C[C@H]2COc3ccn4ncc(c4n3)-c3cc(cc(OC(F)F)c3)NCCN2C1=O] (12R,14S)-4-(difluoromethoxy)-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A8 27% yield as pale yellow solid using DL-cysteine instead of 4-Methylbenzenethiol | LCMS (MA) RT = 2.26 min, m/z = 490.2 $(M + H)^+$ LCMS (MC) RT = 2.26 min, m/z = 490.2 $(M + H)^+$ $^{1}$H NMR (400 MHz, DMSO) 9.00 (1H, d, J = 7.6 Hz), 8.53 (1H, s), 7.70 (1H, s), 7.40-6.90 (1H, m), 6.74-6.66 (2H, m), 6.36 (1H, t, J = 5.8 Hz), 6.23 (1H, t, J = 1.9 Hz), 4.95-4.91 (1H, m), 4.51-4.42 (2H, m), 4.00-3.92 (2H, m), 3.67-3.61 (1H, m), 3.58-3.52 (1H, m), 3.48 (2H, t, J = 4.7 Hz), 3.38 (1H, dd, J = 7.8, 13.9 Hz), 3.31 (1H, s), 3.26-3.26 (5H, m), 2.02-1.94 (1H, m); |
| 114 | 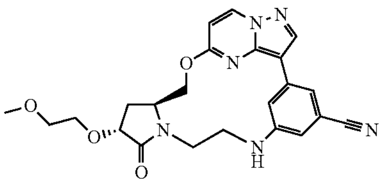 [SMILES: COCCO[C@@H]1C[C@H]2COc3ccn4ncc(c4n3)-c3cc(C#N)cc(c3)NCCN2C1=O] (12R,14S)-12-(2-methoxyethoxy)-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carbonitrile | Scaffold 3-bromo-5-chloro-pyrazolo[1,5-a]pyrimidine Pyrrolidine P7 Aniline A8 48% yield as Beige solid using DL-cysteine instead of 4-Methylbenzenethiol | LCMS (MA) RT = 2.10 min, m/z = 449.3 $(M + H)^+$ LCMS (MC) RT = 2.09 min, m/z = 449.3 $(M + H)^+$ $^{1}$H NMR (400 MHz, DMSO) 9.02 (1H, d, J = 7.6 Hz), 8.63 (1H, s), 8.10 (1H, s), 7.35 (1H, s), 6.79-6.78 (1H, m), 6.70 (1H, d, J = 7.6 Hz), 6.57 (1H, t, J = 5.8 Hz), 4.94 (1H, d, J = 10.4 Hz), 4.50-4.43 (2H, m), 4.00-3.93 (2H, m), 3.68-3.62 (1H, m), 3.60-3.50 (1H, m), 3.48 (2H, t, J = 4.7 Hz), 3.31-3.23 (3H, m), 3.26 (3H, s), 2.47-2.42 (1H, m), 2.01-1.93 (1H, m); |
| 116 | 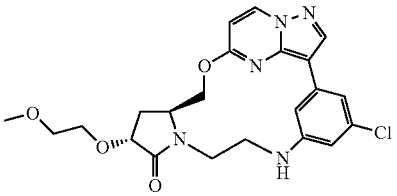 [SMILES: COCCO[C@@H]1C[C@H]2COc3ccn4ncc(c4n3)-c3cc(Cl)cc(c3)NCCN2C1=O] (12R,14S)-4-chloro-12-(2-methoxyethoxy)-16-oxa- | Scaffold 3-bromo-5-chloro-pyrazolo[1,5-a]pyrimidine Pyrrolidine P7 Aniline A2 48% yield as Beige solid using DL-cysteine instead of 4-Methylbenzenethiol | LCMS (MA) RT = 2.31 min, m/z = 458.1 $(M + H)^+$ LCMS (MC) RT = 2.28 min, m/z = 458.2 $(M + H)^+$ $^{1}$H NMR (400 MHz, DMSO) 9.00-8.97 (1H, m), 8.57-8.56 (1H, m), 7.78 (1H, s), 6.97-6.95 (1H, m), 6.68-6.65 (1H, m), 6.49-6.47 (1H, m), 6.35 (1H, t, J = 5.9 Hz), 4.92 (1H, d, J = 11.2 Hz), 4.45 (2H, t, J = 8.9 Hz), 4.00-3.91 (2H, m), 3.68-3.61 (1H, m), 3.58-3.47 |

-continued

| Ex no | Structure/Name | From intermediates | Analytical data |
| --- | --- | --- | --- |
| | 7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | | (3H, m), 3.37-3.32 (1H, m), 3.25-3.21 (5H, m), 2.46-2.40 (1H, m), 2.03-1.93 (1H, m); |
| 117 | 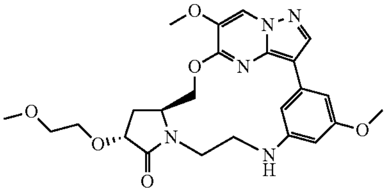 (12R,14S)-4,18-dimethoxy-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold S2 Pyrrolidine P7 Aniline A3 31% yieldas yellowish solid using DL-cysteine instead of 4-Methylbenzenethiol | LCMS (MA) RT = 2.03 min, m/z = 484.3 (M + H)$^+$ LCMS (MC) RT = 2.01 min, m/z = 484.3 (M + H)$^+$ $^1$H NMR (400 MHz, DMSO) 8.74 (1H, s), 8.35 (1H, s), 7.42 (1H, s), 6.51 (1H, s), 6.06-6.01 (2H, m), 4.93 (1H, d, J = 10.6 Hz), 4.44 (2H, t, J = 8.8 Hz), 4.05-3.91 (2H, m), 3.89-3.88 (3H, m), 3.68-3.61 (1H, m), 3.50-3.46 (3H, m), 3.44-3.35 (1H, m), 3.34 (2H, s), 3.27-3.26 (6H, m), 2.48-2.41 (1H, m), 2.02-1.92 (1H, m); |
| 118 | 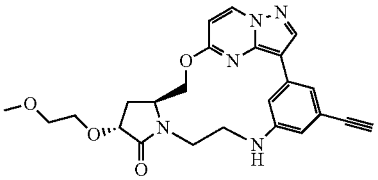 [SMILES: C#Cc1cc2cc(c1)-c1cnn3ccc(nc13)OC[C@@H]1C[C@@H](OCCOC)C(=O)N1CCN2] (12R,14S)-4-ethynyl-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A11 22% yield as white solid using DL-cysteine instead of 4-Methylbenzenethiol | LCMS (MA) RT = 2.21 min, m/z = 448.2 (M + H)$^+$ LCMS (MC) RT = 2.18 min, m/z = 448.2 (M + H)$^+$ $^1$H NMR (400 MHz, DMSO) 8.99 (1H, d, J = 7.4 Hz), 8.57 (1H, s), 7.86 (1H, s), 7.04 (1H, s), 6.66 (1H, d, J = 7.6 Hz), 6.56 (1H, s), 6.26 (1H, t, J = 5.8 Hz), 4.93 (1H, dd, J = 0.9, 10.9 Hz), 4.50-4.42 (2H, m), 4.05-3.94 (3H, m), 3.68-3.61 (1H, m), 3.58-3.51 (1H, m), 3.48 (2H, t, J = 4.8 Hz), 3.37 (1H, s), 3.31 (1H, s), 3.27-3.26 (5H, m), 2.01-1.93 (1H, m); |
| 121 | 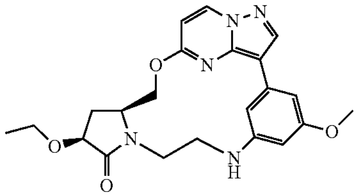 [SMILES: CCO[C@H]1C[C@H]2COc3ccn4ncc(c4n3)-c3cc(cc(OC)c3)NCCN2C1=O] (12S,14S)-12-ethoxy-4-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P14 Aniline A3 27% yield as salmon solid | LCMS (MA) RT = 2.22 min, m/z = 424.4 (M + H)$^+$ LCMS (MC) RT = 2.21 min, m/z = 424.4 (M + H)$^+$ $^1$H NMR (400 MHz, DMSO) 8.98-8.94 (1H, m), 8.50 (1H, s), 7.49-7.44 (1H, m), 6.65-6.62 (1H, m), 6.55 (1H, s), 6.03 (2H, s), 5.07 (1H, d, J = 10.6 Hz), 4.44 (1H, t, J = 7.4 Hz), 3.95-3.86 (2H, m), 3.74 (4H, m), 3.63-3.59 (2H, m), 3.48-3.43 (1H, m), 3.27-3.11 (2H, m), 2.40-2.31 (1H, m), 1.95 (1H, d, J = 14.2 Hz), 1.15 (3H, t, J = 7.0 Hz); |
| 129 | 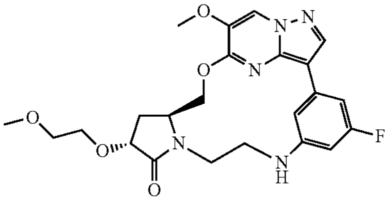 [SMILES: COCCO[C@@H]1C[C@H]2COc3nc4c(cnn4cc3OC)-c3cc(F)cc(c3)NCCN2C1=O] (12R,14S)-4-fluoro-18-methoxy-12-(2-methoxyethoxy)-16-oxa- | Scaffold S2 Pyrrolidine P7 Aniline A1 11 mg, 13% yield as Beige solid | LCMS (MA) RT = 2.19 min, m/z = 472.2 (M + H)$^+$ LCMS (MC) RT = 2.13 min, m/z = 472.3 (M + H)$^+$ $^1$H NMR (400 MHz, DMSO) 8.79 (1H, s), 8.40 (1H, s), 7.63-7.62 (1H, m), 6.74-6.71 (1H, m), 6.33 (1H, t, J = 5.8 Hz), 6.20 (1H, d, J = 12.3 Hz), 4.96 (1H, d, J = 10.7 Hz), 4.49-4.43 (2H, m), 4.03 (1H, t, J = 11.3 Hz), 3.98-3.92 (1H, m), 3.89 (3H, s), 3.67-3.62 (1H, m), 3.59-3.52 (1H, m), 3.48 (3H, t, |

-continued

| Ex no | Structure/Name | From intermediates | Analytical data |
|---|---|---|---|
| | 7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | | J = 4.7 Hz), 3.28-3.22 (5H, m), 2.46-2.42 (1H, m), 2.00-1.95 (1H, m). |
| 145 | 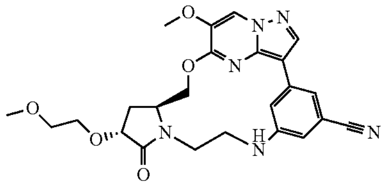 [SMILES: COCCO[C@@H]1C[C@H]2COc3nc4c(cnn4cc3OC)-c3cc(C#N)cc(c3)NCCN2C1=O] (12R,14S)-18-methoxy-12-(2-methoxyethoxy)-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carbonitrile | Scaffold S2 Pyrrolidine P7 Aniline A6 40 mg, 22% yield as Beige solid | LCMS (MA) RT = 2.10 min, m/z = 479.3 (M + H)$^+$ LCMS (MC) RT = 2.08 min, m/z = 479.3 (M + H)$^+$ $^1$H NMR (400 MHz, DMSO) 8.82 (1H, s), 8.49 (1H, s), 8.05 (1H, s), 7.32 (1H, s), 6.77 (1H, s), 6.56 (1H, t, J = 5.9 Hz), 4.95 (1H, d, J = 9.9 Hz), 4.46 (2H, t, J = 8.7 Hz), 3.91-3.89 (6H, m), 3.68-3.62 (1H, m), 3.57 (1H, s), 3.48 (2H, t, J = 4.7 Hz), 3.31 (1H, s), 3.26 (4H, s), 2.48-2.42 (1H, m), 1.99-1.92 (1H, m). |

Example 44: (12R,14S)-12-methoxy-4-(pyridin-3-ylmethoxy)-16-oxa-7,10,20,21,24-pentaazapentacyclo[15.5.2.1$^{2}$,6.0$^{1o}$,$^{1}$4.0$^{2o}$,$^{23}$]pentacosa-1 (23),2(25),3,5,17(24),18,21-heptaen-11-one

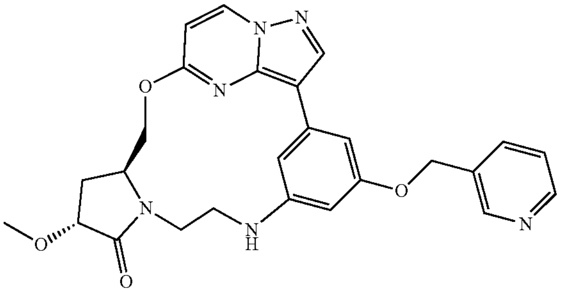 [SMILES: CO[C@@H]1C[C@H]2COc3ccn4ncc(c4n3)-c3cc(cc(OCc4cccnc4)c3)NCCN2C1=O]

Following the general synthetic scheme 1, as depicted for the synthesis of Example 1, (12R,14S)-4-(benzyloxy)-12-methoxy-7-(2-nitrobenzenesulfonyl)-16-oxa-7,10,20,21,24-pentaazapentacyclo[15.5.2.12,6.010,14.020,23]pentacosa-1 (23),2,4,6(25),17(24),18,21-heptaen-11-one was obtained as Intermediate I18 using Scaffold 3-bromo-5-chloro-pyrazolo [1,5-a]pyrimidine, Pyrrolidine P1 and Aniline A9.

Step 1

A solution of Intermediate I18 (1 g, 1.491 mmol) in TFA (5 mL) and Anisole (15 mL) was heated at 130° C. for 4 hours. LCMS showed complete reaction. The mixture was allowed to cooled to room temperature. The solvent was evaporated under reduced pressure. The gummy residue was triturated with DCM/i$Pr_2O$ (1/1). The resulting precipitate was filtered, washed with Diisopropyl ether then pentane and dried to afford the title compound (Intermediate I19, (12R,14S)-4-hydroxy-12-methoxy-7-(2-nitrobenzenesulfonyl)-16-oxa-7,10,20,21,24-pentaazapentacyclo[15.5.2.12, 6.010, 14.020,23]pentacosa-1(23),2,4,6(25),17(24),18,21-heptaen-11-one) (0.81 g, 93.6% yield) as a cream solid.

LCMS (MA) RT=2.20 min m/z=581.1 (M+H)$^+$.

Step 2

To a solution of the title compound from Step 1 (50 mg, 0.0861 mmol) under Nitrogen in DMF (3 mL) were added 3-(bromomethyl)pyridine, hydrobromide (65 mg, 0.258 mmol) and Cesium carbonate (168 mg, 0.517 mmol). The solution was stirred to 80° C. for 1H. Monitoring by LCMS showed completed reaction. The crude was evaporated under vacuum The residue was purified by chromatography on silica eluting with 0%-50% gradient of (3:1 EtOAc: EtOH)/Cyclohexane to afford the expected compound (75 mg, 65% yield) as a yellow glassy solid.

LCMS (MA) RT=2.02 min m/z=672.1 (M+H)$^+$.

Step 3

To a suspension of the title compound from Step 2 (75 mg, 0.112 mmol) in DMF (5 mL) was added cesium carbonate (73 mg, 0.224 mmol) and 4-methylbenzenethiol (17 mg, 0.134 mmol). The reaction mixture was stirred at room temperature for 2 h, then overnight. The mixture was portioned between water and EtOAc, the organic layer was dried over $Na_2SO_4$ and evaporated under vacuum. The residue was purified by chromatography on silica eluting with 0%-50% gradient of (3:1 EtOAc: EtOH)/Cyclohexane. The appropriate fractions were evaporated under vacuum and the residue was treated by $CH_3CN$, a solid cream crystallized, it was filtered, washed with water and dried under vacuum at 60° C. to afford the expected product (26 mg, 48% yield) as a cream solid.

LCMS (MA) RT=1.67 min m/z=487.1 (M+H)$^+$.

LCMS (MC) RT=2.10 min m/z=487.1 (M+H)$^+$.

$^1$H NMR (400 MHz, DMSO) 8.97 (1H, d, J=7.6 Hz), 8.69 (1H, d, J=1.7 Hz), 8.56-8.51 (2H, m), 7.90-7.86 (1H, m), 7.52-7.42 (2H, m), 6.67-6.63 (2H, m), 6.13-6.05 (2H, m), 5.14-5.13 (2H, m), 4.92 (1H, d, J=10.8 Hz), 4.49-4.46 (1H, m), 4.36-4.30, (1H, m), 3.94 (1H, t, J=10.7 Hz), 3.58-3.48 (1H, m), 3.44-3.36 (1H, m), 3.33 (3H, s), 3.25-3.16 (2H, m), 2.46-2.40 (1H, m), 2.01-1.92 (1H, m) Similarly prepared:

| Ex no | Structure/Name | From intermediates | Analytical data |
|---|---|---|---|
| 45 | 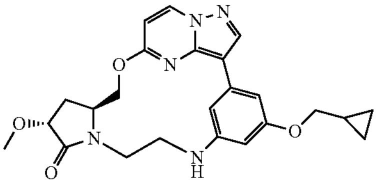 [SMILES: CO[C@@H]1C[C@H]2COc3ccn4ncc(c4n3)-c3cc(cc(OCC4CC4)c3)NCCN2C1=O] (12R,14S)-4-(cyclopropylmethoxy)-12-methoxy-16-oxa-7,10,20,21,24-pentaazapentacyclo[15.5.2.$1^2$,6.$0^{10}$,$^{1}$4.$0^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A9 49% yield as a cream solid | LCMS (MA) RT = 2.38 min, m/z = 450.2 $(M + H)^+$. LCMS (MC) RT = 2.38 min, m/z = 450.2 $(M + H)^+$. $^1$H NMR (400 MHz, DMSO): 8.96 (1H, d, J = 7.4 Hz), 8.50 (1H, s), 7.45 (1H, s), 6.63 (1H, d, J = 7.4 Hz), 6.55 (1H, s), 6.03-5.97 (2H, m), 4.95-4.88 (1H, m), 4.48-4.44 (1H, m), 4.36-4.30 (1H, m), 3.93 (1H, t, J = 10.7 Hz), 3.82-3.73 (2H, m), 3.64-3.49 (2H, m), 3.45 (3H, s), 3.27-3.17 (2H, m), 2.47-2.41 (1H, m) 2.02-1.92 (1H, m), 1.26-1.18 (1H, m), 0.61-0.54 (2H, m), 0.35-0.29 (2H, m). |
| 46 | 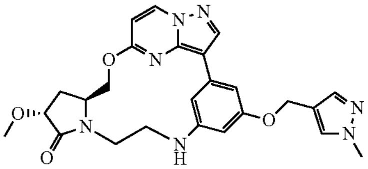 (12R,14S)-12-methoxy-4-[(1-methyl-1H-pyrazol-4-yl)methoxy]-16-oxa-7,10,20,21,24-pentaazapentacyclo[15.5.2.$1^2$,6.$0^{10}$,$^{1}$4.$0^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P1 Aniline A9 35% yield as a white solid | LCMS (MA) RT = 2.03 min, m/z = 490.3 $(M + H)^+$ LCMS (MC) RT = 2.02 min, m/z = 490.3 $(M + H)^+$. $^1$H NMR (400 MHz, DMSO): 8.98-8.95 (1H, m), 8.51 (1H, s), 7.78 (1H, s), 7.51-7.50 (2H, m), 6.65-6.60 (2H, m), 6.09-6.00 (2H, m), 4.93-4.90 (3H, m), 4.49-4.44 (1H, m),4.33 (1H, t, J = 8.8 Hz), 3.94 (1H,t, J = 10.7 Hz), 3.83 (3H, s), 3.57-3.38 (3H, m), 3.32 (3H, s), 3.28-3.13 (2H, m), 2.47-2.40 (1H, m), 2.01-1.92 (1H, m). |
| 47 | 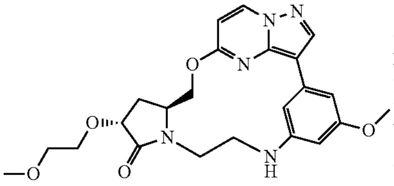 (12R,14S)-4-methoxy-12-(2-methoxyethoxy)-16-oxa-7,10,20,21,24-pentaazapentacyclo[15.5.2.$1^2$,6.$0^{10}$,$^{1}$4.$0^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A9 81% yield as a white solid using $K_2CO_3$ instead of $CS_2CO_3$ in alkylation step | LCMS (MD) RT = 2.72 min, m/z = 454.1 $(M + H)^+$. LCMS (ME) RT = 3.20 min, m/z = 454.1 $(M + H)^+$. $^1$H NMR (400 MHz, DMSO) d 8.96 (d, J = 7.5 Hz, 1H), 8.51 (s, 1H), 7.47 (s, 1H), 6.64 (d, J = 7.5 Hz, 1H), 6.54 (s, 1H), 6.09-5.99 (m, 2H), 4.92 (d, J = 10.9 Hz, 1H), 4.54-4.38 (m, 2H), 3.95 (ddd, J = 17.7, 11.3, 7.7 Hz, 2H), 3.73 (s, 3H), 3.70-3.60 (m, 1H), 3.59-3.50 (m, 1H), 3.48 (t, J = 4.8 Hz, 2H), 3.40 (dd, J = 17.0, 6.9 Hz, 1H), 3.26 (s, 3H), 3.24-3.12 (m, 2H), 2.44 (dd, J = 12.7, 8.2 Hz, 1H), 1.98 (dt, J = 11.8, 8.9 Hz, 1H). |
| 48 | 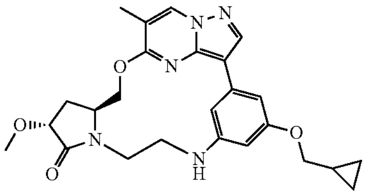 [SMILES: CO[C@@H]1C[C@H]2COc3nc4c(cnn4cc3C)-c3cc(cc(OCC4CC4)c3)NCCN2C1=O] (12R,14S)-4-(cyclopropylmethoxy)-12-methoxy-18-methyl-16-oxa-7,10,20,21,24-pentaazapentacyclo[15.5.2.$1^2$,6.$0^{10}$,$^{1}$4.$0^{20}$,$^{23}$]pentacosa-1(23),2,4,6(25),17(24),18,21-heptaen-11-one | Scaffold S1 Pyrrolidine P1 Aniline A9 47% yield as a white solid | LCMS (MD) RT = 3.36 min, m/z = 464.2 $(M + H)^+$. LCMS (ME) RT = 3.70 min, m/z = 464.2 $(M + H)^+$. 1H NMR (400 MHz, DMSO) d 8.87 (d, J = 1.2 Hz, 1H), 8.41 (s, 1H), 7.44 (s, 1H), 6.53 (s, 1H), 6.00 (t, J = 2.0 Hz, 1H), 5.98 (d, J = 5.9 Hz, 1H), 4.94 (d, J = 10.7 Hz, 1H), 4.45 (s, 1H), 4.35 (t, J = 8.9 Hz, 1H), 3.98 (t, J = 10.7 Hz, 1H), 3.85-3.70 (m, 2H), 3.60-3.49 (m, 1H), 3.44 (s, 3H), 3.40 (dd, J = 15.5, 8.4 Hz, 1H), 3.27-3.06 (m, 2H), 2.48-2.43 (m, 1H), 2.17 (s, 3H), 2.03-1.88 (m, 1H), 1.28-1.16 (m, 1H), 0.61-0.53 (m, 2H), 0.35-0.27 (m, 2H). |

-continued

| Ex no | Structure/Name | From intermediates | Analytical data |
|---|---|---|---|
| 49 | 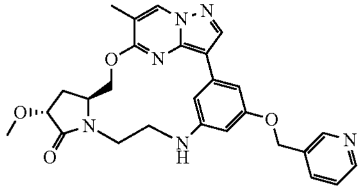 [SMILES: CO[C@@H]1C[C@H]2COc3nc4c(cnn4cc3C)-c3cc(cc(OCc4cccnc4)c3)NCCN2C1=O] (12R,14S)-12-methoxy-18-methyl-4-(pyridin-3-ylmethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold S1 Pyrrolidine P1 Aniline A9 62% yield as a white solid | LCMS (MD) RT = 2.33 min, m/z = 501.2 (M + H)$^{+}$. LCMS (ME) RT = 3.54 min m/z = 501.1 (M + H)$^{+}$. $^{1}$H NMR (400 MHz, DMSO) d 8.88 (d, J = 1.1 Hz, 1H), 8.69 (d, J = 1.5 Hz, 1H), 8.55 (dd, J = 4.8, 1.7 Hz, 1H), 8.42 (s, 1H), 7.88 (dt, J = 7.8, 1.8 Hz, 1H), 7.49 (s, 1H), 7.44 (ddd, J = 7.8, 4.8, 0.8 Hz, 1H), 6.65 (s, 1H), 6.11 (t, J = 2.1 Hz, 1H), 6.06 (t, J = 5.8 Hz, 1H), 5.13 (s, 2H), 4.95 (d, J = 10.4 Hz, 1H), 4.46 (s, 1H), 4.35 (t, J = 8.9 Hz, 1H), 3.97 (dd, J = 21.8, 11.1 Hz, 1H), 3.53 (dd, J = 11.1,7.6 Hz, 1H), 3.45 (s, 3H), 3.40 (t, J = 11.9 Hz, 1H), 3.20 (dd, J = 17.1, 10.8 Hz, 2H), 2.48-2.41 (m, 1H), 2.18 (d, J = 0.7 Hz, 3H), 2.05- 1.84 (m, 1H). |
| 50 | 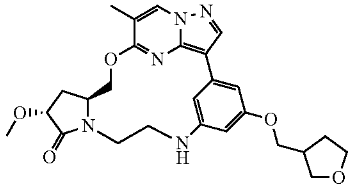 [SMILES: CO[C@@H]1C[C@H]2COc3nc4c(cnn4cc3C)-c3cc(cc(OCC4CCOC4)c3)NCCN2C1=O] (12R,14S)-12-methoxy-18-methyl-4-(oxolan-3-ylmethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold S1 Pyrrolidine P1 Aniline A9 60% yield as a white solid | LCMS (MD) RT = 3.01 min, m/z = 494.2(M + H)$^{+}$. LCMS (ME) RT = 3.52 min, m/z = 494.2 (M + H)$^{+}$. $^{1}$H NMR (400 MHz, DMSO) d 8.99 (d, J = 7.5 Hz, 1H), 8.54 (s, 1H), 7.71 (s, 1H), 6.75 (d, J = 10.2 Hz, 1H), 6.67 (d, J = 7.5 Hz, 1H), 6.32 (t, J = 5.9 Hz, 1H), 6.21 (dt, J = 11.8, 2.1 Hz, 1H), 4.94 (d, J = 10.9 Hz, 1H), 4.41 (s, 1H), 3.99 (t, J = 10.6 Hz, 1H), 3.60 (dd, J = 11.4, 8.9 Hz, 1H), 3.55 (dd, J = 9.5, 3.8 Hz, 1H), 3.49 (dd, J = 9.5, 5.8 Hz, 1H), 3.40 (dt, 1H), 3.25 (s, 3H), 3.18 (dd, J = 14.2, 9.0 Hz, 2H), 2.91 (tdd, J = 9.7, 5.5, 4.0 Hz, 1H), 2.10 (t, J = 10.6 Hz, 2H). |
| 51 | 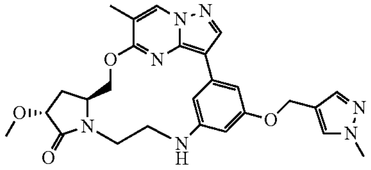 (12R,14S)-12-methoxy-18-methyl-4-[(1-methyl-1H-pyrazol-4-yl)methoxy]-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold S1 Pyrrolidine P1 Aniline A9 17% yield as a green solid | LCMS (MD) RT = 2.78 min, m/z = 504.2(M + H)$^{+}$. LCMS (MF) RT = 2.71 min, m/z = 504.2 (M + H)$^{+}$. $^{1}$H NMR (400 MHz, DMSO) D 8.88 (d, J = 1.2 Hz, 1H), 8.42 (s, 1H), 7.78 (s, 1H), 7.50 (s, 1H), 7.46 (s, 1H), 6.58 (s, 1H), 6.07 (t, J = 2.0 Hz, 1H), 6.01 (t, J = 5.8 Hz, 1H), 4.95 (d, J = 9.0 Hz, 1H), 4.89 (s, 2H), 4.47 (t, J = 9.5 Hz, 1H), 4.35 (d, J = 6.0 Hz, 1H), 3.99 (t, J = 10.7 Hz, 1H), 3.83 (s, 3H), 3.57-3.49 (m, 1H), 3.45 (s, 3H), 3.41-3.36 (m, 1H), 3.24-3.15 (m, 3H), 2.18 (d, J = 1.0 Hz, 3H), 1.96 (dd, J = 21.6, 8.6 Hz, 1H). |
| 52 | 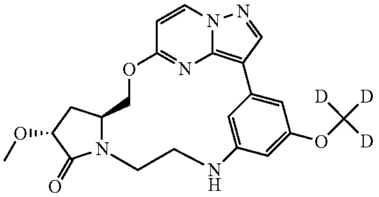 [SMILES: [2H]C([2H])([2H])Oc1cc2cc(c1)-c1cnn3ccc(nc13)OC[C@@H]1C[C@@H](OC)C(=O)N1CCN2] (12R,14S)-4-($^{2}$H3)methoxy-12-methoxy-16-oxa-7,10,20,21,24- | Scaffold 3-bromo-5-chloro-pyrazolo[1,5-a]pyrimidine Pyrrolidine P1 Aniline A9 50% yield as a cream solid | LCMS (MA) RT = 2.07 min, m/z = 413.2 (M + H)$^{+}$ LCMS (MC) RT = 2.08 min, m/z = 412.2 (M + H)$^{+}$. $^{1}$H NMR (400 MHz, DMSO): 8.98-8.95 (1H, m), 8.50 (1H, s), 7.47 (1H, s), 6.65-6.62 (1H, m), 6.54 (1H, d, J = 0.8 Hz), 6.07-6.02 (2H, m), 4.96-4.89 (1H, m), 4.47 (1H, t, J = 8.0 Hz), 4.33 (1H, t, J = 8.8 Hz), 3.94 (1H, t, J = 10.7 Hz), 3.57-3.37 (2H, m), 3.33 (3H, |

-continued

| Ex no | Structure/Name | From intermediates | Analytical data |
|---|---|---|---|
| | pentaazapentacyclo[15.5.2.$1^{2}$, $6.0^{10}$,$^{1}4.0^{20}$,$^{23}$]pentacosa-1(23),2,4,6(25),17(24),18,2 1-heptaen-11-one | | s), 3.27-3.16 (2H, m), 2.46-2.41 (1H, m), 2.02-1.92 (1H, m). |
| 53 | 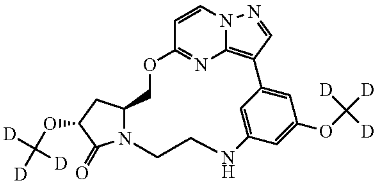 [SMILES: [2H]C([2H])([2H])Oc1cc2cc(c1)-c1cnn3ccc(nc13)OC[C@@H]1C[C@@H](OC([2H])([2H])[2H])C(=O)N1CCN2] (12R,14S)-4,12-bis($^{2}$H3)methoxy-16-oxa-7,10,20,21,24-pentaazapentacyclo[[15.5.2.$1^{2}$,$6.0^{10}$,$^{1}4.0^{20}$,$^{23}$]pentacosa-1(23),2,4,6(25),17(24),18,2 1-heptaen-11-one | Scaffold S1 Pyrrolidine P6 Aniline A9 20% yield as a white solid | LCMS (MD) RT = 2.66 min, m/z = 416.2 (M + H)$^{+}$. LCMS (ME) RT = 3.09 min, m/z = 416.2 (M + H)$^{+}$. $^{1}$H NMR (400 MHz, DMSO) d 8.89 (d, J = 7.5 Hz, 1H), 8.43 (s, 1H), 7.39 (s, 1H), 6.56 (d, J = 7.5 Hz, 1H), 6.47 (dd, J = 1.9, 1.1 Hz, 1H), 5.98 (d, J = 5.9 Hz, 1H), 5.96 (t, J = 2.1 Hz, 1H), 4.85 (d, J = 10.9 Hz, 1H), 4.39 (t, J = 8.8 Hz, 1H), 4.25 (t, J = 8.8 Hz, 1H), 3.86 (t, J = 10.7 Hz, 1H), 3.51-3.40 (m, 1H), 3.38-3.28 (m, 1H), 3.18-3.04 (m, 2H), 2.36 (dd, J = 12.7, 8.2 Hz, 1H), 1.89 (dt, J = 12.0, 8.8 Hz, 1H). |
| 94 | 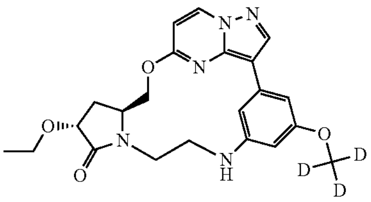 (12R,14S)-12-ethoxy-4-($^{2}$H3)methoxy-16-oxa-7,10,20,21,24-pentaazapentacyclo[15.5.2.$1^{2}$,$6.0^{10}$,$^{1}4.0^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P2 Aniline A9 24% yield as a green solid | LCMS (MA) RT = 1.81 min, m/z = 410.4 (M + H)$^{+}$. LCMS (MC) RT = 1.80 min, m/z = 410.4 (M + H)$^{+}$. $^{1}$H NMR (400 MHz, DMSO) 8.97-8.94 (2H, m), 8.39-8.38 (1H, m), 7.97-7.95 (1H, m), 7.35-7.32 (1H, m), 6.64-6.61 (1H, m), 6.35 (1H, s), 5.93 (1H, t, J = 2.0 Hz), 4.94-4.89 (1H, m), 4.44-4.38 (2H, m), 3.98-3.82 (2H, m), 3.48 (4H, d, J = 10.4 Hz), 3.20-3.14 (1H, m), 2.01-1.91 (1H, m), 1.17-1.04 (4H, m); |
| 95 | 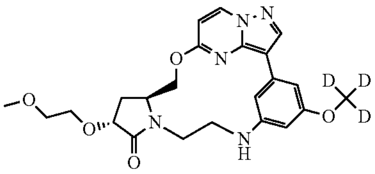 (12R,14S)-4-($^{2}$H3)methoxy-12-(2-methoxyethoxy)-16-oxa-7,10,20,21,24-pentaazapentacyclo[15.5.2.$1^{2}$, $6.0^{10}$,$^{1}4.0^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A9 27% yield as a yellow solid using DL-cysteine instead of 4-Methylbenzenethiol | LCMS (MA) RT = 2.11 min, m/z = 427.5 (M + H)$^{+}$. LCMS (MC) RT = 2.10 min, m/z = 427.4 (M + H)$^{+}$. $^{1}$H NMR (400 MHz, DMSO) 8.98-8.96 (1H, m), 8.51-8.50 (1H, m), 7.46-7.45 (1H, m), 6.65-6.63 (1H, m), 6.55 (1H, d, J = 2.3 Hz), 6.06-6.02 (2H, m), 4.95-4.90 (1H, m), 4.44-4.39 (2H, m), 3.98-3.83 (2H, m), 3.60-3.49 (2H, m), 3.45-3.35 (1H, m), 3.24-3.16 (2H, m), 2.45-2.35 (1H, m), 2.01-1.93 (1H, m), 1.17-1.08 (3H, m) |
| 112 | 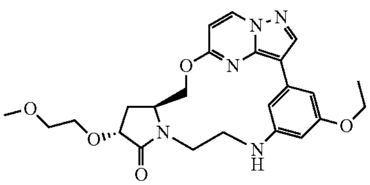 [SMILES: CCOc1cc2cc(c1)-c1cnn3ccc(nc13)OC[C@@H]1C[C@@H](OCCOC)C(=O)N1CCN2] (12R,14S)-4-ethoxy-12-(2-methoxyethoxy)-16-oxa-7,10,20,21,24-pentaazapentacyclo[15.5.2.$1^{2}$, $6.0^{10}$,$^{1}4.0^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A9 66 mg, 68% yield as a white solid using DL-cysteine instead of 4-Methylbenzenethiol | LCMS (MA) RT = 2.17 min, m/z = 468.2 (M + H)$^{+}$. LCMS (MC) RT = 2.15 min, m/z = 468.5 (M + H)$^{+}$. $^{1}$H NMR (400 MHz, DMSO) 8.98-8.95 (1H, m), 8.51 (1H, s), 7.46 (1H, s), 6.64 (1H, d, J = 7.6 Hz), 6.54 (1H, dd, J = 1.3, 1.9 Hz), 6.02 (2H, t, J = 2.1 Hz), 4.92 (1H, dd, J = 1.0, 9.4 Hz), 4.47-4.42 (2H, m), 4.01-3.93 (4H, m), 3.67-3.61 (1H, m), 3.51 (1H, s), 3.48 (2H, t, J = 4.8 Hz), 3.30 (2H, s), 3.26-3.26 (3H, m), 3.20-3.16 (2H, m), 2.03-1.94 (1H, m), 1.35-1.31 (3H, m); |

-continued

| Ex no | Structure/Name | From intermediates | Analytical data |
|---|---|---|---|
| 113 | 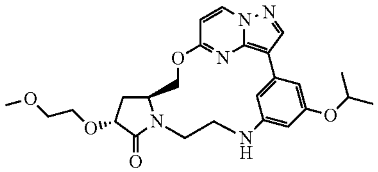 [SMILES: COCCO[C@@H]1C[C@H]2COc3ccn4ncc(c4n3)-c3cc(cc(OC(C)C)c3)NCCN2C1=O]<br>(12R,14S)-12-(2-methoxyethoxy)-4-(propan-2-yloxy)-16-oxa-7,10,20,21,24-pentaazapentacyclo[15.5.2.1$^{2}$,6.0$^{10}$,$^{14}$.0$^{20}$,$^{23}$]pentacosa-1(23),2(25),3,5,17(24),18,21-heptaen-11-one | Scaffold 3-bromo-5-chloro-pyrazolo[1,5-a]pyrimidine Pyrrolidine P7 Aniline A9 41 mg, 41% yield as a white solid using DL-cysteine instead of 4-Methylbenzenethiol | LCMS (MA) RT = 2.26 min, m/z = 482.5 $(M + H)^+$. LCMS (MC) RT = 2.26 min, m/z = 482.5 $(M + H)^+$. $^1$H NMR (400 MHz, DMSO) 8.98-8.95 (1H, m), 8.51 (1H, s), 7.45-7.43 (1H, m), 6.65-6.62 (1H, m), 6.53-6.52 (1H, m), 6.03-5.98 (2H, m), 4.94-4.91 (1H, m), 4.59-4.52 (1H, m), 4.45 (2H, dd, J = 8.3, 9.4 Hz), 4.00-3.90 (2H, m), 3.67-3.61 (1H, m), 3.52-3.50 (1H, m), 3.50-3.35 (3H, m), 3.31 (1H, s), 3.26-3.26 (5H, m), 2.02-1.94 (1H, m), 1.27 (6H,t, J = 5.6 Hz); |
| 131 | 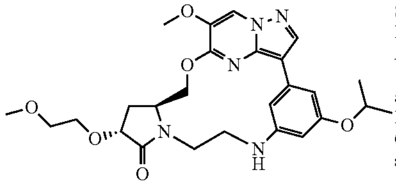 [SMILES: COCCO[C@@H]1C[C@H]2COc3nc4c(cnn4cc3OC)-c3cc(cc(OC(C)C)c3)NCCN2C1=O]<br>(12R,14S)-18-methoxy-12-(2-methoxyethoxy)-4-(propan-2-yloxy)-16-oxa-7,10,20,21,24-pentaazapentacyclo[15.5.2.1$^{2}$,6.0$^{10}$,$^{14}$.0$^{20}$,$^{23}$]pentacosa-1(23),2,4,6(25),17(24),18,21-heptaen-11-one | Scaffold S2 Pyrrolidine P7 Aniline A9 10 mg, 26% yield as a Beige solid using $K_2CO_3$ instead of $Cs_2CO_3$ at alkylation step | LCMS (MA) RT = 2.23 min, m/z = 512.4 $(M + H)^+$. LCMS (MC) RT = 2.22 min, m/z = 512.4 $(M + H)^+$. 1H NMR (400 MHz, $CDCl_3$) 8.19 (1H, s), 8.14 (1H,S), 7.48-7.45 (1H, m), 6.58 (1H, s), 6.07 (1H, t, J = 2.0 Hz), 5.13 (1H, d, J = 10.8 Hz), 4.61-4.50 (2H, m), 4.38-4.32 (1H, m), 4.21-4.08 (2H, m), 3.96-3.94 (6H, m), 3.70-3.53 (4H, m), 3.42-3.41 (4H, m), 2.73 (1H, dd, J = 8.2, 13.1 Hz), 2.24-2.17 (1H, m), 1.38 (6H, dd, J = 2.3, 6.1 Hz); |
| 140 | 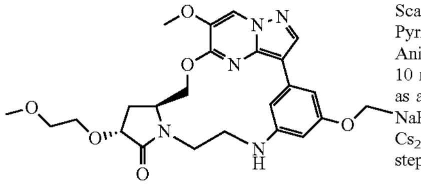<br>(12R,14S)-4-ethoxy-18-methoxy-12-(2-methoxyethoxy)-16-oxa-7,10,20,21,24-pentaazapentacyclo[15.5.2.1$^{2}$,6.0$^{10}$,$^{14}$.0$^{20}$,$^{23}$]pentacosa-1(23),2,4,6(25),17(24),18,21-heptaen-11-one | Scaffold S2 Pyrrolidine P7 Aniline A9 10 mg, 31% yield as a Beige solid using NaH instead of $Cs_2CO_3$ at alkylation step | LCMS (MA) RT = 2.15 min, m/z = 498.4 $(M + H)^+$. LCMS (MC) RT = 2.13 min, m/z = 498.4 $(M + H)^+$. 1H NMR (400 MHz, $CDCl_3$) 8.20-8.19 (1H, m), 8.14-8.13 (1H, m), 7.49-7.46 (1H, m), 6.59 (1H, dd, J = 1.3, 2.1 Hz), 6.07 (1H, t, J = 2.2 Hz), 5.15-5.10 (1H, m), 4.54-4.49 (1H, m), 4.38-4.32 (1H, m), 4.20-4.14 (1H, m), 4.09-4.03 (3H, m), 3.95-3.94 (6H, m), 3.70-3.49 (4H, m), 3.42-3.42 (3H, m), 3.30-3.23 (1H, m), 2.73 (1H, dd, J = 8.2, 13.1 Hz), 2.25-2.16 (1H, m), 1.44 (3H,t, J = 7.0 Hz); |
| 141 | 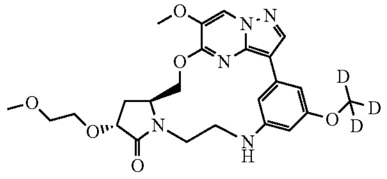 [SMILES: [2H]C([2H])([2H])Oc1cc2cc(c1)-c1cnn3cc(OC)c(nc13)OC[C@@H]1C[C@@H](OCCOC)C(=O)N1CCN2]<br>(12R,14S)-4-($^2$H3)methoxy-18-methoxy-12-(2-methoxyethoxy)-16-oxa-7,10,20,21,24-pentaazapentacyclo[15.5.2.1$^{2}$,6.0$^{10}$,$^{14}$.0$^{20}$,$^{23}$]pentacosa-1(23),2,4,6(25),17(24),18,21-heptaen-11-one | Scaffold S2 Pyrrolidine P7 Aniline A9 9 mg, 25% yield as a Light brown solid using NaH instead of $Cs_2CO_3$ at alkylation step | LCMS (MA) RT = 2.02 min, m/z = 487.4 $(M + H)^+$. LCMS (MC) RT = 1.99 min, m/z = 487.4 $(M + H)^+$. $^1$H NMR (400 MHz, $CDCl_3$) 8.21-8.21 (1H, m), 8.15-8.14 (1H, m), 7.50-7.47 (1H, m), 6.59 (1H, dd, J = 1.2, 2.2 Hz), 6.08 (1H, t, J = 2.2 Hz), 5.13 (1H, d, J = 10.8 Hz), 4.52 (1H, t, J = 8.8 Hz), 4.35 (1H, dd, J = 8.2, 9.5 Hz), 4.21-4.13 (2H, m), 3.96-3.95 (6H, m), 3.70-3.57 (4H, m), 3.42-3.42 (3H, m), 3.30-3.23 (1H, m), 2.73 (1H, dd, J = 8.1, 13.2 Hz), 2.25-2.16 (1H, m); |

Example 54: (12R,14S)-4-acetyl-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one

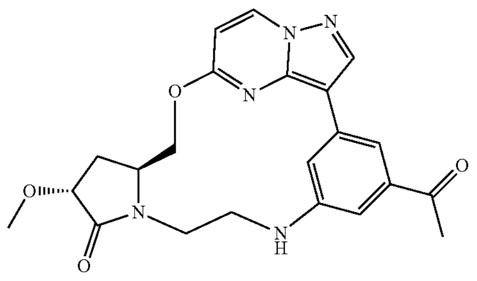 [SMILES: CO[C@@H]1C[C@H]2COc3ccn4ncc(c4n3)-c3cc(cc(C(C)=O)c3)NCCN2C1=O]

Step 1

To a solution of Triethylamine (0.13 mL, 0.956 mmol) and Intermediate I19 (370 mg, 0.637 mmol) in Dichloromethane (30 mL) was added portionwise N-phenyl-bis (trifluoromethanesulfonimide) (250 mg, 0.701 mmol). The reaction mixture was stirred at room temperature for 5 h. Water (30 mL) was added to the reaction and extracted with Dichloromethane. The combined organic layers were washed with Brine, dried over anhydrous sodium sulfate, filtered and evaporated under reduced pressure. The residue was purified by silica gel chromatography (eluting gradient 0-50% cyclohexane/ethyl acetate) to afford the title compound (430 mg, 95% yield) as a yellowish solid.

LCMS (MA) RT=2.91 min, m/z=713.2 $(M+H)^+$.

Step 2

To a solution of the title compound from Step 1 (100 mg, 0.140 mmol) in DMF (3.5 mL) was added Cesium carbonate (91 mg, 0.280 mmol) and 4-Methylbenzenethiol (21 mg, 0.168 mmol). The reaction mixture was stirred at room temperature for 30 min. The mixture was diluted with water (3 mL) and EtOAc (3 mL) and the two layers were separated. The aqueous layer was extracted three times (3×5 mL) with ethyl acetate. The organic layers were combined, washed with Brine (5 mL) and dried over sodium sulfate. The crude residue was purified by silica gel chromatography using cyclohexane/ethyl acetate 100:0 to 0:100 as eluent s to afford the title compound (65 mg, 88% yield) as a white amorphous solid.

LCMS (MA) RT=2.62 min, m/z=528.1 $(M+H)^+$.

Step 3

In a microwave vial, the title compound from Step 2 (31 mg, 0.059 mmol) and LiCl (8 mg, 0.177 mmol) were dissolved in Dioxane (1 mL) and the mixture was degassed with Ar for 10 minutes. Tributyl(1-ethoxyvinyl)stannane (0.024 mL, 0.070 mmol) and $Pd(PPh_3)_4$ (7 mg, 0.006 mmol) were added and the vial containing the resulting transparent solution was sealed and heated to 100° C. for 1 h. The reaction mixture was partitioned between a 1M solution of HCl (2 mL) and Ethyl acetate (2 mL). The two layers were separated, the aqueous layer was extracted three times with Ethyl acetate (3×2 mL). The combined organic layers were washed with Brine (2 mL), dried over sodium sulfate and concentrated in vacuum. The crude residue was purified by silica gel chromatography using cyclohexane/ethyl acetate 50:50 to 0:100 as eluents to afford the expected product (13 mg, 52% yield) as a yellowish amorphous solid.

LCMS (MA) RT=2.00 min, m/z=422.2 $(M+H)^+$.

LCMS (MC) RT=2.02 min, m/z=422.3 $(M+H)^+$.

$^1$H NMR (400 MHz, DMSO) 9.00 (1H, d, J=7.6 Hz), 8.63 (1H, s), 8.04-8.03 (1H, m), 7.50 (1H, s), 7.05 (1H, dd, J=1.4, 2.4 Hz), 6.67 (1H, d, J=7.4 Hz), 6.37 (1H, s), 4.93 (1H, d, J=10.4 Hz), 4.52-4.47 (1H, m), 4.37-4.31 (1H, m), 3.95 (1H, t, J=10.8 Hz), 3.46-3.45 (4H, m), 3.28-3.24 (2H, m), 2.58-2.57 (3H, m), 2.44 (1H, dd, J=8.6, 15.4 Hz), 2.05-1.92 (1H, m). One proton was overlapped by the water signal.

Similarly Prepared:

| Ex no | Structure/Name | From intermediates | Analytical data |
|---|---|---|---|
| 98 | 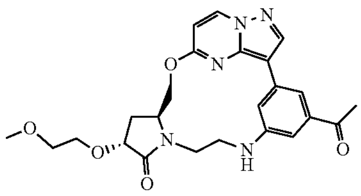 [SMILES: COCCO[C@@H]1C[C@H]2COc3ccn4ncc(c4n3)-c3cc(cc(C(C)=O)c3)NCCN2C1=O] (12R,14S)-4-acetyl-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaen-11-one | Scaffold 3-bromo-5-chloro-pyrazolo[1,5-a]pyrimidine Pyrrolidine P7 Aniline A9 64% yield as yellow solid | LCMS (MA) RT = 1.96 min, m/z = 466.4 $(M + H)^+$. LCMS (MC) RT = 1.96 min, m/z = 466.4 $(M + H)^+$. $^1$H NMR (400 MHz, DMSO) 9.00 (1H, d, J = 7.4 Hz), 8.64 (1H, s), 8.04 (1H, Is), 7.50-7.49 (1H, m), 7.05-7.04 (1H, m), 6.68 (1H, d, J = 7.6 Hz), 6.37 (1H, t, J = 5.9 Hz), 4.95-4.91 (1H, m), 4.52-4.43 (2H, m), 4.00-3.92 (2H, m), 3.68-3.62 (1H, m), 3.58-3.48 (1H, m), 3.48 (2H, t, J = 4.8 Hz), 3.41-3.35 (1H, m), 3.29-3.23 (2H, m), 3.26 (3H, s), 2.57 (3H, s), 2.47-2.42 (1H, m), 2.02-1.91 (1H, m). |

-continued

| Ex no | Structure/Name | From intermediates | Analytical data |
|---|---|---|---|
| 99 | 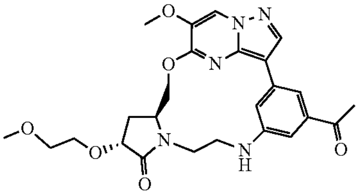 [SMILES: COCCO[C@@H]1C[C@H]2COc3nc4c(cnn4cc3OC)-c3cc(cc(C(C)=O)c3)NCCN2C1=O] (12R,14S)-4-acetyl-18-methoxy-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S2 Pyrrolidine P7 Aniline A9 64% yield as yellow solid | LCMS (MA) RT = 1.97 min, m/z = 496.4 (M + H)$^{+}$. LCMS (MC) RT = 1.97 min, m/z = 496.4 (M + H)$^{+}$. $^{1}$H NMR (400 MHz, DMSO) 8.79 (1H, s), 8.49 (1H, s), 7.99-7.99 (1H, m), 7.47 (1H, s), 7.03 (1H, t, J = 1.9 Hz), 6.36 (1H, t, J = 5.7 Hz), 4.95 (1H, d, J = 10.2 Hz), 4.48-4.43 (2H, m), 3.91-3.90 (6H, m), 3.68-3.62 (1H, m), 3.50-3.46 (3H, m), 3.27-3.26 (6H, m), 2.65-2.55 (3H, m); 2.01-1.93 (1H, m) |

Example 55: (12R,14S)—N,12-dimethoxy-N-methyl-11-oxo-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaene-4-carboxamide

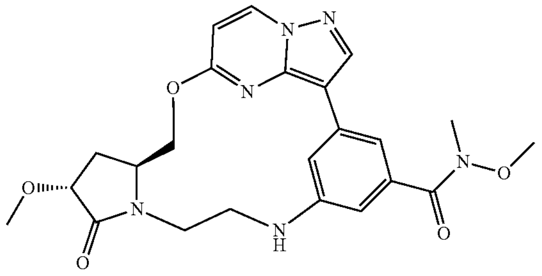

Following the general synthetic scheme 1, as depicted for the synthesis of Example 1, Methyl (12R,14S)-12-methoxy-11-oxo-16-oxa-7,10,20,21,24-pentaazapentacyclo[15.5.2.12,6.010,14.020,23]pentacosa-1(23),2,4,6(25),17(24),18,21-heptaene-4-carboxylate was obtained as Intermediate I20 using Scaffold 3-bromo-5-chloro-pyrazolo[1,5-a]pyrimidine, Pyrrolidine P1 and Aniline A18.

Step 1

To a solution of Intermediate I20 (0.32 g, 0.731 mmol) in Methanol (15 mL), Tetrahydrofuran (15 mL) and water (15 mL) was added 1N sodium hydroxide solution (3.6 mL, 3.657 mmol). The reaction mixture was stirred at 50° C. for 3 h. The reaction mixture was cooled to room temperature, then slightly acidified with a of 1N HCl solution (~pH=4-5) and concentrated under reduced pressure. Water was added to the residue. The resulting precipitate was filtered, washed with water, then pentane and dried to afford the title compound (280 mg, 90% yield) as an off-white solid.

L36119-1 LCMS (MA) RT=1.89 min, m/z=424.1 (M+H)$^{+}$.

Step 2

To a solution of the title compound from Step 1 (50 mg, 0.118 mmol) in N,N-dimethylformamide (5 mL) were added HATU (67 mg, 0.177 mmol), N-Methoxymethanamine hydrochloride (35 mg, 0.354 mmol) and Triethylamine (0.08 mL, 0.59 mmol). The reaction mixture was stirred at room temperature for 1 h. The reaction mixture was concentrated under reduced pressure. Water was added to the residue and after extraction with Dichloromethane, the combined organic phases were dried over anhydrous sodium sulfate, filtered and concentrated under reduced pressure. The residue was purified by preparative TLC (eluting solvent 90-10% Dichloromethane/methanol). The gummy residue was triturated with Dichloromethane/pentane (1:4). The resulting precipitate was filtered, washed with pentane and dried under reduced pressure to afford the expected product (35 mg, 63% yield) as a white solid.

LCMS (MA) RT=1.90 min, m/z=467.1 (M+H)$^{+}$.

LCMS (MC) RT=1.89 min, m/z=467.2 (M+H)$^{+}$.

$^{1}$H NMR (400 MHz, DMSO): 8.99 (1H, d, J=7.4 Hz), 8.55 (1H, s), 7.93-7.89 (1H, m), 7.06 (1H, s), 6.67-6.62 (2H, m), 6.31-6.26 (1H, m), 4.95 (1H, d, J=10.6 Hz), 4.49 (1H, t, J=8.1 Hz), 4.37-4.31 (1H, m), 3.95 (1H, t, J=10.7 Hz), 3.61 (3H, s), 3.58-3.51 (1H, m), 3.46 (3H, s), 3.44-3.36 (1H, m), 3.26 (3H, m), 3.26-3.17 (2H, m), 2.47-2.42 (1H, m), 2.02-1.93 (1H, m).

Similarly Prepared:

| Ex no | Structure/Name | From intermediates | Analytical data |
|---|---|---|---|
| 56 | 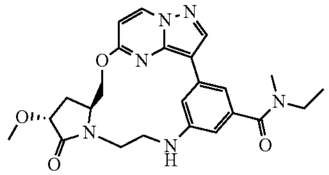 [SMILES: CCN(C)C(=O)c1cc2cc(c1)-c1cnn3ccc(nc13)OC[C@@H]1C[C@@H](OC)C(=O)N1CCN2] (12R,14S)-N-ethyl-12-methoxy-N-methyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carboxamide | Scaffold 3-bromo-5-chloro-pyrazolo[1,5-a]pyrimidine Pyrrolidine P1 Aniline A18 76.5% yield as an off-white solid | LCMS (MA) RT = 1.96 min, m/z = 465.1 $(M + H)^+$. LCMS (MC) RT = 1.97 min, m/z = 465.1 $(M + H)^+$. $^1$H NMR (400 MHz, DMSO): 8.99 (1H, d, J = 7.6 Hz), 8.56 (1H, s), 7.87 (1H, brs), 6.88 (1H, s), 6.67-6.65 (1H, d, J = 7.4 Hz), 6.40 (1H, s), 6.25 (1H, brs), 4.95 (1H, d, J = 10.2 Hz), 4.50 (1H, t, J = 8.1 Hz), 4.37-4.31 (1H, m), 3.96 (1H, t, J = 10.8 Hz), 3.60-3.51 (1H, m), 3.46 (3H, s), 3.44-3.38 (1H, m), 3.30-3.21 (2H, m), 2.95-2.83 (5H, m), 2.47 2.42 (1H, m), 2.02-1.93 (1H, m), 1.14 (3H, t, J = 7.2 Hz). |
| 57 | 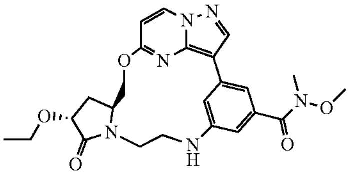 [SMILES: CCO[C@@H]1C[C@H]2COc3ccn4ncc(c4n3)-c3cc(cc(C(=O)N(C)OC)c3)NCCN2C1=O] (12R,14S)-12-ethoxy-N-methoxy-N-methyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaene-4-carboxamide | Scaffold 3-bromo-5-chloro-pyrazolo[1,5-a]pyrimidine Pyrrolidine P1 Aniline A18 14% yield as an pale yellow solid | LCMS (MA) RT = 2.02 min, m/z = 481 $(M + H)^+$. LCMS (MC) RT = 1.96 min, m/z = 481.2 $(M + H)^+$. $^1$H NMR (400 MHz, DMSO): 8.99 (1H, d, J = 7.6 Hz), 8.55 (1H, s), 7.96-7.91 (1H, m), 7.06 (1H, s), 6.68-6.62 (2H, m), 6.29 (1H, t, J = 6.1 Hz), 4.95 (1H, d, J = 10.8 Hz), 4.51-4.39 (2H, m), 4.00-3.83 (2H, m), 3.33-3.32 (4H, m), 3.30 (1H, s), 3.26-3.25 (5H, m), 2.45-2.40 (1H, m), 2.01-1.93 (1H, m), 1.17-1.13 (4H, m). |
| 58 | 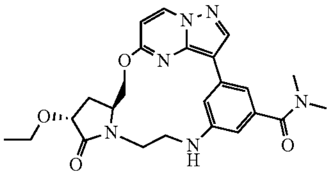 [SMILES: CCO[C@@H]1C[C@H]2COc3ccn4ncc(c4n3)-c3cc(cc(C(=O)N(C)C)c3)NCCN2C1=O] (12R,14S)-12-ethoxy-N,N-dimethyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaene-4-carboxamide | Scaffold 3-bromo-5-chloro-pyrazolo[1,5-a]pyrimidine Pyrrolidine P2 Aniline A18 62% yield as a yellow solid | LCMS (MA) RT = 1.98 min, m/z = 465 $(M + H)^+$. LCMS (MC) RT = 1.97 min, m/z = 465.2 $(M + H)^+$. $^1$H NMR (400 MHz, DMSO): 9.00-8.97 (1H, m), 8.55-8.55 (1H, m), 7.86 (1H, s), 6.90 (1H, s), 6.66 (1H, d, J = 7.6 Hz), 6.44-6.42 (1H, m), 6.27 6.22 (1H, m), 4.94 (1H, d, J = 11.6 Hz), 4.51-4.39 (2H, m), 4.00-3.83 (2H, m), 3.62-3.51 (2H, m), 2.97 (6H, s), 2.70-2.69 (2H, m), 2.45-2.40 (1H, m), 2.02-1.91 (1H, m), 1.18-1.10 (4H, m). |
| 59 | 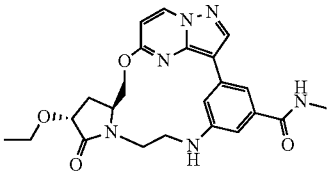 [SMILES: CCO[C@@H]1C[C@H]2COc3ccn4ncc(c4n3)-c3cc(cc(C(=O)NC)c3)NCCN2C1=O] (12R,14S)-12-ethoxy-N-methyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaene-4-carboxamide | Scaffold 3-bromo-5-chloro-pyrazolo[1,5-a]pyrimidine Pyrrolidine P2 Aniline A18 39% yield as a white solid | LCMS (MA) RT = 1.92 min, m/z = 451 $(M + H)^+$. LCMS (MC) RT = 1.91 min, m/z = 451.3 $(M + H)^+$. $^1$H NMR (400 MHz, DMSO): 9.00-8.98 (1H, m), 8.49 (1H, s), 8.28 (1H, q, J = 4.5 Hz), 7.94-7.92 (1H, m), 7.36 (1H, s), 6.94 (1H, dd, J = 1.4, 2.4 Hz), 6.68-6.65 (1H, m), 6.25 (1H, t, J = 5.9 Hz), 4.93 (1H, d, J = 11.0 Hz), 4.49-4.39 (2H, m), 4.00-3.83 (2H, m), 3.67-3.51 (2H, m), 3.45-3.35 (1H, m), 3.25-3.15 (2H, m), 2.79 (3H, d, J = 4.6 Hz), 2.01-1.91 (1H, m), 1.17-1.13 (4H, m). |

-continued

| Ex no | Structure/Name | From intermediates | Analytical data |
|---|---|---|---|
| 60 | 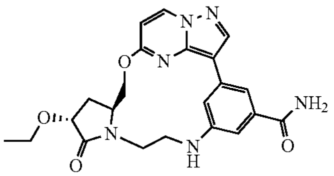 [SMILES: CCO[C@@H]1C[C@H]2COc3ccn4ncc(c4n3)-c3cc(cc(C(N)=O)c3)NCCN2C1=O] (12R,14S)-12-ethoxy-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaene-4-carboxamide | Scaffold 3-bromo-5-chloro-pyrazolo[1,5-a]pyrimidine Pyrrolidine P2 Aniline A18 68% yield as a yellow solid | LCMS (MA) RT = 1.85 min, m/z = 437 $(M + H)^+$. LCMS (MC) RT = 1.83 min, m/z = 437.2 $(M + H)^+$. $^1$H NMR (400 MHz, DMSO): 8.99 (1H, d, J = 7.4 Hz), 8.50-8.50 (1H, m), 7.93-7.93 (1H, m), 7.81-7.79 (1H, m), 7.42 (1H, s), 7.24 (1H, s), 6.97 (1H, dd, J = 1.5, 2.3 Hz), 6.66 (1H, d, J = 7.4 Hz), 6.25-6.20 (1H, m), 4.94 (1H, d, J = 10.4 Hz), 4.51-4.39 (2H, m), 4.00-3.83 (2H, m), 3.61-3.52 (2H, m), 3.29-3.20 (1H, m), 2.70-2.69 (2H, m), 2.01-1.93 (1H, m), 1.18-1.10 (4H, m). |
| 61 | 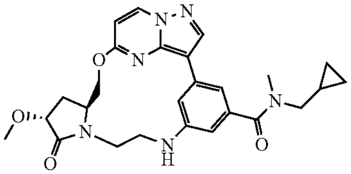 [SMILES: CO[C@@H]1C[C@H]2COc3ccn4ncc(c4n3)-c3cc(cc(C(=O)N(C)CC4CC4)c3)NCCN2C1=O] (12R,14S)-N-(cyclopropylmethyl)-12-methoxy-N-methyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carboxamide | Scaffold 3-bromo-5-chloro-pyrazolo[1,5-a]pyrimidine Pyrrolidine P1 Aniline A18 60% yield as an off-white solid | LCMS (MA) RT = 2.12 min, m/z = 491.2 $(M + H)^+$ LCMS (MC) RT = 2.12 min, m/z = 491.2 $(M + H)^+$ $^1$H NMR (400 MHz, DMSO): 8.98 (1H, d, J = 7.6Hz), 8.56 (1H, s), 7.89-7.87 (1H, m), 6.88 (1H, s), 6.65 (1H, d, J = 7.4 Hz), 6.41 (1H, d, J = 0.8 Hz), 6.25 (1H, t, J = 5.8 Hz), 4.96 (1H, d, J = 11.2 Hz), 4.50-4.48 (1H, m), 4.37-4.31 (1H, m), 3.95 (1H, t, J = 10.7 Hz), 3.59-3.51 (1H, m), 3.45 (3H, s), 3.27-3.21 (2H, m), 3.04-2.98 (3H, m), 2.9-2.85 (3H, m), 2.47-2.42 (1H, m), 2.02-1.93 (1H, m), 1.08-0.9 (1H, m), 0.54-0.43 (3H, m), 0.34-0.26 (1H, m). |
| 62 | 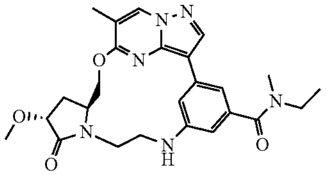 [SMILES: CCN(C)C(=O)c1cc2cc(c1)-c1cnn3cc(C)c(nc13)OC[C@@H]1C[C@@H](OC)C(=O)N1CCN2] (12R,14S)-N-ethyl-12-methoxy-N,18-dimethyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaene-4-carboxamide | Scaffold S2 Pyrrolidine P1 Aniline A18 5% yield as a white solid | LCMS (MD) RT = 2.668 min, m/z = 479.2 $(M + H)^+$. LCMS (ME) RT = 3.203 min, m/z = 479.1 $(M + H)^+$. $^1$H NMR (400 MHz, DMSO) d 8.90 (d, J = 0.9 Hz, 1H), 8.46 (s, 1H), 7.86 (s, 1H), 6.86 (s, 1H), 6.39 (s, 1H), 6.23 (s, 1H), 4.97 (d, J = 10.5 Hz, 1H), 4.49 (t, J = 8.1 Hz, 1H), 4.36 (t, J = 8.9 Hz, 1H), 4.00 (t, J = 10.7 Hz, 1H), 3.66-3.50 (m, 1H), 3.45 (s, 3H), 3.43 (d, J = 3.6 Hz, 1H), 3.38 (dd, J = 13.0, 3.2 Hz, 1H), 3.29-3.17 (m, 3H), 2.93 (s, 3H), 2.49-2.44 (m, 1H), 2.19 (s, 3H), 1.96 (dt, J = 12.2, 9.1 Hz, 1H), 1.11 (brs, 3H). |
| 63 | 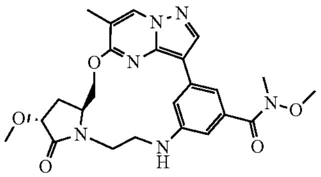 (12R,14S)-N,12-dimethoxy-N,18-dimethyl-11-oxo-16-oxa-7,10,20,21,24-pentaazapentacyclo[15.5.2.1$^{2}$,6.0$^{10}$,$^{1}$4.0$^{20}$,$^{23}$]pentacosa-1(23),2,4,6(25),17(24),18,21-heptaene-4-carboxamide | Scaffold S2 Pyrrolidine P1 Aniline A18 37% yield as a white solid | LCMS (MD) RT = 2.401 min, m/z = 481.2 $(M + H)^+$ LCMS (ME) RT = 3.153 min, m/z = 481.1 $(M + H)^+$ $^1$H NMR (400 MHz, DMSO) 8.91 (d, J = 1.2 Hz, 1H), 8.45 (s, 1H), 7.90 (s, 1H), 7.05 (s, 1H), 6.61 (d, J = 1.3 Hz, 1H), 6.27 (t, J = 5.8 Hz, 1H), 4.98 (d, J = 10.8 Hz, 1H), 4.49 (t, J = 9.0 Hz, 1H), 4.36 (t, J = 8.8 Hz, 1H), 4.00 (t, J = 10.8 Hz, 1H), 3.61 (s, 2H), 3.55 (dd, J = 13.0, 7.9 Hz, 2H), 3.45 (s, 2H), 3.40 (dd, J = 18.2, 8.3 Hz, 1H), 3.30 (s, 2H), 3.25 (s, 3H), 3.19 |

-continued

| Ex no | Structure/Name | From intermediates | Analytical data |
|---|---|---|---|
| | | | (dd, J = 15.7, 4.7 Hz, 2H), 2.19 (d, J = 1.0 Hz, 3H), 1.96 (dd, J = 21.5, 8.9 Hz, 1H). |
| 107 | 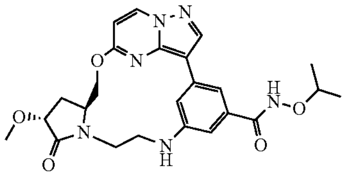 [SMILES: CO[C@@H]1C[C@H]2COc3ccn4ncc(c4n3)-c3cc(cc(C(=O)NOC(C)C)c3)NCCN2C1=O] (12R,14S)-12-methoxy-11-oxo-N-(propan-2-yloxy)-16-oxa-7,10,20,21,24-pentaazapentacyclo[15.5.2.$1^{2}$,6.$0^{10}$,$^{1}$4.$0^{20}$,$^{23}$]pentacosa-1(23),2,4,6(25),17(24),18,21-heptaene-4-carboxamide | Scaffold 3-bromo-5-chloro-pyrazolo[1,5-a]pyrimidine Pyrrolidine P1 Aniline A18 88% yield as an beige solid | LCMS (MA) RT = 1.870 min, m/z = 481.3 $(M + H)^+$ LCMS (MC) RT = 2.84 min, m/z = 481.4 $(M + H)^+$ $^1$H NMR (400 MHz, $CDCl_3$) 9.24-9.21 (1H, m), 8.52-8.48 (1H, m), 8.35 (1H, s), 7.97 (1H, s), 7.26 (1H, m), 6.90-6.87 (1H, m), 6.41-6.38 (1H, m), 4.99 (1H, d, J = 10.6 Hz), 4.54-4.20 (4H, m), 3.81-3.64 (2H, m), 3.60 (3H, s), 3.56-3.44 (2H, m), 3.23 (1H, q, J = 7.3 Hz), 2.66-2.58 (1H, m), 2.14-2.06 (1H, m), 1.40-1.33 (6H, m). |

Example 64: (12R,14S)-4-(hydroxymethyl)-12-methoxy-18-methyl-16-oxa-7,10,20,21,24-pentaaza-pentacyclo[15.5.2.$1^{2}$,6.$0^{1o}$,$^{1}$4.$0^{2o}$,$^{23}$]pentacosa-1(23),2,4,6(25),17(24),18,21-heptaen-11-one

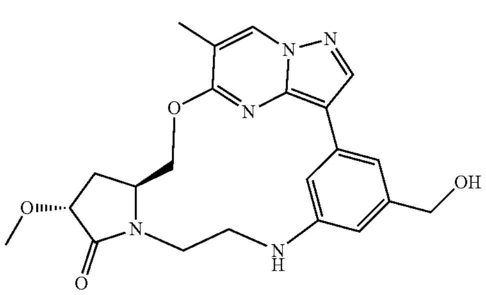 [SMILES: CO[C@@H]1C[C@H]2COc3nc4c(cnn4cc3C)-c3cc(CO)cc(c3)NCCN2C1=O]

Following the general synthetic scheme 1, as depicted for the synthesis of Example 1, Methyl (12R,14S)-12-methoxy-18-methyl-11-oxo-16-oxa-7,10,20,21,24-pentaazapentacyclo[15.5.2.12,6.010,14.020,23]pentacosa-1(23),2,4,6(25),17(24),18,21-heptaene-4-carboxylate was obtained as Intermediate I21 using Scaffold S1, Pyrrolidine P1 and Aniline A18.

Step 1 Intermediate I21 (50 mg, 0.11 mmol) was suspended in water (2 mL) and hydrochloric acid 37% solution (2 mL) was added. The reaction mixture was stirred at room temperature for 16 h. The mixture was concentrated under reduced pressure and co-evaporated with Heptane. The crude residue was dried under vacuum to afford the expected compound as pink solid. The crude was used in the next step without further purifications.

LCMS (MH) RT=0.696 min, m/z=438.1 $(M+H)^+$.

Step 2 Borane dimethyl sulfide complex (2M/THF) (1.14 mL, 2.11 mmol) was added to a stirred solution of the title compound from Step 1 (100 m g, 0.211 mmol) in dry THE (3 mL) under Nitrogen atmosphere at 0° C. The reaction mixture was warmed to ambient temperature and stirred for 1 h. The reaction mixture was cooled down to 0° C. and quenched with a few drops of methanol. The solvent was removed under reduced pressure. The residue was purified by silica gel chromatography (eluting gradient 0-2.5% Dichloromethane/methanol) to afford the expected product (40 mg. 45% yield) as a white solid.

LCMS (MD) RT=2.374 min, m/z=424.1 $(M+H)^+$.

LCMS (ME) RT=2.977 min, m/z=424.1 $(M+H)^+$.

$^1$H NMR (400 MHz, DMSO) δ 8.88 (d, J=1.2 Hz, 1H), 8.34 (s, 1H), 7.67 (s, 1H), 6.83 (s, 1H), 6.45 (s, 1H), 6.02 (t, J=5.9 Hz, 1H), 5.04 (t, J=5.7 Hz, 1H), 4.94 (d, J=10.7 Hz, 1H), 4.46 (t, J=8.5 Hz, 1H), 4.42 (d, J=5.8 Hz, 2H), 4.36 (d, J=8.0 Hz, 1H), 3.99 (t, J=10.7 Hz, 1H), 3.60-3.48 (m, 1H), 3.45 (s, 3H), 3.38 (dd, J=9.6, 3.6 Hz, 1H), 3.25-3.12 (m, 2H), 2.46 (dd, J=12.0, 6.0 Hz, 1H), 2.18 (d, J=1.0 Hz, 3H), 1.96 (dd, J=21.4, 8.7 Hz, 1H).

Examples 65 & 66: (12R or S,14S)-12-methoxy-4-(methoxymethyl)-18-methyl-16-oxa-7,10,20,21,24-pentaazapenta cyclo[15.5.2.$1^{2,6}$.$0^{10,14}$.$0^{20,23}$]pentacosa-1(23),2,4,6(25),17(24), 18,21-heptaen-11-one (single unknown isomer 1, single unknown isomer 2)

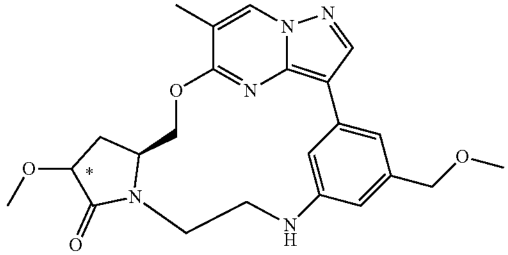

Step 1

To a stirred solution of Example 64 (150 mg, 0.354 mmol) in Dichloromethane (4.5 mL) was added Thionyl chloride (0.129 mL, 1.170 mmol). The reaction was stirred at room temperature for 1 h. The solvent was removed under reduced pressure. The residue was diluted with toluene and evaporated to dryness to afford the title compound (160 mg) as a beige solid, which was used without further purifications.

LCMS (MD) RT=0.860 min, m/z=444.1 $(M+H)^+$.

Step 2

To a solution of the title compound from Step 1 (160 mg, 0.362 mmol) in Methanol (6 mL) was added Sodium methoxide solution (25 Wt. % in methanol) (1.6 mL). The reaction mixture was stirred at 80° C. for 3 h. A saturated aqueous sodium bicarbonate solution was added and the mixture was extracted with ethyl acetate. The combined organic layers were dried over anhydrous magnesium sulfate, filtered and concentrated under reduced pressure.

Reverse Phase Purification:

72% [25 mM $NH_4HCO_3$]-28% [Acetonitrile:Methanol 1:1] 36% [25 mM $NH_4HCO_3$]-64% [Acetonitrile:Methanol 1:1]

Example 65: Single Unknown Isomer 1

70 mg, 44.3% yield as a white solid

LCMS (MD) RT=2857 min, m/z=438.1 $(M+H)^+$.

LCMS (ME) RT=3.349 min, m/z=438.2 $(M+H)^+$.

$^1$H NMR (400 MHz, DMSO) δ 8.88 (dd, J=12.0, 6.0 Hz, 1H), 8.38 (s, 1H), 7.73 (s, 1H), 6.84 (s, 1H), 6.42 (s, 1H), 6.07 (t, J=5.8 Hz, 1H), 4.95 (d, J=10.6 Hz, 1H), 4.48 (t, J=9.1 Hz, 1H), 4.36 (d, J=8.0 Hz, 1H), 4.32 (s, 2H), 3.99 (t, J=10.7 Hz, 1H), 3.60-3.48 (m, 1H), 3.45 (s, 3H), 3.43-3.35 (m, 1H), 3.29 (s, 3H), 3.27-3.16 (m, 2H), 2.48-2.42 (m, 1H), 2.18 (s, 3H), 1.96 (dt, J=12.3, 8.3 Hz, 1H)

Example 66: Single Unknown Isomer 2

8.1 mg, 5.1% yield as a white solid.

LCMS (MD) RT=3.007 min, m/z=438.2 $(M+H)^+$.

LCMS (ME) RT=3.390 min, m/z=: 438.1 $(M+H)^+$.

$^1$H NMR (400 MHz, DMSO) δ 8.88 (d, J=1.2 Hz, 1H), 8.38 (s, 1H), 7.73 (s, 1H), 6.84 (s, 1H), 6.42 (s, 1H), 6.07 (t, J=5.8 Hz, 1H), 5.11 (d, J=10.6 Hz, 1H), 4.50-4.40 (m, 1H), 4.33 (s, 2H), 3.93 (t, J=10.5 Hz, 1H), 3.80 (d, J=6.4 Hz, 1H), 3.67-3.53 (m, 1H), 3.45 (s, 3H), 3.30 (d, J=3.8 Hz, 4H), 3.24 (dd, J=11.0, 6.1 Hz, 1H), 3.19-3.06 (m, 1H), 2.41-2.30 (m, 1H), 2.18 (d, J=0.7 Hz, 3H), 1.98 (d, J=14.1 Hz, 1H).

Example 67: (12R,14S)-4-fluoro-12-methoxy-18-(1-methyl-1H-pyrazol-4-yl)-16-oxa-7,10,20,21,24-pentaazapentacyclo[15.5.2.1$^2$,6.0$^{1o}$,$^1$4.0$^{2o}$,$^{23}$]pentacosa-1(23),2(25),3,5,17(24), 18,21-heptaen-11-one

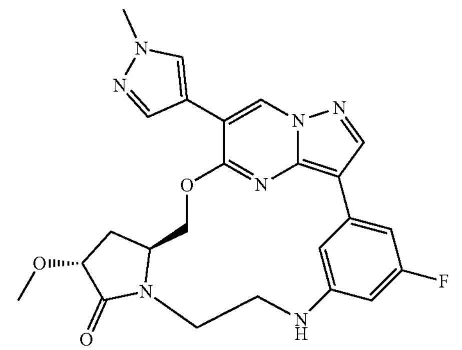 [SMILES: CO[C@@H]1C[C@H]2COc3nc4c(cnn4cc3-c3cnn(C)c3)-c3cc(F)cc(c3)NCCN2C1=O]

Following the general synthetic scheme 1, as depicted for the synthesis of Example 1, (12R,14S)-18-(benzyloxy)-4-fluoro-12-methoxy-7-(2-nitrobenzenesulfonyl)-16-oxa-7,10,20,21,24-pentaazapentacyclo[15.5.2.12,6.010,14.020,23]pentacosa-1(23),2,4,6(25),17(24),18,21-heptaen-11-one was obtained as Intermediate I22 using Scaffold S3, Pyrrolidine P1 and Aniline A1.

Step 1

In a sealed tube was added Intermediate I22 (664 mg, 0.964 mmol), Anisole (4.212 mL, 38.56 mmol) and trifluoroacetic acid (4.5 mL). The reaction mixture was stirred at 130° C. for 16 h.

Solvent was removed under reduced pressure and the product was crystallized in Acetonitrile to afford the title compound (Intermediate I28, (12R,14S)-4-fluoro-18-hydroxy-12-methoxy-7-(2-nitrobenzenesulfonyl)-16-oxa-7,10,20,21,24-pentaazapentacyclo[15.5.2.12,6.010, 14.020, 23]pentacosa-1 (23),2,4,6(25),17(24),18,21-heptaen-11-one) (432 mg, 75% yield) as a brown solid.

LCMS (MH) RT=0.821 min, m/z=599 $(M+H)^+$.

Step 2

Trifluoromethanesulfonic anhydride (0.061 mL, 0.367 mmol) was added to a stirred solution of the title compound from Step 1 (200 mg, 0.334 mmol) and Pyridine (0.079 mL, 1.002 mmol) in dry Dichloromethane (2 mL). The reaction mixture was stirred at room temperature for 1 h. An aqueous saturated solution of sodium bicarbonate was added and extracted with ethyl acetate. The combined organic phases were dried over anhydrous magnesium sulfate, filtered and concentrated under reduced pressure. The residue was purified by silica gel chromatography (eluting gradient 0-2% Dichloromethane/methanol) to afford expected compound (220 mg, 90% yield) as a brown solid.

LCMS (MH) RT=1.084 min, m/z=730.9 $(M+H)^+$.

Step 3

In a pressure flask, the title compound from Step 2 (100 mg, 0.137 mmol), 1,5-dimethyl-1H-pyrazole-4-boronic acid, pinacol ester (36 mg, 0.164 mmol), and Potassium phosphate tribasic (87 mg, 0.411 mmol) were mixed in Dioxane/water (4:1) (2 mL). The reaction mixture was bubbled with a Nitrogen stream for 5 min. Then Tetrakis (triphenylphosphine)palladium(0) (9 mg, 0.008 mmol) and Xphos (8 mg, 0.016 mmol) were added and the mixture was stirred at 80° C. for 2 h. Water was added and extracted with ethyl acetate. The combined organic phases were dried over anhydrous magnesium sulfate, filtered and concentrated under reduced pressure. The residue was purified by silica gel chromatography (eluting gradient 0-2% Dichloromethane/methanol) to afford the expected compound (22 mg, 24% yield) as a brown solid.

LCMS (MD) RT=3.423 min, m/z=677.1 $(M+H)^+$.

Step 4

Thiophenol (0.028 mL, 0.273 mmol) was added to a stirred solution of the title compound from Step 3 (0.060 g, 0.091 mmol) and Cesium carbonate (0.089 g, 0.273 mmol) in DMF (2.0 mL) at 0° C. The mixture was stirred at room temperature for 1 hour. Upon complete conversion, monitored by LCMS, an aqueous saturated solution of $NaHCO_3$ was added and the mixture was extracted with EtOAc. (×3). The combined organic layer was dried overmg$SO_4$, filtered and concentrated under vacuum. The product was purified by flash chromatography (on silica gel) using DCM/MeOH as eluents (100:0 to 97:3) to afford the expected product as a white solid (10 mg, 23.01%).

LCMS (MD) RT=2.977 min, m/z=478.1 $(M+H)^+$.

LCMS (ME) RT=3.551 min, m/z=478.1 $(M+H)^+$.

$^1$H NMR (400 MHz, DMSO) 9.38 (s, 1H), 8.52 (s, 1H), 8.29 (s, 1H), 8.11 (s, 1H), 7.68 (s, 1H), 6.76 (d, J=9.4 Hz, 1H), 6.34 (t, J=5.8 Hz, 1H), 6.21 (dt, J=11.8, 2.1 Hz, 1H), 5.06 (d, J=10.5 Hz, 1H), 4.53 (brs, 1H), 4.35 (t, J=8.9 Hz, 1H), 4.08 (t, J=10.7 Hz, 1H), 3.93 (s, 3H), 3.63-3.52 (m, 1H), 3.48 (s, 3H), 3.44-3.36 (m, 1H), 3.28-3.19 (m, 2H), 2.64 (dd, J=12.7, 8.2 Hz, 1H), 1.97 (dt, J=11.9, 9.0 Hz, 1H).

Similarly Prepared:

| Ex no | Structure/Name | From intermediates | Analytical data |
|---|---|---|---|
| 68 | 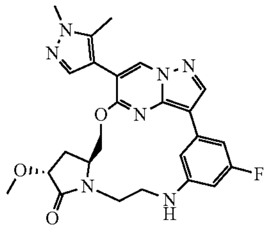 [SMILES: CO[C@@H]1C[C@H]2COc3nc4c(cnn4cc3-c3cnn(C)c3C)-c3cc(F)cc(c3)NCCN2C1=O] (12R,14S)-18-(1,5-dimethyl-1H-pyrazol-4-yl)-4-fluoro-12-methoxy-16-oxa-7,10,20,21,24-2.1$^{2}$,6.0$^{10}$,$^{1}$4.0$^{20}$,$^{23}$]pentacosa-1(23),2(25),3,5,17(24),18,21-heptaen-11-one | 1,5-dimethyl-1H-pyrazole-4-boronic acid, pinacol ester 67% yield as a beige solid | LCMS (MG) RT = 3.133 min, m/z = 492.05 $(M + H)^+$. LCMS (MD) RT = 4.550 min, m/z = 492.2 $(M + H)^+$. $^1$H NMR (400 MHz, DMSO) d 8.92 (s, 1H), 8.55 (s, 1H), 7.71 (s, 1H), 7.58 (s, 1H), 6.77 (d, J = 9.4 Hz, 1H), 6.35 (t, J = 5.8 Hz, 1H), 6.22 (dt, J = 11.8, 2.1 Hz, 1H), 4.98 (d, J = 10.4 Hz, 1H), 4.54 (t, J = 9.9 Hz, 1H), 4.32 (t, J = 8.8 Hz, 1H), 3.95 (t, J = 10.7 Hz, 1H), 3.82 (s, 3H), 3.64-3.51 (m, 1H), 3.44 (s, 3H), 3.42-3.36 (m, 1H), 3.28-3.19 (m, 2H), 2.44 (dd, J = 12.6, 8.2 Hz, 1H), 2.32 (s, 3H), 1.97 (dt, J = 12.0, 8.8 Hz, 1H). |
| 69 | 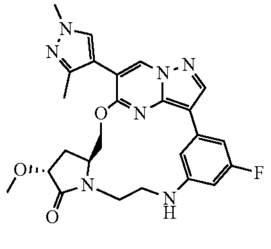 [SMILES: CO[C@@H]1C[C@H]2COc3nc4c(cnn4cc3-c3cn(C)nc3C)-c3cc(F)cc(c3)NCCN2C1=O] (12R,14S)-18-(1,3-dimethyl-1H-pyrazol-4-yl)-4-fluoro-12-methoxy-16-oxa-7,10,20,21,24-2.1$^{2}$,6.0$^{10}$,$^{1}$4.0$^{20}$,$^{23}$]pentacosa-1(23),2(25),3,5,17(24),18,21-heptaen-11-one | 1,3-dimethyl-1H-pyrazole-4-boronic acid, pinacol ester 62% yield as a beige solid | LCMS (MD) RT = 3.003 min m/z = 492.1 $(M + H)^+$ LCMS (ME) RT = 3.590 min m/z = 492.1 $(M + H)^+$. $^1$H NMR (400 MHz, DMSO) d 8.93 (s, 1H), 8.54 (s, 1H), 7.91 (s, 1H), 7.70 (s, 1H), 6.77 (d, J = 9.3 Hz, 1H), 6.35 (t, J = 5.8 Hz, 1H), 6.22 (dd, J = 11.8, 2.1 Hz, 1H), 4.99 (d, J = 10.4 Hz, 1H), 4.54 (s, 1H), 4.34 (t, J = 8.8 Hz, 1H), 3.97 (t, J = 10.7 Hz, 1H), 3.84 (s, 3H), 3.64-3.52 (m, 2H), 3.46 (s, 3H), 3.43-3.36 (m, 1H), 3.28-3.19 (m, 2H), 2.27 (s, 3H), 1.97 (dd, J = 21.6, 8.8 Hz, 1H). |

Example 70: (12R,14S)-4-ethynyl-12-methoxy-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one

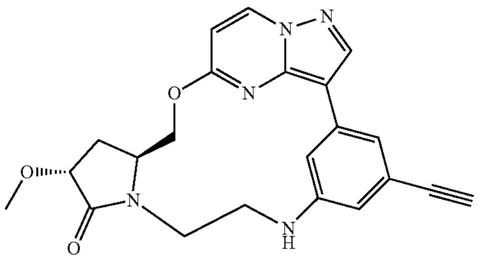 [SMILES: C#Cc1cc2cc(c1)-c1cnn3ccc(nc13)OC[C@@H]1C[C@@H](OC)C(=O)N1CCN2]

Step 1

To a solution of tert-butyl (2S,4R)-2-(hydroxymethyl)-4-methoxy-pyrrolidine-1-carboxylate (4.674 g, 20.21 mmol) in dry DMF (65 mL) was added sodium hydride, 60% in mineral oil (1.347 g, 33.68 mmol) at 0° C. After 30 min 3-Bromo-5-chloropyrazolo[1,5-a]pyrimidine (3.915 g, 16.84 mmol) was added and the mixture was stirred at 0° C. for 1 h. Monitoring by LCMS showed complete reaction. Water was added dropwise carefully at 0° C. and the mixture was extracted with EtOAc (4×50 mL). The combined organic layer was washed with Brine then dried over $Na_2SO_4$, filtered and concentrated under vacuum. the residue was purified by flash column chromatography using Cyclohexane/EtOAc (100/0 to 60/40) as eluent to afford the title compound as a yellow oil (3.831 g, 53% yield).

LCMS (MA) RT=2.73 min, m/z=428 $(M+H)^+$.

Step 2

A mixture of the title compound from Step 1 (0.327 g, 0.77 mmol), Aniline A11 (0.356 g, 0.99 mmol), Xphos (0.015 g, 0.03 mmol), and $K_3PO_4$ (0.487 g, 2.30 mmol) were dissolved in 1,4-Dioxane/Water (3 mL/1 mL) and degassed with Argon during 15 min.

Tetrakis(triphenylphosphine)palladium(0) (0.018 g, 0.02 mmol) was added and the reaction mixture was stirred at 110° C. for 3 h. Monitoring of the reaction mixture by LCMS showed the reaction was completed. The reaction mixture was cooled down and filtered over Celite then solvent was evaporated. The residue was purified by column chromatography using Cyclohexane/EtOAc (100/0 to 50/50) as eluent to afford the title compound as a yellow oil (0.272 g, 62% yield).

LCMS (MA) RT=3.55 min, m/z=578 $(M+H)^+$.

Step 3

To a solution of the title compound from Step 2 (0.272 g, 0.47 mmol) in Acetonitrile (3.4 mL) were added Pyridine (0.057 mL, 0.71 mmol) and 2-Nitrobenzene-1-sulfonyl chloride (0.136 g, 0.61 mmol). The reaction mixture was stirred at rt overnight. Monitoring reaction by LCMS showed complete reaction. The solvent was removed under reduced pressure and the residue was poured into water (40 mL) and EtOAc (80 mL). The aqueous layer was extracted with EtOAc (3×40 mL) and the organic layer was washed with Brine (2×40 mL), dried ($Na_2SO_4$), filtered and concentrated under reduced pressure to afford the title compound (0.485 g, quantitative yield) as an orange solid.

LCMS (MA) RT=3.72 min, m/z=763.3 $(M+H)^+$.

Step 4

To a solution of the title compound from Step 3 (0.485 g, 0.64 mmol) in Acetonitrile (4 mL) were added Cesium carbonate (0.621 g, 1.91 mmol) and 1,2-Dibromoethane (0.822 mL, 9.54 mmol). The reaction mixture was heated to reflux for 4 h. Monitoring of the reaction mixture by LCMS showed the reaction was completed. The mixture was taken in EtOAc (50 mL) extracted with Water (50 mL) then Brine (2×40 mL), the organic layer was dried over $Na_2SO_4$ anh. filtered and dried under vacuum. The residue was purified by column chromatography using Cyclohexane/EtOAc (100/0 to 60/40) as eluent to afford the title compound (0.301 g, 54% yield) as a yellow oil.

LCMS (MA) RT=3.82 min, m/z=870 $(M+H)^+$.

Step 5

To a suspension of the title compound from Step 4 (0.301 g, 0.35 mmol) in DCM (3 mL) was added Hydrogen Chloride solution 4M in 1,4-Dioxane (0.865 mL, 3.46 mmol). The reaction mixture was left stirring overnight. LCMS showed complete reaction. The solvent was removed under reduced pressure to afford the title compound as a yellow oil (0.489 g, quantitative yield).

LCMS (MA) Rt=2.60 min, m/z=770 $(M+H)^+$.

Step 6

To a solution of the title compound from Step 5 (0.489 g, 0.35 mmol postulated) in Acetonitrile (48 mL) were added Sodium hydrogenocarbonate (0.255 g, 3.03 mmol), Cesium carbonate (0.593 g, 1.82 mmol) then Potassium iodide (0.302 g, 1.82 mmol). The resulting mixture was heated at 90° C. for 6 h. Monitoring by LC/MS showed reaction was complete. The mixture was taken in EtOAc (50 mL) washed with Water (50 mL) and Brine (2×40 mL). The organic layer was dried over $Na_2SO_4$ anh. filtered and dried under vacuum. The residue was purified on silica gel column chromatography using Cyclohexane/EtOAc (100/0 to 50/50) as eluent to afford the title compound as a white solid (0.067 g, 28% yield) solid.

LCMS (MA) RT=3.31 min m/z=689 $(M+H)^+$.

Step 7

To a mixture of the title compound from Step 6 (0.067 g, 0.10 mmol) in THF/$H_2O$ (5 mL/2 mL) was added Sodium bicarbonate (0.163 g, 1.95 mmol). The reaction mixture was stirred 10 min at room temperature then Iodine (0.370 g, 1.46 mmol) was added. The reaction mixture was stirred at 60° C. for 2 h. Monitoring by LC/MS showed complete reaction. The reaction mixture was quenched by saturated Sodium thiosulfate solution then extracted by ethyl acetate. The organic layer was dried over anhydrous Sodium sulfate, filtered and evaporated under reduced pressure to afford the title compound as a purple solid (Intermediate I32, (12R, 14S)-12-methoxy-7-(2-nitrobenzenesulfonyl)-4-[2-(triethylsilyl)ethynyl]-16-oxa-7,10,20,21,24-pentaazapentacyclo [15.5.2.12,6.010,14.020,23]pentacosa-1(23),2,4,6(25),17 (24),18,21-heptaen-11-one, 0.150 g, quantitative yield).

LCMS (MA) RT=3.44 min, m/z=703 $(M+H)^+$.

Step 8

The title compound from Step 7 (150 mg, 0.10 mmol) and Cesium carbonate (139 mg, 0.43 mmol) were dissolved in N,N-Dimethylformamide (8 mL). 4-Methylbenzenethiol (32 mg, 0.26 mmol) was added and the mixture was stirred at room temperature for 2 h. The reaction mixture was filtered. Solvent was evaporated under reduced pressure. The residue was purified by silica gel chromatography using Dichloromethane/Methanol (100:0 to 98:2) as eluent) to afford the title compound (28 mg, 25% yield) as a yellow solid.

LCMS (MA) RT=3.34 min, m/z=518 $(M+H)^+$.

Step 9

To a solution of the title compound from Step 8 (28 mg, 0.05 mmol) in Methanol (2 mL) at room temperature, was added Potassium carbonate (37 mg, 0.27 mmol). The reaction mixture was heated at 50° C. for 16 h. The reaction mixture was poured in water and extracted with Ethyl acetate. The organic layer was washed with Brine, dried over anhydrous sodium sulfate, filtered and evaporated under reduced pressure. The residue was purified by silica gel chromatography using Cyclohexane/EtOAc (100:0 to 80:20) as eluent to afford the expected product (17 mg, 0.04 mmol) as a beige powder.

LCMS (MA) RT=2.25 min, m/z=404 $(M+H)^+$.

LCMS (MC) RT=2.25 min, m/z=404 $(M+H)^+$.

$^1$H NMR (400 MHz, DMSO) 9.00-8.97 (1H, m), 8.56-8.56 (1H, m), 7.87-7.86 (1H, m), 7.04 (1H, s), 6.66 (1H, d, J=7.4 Hz), 6.57-6.55 (1H, m), 6.23 (1H, t, J=6.0 Hz), 4.96-4.92 (1H, m), 4.50-4.45 (1H, m), 4.36-4.31 (1H, m), 4.03 (1H, s), 3.95 (1H, t, J=10.8 Hz), 3.58-3.52 (1H, m), 3.41-3.33 (1H, m), 3.32-3.31 (5H, m), 2.48-2.41 (1H, m), 2.00-1.94 (1H, m).

Similarly Prepared:

| Ex no | Structure/Name | From intermediates | Analytical data |
| --- | --- | --- | --- |
| 71 | 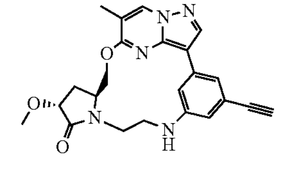 [SMILES: C#Cc1cc2cc(c1)-c1cnn3cc(C)c(nc13)OC[C@@H]1C[C@@H](OC)C(=O)N1CCN2] (12R,14S)-4-ethynyl-12-methoxy-18-methyl-16-oxa-7,10,20,21,24-$2.1^2,6.0^{10},{}^{14}.0^{20},{}^{23}$]pentacosa-1(23),2(25),3,5,17(24),18,21-heptaen-11-one | Scaffold S2<br>Pyrrolidine P1<br>Aniline A11<br>16% yield<br>as a beige solid | LCMS (MA) RT = 2.41 min, m/z = 418$(M + H)^+$. LCMS (MC) RT = 2.36 min, m/z = 418$(M + H)^+$. $^1$H NMR (400 MHz, DMSO) 8.90 (1H, d, J = 1.1 Hz), 8.47 (1H, s), 7.85 (1H, d, J = 1.1 Hz), 7.02 (1H, s), 6.56-6.54 (1H,m),6.22 (1H, t, J = 5.9 Hz), 4.98-4.95 (1H, m), 4.47 (1H, s), 4.38-4.33 (1H, m), 4.03-4.02 (2H, m), 3.54 (1H, dd, J = 6.6, 11.0 Hz), 3.45 (3H, s), 3.36-3.35 (1H, m), 3.25-3.10 (2H, m), 2.45-2.40 (1H, m), 2.19-2.18 (3H, m), 2.00-1.91 (1H, m). |

-continued

| Ex no | Structure/Name | From intermediates | Analytical data |
|---|---|---|---|
| 72 | 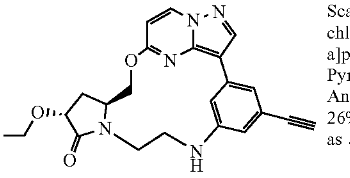 (12R,14S)-12-ethoxy-4-ethynyl-16-oxa-7,10,20,21,24-pentaazapentacyclo[15.5.2.1$^{2}$,6.0$^{10}$,$^{14}$.0$^{20}$,$^{23}$]pentacosa-21-heptaen-11-one | Scaffold 3-bromo-5-chloropyrazolo[1,5-a]pyrimidine Pyrrolidine P2 Aniline A11 26% yield as a white solid | LCMS (MA) RT = 2.50 min, m/z = 418.3 $(M + H)^+$. LCMS (MC) RT = 2.47 min, m/z = 418.2 $(M + H)^+$. $^1$H NMR (400 MHz, DMSO) 8.99 (1H, d, J = 7.4 Hz), 8.56 (1H, s), 7.86 (1H, s), 7.04 (1H, s), 6.66 (1H, d, J = 7.6 Hz), 6.57-6.55 (1H, m), 6.27-6.22 (1H, m), 4.96-4.90 (1H, m), 4.47-4.39 (2H, m), 4.04 (1H, s), 3.99-3.82 (2H, m), 3.61-3.49 (3H, m), 3.25-3.18 (2H, m), 2.46-2.41 (1H, m), 2.01-1.92 (1H, m), 1.15 (3H, t, J = 7.0 Hz). |

Example 73: Ethyl (12R,14S)-4-fluoro-12-methoxy-11-oxo-16-oxa-7,10,20,21,24-pentaazapentacyclo[15.5.2.1$^{2}$,6.0$^{10}$,$^{14}$.0$^{20}$,$^{23}$]pentacosa-1(23),2,4,6(25),17(24),18,21-heptaene-7-carboxylate

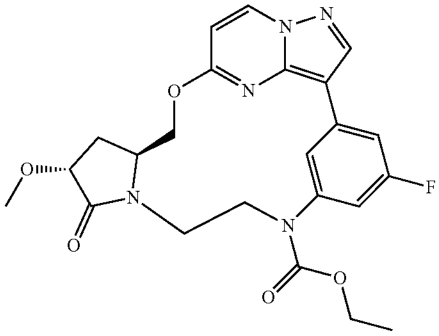 [SMILES: CCOC(=O)N1CCN2C(=O)[C@H](OC)C[C@H]2COc2ccn3ncc(c3n2)-c2cc(F)cc1c2]

To a solution of Example 3 (50 mg, 0.13 mmol) in Tetrahydrofuran (3 mL) was added Triethylamine (53 μL, 0.38 mmol) and Ethyl chloroformate (36 μL, 0.38 mmol) dropwise. The solution was stirred at room temperature for 36 h. Solvent was removed under reduced pressure. The residue was purified by preparative HPLC (Column XSELECT C18 19*100 mm 5 μm, $[(NH_4)_2CO_3$ aq 2 g/L/Acetonitrile] 45% B to 55% B in 7 min—19 mL/min R.T) to afford the expected product (33 mg, 56% yield) as a light yellow solid.

LCMS (MA) RT=2.47 min, m/z=470.2 $(M+H)^+$.

LCMS (MC) RT=2.47 min, m/z=470.3 $(M+H)^+$.

$^1$H NMR (400 MHz, DMSO) 9.02 (1H, d, J=7.4 Hz), 8.77-8.76 (1H, m), 8.54 (1H, s), 7.53-7.48 (1H, m), 7.37-7.31 (1H, m), 6.70 (1H, d, J=7.4 Hz), 5.06 (1H, d, J=11.2 Hz), 4.61 (1H, t, J=8.6 Hz), 4.37-4.17 (4H, m), 4.09-3.94 (2H, m), 3.63-3.52 (1H, m), 3.46 (3H, s), 3.41 (1H, d, J=12.2 Hz), 2.46-2.39 (1H, m), 2.00-1.88 (1H, m), 1.30 (3H, t, J=7.3 Hz).

Example 74: (12R,14S)-7-acetyl-4-fluoro-12-methoxy-16-oxa-7,10,20,21,24-pentaazapentacyclo[15.5.2.1$^{2}$,6.0$^{10}$,$^{14}$.0$^{20}$,$^{23}$]pentacosa-1(23),2,4,6(25),17(24),18,21-heptaen-11-one

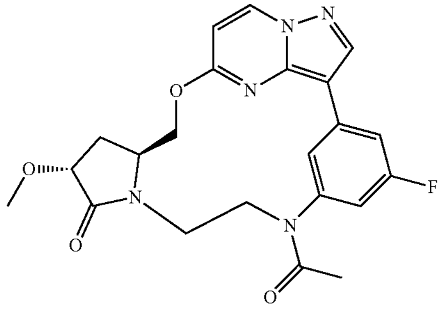 [SMILES: CO[C@@H]1C[C@H]2COc3ccn4ncc(c4n3)-c3cc(F)cc(c3)N(C(C)=O)CCN2C1=O]

To a solution of Example 3 (50 mg, 0.13 mmol) in Tetrahydrofuran (3 mL) was added Triethylamine (70 μL, 0.50 mmol) and acetyl chloride (20 μL, 0.28 mmol) dropwise. The reaction mixture was stirred at room temperature for 48 h. Solvent was removed under reduced pressure. The residue was purified by preparative HPLC. (Column XSELECT PHENYL-HEXYL 19*100 mm 5 μm $[(NH_4)_2CO_3$ aq. 2 g/L/Acetonitrile] 35% B to 45% B in 7 min 19 mL/min R.T) to afford the expected product (40 mg, 72% yield) as a white solid.

LCMS (MA) RT=2.12 min, m/z=440.2 $(M+H)^+$.

LCMS (MC) RT=2.13 min, m/z=440.3 $(M+H)^+$.

$^1$H NMR (400 MHz, DMSO) 9.03 (1H, d, J=7.6 Hz), 8.78 (1H, s), 8.62 (1H, s), 7.59 (1H, d, J=10.2 Hz), 7.25 (1H, s), 6.71 (1H, d, J=7.4 Hz), 5.06 (1H, d, J=10.6 Hz), 4.68-4.63 (1H, m), 4.33 (2H, t, J=8.9 Hz), 4.20-4.14 (1H, m), 3.98 (1H, t, J=10.9 Hz), 3.44 (3H, s), 3.35 (2H, s), 2.39 (1H, dd, J=8.1, 12.6 Hz), 2.20 (3H, s), 1.94-1.86 (1H, m).

Example 75: (12R,14S)-4-fluoro-12-methoxy-7-methyl-16-oxa-7,10,20,21,24-pentaazapentacyclo[15.5.2.1$^2$,6.0$^{1o}$,$^1$4.0$^{2o}$,$^{23}$]pentacosa-1(23),2(25),3,5,17(24),18,21-heptaen-11-one

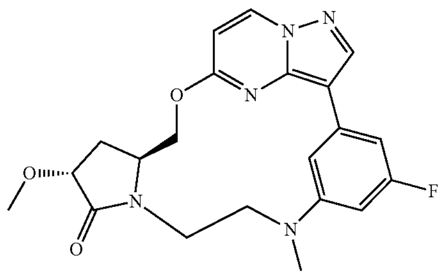 [SMILES: CO[C@@H]1C[C@H]2COc3ccn4ncc(c4n3)-c3cc(F)cc(c3)N(C)CCN2C1=O]

To a solution of Example 3 (50 mg, 0.13 mmol) in N,N-Dimethylformamide (5 mL) under argon atmosphere was added sodium hydride, (60% dispersion in mineral oil) (10 mg, 0.25 mmol) at room temperature. After 30 min Iodomethane (0.117 mL, 1.89 mmol) was added and the reaction mixture was stirred at room temperature for 2 h. Additional sodium hydride (60% dispersion in mineral oil) (10 mg, 0.25 mmol) and Iodomethane (0.117 mL, 1.89 mmol) were successively added after 2 h, 18 h, 20 h, 24 h, 40 h, 44 h until total conversion of starting material. Water and ethyl acetate were added to the reaction mixture. After extraction with Ethyl acetate (3×30 ml), the combined organic phase was dried over anhydrous sodium sulfate, filtered and concentrated under reduced pressure. Water and ethyl acetate were added to the reaction mixture. After extraction with ethyl acetate, the combined organic phases were dried over anhydrous sodium sulfate, filtered and concentrated under reduced pressure. The residue was purified by preparative HPLC (Column XSELECT C18 19*100 mm 5 μm [$(NH_4)_2CO_3$ aq 2 g/L/Acetonitrile] 45% B to 50% B in 7 min 19 mL/min R.T) to afford the expected product (15 mg, 29% yield) as a white solid.

LCMS (MA) RT=2.42 min, m/z=412 $(M+H)^+$.

LCMS (MC) RT=2.41 min, m/z=412 $(M+H)^+$.

$^1$H NMR (400 MHz, DMSO) 9.00 (1H, d, J=7.4 Hz), 8.56 (1H, s), 7.78 (1H, s), 6.83 (1H, d, J=9.9 Hz), 6.67 (1H, d, J=7.4 Hz), 6.33 (1H, d, J=12.9 Hz), 4.95 (1H, d, J=10.2 Hz), 4.49-4.46 (1H, m), 4.35 (1H, t, J=8.7 Hz), 3.96 (1H, t, J=10.5 Hz), 3.73 (2H, dd, J=12.6, 21.2 Hz), 3.46 (3H, s), 3.03-3.01 (3H, m), 2.00-1.91 (1H, m), 1.25-1.23 (2H, m), 0.87-0.83 (1H, m)

Example 76: (12R,14S)-12-methoxy-4-(1,2,4-oxadiazol-3-yl)-16-oxa-7,10,20,21,24-pentaazapentacyclo[15.5.2.1$^2$,6.0$^{1o}$,$^1$4.0$^{2o}$,$^{23}$]pentacosa-1(23),2(25),3,5,17(24),18,21-heptaen-11-one

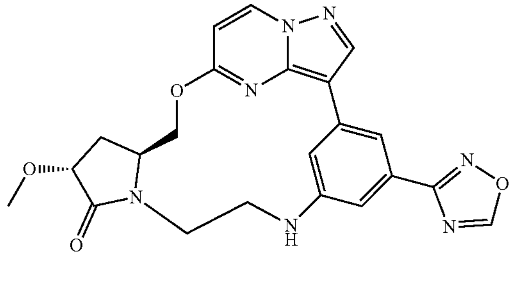 [SMILES: CO[C@@H]1C[C@H]2COc3ccn4ncc(c4n3)-c3cc(cc(-c4ncon4)c3)NCCN2C1=O]

Following the general synthetic scheme 1, as depicted for the synthesis of Example 1, (12R,14S)-12-methoxy-7-(2-nitrobenzenesulfonyl)-11-oxo-16-oxa-7,10,20,21,24-pentaazapentacyclo[15.5.2.12,6.010,14.020,23]pentacosa-1(23),2(25),3,5,17(24),18,21-heptaene-4-carbonitrile was obtained as Intermediate I23 using Scaffold 3-bromo-5-chloropyrazolo[1,5-a]pyrimidine, Pyrrolidine P1 and Aniline A6.

LCMS (MA) RT=2.38 min, m/z=590.2 $(M+H)^+$.

Step 1

To a solution of Intermediate I23 (589 mg, 1 mmol) in Ethanol/Water mixture (10 mL/4 mL) was added Sodium carbonate (318 mg, 3 mmol) and Hydroxylamine hydrochloride (271 mg, 3.9 mmol). The reaction mixture was stirred and heated to 65° C. for 2 h. The reaction mixture was cooled down and a precipitate appeared. The resulting precipitate was filtered and rinsed with cold diethyl ether then dried under reduced pressure to afford the title compound (520 mg, 83% yield) as a yellow solid.

LCMS (MA) RT=1.75 min, m/z=623.2 $(M+H)^+$.

Step 2

To a stirred solution of the title compound from Step 1 (520 mg, 0.83 mmol) in Tetrahydrofuran (5 mL) was added Triethyl orthoformate (0.415 mL, 2.5 mmol). The mixture was cooled 0° C. Boron trifluoride ethyl etherate (0.123 mL, 1 mmol) was then added dropwise and the reaction mixture was stirred at ambient temperature for 16 h. Additional Ethanol (5 mL) and Triethyl orthoformate (0.415 mL, 2.5 mmol) were added and the mixture was heated to reflux for 24 h. The reaction mixture was cooled down and the precipitate was filtered off and dried under reduced pressure. The residue was triturated with diethyl ether and dried to afford the title compound (454 mg, 87% yield) as a cream solid.

LCMS (MA) RT=2.44 min, m/z=633.1 $(M+H)^+$.

Step 3

To the title compound from Step 2 (0.454 g, 0.72 mmol) in DMF (3 mL) was added Cesium carbonate (469 mg, 1.44 mmol) and 4-Methylbenzenethiol (107 mg, 0.86 mmol), the reaction mixture was stirred at rt for 1 h. Monitoring of the reaction mixture by LCMS showed the reaction was completed. The reaction mixture was adsorbed on silica and evaporated to dryness. The residue was purified by chromatography using DCM/MeOH (98/2 to 85/15) as eluent. The expected fractions were combined and evaporated under reduced pressure. The residue was triturated in MeOH, filtered and dried under vacuum to afford the expected product (99 mg, 31%) a as a cream solid.

LCMS (MA) RT=2.12 min, m/z=448.1 $(M+H)^+$.

LCMS (MC) RT=2.18 min, m/z=448 $(M+H)^+$.

$^1$H NMR (400 MHz, DMSO) 9.69-9.68 (1H, m), 9.02-8.99 (1H, m), 8.61-8.59 (1H, m), 7.99 (1H, s), 7.54 (1H, s), 7.20 (1H, s), 6.68 (1H, d, J=7.6 Hz), 6.49 (1H, t, J=6.0 Hz), 4.96 (1H, d, J=11.2 Hz), 4.50-4.31 (2H, m), 3.96 (1H, t, J=10.6 Hz), 3.61-3.52 (1H, m), 3.46 (3H, s), 3.43-3.36 (1H, m), 3.32-3.25 (2H, m), 2.48-2.41 (1H, m), 2.02-1.94 (1H, m);

Example 77: (12R,14S)-4-fluoro-12-methoxy-18-(2-methoxyethyl)-16-oxa-7,10,20,21,24-pentaazapentacyclo[15.5.2.1$^{2}$,6.0$^{10}$,$^{14}$.0$^{20}$,$^{23}$]pentacosa-1(23),2(25),3,5,17(24),18,21-heptaen-11-one

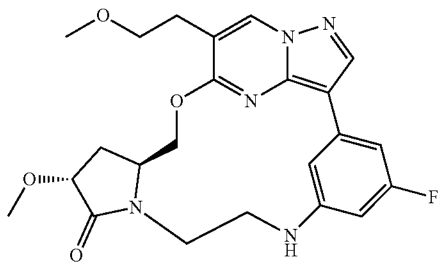 [SMILES: COCCc1cn2ncc3c2nc1OC[C@@H]1C[C@@H](OC)C(=O)N1CCNc1cc(F)cc-3c1]

Step 1

Pyrrolidine P1 (0.720 g, 3.113 mmol) in 16 mL of dry DMF (5 mL/mmol) was added sodium hydride, 60% in mineral oil (C, 0.373 g, 9.339 mmol), at 0° C., after 30 min Scaffold S8 (1.043 g, 3.424 mmol) was added and the mixture was stirred at 4-5° C. for 15 min. Upon complete conversion, monitored by TLC, EtOAc was added and the mixture was quenched carefully by dropwise water at 0° C. Then, it was extracted with EtOAc (×3) and the combined organic layers were dried overmg$SO_4$, filtered and concentrated under vacuum. The product was purified by flash chromatography on silica gel using Heptane/EtOAc (100:0 to 60:40) as eluents to afford the expected compound as a yellow oil (2.253 g, 54.9% yield).

LCMS (MI) RT=0.884 min, m/z=499-401 $(M+H)^+$-Boc.

Step 2

To a solution of the title compound from Step 1 (2.253 g, 4.512 mmol) in Dichloromethane (7 mL) was added Trifluoroacetic acid (7 mL). The reaction mixture was stirred at room temperature for 16 h. The solvent was evaporated under reduced pressure the title compound (2.804 g, 100% yield) as a dark orange oil which was used without further purification.

LCMS (MI) RT=0.303 min, m/z=355-357 $(M+H)^+$.

Step 3

To a solution of the title compound from Step 2 (2.804 g, 4.512 mmol) in Dichloromethane (14 mL) was added di-tert-butyl Dicarbonate (2.954 g, 13.536 mmol) followed by Triethylamine (1.887 mL, 13.536 mmol) at 0° C. The reaction mixture was stirred at room temperature for 1 h. Solvent was removed under reduced pressure. The residue was purified by silica gel chromatography (eluting solvent 70-30% Heptane/ethyl acetate) to afford the title compound (1.332 g, 65% yield) as a yellow solid.

LCMS (MH) RT=0.987 min, m/z=355-357 $(M+H)^+$-Boc.

Step 4

To a solution of methoxymethyl)triphenylphosphonium chloride (2.579 g, 7.524 mmol) in dry THE (14 mL) was added potassium bis(trimethylsilyl)amide solution (1M/THF) (12.54 mL, 12.540 mmol) in one portion at −78° C. The reaction mixture was stirred at −78° C. for 1 h. The title compound from Step 3 (1.142 g, 2.508 mmol) in dry THE (9 mL) was added dropwise and the reaction mixture was stirred at −78° C. for 2 h. Methyl-tert-butyl-ether and saturated aqueous sodium bicarbonate solution were added and the reaction mixture was warmed to room temperature. The reaction mixture was heated up to 60° C. and stirred for 16 h. The phases were separated and the aqueous phase was extracted with MTBE. The combined organic layers were dried over anhydrous magnesium sulfate, filtered and concentrated under reduced pressure. The residue was purified by silica gel chromatography (eluting gradient 0-30% Heptane/ethyl acetate) to afford the title compound (314 mg, 26% yield) as a yellow sticky solid.

LCMS (MH) RT=1.216 min, m/z=483-485 $(M+H)^+$.

Step 5

The title compound from Step 4 (0.300 g, 0.621 mmol), Aniline A1 (0.191 g, 0.807 mmol), Potassium phosphate tribasic (0.264 g, 1.242 mmol) and Xphos (0.030 g, 0.062 mmol) were mixed in Dioxane/water (4:1) (7 mL/mmol) (4.30 mL) and the mixture was bubbled with nitrogen for 5 min. Then, Tetrakis (triphenylphosphine)palladium(0) (C, 0.036 g, 0.031 mmol) was added and the mixture was stirred at 90° C. in a pressure flask for 16 hours. Water was added and the mixture was extracted with EtOAc (×2). The combined organic layers were dried overmg$SO_4$, filtered and concentrated under vacuum giving the crude which was purified by flash chromatography on silica gel using Heptane/EtOAc (100:0 to 40:60) as eluents to afford the title compound (0.168 g, 52.68% yield) as a yellow solid.

LCMS (MH) RT=1.107 min, m/z=514.2 $(M+H)^+$.

Step 6

To a solution of the title compound from Step 5 (168 mg, 0.327 mmol) in Ethyl acetate (33 mL) under nitrogen atmosphere was added Pd/C 10% (67 mg). The reaction mixture was stirred at room temperature under hydrogen atmosphere for 16 h. Additional Palladium/C 10% (67 mg) was added and the reaction mixture was stirred at room temperature under hydrogen atmosphere for 16 h. The reaction was filtered over Celite pad and washed with Dichloromethane/Methanol (4:1) mixture. The filtrate was concentrated under reduced pressure to afford the title compound (143 mg, 85% yield) as an orange sticky solid, which was used in the next step without further purification.

LCMS (MH) RT=1.029 min, m/z=516.2 $(M+H)^+$.

Step 7

A solution of the title compound from Step 6 (0.143 g, 0.277 mmol) and Pyridine (0.066 mL, 0.831 mmol) in DCM (1.4 mL, 5 mL/mmol) was cooled to 0° C. Then, 2-nitrobenzenesulfonyl chloride (0.068 g, 0.305 mmol) was added portionwise and the mixture was allowed to stir at room temperature for 16 h. A solution of $NaHCO_3$ 10% was added and the mixture was extracted with DCM (×2). The combined organic layers were dried overmg$SO_4$, filtered and concentrated under vacuum. The product was purified by flash chromatography on silica gel using Heptane/EtOAc (100:0 to 20:80) as eluents to afford the title compound (0.136 g, 70.1% yield) as a yellow solid.

LCMS (MH) RT=1.173 min, m/z=701.1 $(M+H)^+$.

Step 8

1,2-Dibromoethane (0.364 mL, 1.940 mmol) was added to a stirred solution of the title compound from Step 7 (0.136 g, 0.194 mmol) and Cesium carbonate (0.316 g, 0.970 mmol) in 1.65 mL of DMA (8.5 mL/mmol). The mixture was stirred at 50° C. for 16 hours. Water was added and the mixture was extracted with EtOAc (×2). The combined organic layers were dried overmg$SO_4$, filtered and concentrated under vacuum affording the crude which was purified by flash chromatography on silica gel using Heptane/EtOAc (100:0 to 50:50) as eluents to afford the title compound (0.100 g, 63.8% yield) as a colorless sticky solid.

LCMS (MH) RT=1.281 min, m/z=707.0-708.9 $(M+H)^+$-Boc.

Step 9

The title compound from Step 8 (0.100 g, 0.124 mmol) was dissolved in Hydrochloric acid [4M] in Dioxane (2 mL) and the resulting mixture was stirred at rt for 16 hours. The mixture was concentrated under vacuum co-evaporated with Heptane to afford the title compound (0.090 g) as an orange sticky solid. The crude was used in the next step without purification.

LCMS (MH) RT=0.959 min, m/z=707-709 $(M+H)^+$.

Step 10

The title compound from Step 9 (0.087 g, 0.117 mmol) in 12 mL of Acetonitrile, Sodium hydrogen carbonate (0.098 g, 1.170 mmol) and Potassium iodide (0.058 g, 0.351 mmol) were added and the mixture was stirred at 90° C. for 16 hours. Further Sodium hydrogen carbonate (0.098 g, 1.170 mmol) and Potassium iodide (0.058 g, 0.351 mmol) were added and the mixture was stirred at 90° C. for 16 hours. EtOAc and water were added and the product was extracted with EtOAc (×3). The combined organic layer was dried over $MgSO_4$, filtered and concentrated under vacuum affording the title compound (0.069 g) as a cream solid. The crude was used in the next step without purification.

LCMS (MI) RT=0.803 min, m/z=627.2 $(M+H)^+$.

Step 11

To a mixture of the title compound from Step 10 (0.066 g, 0.105 mmol) in THF:$H_2O$ (2.5:1) (1.00 mL) was added Sodium bicarbonate (0.176 g, 2.100 mmol). The reaction mixture was stirred 10 min at room temperature. Then, Iodine (0.400 g, 1.575 mmol) was added and stirred at rt for 1 h. The mixture was diluted with EtOAc and washed with Sodium thiosulfate 10% aqueous solution. The aqueous phase was extracted with EtOAc (×3) and the combined organic layer was dried overmgSO$_4$, filtered and concentrated under vacuum. Finally, the product was purified on silica gel column chromatography using DCM/EtOAc (100:0 to 40:60) as eluents to afford the title compound (0.025 g, 37.2% yield) as a white solid.

LCMS (MH) RT=1.041 min, m/z=641.0 $(M+H)^+$.

Step 12

Thiophenol (0.013 mL, 0.117 mmol) was added to a suspension of the title compound from Step 11 (0.025 g, 0.039 mmol) and Cesium carbonate (0.038 g, 0.117 mmol) in 0.50 mL of DMF at 0° C. The mixture was stirred at rt for 1 hour. EtOAc and water were added and the mixture was extracted with EtOAc (×2). The combined organic layers were dried overmgSO$_4$, filtered and concentrated under vacuum yielding the crude which was purified by flash chromatography on silica gel using Heptane/EtOAc (100:0 to 40:60) as eluents to afford the expected product (0.004 g, 22.52% yield) as a beige solid.

LCMS (MD) RT=3.081 min, m/z=456.2 $(M+H)^+$.

LCMS (MF) RT=4.575 min, m/z=456.2 $(M+H)^+$.

$^1H$ NMR (400 MHz, DMSO) δ 8.88 (s, 1H), 8.48 (s, 1H), 7.65 (s, 1H), 6.74 (d, J=9.4 Hz, 1H), 6.32 (t, J=5.8 Hz, 1H), 6.20 (dt, J=11.8, 2.0 Hz, 1H), 4.98 (d, J=10.5 Hz, 1H), 4.49 (t, J=9.9 Hz, 1H), 4.36 (t, J=8.9 Hz, 1H), 4.00 (t, J=10.7 Hz, 1H), 3.60 (t, J=6.5 Hz, 2H), 3.55 (dd, J=11.9, 7.2 Hz, 1H), 3.45 (s, 3H), 3.42-3.34 (m, 1H), 3.28 (s, 3H), 3.26-3.16 (m, 2H), 2.83 (t, J=6.5 Hz, 2H), 2.48-2.42 (m, 1H), 1.96 (dt, J=11.7, 8.8 Hz, 1H).

Similarly Prepared:

| Ex no | Structure/Name | From intermediates | Analytical data |
|---|---|---|---|
| 78 | 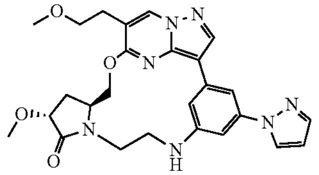 [SMILES: COCCc1cn2ncc3c2nc1OC[C@@H]1C[C@@H](OC)C(=O)N1CCNc1cc-3cc(-n2cccn2)c1] (12R,14S)-12-methoxy-18-(2-methoxyethyl)-4-(1H-pyrazol-1-yl)-16-oxa-7,10,20,21,24-pentaazapentacyclo[15.5.2.$1^2$,$6.0^{10}$,$^14.0^{20}$,$^{23}$]pentacosa-1(23),2(25),3,5,17(24),18,21-heptaen-11-one | Scaffold S8 Pyrrolidine P1 Aniline A15 45% yield as a beige solid | LCMS (MD) RT = 2.938 min, m/z = 504.2 $(M + H)^+$. LCMS (MF) RT = 4.533 min, m/z = 504.2 $(M + H)^+$. 1H NMR (400 MHz, DMSO) d 8.89 (s, 1H), 8.56 (s, 1H), 8.45 (d, J = 2.3 Hz, 1H), 7.76 (s, 1H), 7.71 (d, J = 1.5 Hz, 1H), 7.35 (s, 1H), 6.97 (t, J = 2.0 Hz, 1H), 6.58-6.46 (m, 1H), 6.35 (t, J = 5.8 Hz, 1H), 4.99 (d, J = 10.4 Hz, 1H), 4.51 (brs, 1H), 4.37 (t, J = 8.9 Hz, 1H), 4.09-3.92 (m, 1H), 3.61 (t, J = 6.5 Hz, 2H), 3.56 (d, J = 13.1 Hz, 1H), 3.46 (s, 3H), 3.44-3.36 (m, 1H), 3.33 (s, 3H), 3.26 (d, J = 6.1 Hz, 2H), 2.84 (t, J = 6.5 Hz, 2H), 2.49-2.41 (m, 2H). |

Example 79: (12R,14S)-4-fluoro-12-(2-hydroxyethoxy)-16-oxa-7,10,20,21,24-pentaazapentacyclo[15.5.2.$1^2$,$6.0^{1o}$,$^14.0^{2o}$,$^{23}$]pentacosa-1(23),2(25),3,5,17(24),18,21-heptaen-11-one

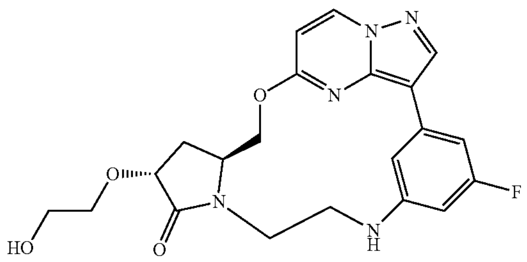 [SMILES: O=C1[C@H](OCCO)C[C@H]2COc3ccn4ncc(c4n3)-c3cc(F)cc(c3)NCCN12]

Following the general synthetic scheme 1, as depicted for the synthesis of Example 1, (12R,14S)-12-[2-(benzyloxy)ethoxy]-4-fluoro-16-oxa-7,10,20,21,24-pentaazapentacyclo[15.5.2.12,6.010,14.020,23]pentacosa-1(23),2,4,6(25),17(24),18,21-heptaen-11-one was obtained as Intermediate I24 using Scaffold 3-bromo-5-chloropyrazolo[1,5-a]pyrimidine, Pyrrolidine P8 and Aniline A1.

Step 1

To a solution of Intermediate I24 (100 mg, 0.193 mmol) in Ethyl acetate (2 mL) under nitrogen atmosphere was added 10% Palladium/C (20 mg). The reaction mixture was stirred at room temperature under hydrogen atmosphere for 16 h. Additional palladium/C 10% (67 mg) was added and the reaction mixture was stirred at room temperature under hydrogen atmosphere for 16 h. The crude was filtered off over a Celite pad rinsing with ethyl acetate, and the filtrate was concentrated under reduced pressure. The residue was purified by silica gel chromatography (eluting gradient 0-2% Dichloromethane/methanol) to afford the expected product (40 mg, 48.49% yield) as a white solid.

LCMS (MG) RT=2.813 min, m/z=428.1 $(M+H)^+$.

LCMS (MF) RT=4.652 min, m/z=428.1 $(M+H)^+$.

1H NMR (400 MHz, DMSO) δ 8.98 (d, J=7.5 Hz, 1H), 8.53 (s, 1H), 7.67 (s, 1H), 6.79-6.70 (m, 1H), 6.66 (d, J=7.5 Hz, 1H), 6.33 (t, J=5.8 Hz, 1H), 6.21 (dt, J=11.8, 2.1 Hz, 1H), 4.93 (d, J=10.9 Hz, 1H), 4.71 (t, J=5.5 Hz, 1H), 4.56-4.36 (m, 2H), 3.95 (t, J=10.8 Hz, 1H), 3.82 (dt, J=9.6, 4.7 Hz, 1H), 3.62-3.47 (m, 4H), 3.45-3.34 (m, 1H), 3.27-3.12 (m, 2H), 2.44 (dd, J=12.7, 8.2 Hz, 1H), 2.05-1.90 (m, 1H).

Example 80: (12R,14S)-12-cyclopropoxy-4-fluoro-16-oxa-7,10,20,21,24-pentaazapentacyclo[15.5.2.1$^{2}$,6.0$^{10}$,$^{14}$.0$^{20}$,$^{23}$]pentacosa-1(23),2(25),3,5,17(24),18,21-heptaen-11-one

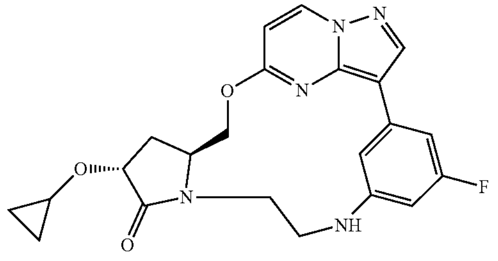 [SMILES: O=C1[C@H](OC2CC2)C[C@H]2COc3ccn4ncc(c4n3)-c3cc(F)cc(c3)NCCN12]

Step 1

To a solution of Pyrrolidine P9 (0.500 g, 1.943 mmol) in dry DMF (10 mL) was added Sodium hydride, 60% in mineral oil (0.233 g, 5.829 mmol), at 0° C. After 30 min stirring, 3-bromo-5-chloropyrazolo[1,5-a]pyrimidine (0.903 g, 3.886 mmol) was added and the mixture was stirred at 4-5° C. for 30 min. Water was added dropwise carefully at 4-5° C. and the mixture was extracted with EtOAc (×4). The combined organic layers were dried overmgSO$_4$, filtered and concentrated under vacuum. The product was purified on column of silica gel using as eluent Heptane/EtOAc (from 100:0 to 85:15) to afford the title compound (0.471 g, yield: 53.47%) as yellowish gum.

LCMS (MH) RT=1.142 min, m/z=353.0 (M-100)

Step 2

In a pressure flask the title compound from Step 1 (0.450 g, 0.993 mmol), Aniline A1 (0.283 g, 1.192 mmol), and $K_3PO_4$ (0.632 g, 2.979 mmol) were mixed in Dioxane/$H_2O$ (4:1) (6 mL), and the reaction mixture was bubbled with a Nitrogen stream for 5 min. Tetrakis(triphenylphosphine) palladium(0) (0.070 g, 0.060 mmol) and Xphos (0.057 g, 0.119 mmol) were added and the mixture was stirred at 80° C. for 16 hours. Upon complete conversion, monitored by LCMS, water was added and extracted with EtOAc (×3). The combined organic phases were dried overmgSO$_4$, filtered and concentrated under reduced pressure. The crude was purified by flash chromatography (on silica gel) using DCM/MeOH as eluents (100:0 to 97:3) to afford the title compound (0.291 g, 61% yield) as a brown solid.

LCMS (MH) RT=1.082 min, m/z=484.1 $(M+H)^+$.

Step 3

A solution of the title compound from Step 2 (0.293 g, 0.606 mmol) and Pyridine (0.13 mL, 1.82 mmol) in DCM (3 mL) was cooled down to 0° C., then 2-Nitrobenzenesulfonyl chloride (0.15 g, 0.67 mmol) was added dropwise and the mixture was allowed to stir at room temperature for 16 h. An aqueous solution of $NaHCO_3$ (10%) was added and the mixture was extracted with DCM (×3). The combined organic layers were dried over $MgSO_4$, filtered and concentrated under reduced pressure. The crude was purified by flash chromatography (on silica gel) using DCM/MeOH as eluents (100:0 to 96:4) to afford the title compound (0.370 g, 91.3% yield) as a brown gum.

LCMS (MH) RT=1.215 min, m/z=569.0 $(M+H)^+$.

Step 4

The title compound from Step 3 (0.360 g, 0.538 mmol) was dissolved in DMA (18 mL, 33 mL/mmol). Then Cesium carbonate (0.876 g, 2.69 mmol) and 1,2-Dibromoethane (0.464 mL, 5.380 mmol) were added and stirred at 50° C. for 16 hours. Upon complete conversion, monitored by LCMS, water was added and extracted with EtOAc (×3). The combined organic phases were dried overmgSO$_4$, filtered and concentrated under reduced pressure. The crude was purified by flash chromatography using DCM/MeOH as eluents (100:0 to 98:2) to afford the title compound (0.380 g, 91.06% yield) as a brown solid.

LCMS (MH) RT=1.342 min, m/z=675.0/677.0 (M-100).

Step 5

The title compound from Step 4 (0.357 g, 0.460 mmol) was cooled down to 0° C. DCM/TFA 1:1 (4 mL) was added and stirred from 0° C. to rt for 16 hours. The reaction mixture was concentrated under reduced pressure to afford the title compound as crude brown sticky solid (0.320 g), was used as such in the next step without further purification.

LCMS (MH) RT=0.901 min, m/z=675.0/677.0 $(M+H)^+$.

Step 6

To a solution of the title compound from Step 5 (crude, 0.36 g, 0.46 mmol) in Acetonitrile (138 mL), Sodium hydrogen carbonate (0.386 g, 4.600 mmol) and Potassium iodide (0.076 g, 0.460 mmol) were added and the mixture was stirred at 90° C. for 16 hours. Water was added and extracted with EtOAc (×3). The combined organic phases were dried overmgSO$_4$, filtered and concentrated under reduced pressure. The crude was purified by flash chromatography (on silica gel) using DCM/MeOH as eluents (100:0 to 98:2) to afford the title compound (0.202 g, 73.8% yield) as a yellow solid.

LCMS (MH) RT=1.047 min, m/z=595.0 $(M+H)^+$.

Step 7

To the mixture of the title compound from Step 6 (0.125 g, 0.210 mmol) in DMF (5 mL) was added Cesium carbonate (0.205 g, 0.630 mmol). The mixture was cooled in a bath of ice/water, and then, Thiophenol (0.065 mL, 0.630 mmol) was added. The mixture was stirred at room temperature for 30 minutes. The mixture was diluted with EtOAc, water was added and the mixture was extracted with EtOAc (×4). The combined organic layers were dried overmgSO$_4$, filtered and concentrated under vacuum. The crude was purified by flash chromatography on silica gel, using as eluents DCM/MeOH (from 100:0 to 97.5:2.5), to afford the title compound (0.068 g, 79.08% yield) as yellowish solid.

LCMS (MH) RT=0.710 min, m/z=410.1 $(M+H)^+$.

Step 8

To a solution of the title compound from Step 7 (0.058 g, 0.142 mmol) in THF:$H_2O$ (9:1) (8.5 mL) was added Sodium bicarbonate (0.179 g, 2.130 mmol). The reaction mixture was stirred 10 min at room temperature. Then, Iodine (0.252 g, 0.994 mmol) was added and stirred at room temperature. LCMS showed the partial conversion. The mixture was heated at 50° C. and stirred for 6 h. The mixture was diluted with EtOAc, water was added and the mixture was extracted with EtOAc (×4). The combined organic layers were dried overmg$SO_4$, filtered and concentrated under vacuum. The crude was purified by flash chromatography on silica gel, using as eluents DCM/MeOH (from 100:0 to 90:10) to Hz, 1H), 6.24 (d, J=10.8 Hz, 1H), 5.06 (d, J=11.0 Hz, 1H), 3.91-3.83 (m, 1H), 3.81 (dd, J=6.1, 3.0 Hz, 1H), 3.76 (t, J=10.8 Hz, 1H), 3.63-3.50 (m, 3H), 3.26 (t, J=11.5 Hz, 1H), 2.61 (dd, J=13.1, 8.1 Hz, 1H), 2.14 (dd, J=21.9, 9.0 Hz, 2H), 0.90-0.81 (m, 1H), 0.80-0.73 (m, 1H), 0.70-0.63 (m, 1H), 0.60-0.48 (in, 2H).

Similarly Prepared:

| Ex no | Structure/Name | From intermediates | Analytical data |
|---|---|---|---|
| 81 | 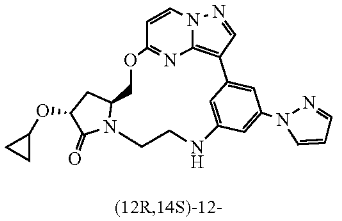 (12R,14S)-12-cyclopropoxy-4-(1H-pyrazol-1-yl)-16-oxa-7,10,20,21,24-pentaazapentacyclo[15.5.2.$1^{2}$,6.$0^{10}$,$^{1}$4.$0^{20}$,$^{23}$]pentacosa-1(23),2(25),3,5,17(24),18,21-heptaen-11-one | Scaffold 3-bromo-5-chloropyrazolo[1,5-a]pyrimidine Pyrrolidine P9 Aniline A15 5.1 mg, 47% yield | LCMS (MD) RT = 3.092 min, m/z = 472.2 $(M + H)^+$. LCMS (ME) RT = 3.472 min, m/z = 472.2 $(M + H)^+$. $^1$H NMR (400 MHz, DMSO) d 9.00 (d, J = 7.5 Hz, 1H), 8.63 (s, 1H), 8.45 (d, J = 2.4 Hz, 1H), 7.79 (s, 1H), 7.71 (d, J = 1.6 Hz, 1H), 7.36 (s, 1H), 6.98 (t, J = 1.9 Hz, 1H), 6.67 (d, J = 7.5 Hz, 1H), 6.56-6.50 (m, 1H), 6.36 (t, J = 5.8 Hz, 1H), 4.95 (d, J = 10.8 Hz, 1H), 4.57-4.48 (m, 1H), 4.02 (t, J = 10.8 Hz, 1H), 3.74 (ddd, J = 9.2, 6.0, 3.0 Hz, 1H), 3.58 (dd, J = 21.6, 10.0 Hz, 2H), 3.49-3.37 (m, 2H), 3.30-3.21 (m, 1H), 2.49-2.40 (m, 1H), 2.05-1.92 (m, 1H), 0.68-0.55 (m, 2H), 0.51 (dd, J = 12.0, 4.0 Hz, 2H). |
| 82 | 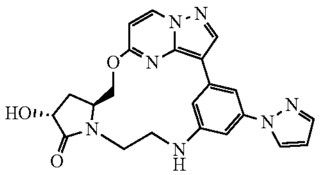 [SMILES: O=C1[C@H](O)C[C@H]2COc3ccn4ncc(c4n3)-c3cc(cc(-n4cccn4)c3)NCCN12] (12R,14S)-12-hydroxy-4-(1H-pyrazol-1-yl)-16-oxa-7,10,20,21,24-pentaazapentacyclo[15.5.2.$1^{2}$,6.$0^{10}$,$^{1}$4.$0^{20}$,$^{23}$]pentacosa-1(23),2(25),3,5,17(24),18,21-heptaen-11-one | Scaffold 3-bromo-5-chloropyrazolo[1,5-a]pyrimidine Pyrrolidine P9 Aniline A15 4.7 mg, 47% yield | LCMS (MD) RT = 2.452 min, m/z = 432.1 $(M + H)^+$. LCMS (ME) RT = 2.947 min, m/z = 432.1 $(M + H)^+$. $^1$H NMR (400 MHz, DMSO) d 9.00 (d, J = 7.5 Hz, 1H), 8.63 (s, 1H), 8.45 (d, J = 2.2 Hz, 1H), 7.81 (d, J = 1.5 Hz, 1H), 7.71 (d, J = 1.5 Hz, 1H), 7.36 (s, 1H), 6.98 (t, J = 2.0 Hz, 1H), 6.68 (d, J = 7.5 Hz, 1H), 6.58-6.50 (m, 1H), 6.35 (t, J = 5.8 Hz, 1H), 5.61 (brs, 1H), 4.95 (d, J = 11.0 Hz, 1H), 4.48 (t, J = 9.0 Hz, 2H), 3.98 (t, J = 10.8 Hz, 1H), 3.58 (dt, J = 12.6, 8.6 Hz, 1H), 3.50-3.40 (m, 1H), 3.28-3.17 (m, 2H), 2.39 (dd, J = 12.5, 8.2 Hz, 1H), 2.00-1.85 (m, 1H). |

afford the title compound (0.019 g) contaminated with di-iodo derivative as yellowish solid.

LCMS (MH) RT=0.710 min, m/z=410.1 $(M+H)^+$.

Step 9

A vial equipped with a magnetic stir bar was charged with the title compound from Step 8 (0.005 g, 0.009 mmol) and (Ir[dF(CF3)ppy]2(dtbpy))PF6 (0.001 g, 0.0009 mmol). Acetonitrile (0.2 mL) was added to the vial followed by DIPEA (0.006 g, 0.036 mmol) followed by Tris(trimethylsilyl)silane (0.006 g, 0.018 mmol). The mixture was stirred keeping the vial open to air and then illuminated with a 42 W blue LED strip for 45 min. The temperature near the surface of the vial was 40° C. Upon completion, monitored by LCMS, solvent was removed under reduced pressure and the crude was purified on column of silica gel using DCM/MeOH (98:2) as eluents to afford the expected product (4.2 mg, 55%) as white solid.

LCMS (MD) RT=3.250 min m/z=424.1 $(M+H)^+$.

1H NMR (400 MHz, $CDCl_3$): 8.51 (d, J=7.5 Hz, 1H), 8.26 (s, 1H), 7.69 (s, 1H), 6.69 (d, J=9.6 Hz, 1H), 6.41 (d, J=7.5

Example 83: (12R,14S)-4-(3,5-dimethyl-1H-pyrazol-1-yl)-12-methoxy-16-oxa-7,10,20,21,24-pentaazapentacyclo[15.5.2.$1^{2}$,6.$0^{1o}$,$^{1}$4.$0^{2o}$,$^{23}$]pentacosa-1(23),2(25),3,5,17(24),18,21-heptaen-11-one

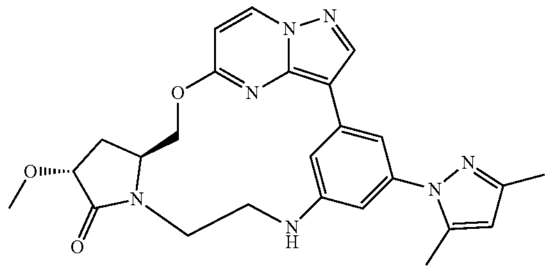

Following the general synthetic scheme 1, as depicted for the synthesis of Example 1, (12R,14S)-4-(4-iodo-3,5-dimethyl-1H-pyrazol-1-yl)-12-methoxy-16-oxa-7,10,20,21,24- pentaazapentacyclo[15.5.2.12,6.010,14.020,23]pentacosa-1(23),2,4,6(25),17(24),18,21-heptaen-11-one was obtained as Intermediate I25 using Scaffold 3-bromo-5-chloropyrazolo[1,5-a]pyrimidine, Pyrrolidine P1 and Aniline A16.

Step 1

To a solution of Intermediate I25 (93 mg, 0.155 mmol) in Acetonitrile (4 mL), was added N,N-Diisopropylethylamine (0.379 mL, 2.17 mmol) followed by Tris(trimethylsilyl) silane (0.385 mL, 1.240 mmol) and (Ir[dF($CF_3$)ppy]$_2$(dtbpy))$PF_6$ (18 mg, 0.016 mmol). The reaction mixture was stirred keeping the vial open to air and then illuminated with a 42 W blue LED strip for 2 h. The mixture was diluted with Ethyl acetate, water was added and the reaction mixture was extracted with ethyl acetate. The combined organic layers were dried over anhydrous sodium sulfate, filtered and concentrated under reduced pressure. The residue was purified by silica gel chromatography (eluting gradient 0-2% Dichloromethane/methanol) to afford the expected product (55 mg. 75% yield) as a beige solid.

LCMS (MD) RT=2.881 min, m/z=474.2 $(M+H)^+$.

LCMS (ME) RT=3.361 min, m/z=474.2 $(M+H)^+$.

$^1$H NMR (400 MHz, DMSO) δ 8.91 (d, J=7.5 Hz, 1H), 8.50 (s, 1H), 7.75 (s, 1H), 6.89 (s, 1H), 6.58 (d, J=7.5 Hz, 1H), 6.46 (t, J=2.0 Hz, 1H), 6.22 (t, J=5.8 Hz, 1H), 5.95 (s, 1H), 4.88 (d, J=10.9 Hz, 1H), 4.26 (t, J=8.9 Hz, 1H), 3.88 (t, J=10.7 Hz, 1H), 3.48 (dt, J=12.7, 8.9 Hz, 1H), 3.35-3.29 (m, 1H), 3.24 (s, 3H), 3.21 (s, 1H), 3.20-3.11 (m, 2H), 2.36 (dd, J=12.6, 8.2 Hz, 1H), 2.23 (s, 3H), 2.09 (s, 3H), 1.89 (dt, J=12.1, 8.9 Hz, 1H).

Example 84: (12R,14S)-4-(4,5-dimethyl-1H-pyrazol-1-yl)-12-methoxy-16-oxa-7,10,20,21,24-pentaazapentacyclo[15.5.2.1$^{2}$,6.0$^{1o}$,$^{1}$4.0$^{2o}$,$^{23}$]pentacosa-1(23),2(25),3,5,17(24),18,21-heptaen-11-one

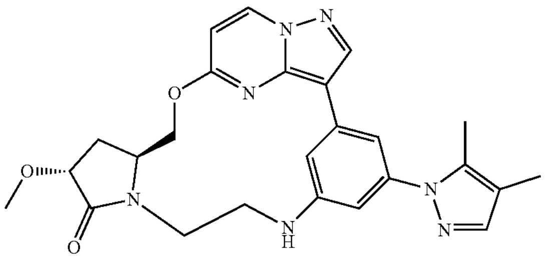

Step 1

Intermediate I17 (60 mg, 0.102 mmol), Methylboronic acid (18 mg, 0.306 mmol), Potassium phosphate tribasic (65 mg, 0.306 mmol) were mixed in Dioxane/water (4:1) (1.8 mL). The reaction mixture was bubbled with nitrogen for 5 min and [1,1'-Bis(diphenylphosphino)ferrocene]dichloropalladium(II) (5 mg, 0.006 mmol) was added. The reaction mixture was stirred at 80° C. in a pressure flask for 6 h. Water was added and the mixture was extracted with Ethyl acetate. The combined organic layers were dried over anhydrous magnesium sulfate, filtered and concentrated under reduced pressure. The residue was purified by reverse phase chromatography (Purification method PB) 70% [25 mM $NH_4HCO_3$]-30% [Acetonitrile: MeOH 1:1] 27% [25 mM $NH_4HCO_3$]-73% [Acetonitrile: MeOH 1:1] to afford the expected product (26 mg, 53% yield) as a white solid.

LCMS (MD) RT=3.093 min, m/z=474.2 $(M+H)^+$.

LCMS (ME) RT=3.450 min, m/z=474.2 $(M+H)^+$.

$^1$H NMR (400 MHz, DMSO) δ 9.00 (d, J=7.5 Hz, 1H), 8.58 (s, 1H), 7.85 (s, 1H), 7.40 (s, 1H), 6.98 (s, 1H), 6.68 (d, J=7.5 Hz, 1H), 6.53 (t, J=1.9 Hz, 1H), 6.34 (t, J=5.9 Hz, 1H), 4.97 (d, J=10.8 Hz, 1H), 4.52 (t, J=8.5 Hz, 1H), 4.35 (t, J=8.9 Hz, 1H), 3.57 (dd, J=16.4, 5.9 Hz, 1H), 3.46 (s, 3H), 3.44-3.38 (m, 1H), 3.30-3.16 (m, 2H), 2.47-2.39 (m, 2H), 2.26 (s, 3H), 2.02 (s, 3H), 1.97 (dd, J=12.5, 9.0 Hz, 1H)

Example 88: (12R,14S)-12-methoxy-4-(prop-1-yn-1-yl)-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaen-11-one

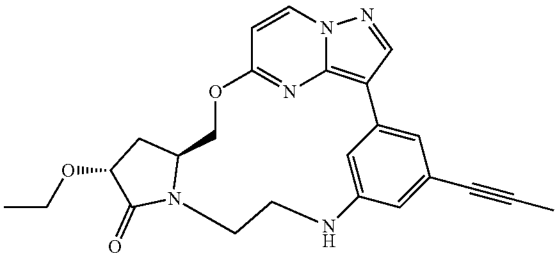 [SMILES: CC#Cc1cc2cc(c1)-c1cnn3ccc(nc13)OC[C@@H]1C[C@@H](OCC)C(=O)N1CCN2]

Step 1

In a microwave vial (5 mL), Example 20 (205 mg, 0.5 mmol) was suspended in Acetonitrile (5 mL). At room temperature, were added Xphos (50 mg, 0.1 mmol) and Cesium carbonate (490 mg, 1.5 mmol). The resulting mixture was degassed by bubbling Argon for 10 min before addition of Bis(acetonitrile)dichloropalladium(II) (15 mg, 0.05 mmol). The reaction mixture was stirred 10 min at room temperature. Then, Trimethyl(propargyl)silane (0.375 mL, 2.5 mmol) was added. The reaction vessel was sealed and heated for 5 hr under microwave irradiation using Biotage Initiator at 120° C. Monitoring by LCMS showed the reaction was completed. The reaction mixture was adsorbed on silica and purified by silica gel column chromatography using DCM/MeOH (100/0 to 9/1) as eluent. The expected fractions were combined and evaporated under reduced pressure. The residue was recrystallized in EtOH twice. The expect product was obtained as a cream-colored solid (35 mg, 0.08 mmol, 17%).

LCMS (MA) RT=2.28 min, m/z=418.4 $(M+H)^+$.

LCMS (MC) RT=2.28 min, m/z=418.4 $(M+H)^+$.

$^1$H NMR (400 MHz, DMSO) 9.00-8.96 (1H, m), 8.55-8.53 (1H, m), 7.79-7.76 (1H, m), 6.96 (1H, s), 6.67-6.63 (1H, m), 6.49-6.47 (1H, m), 6.18-6.17 (1H, m), 4.94 (1H, t, J=10.3 Hz), 4.46 (1H, s), 4.33 (1H, t, J=8.7 Hz), 3.94 (1H, t, J=10.6 Hz), 3.54 (1H, d, J=18.3 Hz), 3.35-3.32 (6H, m), 2.46-2.40 (1H, m), 2.05-2.01 (4H, m)

Example 89: (12R,14S)-4,12-dimethoxy-8-methyl-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaen-11-one

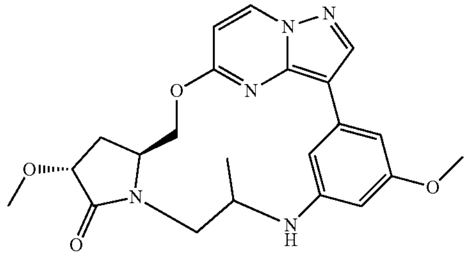

Step 1

To a suspension Sodium hydride, 60% in oil (3.2 g, 80.0 mmol) in dry THE (25 mL) was added at 0° C. a solution of Pyrrolidine P1 (9.25 g, 40.0 mmol) in THE (25 mL). After 30 min, 3-bromo-5-chloro-pyrazolo[1,5-a]pyrimidine (9.3 g, 40.01 mmol) was added and the mixture was stirred at 0° C. for 15 min, and then at rt for 4 h. The mixture was carefully diluted with water and EtOAc (250 ml) was added. The layers were separated. The aqueous layer was extracted with EtOAc (2×100 mL). The combined organic layer was dried over anhydrous sodium sulfate, filtered and evaporated under reduced pressure to afford the title compound as a yellow (17 g, 39.79 mmol, 99%).

LCMS (MA) RT=2.84 min, m/z=429.1 (M+H)$^{+}$.

Step 2

To a suspension of the title compound from Step 1 (3.33 g, 7.79 mmol) in Acetonitrile (10 mL) was added HCl in 1,4-Dioxane 4M (9.75 mL, 38.9 mmol). The mixture was stirred at room temperature for 1 h. The solvent was evaporated under reduced pressure to afford the title compound as a yellow foam (2.83 g), which was directly engaged in the next step without further purification.

LCMS (MA) RT=1.29 min, m/z=329.1 (M+H)$^{+}$.

Step 3

To a solution of the title compound from Step 2 (363 mg, 1 mmol) in DCM (20 mL) was added Triethylamine (0.418 mL, 3 mmol). The resulting mixture was stirred at room temperature for 15 min then 2-(tert-Butyldimethylsilyloxy) propanal was added (375 mg, 1.2 mmol). After further stirring for 15 min was added Sodium triacetoxyborohydride (318 mg, 1.5 mmol). The reaction mixture was left stirring at room temperature for 3 hr. Monitoring of the reaction mixture by LCMS showed the reaction was completed. The reaction mixture was diluted in DCM (50 ml) and water was added. The water layer was extracted with DCM. The combined organic layers were washed with saturated Brine, dried over anhydrous sodium sulfate, and concentrated under reduced pressure. The crude was purified by flash chromatography using Cyclohexane/EtOAc (100/0 to 6/4) as eluent to afford the title compound as a colorless oil (0.39 g, 79%).

LCMS (MA) RT=2.20 min, m/z=421.1 (M+H)$^{+}$.

Step 4

To a solution of the title compound from Step 3 (3.06 g, 6.12 mmol) in Dioxane/water (30/7 mL) was added Aniline A3 (1.98 g, 7.96 mmol), Tetrakis(triphenylphosphine)palladium(0) (139 mg, 0.12 mmol), Xphos (114 mg, 0.24 mmol) and Potassium phosphate tribasic (3.9 g, 18.36 mmol). The reaction mixture was degassed by bubbling under argon for 15 min and stirred at 90° C. for 4 h. Upon complete conversion, monitored by LCMS, the mixture was allowed to cooled to room temperature and was diluted with water and EtOAc. Layers were separated and the water layer was extracted with EtOAc. The combined organic layers were dried over anhydrous sodium sulfate, filtered and concentrated under reduced pressure. The crude was purified by flash chromatography using Cyclohexane/EtOAc-EtOH (3:1) (100:0 to 6:4) as eluent to afford the title compound as a yellow oil (3.21 g, 97%).

LCMS (MA) RT=2.04 min, m/z=542.4 (M+H)$^{+}$.

Step 5

To a solution of the title compound from Step 4 (3.21 g, 5.9 mmol) in Acetonitrile (45 mL) was added Pyridine (0.62 mL, 7.7 mmol) and 2-nitrobenzenesulfonyl chloride (1.44 g, 6.5 mmol) portionwise. The reaction mixture was stirred at room temperature for 2 h. Upon complete conversion, monitored by LCMS, the solvent was evaporated under reduced pressure. The crude was purified by flash chromatography using Cyclohexane/EtOAc-EtOH (3:1) (100:0 to 6:4) as eluent to afford the title compound as a yellow foam (3.8 g, 88%).

LCMS (MA) RT=2.49 min, m/z=727.3 (M+H)$^{+}$.

Step 6

To a solution of the title compound from Step 5 (3.8 g, 5.23 mmol) in THE (100 mL) was added a solution of TBAF (5.75 mL, 5.75 mmol). The reaction mixture was stirred at room temperature for 72 h. Upon complete conversion, monitored by LCMS, the solvent was evaporated under reduced pressure. The crude was purified by flash chromatography using DCM/MeOH (100/0 to 9/1) as eluent to afford the title compound as a yellow foam (3.62 g, 100%).

LCMS (MA) RT=1.78 min, m/z=613.3 (M+H)$^{+}$.

Step 7

A solution of the title compound from Step 6 (3.31 g, 5.4 mmol) in THE (30 mL) and a solution of DIAD (3.18 mL, 16.2 mmol) in Toluene (30 mL) were added dropwise (over 1 hr) and simultaneously to a solution of Triphenylphosphine (4.25 g, 16.2 mmol) in Toluene (300 mL) heated at 90° C. The reaction mixture was heated at 90° C. for 1 h. Upon complete conversion, monitored by LCMS, solvents were removed under reduced pressure and the crude was purified by column chromatography using DCM/MeOH (100/0 to 9/1) as eluent. The purification was repeated using Cyclohexane/EtOAc-EtOH (3:1) (100/0 to 3/7) as eluent to afford the title compound as a cream foam (700 mg, 22% yield).

LCMS (MA) RT=2.05 min, m/z=595.2 (M+H)$^{+}$.

Step 8

To a solution of the title compound from Step 7 (700 mg, 1.17 mmol) in Acetonitrile/water (60 mL/20 mL) was added Sodium bicarbonate (0.98 g, 11.7 mmol). The reaction mixture was stirred 30 min at 45° C., then Iodine (1.9 g, 8.77 mmol) was added. The reaction mixture was stirred at 45° C. for 3 h. Upon complete conversion, monitored by LCMS, the reaction mixture was quenched by a saturated Sodium thiosulfate solution (100 mL). To the mixture was added DCM (200 mL), which was extracted with water (100 mL) and Brine (100 mL). The organic layers were combined, dried over anhydrous sodium sulfate, filtered and evaporated under reduced pressure. The crude was purified by column chromatography using DCM/MeOH (100/0 to 9/1) as eluent to afford the title compound as a cream solid (0.5 g, 70% yield).

LCMS (MA) RT=2.50 min, m/z=609.2 (M+H)$^{+}$.

Step 9

To a suspension of the title compound from Step 8 (0.5 g, 0.82 mmol) in THE/Acetonitrile (40 mL/4 mL) was added Cesium carbonate (0.53 g, 1.64 mmol) and 4-Methylbenzenethiol (0.12 g, 0.98 mmol). The reaction mixture was stirred at room temperature overnight. The mixture was filtered and evaporated under reduced pressure. The crude was purified by flash chromatography using DCM/MeOH (100:0 to 90:10) as eluent. The expected fractions were combined and evaporated under reduced pressure. The residue was triturated in Diethylether/Acetonitrile (98/2) to afford the expected product as a cream solid (0.18 g, 52% yield).

LCMS (MA) RT=2.09 min, m/z=424.4 $(M+H)^+$.

LCMS (MC) RT=2.90 min, m/z=424.4 $(M+H)^+$.

$^1$H NMR (400 MHz, DMSO) 8.99-8.95 (1H, m), 8.60-8.60 (1H, m), 7.98 (1H, s), 6.65 (1H, d, J=7.7 Hz), 6.61-6.59 (1H, m), 6.14-6.10 (1H, m), 6.03 (1H, t, J=2.1 Hz), 5.30-5.25 (1H, m), 4.39-4.33 (1H, m), 4.23-4.19 (1H, m), 4.08 (1H, t, J=11.4 Hz), 3.75 (1H, d, J=12.6 Hz), 3.63-3.55 (1H, m), 3.45-3.44 (6H, m), 2.47-2.41 (1H, m), 2.02-1.94 (1H, m), 1.28 (3H, d, J=6.8 Hz), 1.15-1.12 (1H, m)

Example 90: (12R,14S)-12-hydroxy-4-methoxy-16-oxa-7,10,20,21,24-pentaazapentacyclo[15.5.2.1$^{2}$,6.0$^{10}$,$^{14}$.0$^{20}$,$^{23}$]pentacosa-1 (23),2,4,6(25),17(24),18,21-heptaen-11-one

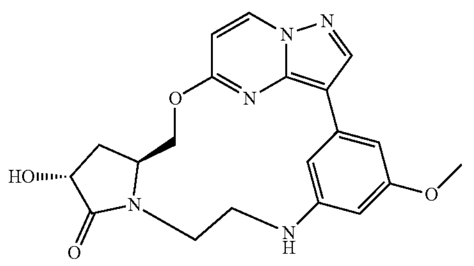 [SMILES: COc1cc2cc(c1)-c1cnn3ccc(nc13)OC[C@@H]1C[C@@H](O)C(=O)N1CCN2]

Following the general synthetic scheme 1, as depicted for the synthesis of Example 1, (12R,14S)-4-methoxy-7-(2-nitrobenzenesulfonyl)-12-(prop-2-en-1-yloxy)-16-oxa-7,10,20,21,24-pentaazapentacyclo[15.5.2.12,6.010,14.020,23]pentacosa-1(23),2,4,6(25),17(24),18,21-heptaene was obtained as Intermediate I26 using Scaffold 3-bromo-5-chloropyrazolo[1,5-a]pyrimidine, Pyrrolidine P13 and Aniline A3.

LCMS (MA) RT=2.29 min, m/z=607.2 $(M+H)^+$.

Step 1

Under argon, to a suspension of Intermediate I26 (315 mg, 0.52 mmol) in EtOH/TFA (4.5/0.4 mL) was added Tetrakis (triphenylphosphine)palladium(0) (120 mg, 0.10 mmol). The reaction mixture was stirred at 80° C. for 14 h. Upon complete conversion, monitored by LCMS, the reaction mixture was cooled to room temperature and was carefully quenched with a saturated solution of $NaHCO_3$. An emulsion was observed so the mixture was filtered and the layers were separated. The aqueous layer was extracted with EtOAc (2×15 mL) and the combined organic layer was dried over anhydrous sodium sulfate, filtered and evaporated under reduced pressure. The residue was purified on silica gel column using Cyclohexane/(EtOAc/EtOH 3:1) (100:0 to 50:50) as eluent to afford the title compound as an orange foam (184 mg, 62% yield).

LCMS (MA) RT=1.80 min, m/z=567.1 $(M+H)^+$.

Step 2

To a suspension of the title compound from Step 1 (1.38 g, 2.44 mmol) in THF/$H_2O$ (80/16 mL) was added Sodium bicarbonate (4.100 g, 48.80 mmol). The reaction mixture was stirred 10 min at room temperature and then Iodine (9.29 g, 36.60 mmol) was added. The reaction mixture was stirred at 60° C. for 1 h. Upon complete conversion, monitored by LCMS, the reaction mixture was cooled to room temperature, quenched with a saturated solution of sodium thiosulfate and diluted with ethyl acetate. The layers were separated. The aqueous layer was extracted with EtOAc (2×25 mL) and the combined organic layer was dried over anhydrous sodium sulfate, filtered and evaporated under reduced pressure to afford the title compound (Intermediate I27, (12R,14S)-12-hydroxy-4-methoxy-7-(2-nitrobenzenesulfonyl)-16-oxa-7,10,20,21,24-pentaazapentacyclo [15.5.2.12,6.010,14.020,23]pentacosa-1(23),2,4,6(25),17 (24),18,21-heptaen-11-one) as a beige solid (1.679 g). The compound was directly engaged in the next step without further purification.

LCMS (MA) RT=2.27 min, m/z=581.1 $(M+H)^+$.

Step 3

To a suspension of the title compound from Step 2 (100 mg, 0.17 mmol) in DMF (1.5 mL) were added Cesium carbonate (110 mg, 0.34 mmol) and 4-Methylbenzenethiol (25 mg, 0.20 mmol). The reaction was stirred at rt for 30 min. Upon complete conversion, monitored by LCMS, the mixture was diluted with water and ethyl acetate. The layers were separated. The aqueous layer was extracted with EtOAc (2×15 mL) and the combined organic layer was dried over anhydrous Sodium sulfate, filtered and evaporated under reduced pressure. The residue was purified on silica gel column using DCM/MeOH (100:0 to 95:5) as eluent. The compound was triturated into acetonitrile, filtered and dried under reduced pressure to afford the expected product as a pale beige solid (26 mg, 38% yield).

LCMS (MA) RT=1.79 min, m/z=396.4 $(M+H)^+$.

LCMS (MC) RT=1.78 min, m/z=396.4 $(M+H)^+$.

$^1$H NMR (400 MHz, DMSO) 8.96 (1H, d, J=7.6 Hz), 8.51 (1H, s), 7.48 (1H, s), 6.64 (1H, d, J=7.4 Hz), 6.55-6.54 (1H, m), 6.05-6.02 (2H, m), 5.59 (1H, d, J=5.7 Hz), 4.92-4.89 (1H, m), 4.50-4.42 (2H, m), 3.96 (1H, t, J=10.8 Hz), 3.73 (3H, s), 3.57-3.49 (1H, m), 3.44-3.37 (1H, m), 3.26-3.16 (2H, m), 2.40-2.33 (1H, m), 1.96-1.88 (1H, m)

Similarly Prepared:

| Ex no | Structure/Name | From intermediates | Analytical data |
|---|---|---|---|
| 104 | 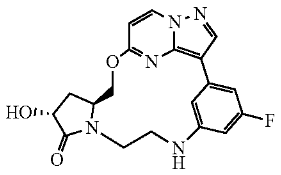 [SMILES: O=C1[C@H](O)C[C@H]2COc3ccn4ncc(c4n3)-c3cc(F)cc(c3)NCCN12] (12R,14S)-4-fluoro-12-hydroxy-16-oxa-7,10,20,21,24-pentaazapentacyclo[15.5.2.$1^{2}$,$6.0^{10}$,$^{1}4.0^{20}$,$^{23}$]pentacosa-1(23),2(25),3,5,17(24),18,21-heptaen-11-one | Scaffold 3-bromo-5-chloropyrazolo[1,5-a]pyrimidine Pyrrolidine P13 Aniline A1 7 mg, 10% yield as white solid | LCMS (MA) RT = 1.92 min, m/z = 384.3 $(M + H)^+$. LCMS (MC) RT = 1.91 min, m/z = 384.3 $(M + H)^+$. $^1$H NMR (400 MHz, DMSO) 8.99 (1H, d, J = 7.6 Hz), 8.54 (1H, s), 7.68 (1H, s), 6.75 (1H, d, J = 9.3 Hz), 6.68 (1H, d, J = 7.4 Hz), 6.33 (1H, t, J = 6.3 Hz),6.24-6.19 (1H, m), 4.91 (1H, s), 4.51-4.44 (2H, m), 3.97 (1H, t, J = 10.6 Hz), 3.53 (1H, s), 3.45-3.35 (1H, m), 3.22 (2H, s), 2.40-2.32 (2H, m), 1.93-1.88 (1H, m); |
| 143 | 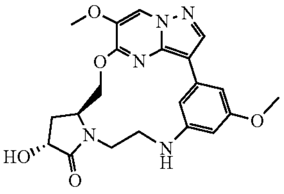 [SMILES: COc1cc2cc(c1)-c1cnn3cc(OC)c(nc13)OC[C@@H]1C[C@@H](O)C(=O)N1CCN2] (12R,14S)-12-hydroxy-4,18-dimethoxy-16-oxa-7,10,20,21,24-pentaazapentacyclo[15.5.2.$1^{2}$,$6.0^{10}$,$^{1}4.0^{20}$,$^{23}$]pentacosa-1(23),2(25),3,5,17(24),18,21-heptaen-11-one | Scaffold S2 Pyrrolidine P13 Aniline A3 9 mg, 53% yield white solid | LCMS (MC) RT = 1.86 min, m/z = 426.2 $(M + H)^+$. LCMS (MC) RT = 1.87 min, m/z = 426.2 $(M + H)^+$. $^1$H NMR (400 MHz, DMSO) 8.76 (1H, s), 8.36 (1H, s), 7.44 (1H, brs), 6.53-6.51 (1H, m), 6.04-6.01 (2H, m), 5.60 (1H, d, J = 5.9 Hz), 4.92 (1H, d, J = 10.1 Hz), 4.51-4.42 (2H, m), 4.04 (1H, t, J = 10.6 Hz), 3.89 (3H, s), 3.72 (3H, s), 3.57-3.49 (1H, m), 3.44-3.37 (1H, m), 3.24-3.16 (2H, m), 2.40-2.33 (1H, m), 1.95-1.87 (1H, m). |

Example 91: (12R,14S)-4-fluoro-12-(oxetan-3-ylmethoxy)-16-oxa-7,10,20,21,24-pentaazapentacyclo[15.5.2.$1^{2}$,$6.0^{1o}$,$^{1}4.0^{2o}$,$^{23}$]pentacosa-1(23),2(25),3,5,17(24),18,21-heptaen-11-one

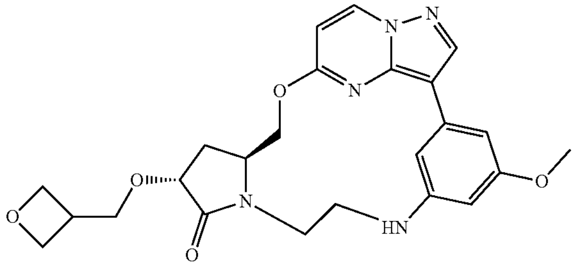 [SMILES: COc1cc2cc(c1)-c1cnn3ccc(nc13)OC[C@@H]1C[C@@H](OCC3COC3)C(=O)N1CCN2]

Step 1

To a solution of Intermediate I27 (0.10 g, 0.18 mmol) and 3-Bromomethyloxetane (0.032 g, 0.21 mmol) in dry DMF (2 mL) was added Potassium tert-butoxide (0.024 g, 0.21 mmol) at 0° C. and the mixture was stirred at 0° C. for 2 h. Upon complete conversion, monitored by LCMS, Water was added dropwise carefully at 0° C. The resulting mixture was extracted with EtOAc (2×10 mL). The combined organic layers were washed with Brine, dried over $Na_2SO_4$, filtered and concentrated under vacuum to afford the title compound as a yellow oil (0.030 g, 27% yield).

LCMS (MA) RT=2.51 min, m/z=639.1 $(M+H)^+$.

Step 2

The title compound from Step 1 (0.03 g, 0.05 mmol) and Cesium carbonate (0.031 g, 0.09 mmol) were dissolved in DMF (1.1 mL). 4-Methylbenzenethiol (0.007 g, 0.06 mmol) was added and the mixture was stirred at rt overnight. Upon complete conversion, monitored by LCMS, the reaction mixture was filtered. Solvent was evaporated and the residue was purified by flash column chromatography using Cyclohexane/EtOAc (100/0 to 0/100) as eluent to afford the expected product as a white solid (0.011 g, 52% Yield).

LCMS (MA) RT=2.12 min, m/z=454.2 $(M+H)^+$.

LCMS (MC) RT=2.11 min, m/z=454.2 $(M+H)^+$.

$^1$H NMR (400 MHz, $CDCl_3$) 8.55-8.52 (1H, m), 8.31-8.30 (1H, m), 7.72-7.71 (1H, m), 6.74-6.69 (1H, m), 6.46-6.43 (1H, m), 6.26-6.21 (1H, m), 5.11 (1H, t, J=6.9 Hz), 4.87-4.82 (1H, m), 4.53-4.49 (3H, m), 4.34-4.29 (2H, m), 3.93-3.57 (6H, m), 3.36-3.25 (1H, m), 2.64 (1H, dd, J=8.0, 12.9 Hz), 2.07-2.07 (1H, m), 1.30-1.26 (2H, m);

Similarly Prepared:

| Ex no | Structure/Name | From intermediates | Analytical data |
|---|---|---|---|
| 110 | 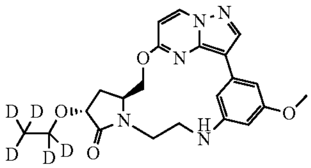 [SMILES: [2H]C([2H])([2H])C([2H])([2H])O[C@@H]1C[C@H]2COc3ccn4ncc(c4n3)-c3cc(cc(OC)c3)NCCN2C1=O] (12R,14S)-12-(H5)ethoxy-4-methoxy-16-oxa-7,10,20,21,24-pentaazapentacyclo[15.5.2.$1^2$,6.$0^{10}$,$^1$4.$0^{20}$,$^{23}$]pentacosa-1(23),2,4,6(25),17(24),18,21-heptaen-11-one | Scaffold 3-bromo-5-chloropyrazolo[1,5-a]pyrimidine Pyrrolidine P13 Aniline A3 48 mg, 53% yield using Sodium Hydride instead of tBuOK at alkylation step | LCMS (MA) RT = 2.13 min, m/z = 429.2 $(M + H)^+$. LCMS (MC) RT = 2.11 min, m/z = 429.3 $(M + H)^+$. $^1$H NMR (400 MHz, DMSO) 8.97 (1H, d, J = 7.6 Hz), 8.51 (1H, s), 7.47 (1H, s), 6.64 (1H, d, J = 7.6 Hz), 6.55-6.54 (1H, m), 6.06-6.02 (2H, m), 4.94-4.90 (1H, m), 4.48-4.38 (2H, m), 3.94 (1H, t, J = 10.6 Hz), 3.73 (3H, s), 3.55-3.49 (1H, m), 3.44-3.40 (1H,m), 3.24-3.16 (2H, m), 2.46-2.40 (1H, m), 2.00-1.92 (1H, m). |
| 132 | 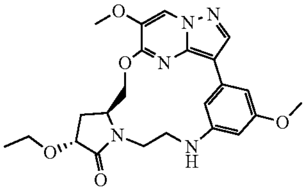 [SMILES: CCO[C@@H]1C[C@H]2COc3nc4c(cnn4cc3OC)-c3cc(cc(OC)c3)NCCN2C1=O] (12R,14S)-12-ethoxy-4,18-dimethoxy-16-oxa-7,10,20,21,24-pentaazapentacyclo[15.5.2.$1^2$,6.$0^{10}$,$^1$4.$0^{20}$,$^{23}$]pentacosa-1(23),2,4,6(25),17(24),18,21-heptaen-11-one | Scaffold S2 Pyrrolidine P13 Aniline A3 18 mg, 51% yield as Pale yellow solid using Sodium Hydride instead of tBuOK at alkylation step | LCMS (MA) RT = 2.10 min, m/z = 454.3 $(M + H)^+$. LCMS (MC) RT = 2.09 min, m/z = 454.3 $(M + H)^+$. $^1$H NMR (400 MHz, DMSO) 8.76 (1H, s), 8.36 (1H, s), 7.43-7.42 (1H, m), 6.52 (1H, dd, J = 1.2, 2.0 Hz), 6.06-6.01 (2H, m), 4.92 (1H, s), 4.45-4.39 (2H, m), 4.06-4.00 (1H, m), 3.89-3.88 (4H, m), 3.72 (3H, s), 3.61-3.49 (2H, m), 3.43-3.36 (1H, m), 3.23-3.16 (2H, m), 2.44 (1H, dd, J = 8.4, 12.8 Hz), 1.99-1.91 (1H, m), 1.15 (3H, t, J = 7.0 Hz). |
| 133 | 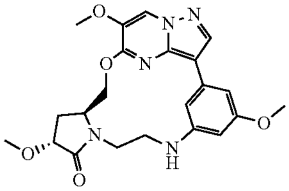 (12R,14S)-4,12,18-trimethoxy-16-oxa-7,10,20,21,24-pentaazapentacyclo[15.5.2.$1^2$,6.$0^{10}$,$^1$4.$0^{20}$,$^{23}$]pentacosa-1(23),2,4,6(25),17(24),18,21-heptaen-11-one | Scaffold S2 Pyrrolidine P13 Aniline A3 12 mg, 42% yield as Pale yellow solid using Sodium Hydride instead of tBuOK at alkylation step | LCMS (MA) RT = 1.98 min, m/z = 440.3 $(M + H)^+$. LCMS (MC) RT = 1.97 min, m/z = 440.4 $(M + H)^+$. $^1$H NMR (400 MHz, DMSO) 8.76 (1H, s), 8.36 (1H, s), 7.42 (1H, brs), 6.52 (1H, dd, J = 1.2, 2.2 Hz), 6.05-6.01 (2H, m), 4.94 (1H, d, J = 11.0 Hz), 4.50-4.43 (1H, m), 4.36-4.30 (1H, m), 4.02 (1H, t, J = 10.9 Hz), 3.89 (3H, s), 3.72 (3H, s), 3.57-3.49 (1H, m), 3.44 (3H, s), 3.41-3.37 (1H, m), 3.23-3.15 (2H, m), 2.47-2.41 (1H, m), 1.99-1.91 (1H, m). |
| 134 | 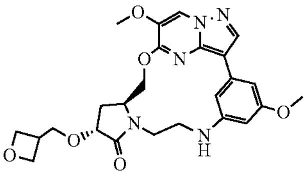 (12R,14S)-4,18-dimethoxy-12-(oxetan-3-ylmethoxy)-16-oxa-7,10,20,21,24-pentaazapentacyclo[15.5.2.$1^2$,6.$0^{10}$,$^1$4.$0^{20}$,$^{23}$]pentacosa-1(23),2,4,6(25),17(24),18,21-heptaen-11-one | Scaffold S2 Pyrrolidine P13 Aniline A3 12 mg, 37% yield as Pale yellow solid using Sodium Hydride instead of tBuOK at alkylation step | LCMS (MA) RT = 2.10 min, m/z = 454.3 $(M + H)^+$. LCMS (MC) RT = 2.09 min, m/z = 454.3 $(M + H)^+$. $^1$H NMR (400 MHz, DMSO) 8.76 (1H, s), 8.36 (1H, s), 7.42 (1H, brs), 6.52 (1H, dd, J = 1.3, 2.1 Hz), 6.06-6.01 (2H, m), 4.97-4.92 (1H, m), 4.64 (2H, dd, J = 5.9, 7.8 Hz), 4.51-4.44 (2H, m), 4.35-4.30 (2H, m), 4.09-4.00 (2H, m), 3.89 (3H, s), 3.77-3.74 (1H, m), 3.72 (3H, s), 3.58-3.49 (1H, m), 3.44-3.36 (1H, m), 3.24-3.14 (3H, m), 2.48-2.42 (1H, m), 2.02-1.93 (1H, m). |

-continued

| Ex no | Structure/Name | From intermediates | Analytical data |
|---|---|---|---|
| 135 | 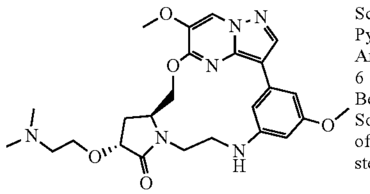 (12R,14S)-12-[2-(dimethylamino)ethoxy]-4,18-dimethoxy-16-oxa-7,10,20,21,24-pentaazapentacyclo[15.5.2.$1^{2}$,6.$0^{10}$,$^{1}$4.$0^{20}$,$^{23}$]pentacosa-1(23),2,4,6(25),17(24),18,21-heptaen-11-one | Scaffold S2 Pyrrolidine P13 Aniline A3 6 mg, 19% yield as Beige solid using Sodium Hydride instead of tBuOK at alkylation step | LCMS (MA) RT = 1.49 min, m/z = 497.4 $(M + H)^+$. LCMS (MC) RT = 1.49 min, m/z = 497.4 $(M + H)^+$. $^1$H NMR (400 MHz, $CDCl_3$) 8.22 (1H, s), 8.15 (1H, s), 7.49 (1H, s), 6.60 (1H, dd, J = 1.3, 2.1 Hz), 6.09 (1H, t, J = 2.2 Hz), 5.14 (1H, d, J = 11.0 Hz), 4.56-4.50 (1H, m), 4.35-4.30 (1H, m), 4.26-4.20 (1H, m), 4.14 (1H, t, J = 5.8 Hz), 3.96 (3H, s), 3.92-3.86 (1H, m), 3.87-3.82 (1H, m), 3.84 (3H, s), 3.67-3.50 (3H, m), 3.32-3.24 (1H, m), 2.81-2.70 (2H, m), 2.48 (6H, s), 2.27-2.17 (1H, m). |
| 115 | 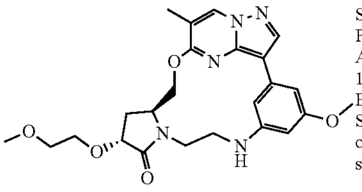 (12R, 14S)-4-methoxy-12-(2-16-oxa-7,10,20,21,24-pentaazapentacyclo[15.5.2.$1^{2}$,6.$0^{10}$,$^{1}$4.$0^{20}$,$^{23}$]pentacosa-1(23),2,4,6(25),17(24),18,21-heptaen-11-one | Scaffold S1 Pyrrolidine P13 Aniline A3 11 mg, 24% yield as Beige solid using Sodium Hydride instead of tBuOK at alkylation step | LCMS (MA) RT = 2.15 min, m/z = 468.4 $(M + H)^+$. LCMS (MC) RT = 2.15 min, m/z = 468.4 $(M + H)^+$. $^1$H NMR (400 MHz, DMSO): 8.88-8.87 (1H, m), 8.41-8.40 (1H, m), 7.46 (1H, s), 6.53 (1H, d, J = 0.8 Hz), 6.06-6.01 (2H, m), 4.94 (1H, d, J = 10.6 Hz), 4.51-4.44 (2H, m), 4.02-3.91 (2H, m), 3.72 (3H, s), 3.69-3.62 (1H, m), 3.58-3.30 (5H, m), 3.26 (3H, s), 3.23-3.15 (1H, m), 2.51-2.44 (1H, m), 2.19-2.17 (3H, m), 2.02-1.93 (1H, m); |
| 147 | 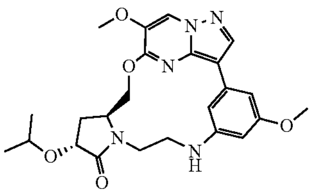 [SMILES: COc1cc2cc(c1)-c1cnn3cc(OC)c(nc13)OC[C@@H]1C[C@@H](OC(C)C)C(=O)N1CCN2] (12R,14S)-4,18-dimethoxy-12-(propan-2-yloxy)-16-oxa-7,10,20,21,24-pentaazapentacyclo[15.5.2.$1^{2}$,6.$0^{10}$,$^{1}$4.$0^{20}$,$^{23}$]pentacosa-1(23),2,4,6(25),17(24),18,21-heptaen-11-one | Scaffold S2 Pyrrolidine P13 Aniline A3 13 mg, 12% yield as Light yellow solid using Sodium Hydride instead of tBuOK at alkylation step | LCMS (MA) RT = 2.24 min, m/z = 468.4 $(M + H)^+$. LCMS (MC) RT = 2.20 min, m/z = 468.4 $(M + H)^+$. $^1$H NMR (400 MHz, CDCl) 8.21 (1H, s), 8.16-8.13 (1H, m), 7.72-7.55 (1H, m), 7.49 (2H, s), 6.59 (1H, t, J = 1.6 Hz), 6.09-6.07 (1H, m), 5.13 (1H, d, J = 10.8 Hz), 4.51 (1H, t, J = 9.2 Hz), 4.35 (1H, dd, J = 8.1, 9.8 Hz), 4.17-4.15 (1H, m), 4.10-4.03 (1H, m), 3.95 (3H, s), 3.94-3.85 (1H, m), 3.84 (3H, s), 3.63-3.53 (1H, m), 3.30-3.23 (1H, m), 2.72-2.66 (1H, m), 2.19-2.08 (1H, m); |

Example 92: (12R,14S)-4-fluoro-18-($^{2}$H3)methoxy-12-methoxy-16-oxa-7,10,20,21,24-pentaazapentacyclo[15.5.2.1$^{2}$,6.0$^{1o}$,$^{1}$4.0$^{2o}$,$^{23}$]pentacosa-1(23),2(25),3,5,17(24),18,21-heptaen-11-one

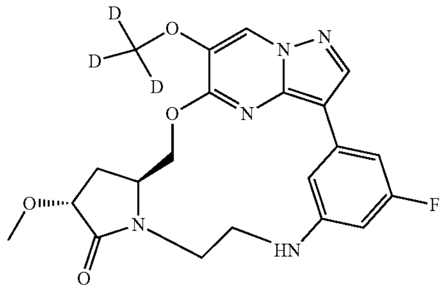 [SMILES: [2H]C([2H])([2H])Oc1cn2ncc3c2nc1OC[C@@H]1C[C@@H](OC)C(=O)N1CCNc1cc(F)cc-3c1]

Step 1

To a suspension of Intermediate I28 (0.064 g, 0.11 mmol) in DMF (3.3 mL) were added Cesium carbonate (0.105 g, 0.32 mmol) and Iodo(2$H_3$)methane (0.046 g, 0.32 mmol). The reaction mixture was stirred at 70° C. for 2 h. Upon complete conversion, monitored by LCMS, the reaction mixture was allowed to cooled to room temperature. The solution was concentrated under reduced pressure and then diluted with water and EtOAc. The layers were separated. The aqueous layer was extracted with EtOAc (3×20 mL) and the combined organic layer was washed with Brine, dried over anhydrous sodium sulfate, filtered and evaporated under reduced pressure to afford the title compound as yellow solid (0.202 g).

LCMS (MA) RT=2.55 min, m/z=616.2 $(M+H)^+$.

Step 2

The title compound from Step 1 (0.066 g, 0.11 mmol) and Cesium carbonate (0.070 g, 0.21 mmol) were dissolved in DMF (2.4 mL). 4-Methylbenzenethiol (0.016 g, 0.13 mmol) was added and the mixture was stirred at rt overnight. Upon complete conversion, monitored by LCMS, the reaction mixture was filtered, solvent was evaporated to dryness. The residue was purified by flash column chromatography using Cyclohexane/EtOAc (100/0 to 20/80) as eluent to afford the expected product as a white solid (25 mg, 54% Yield).

LCMS (MA) RT=2.23 min, m/z=431.2 $(M+H)^+$.

LCMS (MC) RT=2.14 min, m/z=431.3 $(M+H)^+$.

$^{1}$H NMR (400 MHz, DMSO) 8.79-8.78 (1H, m), 8.40-8.39 (1H, m), 7.63-7.62 (1H, m), 6.72 (1H, d, J=9.9 Hz), 6.40-6.25 (1H, m), 6.22-6.17 (1H, m), 4.95 (1H, d, J=10.1 Hz), 4.48 (1H, s), 4.33 (1H, t, J=8.9 Hz), 4.03 (1H, t, J=10.7 Hz), 3.59-3.51 (1H, m), 3.41-3.36 (1H, m), 3.33 (3H, s), 3.31 (1H, s), 3.23-3.16 (2H, m), 1.99-1.91 (1H, m);

Similarly Prepared:

| Ex no | Structure/Name | From intermediates | Analytical data |
|---|---|---|---|
| 122 | 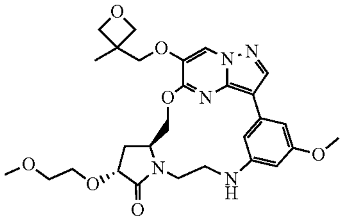 (12R,14S)-18-(cyclopropylmethoxy)-4-methoxy-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S3 Pyrrolidine P7 Aniline A3 35 mg, 69% yield | LCMS (MA) RT = 2.14 min, m/z = 554 $(M + H)^+$. LCMS (MC) RT = 2.36 min, m/z = 554 $(M + H)^+$. $^{1}$H NMR (400 MHz, DMSO) 8.87 (1H, s), 8.37 (1H, s), 7.41 (1H, t, J = 4.5 Hz), 6.52 (1H, dd, J = 1.1, 2.1 Hz), 6.06-6.02 (2H, m), 4.96-4.93 (1H, m), 4.54-4.46 (4H, m), 4.35 (2H, d, J = 5.9 Hz), 4.23 (1H, d, J = 9.5 Hz), 4.16-4.03 (2H, m), 3.97-3.92 (1H, m), 3.73-3.72 (4H, m), 3.47 (3H, t, J = 4.8 Hz), 3.31 (2H, s), 3.26 (3H, s), 3.25-3.10 (2H, m), 2.05-1.85 (1H, m), 1.41 (3H, s); |
| 123 | 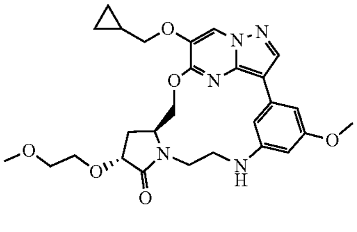 (12R,14S)-18-(cyclopropylmethoxy)-4-methoxy-12-(2-methoxyethoxy)-16-oxa-7,10,20,21,24-pentaazapentacyclo[15.5.2.1$^{2}$,6.0$^{10}$,$^{1}$4.0$^{20}$,$^{23}$]pentacosa-1(23),2(25),3,5,17(24),18,21-heptaen-11-one | Scaffold S3 Pyrrolidine P7 Aniline A3 35 mg, 69% yield using $K_2CO_3$ instead of $Cs_2CO_3$ at alkylation step | LCMS (MA) RT = 2.36 min, m/z = 524 $(M + H)^+$. LCMS (MC) RT = 2.32 min, m/z = 524 $(M + H)^+$. $^{1}$H NMR (400 MHz, DMSO) 8.70 (1H, s), 8.35 (1H, s), 7.43 (1H, s), 6.52-6.51 (1H, m), 6.06-6.01 (2H, m), 4.94-4.91 (1H, m), 4.50-4.44 (2H, m), 4.10-4.04 (1H, m), 3.98-3.86 (3H, m), 3.72-3.72 (4H, m), 3.48 (2H, t, J = 4.7 Hz), 3.30 (2H, s), 3.25 (3H, s), 3.24-3.10 (2H, m), 2.10-1.80 (1H, m), 1.29-1.24 (2H, m), 0.65-0.61 (2H, m), 0.38-0.34 (2H, m); |

-continued

| Ex no | Structure/Name | From intermediates | Analytical data |
|---|---|---|---|
| 124 | 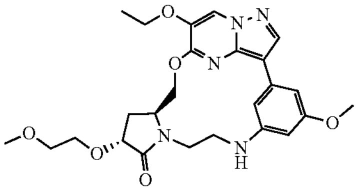 (12R,14S)-18-ethoxy-4-methoxy-12-(2-methoxyethoxy)-16-oxa-7,10,20,21,24-pentaazapentacyclo[15.5.2.1^2,6.0^10,14.0^20,23]pentacosa-1(23),2,4,6(25),17(24),18,21-heptaen-11-one | Scaffold S3 Pyrrolidine P7 Aniline A3 28 mg, 28% yield using $K_2CO_3$ instead of $Cs_2CO_3$ at alkylation step | LCMS (MA) RT = 2.13 min, m/z = 498.3 $(M + H)^+$. LCMS (MC) RT = 2.14 min, m/z = 498.4 $(M + H)^+$. $^1H$ NMR (400 MHz, DMSO) 8.75 (1H, s), 8.36 (1H, s), 7.42 (1H, s), 6.53-6.51 (1H, m), 6.06-6.01 (2H, m), 4.92 (1H, d, J = 10.4 Hz), 4.52-4.43 (2H, m), 4.17-4.09 (2H, m), 4.04 (1H, t, J = 10.6 Hz), 3.96-3.90 (1H, m), 3.72 (3H, s), 3.68-3.62 (1H, m), 3.58-3.51 (1H, m), 3.48 (2H, t, J = 4.8 Hz), 3.42-3.36 (1H, m), 3.26 (3H, s), 3.22-3.16 (2H, m), 2.49-2.42 (1H, m), 2.01-1.93 (1H, m), 1.39 (3H, t, J = 6.9 Hz). |
| 125 | 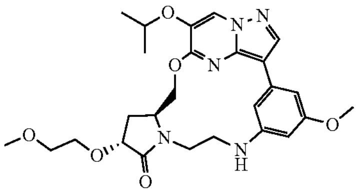 (12R,14S)-4-methoxy-12-(2-methoxyethoxy)-18-(propan-2-yloxy)-16-oxa-7,10,20,21,24-pentaazapentacyclo[15.5.2.1^2,6.0^10,14.0^20,23]pentacosa-1(23),2,4,6(25),17(24),18,21-heptaen-11-one | Scaffold S3 Pyrrolidine P7 Aniline A3 54 mg, 53% yield using $K_2CO_3$ instead of $Cs_2CO_3$ at alkylation step | LCMS (MA) RT = 2.26 min, m/z = 512.4 $(M + H)^+$. LCMS (MC) RT = 2.26 min, m/z = 512.4 $(M + H)^+$. $^1H$ NMR (400 MHz, DMSO) 8.83 (1H, s), 8.37 (1H, s), 7.42 (1H, brs), 6.52 (1H, dd, J = 1.1, 2.1 Hz), 6.06-6.01 (2H, m), 4.92 (1H, d, J = 10.4 Hz), 4.62 (1H, sept, J = 6.03 Hz), 4.51-4.44 (2H, m), 4.03 (1H, t, J = 10.6 Hz), 3.96-3.90 (1H, m), 3.72 (3H, s), 3.68-3.63 (1H, m), 3.58-3.52 (1H, m), 3.50-3.46 (2H, m), 3.42-3.37 (1H, m), 3.27 (3H, s), 3.23-3.16 (2H, m), 2.47-2.42 (1H, m), 2.01-1.93 (1H, m), 1.33 (6H, dd, J = 6.1, 7.4 Hz). |
| 126 | 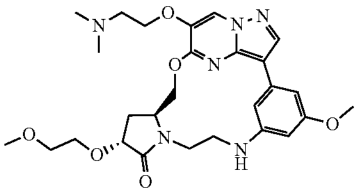 (12R,14S)-18-[2-(dimethylamino)ethoxy]-4-methoxy-12-(2-methoxyethoxy)-16-oxa-7,10,20,21,24-pentaazapentacyclo[15.5.2.1^2,6.0^10,14.0^20,23]pentacosa-1(23),2,4,6(25),17(24),18,21-heptaen-11-one | Scaffold S3 Pyrrolidine P7 Aniline A3 4 mg, 4% yield as white solid using $K_2CO_3$ instead of $Cs_2CO_3$ at alkylation step | LCMS (MA) RT = 1.40 min, m/z = 541.4 $(M + H)^+$. LCMS (MC) RT = 2.01 min, m/z = 541.4 $(M + H)^+$. $^1H$ NMR (400 MHz, $CDCl_3$) 8.22-8.21 (2H, m), 7.49 (1H, brs), 6.59 (1H, dd, J = 1.3, 2.1 Hz), 6.08 (1H, t, J = 2.2 Hz), 5.11 (1H, d, J = 11.0 Hz), 4.53-4.48 (1H, m), 4.36 (1H, dd, J = 8.2, 9.5 Hz), 4.24-4.20 (1H, m), 4.14 (2H, t, J = 5.7 Hz), 3.90-3.84 (2H, m), 3.84 (3H, s), 3.83-3.80 (1H, m), 3.70-3.52 (4H, m), 3.42 (3H, s), 3.31-3.22 (1H, m), 2.86-2.81 (2H, m), 2.70 (1H, dd, J = 8.3, 13.2 Hz), 2.40 (6H, s), 2.24-2.16 (1H, m). |

-continued

| Ex no | Structure/Name | From intermediates | Analytical data |
|---|---|---|---|
| 127 | 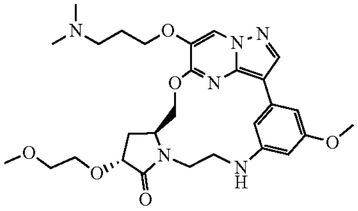 (12R,14S)-18-[3-(dimethylamino)propoxy]-4-methoxy-12-(2-methoxyethoxy)-16-oxa-7,10,20,21,24-pentaazapentacyclo[15.5.2.$1^{2,6}$.$0^{10,14}$.$0^{20,23}$]pentacosa-1(23),2,4,6(25),17(24),18,21-heptaen-11-one | Scaffold S3 Pyrrolidine P7 Aniline A3 17 mg, 15% yield as Beige solid using $K_2CO_3$ instead of $Cs_2CO_3$ at alkylation step | LCMS (MA) RT = 1.46 min, m/z = 555.3 $(M + H)^+$. LCMS (MC) RT = 2.06 min, m/z = 555.4 $(M + H)^+$. $^1$H NMR (400 MHz, DMSO) 8.76 (1H, s), 8.35 (1H, s), 7.41 (1H, brs), 6.53-6.50 (1H, m), 6.06-6.01 (2H, m), 4.95-4.91 (1H, m), 4.52-4.44 (2H, t, J = 8.8 Hz), 4.11 (2H, t, J = 6.2 Hz), 4.04 (1H, t, J = 11.0 Hz), 3.97-3.91 (1H, m), 3.72 (3H, s), 3.68-3.62 (1H, m), 3.58-3.51 (1H, m), 3.48 (2H, t, J = 4.8 Hz), 3.44-3.37 (1H, m), 3.26 (3H, s), 3.23-3.16 (2H, m), 2.48-2.34 (3H, m), 2.16 (6H, s), 1.99-1.87 (3H, m). |
| 130 | 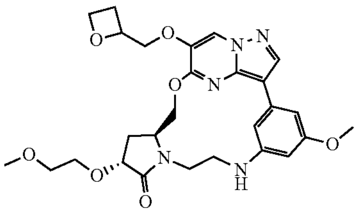 (12R,14S)-4-methoxy-12-(2-methoxyethoxy)-18-(oxetan-2-ylmethoxy)-16-oxa-7,10,20,21,24-pentaazapentacyclo[15.5.2.$1^{2,6}$.$0^{10,14}$.$0^{20,23}$]pentacosa-1(23),2,4,6(25),17(24),18,21-heptaen-11-one | Scaffold S3 Pyrrolidine P7 Aniline A3 15 mg, 43% yield as Off-white solid using $K_2CO_3$ instead of $Cs_2CO_3$ at alkylation step | LCMS (MA) RT = 1.99 min, m/z = 540.3 $(M + H)^+$. LCMS (MC) RT = 2.01 min, m/z = 540.3 $(M + H)^+$. $^1$H NMR (400 MHz, $CDCl_3$) 8.36 (1H, s), 8.22 (1H, s), 7.50 (1H, d, J = 0.4 Hz), 6.59 (1H, dd, J = 1.3, 2.1 Hz), 6.09 (1H, t, J = 2.2 Hz), 5.25-5.11 (2H, m), 4.80-4.66 (2H, m), 4.54-4.49 (1H, m), 4.37 (1H, dd, J = 8.3, 9.6 Hz), 4.27-4.18 (3H, m), 3.85-3.84 (6H, m), 3.70-3.53 (4H, m), 3.42 (3H, s), 3.31-3.24 (1H, m), 2.90-2.67 (3H, m), 2.25-2.16 (1H, m); |
| 136 | 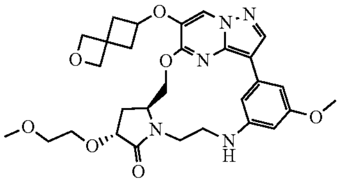 (12R,14S)-4-methoxy-12-(2-methoxyethoxy)-18-{2-oxaspiro[3.3]heptan-6-yloxy}-16-oxa-7,10,20,21,24-pentaazapentacyclo[15.5.2.$1^{2,6}$.$0^{10,14}$.$0^{20,23}$]pentacosa-1(23),2,4,6(25),17(24),18,21-heptaen-11-one | Scaffold S3 Pyrrolidine P7 Aniline A3 20 mg, 23% yield as Beige solid using $K_2CO_3$ instead of $Cs_2CO_3$ at alkylation step | LCMS (MA) RT = 2.07 min, m/z = 566.4 $(M + H)^+$. LCMS (MC) RT = 2.06 min, m/z = 566.4 $(M + H)^+$. $^1$H NMR (400 MHz, DMSO) 8.58 (1H, s), 8.37 (1H, s), 7.40 (1H, s), 6.52 (1H, s), 6.06-6.01 (2H, m), 4.89 (1H, s), 4.66-4.63 (3H, m), 4.57 (2H, s), 4.46 (2H, t, J = 8.7 Hz), 4.05-3.90 (2H, m), 3.72 (3H, s), 3.65 (1H, td, J = 5.1, 10.2 Hz), 3.52-3.46 (3H, m), 3.44-3.38 (1H, m), 3.26 (3H, s), 3.20-3.15 (2H, m), 2.89-2.83 (2H, m), 2.48-2.41 (1H, m), 2.35-2.25 (2H, m), 1.98-1.91 (1H, m); |
| 137 | 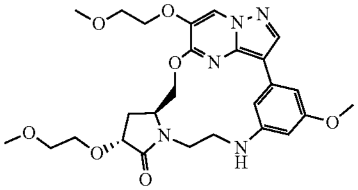 (12R,14S)-4-methoxy-12,18-bis(2-methoxyethoxy)-16-oxa-7,10,20,21,24-pentaazapentacyclo[15.5.2.$1^{2,6}$.$0^{10,14}$.$0^{20,23}$]pentacosa-1(23),2,4,6(25),17(24),18,21-heptaen-11-one | Scaffold S3 Pyrrolidine P7 Aniline A3 30 mg, 29% yield as Pale yellow solid using $K_2CO_3$ instead of $Cs_2CO_3$ at alkylation step | LCMS (MA) RT = 2.05 min, m/z = 528.3 $(M + H)^+$. LCMS (MC) RT = 2.04 min, m/z = 528.4 $(M + H)^+$. $^1$H NMR (400 MHz, DMSO) 8.78 (1H, s), 8.36 (1H, s), 7.42 (1H, brs), 6.53-6.51 (1H, m), 6.06-6.01 (2H, m), 4.93 (1H, d, J = 10.2 Hz), 4.52-4.44 (2H, m), 4.24-4.19 (2H, m), 4.05 (1H, t, J = 10.6 Hz), 3.96-3.88 (1H, m), 3.72 (3H, s), 3.72-3.70 (2H, m), 3.68-3.62 (1H, m), 3.58-3.51 (1H, m), 3.48 (2H, t, J = 4.8 Hz), 3.43-3.36 (1H, m), 3.34 (3H, s), 3.26 (3H, s), |

-continued

| Ex no | Structure/Name | From intermediates | Analytical data |
|---|---|---|---|
| | | | 3.24-3.16 (2H, m), 2.48-2.43 (1H, m), 2.02-1.93 (1H, m). |
| 138 | 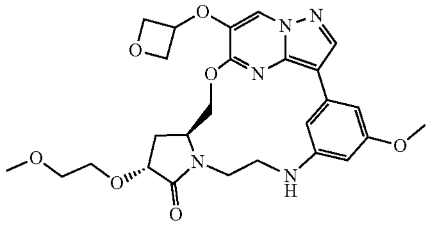<br>(12R,14S)-4-methoxy-12-(2-methoxyethoxy)-18-(oxetan-3-yloxy)-16-oxa-7,10,20,21,24-pentaazapentacyclo[15.5.2.$1^2$,6.$0^{10}$,$^{14}$4.$0^{20}$,$^{23}$]pentacosa-1(23),2,4,6(25),17(24),18,21-heptaen-11-one | Scaffold S3<br>Pyrrolidine P7<br>Aniline A3<br>8 mg, 8% yield as Pale yellow solid using $K_2CO_3$ instead of $Cs_2CO_3$ at alkylation step | LCMS (MA) RT = 1.96 min, m/z = 526.3 $(M + H)^+$.<br>LCMS (MC) RT = 1.94 min, m/z = 526.3 $(M + H)^+$.<br>$^1$H NMR (400 MHz, DMSO) 8.59 (1H, s), 8.39 (1H, s), 7.41 (1H, brs), 6.53-6.51 (1H, m), 6.06 (1H, t, J = 5.5 Hz), 6.02 (1H, t, J = 2.1 Hz), 5.37-5.31 (1H, m), 5.00-4.92 (3H, m), 4.68-4.61 (2H, m), 4.50-4.44 (2H, m), 4.07 (1H, t, J = 10.7 Hz), 3.96-3.91 (1H, m), 3.72 (3H, s), 3.69-3.63 (1H, m), 3.58-3.51 (1H, m), 3.48 (2H, t, J = 4.7 Hz), 3.43-3.36 (1H, m), 3.27 (3H, s), 3.24-3.15 (2H, m), 2.48-2.44 (1H, m), 2.02-1.94 (1H, m). |
| 144 | 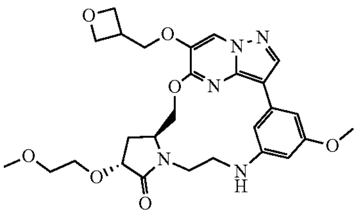<br>(12R,14S)-4-methoxy-12-(2-methoxyethoxy)-18-(oxetan-3-yloxy)-16-oxa-7,10,20,21,24-pentaazapentacyclo[15.5.2.$1^2$,6.$0^{10}$,$^{14}$4.$0^{20}$,$^{23}$]pentacosa-1(23),2,4,6(25),17(24),18,21-heptaen-11-one | Scaffold S3<br>Pyrrolidine P7<br>Aniline A3<br>24 mg, 22% yield as Pale yellow solid using $K_2CO_3$ instead of $Cs_2CO_3$ at alkylation step | LCMS (MA) RT = 2.02 min, m/z = 540.2 $(M + H)^+$.<br>LCMS (MC) RT = 2.03 min, m/z = 540.3 $(M + H)^+$.<br>$^1$H NMR (400 MHz, DMSO) 8.85 (1H, s), 8.38 (1H, s), 7.41 (1H, brs), 6.52 (1H, dd, J = 1.1, 2.1 Hz), 6.07-6.01 (2H, m), 4.93 (1H, d, J = 10.8 Hz), 4.75 (2H, dd, J = 6.1, 7.8 Hz), 4.49-4.47 (2H, m), 4.44 (2H, t, J = 6.0 Hz), 4.35-4.31 (2H, m), 4.05 (1H, t, J = 10.6 Hz), 3.96-3.90 (1H, m), 3.72 (3H, s), 3.68-3.62 (1H, m), 3.58-3.51 (1H, m), 3.47 (2H, t, J = 4.8 Hz), 3.45-3.36 (2H, m), 3.26 (3H, s), 3.23-3.16 (2H, m), 2.47-2.41 (1H, m), 2.01-1.92 (1H, m). |

Example 93: (12R,14S)-4-[1-(2-hydroxyethyl)-1H-pyrazol-4-yl]-12-methoxy-16-oxa-7,10,20,21,24-pentaazapentacyclo[15.5.2.$1^2$,6.$0^{1o}$,$^1$4.$0^{2o}$,$^{23}$]pentacosa-1(23),2,4,6(25),17(24),18,21-heptaen-11-one

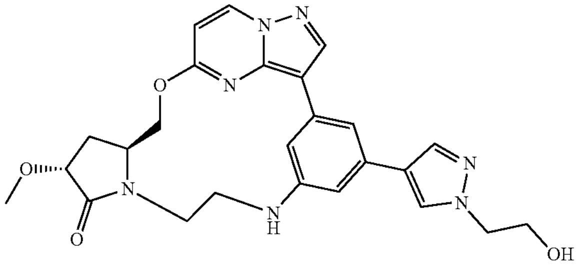 [SMILES: CO[C@@H]1C[C@H]2COc3ccn4ncc(c4n3)-c3cc(cc(-c4cnn(CCO)c4)c3)NCCN2C1=O]

Step 1

To a suspension of Intermediate I29 (170 mg, 0.23 mmol) in THE (1.2 mL) was added TBAF in THE 1 M (0.25 mL, 0.25 mmol). The reaction was stirred at rt for 1 h. Upon complete conversion, monitored by LCMS, the solvent was evaporated under reduced pressure. The residue was purified on silica gel column chromatography using DCM/MeOH (100:0 to 90:10) as eluent. The expected fractions were combined and evaporated under reduced pressure. The resulting solid was triturated into acetonitrile, filtered and dried under vacuum to afford the expected product as a pale pink solid (80 mg, 98%).

LCMS (MA) RT=1.75 min, m/z=490.4 $(M+H)^+$.

LCMS (MC) RT=1.76 min, m/z=490.4 $(M+H)^+$.

$^1$H NMR (400 MHz, DMSO) 8.98 (1H, d, J=7.4 Hz), 8.59 (1H, s), 8.07 (1H, s), 7.82 (1H, s), 7.70 (1H, Is), 7.19-7.18 (1H, m), 6.65 (1H, d, J=7.6 Hz), 6.64-6.63 (1H, m), 6.03 (1H, t, J=5.9 Hz), 4.97-4.93 (1H, m), 4.95 (1H, t, J=5.3 Hz), 4.51-4.50 (1H, m), 4.34 (1H, t, J=9.0 Hz), 4.17 (2H, t, J=5.6 Hz), 3.95 (1H, t, J=10.9 Hz), 3.78 (2H, q, J=5.5 Hz), 3.59-3.51 (1H, m), 3.45 (3H, s), 3.44-3.39 (1H, m), 3.27-3.20 (2H, m), 2.47-2.41 (1H, m), 2.02-1.94 (1H, m).

Example 96: (12R,14S)-12-ethoxy-4-hydroxy-16-oxa-7,10,20,21,24-pentaazapentacyclo[15.5.2.$1^{2}$,$6.0^{10}$,$^{1}4.0^{20,23}$]pentacosa-1(23),2(25),3,5,17(24),18,21-heptaen-11-one

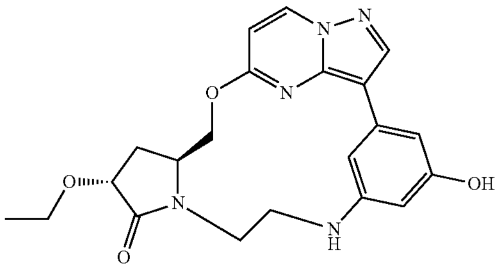 [SMILES: CCO[C@@H]1C[C@H]2COc3ccn4ncc(c4n3)-c3cc(O)cc(c3)NCCN2C1=O]

Following the general synthetic scheme 1, as depicted for the synthesis of Example 1, (12R,14S)-4-(benzyloxy)-12-ethoxy-7-(2-nitrobenzenesulfonyl)-16-oxa-7,10,20,21,24-pentaazapentacyclo[15.5.2.12,6.010,14.020,23]pentacosa-1(23),2,4,6(25),17(24),18,21-heptaen-11-one was obtained as Intermediate I30 using Scaffold 3-bromo-5-chloropyrazolo[1,5-a]pyrimidine, Pyrrolidine P2 and Aniline A9.

LCMS (MA) RT=2.87 min, m/z=685.3 $(M+H)^+$.

Step 1

To a solution of Intermediate I30 (2.38 g, 3.47 mmol) in TFA (43 mL) was added Anisole (15.19 mL, 138.9 mmol). The reaction mixture was stirred at 130° C. for 2 h. Upon complete conversion, monitored by LCMS, the mixture was allowed to cooled at room temperature and the solvent was evaporated under reduced pressure. The residue was purified by flash column chromatography using Cyclohexane/EtOAc (100/0 to 0/100) as eluent to afford the title compound as a brown solid (1.96 g, 95% Yield).

Step 2

The title compound from Step 1 (0.20 g, 0.34 mmol) and Cesium carbonate (0.219 g, 0.67 mmol) were dissolved in DMF (7.4 mL). 4-Methylbenzenethiol (0.050 g, 0.40 mmol) was added and the mixture was stirred at rt overnight. Upon complete conversion, monitored by LCMS, the reaction mixture was filtered and mother liquor was concentrated to dryness. The residue was purified by flash column chromatography using Cyclohexane/EtOAc (100/0 to 20/80) as eluent to afford the expected product as a green solid (33 mg, 24% yield).

LCMS (MA) RT=1.81 min, m/z=410.4 $(M+H)^+$.

LCMS (MC) RT=1.80 min, m/z=410.4 $(M+H)^+$.

$^1$H NMR (400 MHz, DMSO) 8.97-8.94 (2H, m), 8.39-8.38 (1H, m), 7.97-7.95 (1H, m), 7.35-7.32 (1H, m), 6.64-6.61 (1H, m), 6.35 (1H, s), 5.93 (1H, t, J=2.0 Hz), 4.94-4.89 (1H, m), 4.44-4.38 (2H, m), 3.98-3.82 (2H, m), 3.48 (4H, d, J=10.4 Hz), 3.20-3.14 (1H, m), 2.01-1.91 (1H, m), 1.17-1.04 (4H, m);

Similarly Prepared:

| Ex no | Structure/Name | From intermediates | Analytical data |
|---|---|---|---|
| 97 | 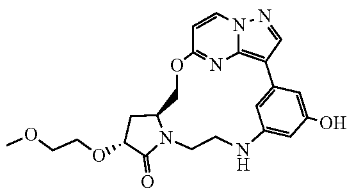 [SMILES: COCCO[C@@H]1C[C@H]2COc3ccn4ncc(c4n3)-c3cc(O)cc(c3)NCCN2C1=O] (12R,14S)-4-hydroxy-12-(2-methoxyethoxy)-16-oxa-7,10,20,21,24-pentaazapentacyclo[15.5.2.$1^{2}$,$6.0^{10}$,$^{1}4.0^{20,23}$]pentacosa-1(23),2,4,6(25),17(24),18,21-heptaen-11-one | Scaffold 3-bromo-5-chloropyrazolo[1,5-a]pyrimidine Pyrrolidine P7 Aniline A9 5.1 mg, 47% yield | LCMS (MA) RT = 1.81 min, m/z = 440.2 $(M + H)^+$. LCMS (MC) RT = 1.74 min, m/z = 440.2 $(M + H)^+$. $^1$H NMR (400 MHz, DMSO) 8.97-8.95 (2H, m), 8.38 (1H, s), 7.34-7.32 (1H, m), 6.63 (1H, d, J = 7.6 Hz), 6.35 (1H, s), 5.95-5.92 (2H, m), 4.90 (1H, s), 4.47-4.42 (2H, m), 3.99-3.90 (2H, m), 3.67-3.61 (1H, m), 3.49-3.46 (3H, m), 3.44-3.40 (1H, m), 3.3-3.25 (3H, m), 3.25-3.00 (2H, m), 2.45-2.35 (1H, m), 2.02-1.94 (1H, m) |
| 128 | 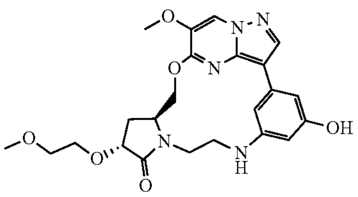 [SMILES: COCCO[C@@H]1C[C@H]2COc3nc4c(cnn4cc3OC)-c3cc(O)cc(c3)NCCN2C1=O] (12R,14S)-4-hydroxy-18-methoxy-12-(2-methoxyethoxy)-16-oxa-7,10,20,21,24-pentaazapentacyclo[15.5.2.$1^{2}$,$6.0^{10}$,$^{1}4.0^{20,23}$]pentacosa-1(23),2,4,6(25),17(24),18,21-heptaen-11-one | Scaffold S2 Pyrrolidine P7 Aniline A9 10 mg, 56% yield Beige solid | LCMS (MA) RT = 1.78 min, m/z = 470.2 $(M + H)^+$. LCMS (MC) RT = 1.81 min, m/z = 470.2 $(M + H)^+$. $^1$H NMR (400 MHz, DMSO) 8.94 (1H, s), 8.75 (1H, s), 8.24 (1H, s), 7.28-7.27 (1H, m), 6.33 (1H, s), 5.94-5.90 (2H, m), 4.96-4.91 (1H, m), 4.44 (2H, t, J = 8.7 Hz), 4.04-3.92 (2H, m), 3.89-3.87 (3H, m), 3.68-3.61 (1H, m), 3.48 (3H, t, J = 4.7 Hz), 3.44-3.39 (1H, m), 3.26 (3H, s), 3.16-3.12 (2H, m), 2.44 (1H, dd, J = 8.2, 13.4 Hz), 2.00-1.92 (1H, m). |

Example 100: (12R,14S)-12-(2-methoxyethoxy)-4-(3-methoxyprop-1-yn-1-yl)-16-oxa-7,10,20,21,24-pentaazapentacyclo[15.5.2.1²,6.0¹°,¹4.0²°,²³]pentacosa-1(23),2(25),3,5,17(24),18,21-heptaen-11-one

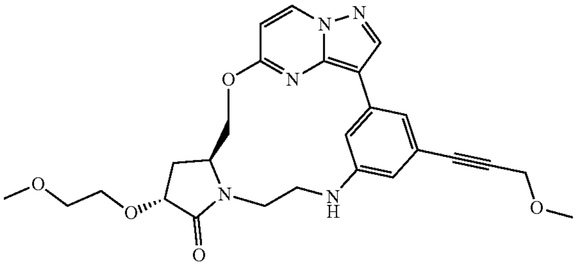

Following the general synthetic scheme 1, as depicted for the synthesis of Example 1, (12R,14S)-4-(benzyloxy)-12-(2-methoxyethoxy)-7-(2-nitrobenzenesulfonyl)-16-oxa-7,10,20,21,24-pentaazapentacyclo[15.5.2.12,6.010,14.020,23]pentacosa-1(23),2,4,6(25),17(24),18,21-heptaen-11-one was obtained as Intermediate I31 using Scaffold 3-bromo-5-chloropyrazolo[1,5-a]pyrimidine, Pyrrolidine P7 and Aniline A9.

LCMS (MA) RT=2.75 min, m/z=715.4 $(M+H)^+$.

Step 1

To a suspension of Intermediate I31 (296 mg, 0.41 mmol) in TFA (6 mL) was added Anisole (1.78 mL, 16.4 mmol). The reaction mixture was stirred at 130° C. overnight. Upon complete conversion, monitored by LCMS, the reaction mixture was cooled to room temperature. The solvent was evaporated under reduced pressure. The residue was purified on silica gel column chromatography using DCM/MeOH (100:0 to 95:5) as eluent to afford the title compound as a beige solid (250 mg, 97% yield).

LCMS (MA) RT=2.15 min, m/z=625.3 $(M+H)^+$.

Step 2

To a suspension of the title compound from Step 1 (250 mg, 0.4 mmol) in DCM (20 mL) was added Triethylamine (0.085 mL, 0.6 mmol). N-phenyl-bis(trifluoromethanesulfonimide) (157 mg, 0.44 mmol) was added portionwise to the slurry. The reaction mixture was stirred at rt overnight. Upon complete conversion, monitored by LCMS, the reaction mixture was diluted with water and the layers were separated. The aqueous layer was extracted with DCM (2×15 mL) and the combined organic layers were dried over anhydrous sodium sulfate, filtered and evaporated under reduced pressure to afford the title compound as a beige foam (450 mg).

The crude was directly engaged in the next step without further purification.

LCMS (MA) RT=2.73 min, m/z=757.3 $(M+H)^+$.

Step 3

To a suspension of the title compound from Step 2 (303 mg, 0.4 mmol) in DMF (3.5 mL) were added Cesium carbonate (260 mg, 0.8 mmol) and then 4-Methylbenzenethiol (60 mg, 0.48 mmol). The reaction was stirred at rt overnight. Upon complete conversion, monitored by LCMS, the reaction mixture was adsorbed on silica and evaporated to dryness. The residue was purified by silica gel column chromatography using DCM/MeOH (100/0 to 9/1) as eluent to afford the title compound as a white solid (Intermediate I33, (12R,14S)-12-(2-methoxyethoxy)-11-oxo-16-oxa-7,10,20,21,24-pentaazapentacyclo[15.5.2.12,6.010,14.020,23]pentacosa-1(23),2,4,6(25),17(24),18,21-heptaen-4-yltrifluoromethanesulfonate, 150 mg, 66% yield).

LCMS (MA) RT=2.54 min, m/z=572.2 $(M+H)^+$.

Step 4

In a sealed tube, to a suspension of the title compound from Step 3 (0.050 g, 0.09 mmol) in dry 1,4-Dioxane (1.5 mL), was added Lithium chloride (0.011 g, 0.26 mmol). The mixture was degassed by bubbling argon for 10 min. Tributyl(vinyl)stannane (0.038 g, 0.10 mmol) and $Pd(PPh_3)_4$ (0.010 g, 0.01 mmol) were added and the reaction was stirred at 100° C. with a sand bath for 2 h. Upon complete conversion, monitored by LCMS, the reaction mixture was cooled down and filtered over Celite then solvent was evaporated. The residue was purified by column chromatography using Cyclohexane/EtOAc (100/0 to 0/100) as eluent to afford the expected product as a white solid (17 mg, 40% yield).

LCMS (MA) RT=2.22 min, m/z=492.4 $(M+H)^+$.

LCMS (MC) RT=2.21 min, m/z=492.4 $(M+H)^+$.

$^1$H NMR (400 MHz, DMSO) 9.00-8.98 (1H, m), 8.57 (1H, s), 7.85 (1H, s), 7.03 (1H, d, J=1.3 Hz), 6.66 (1H, d, J=7.4 Hz), 6.54 (1H, dd, J=1.5, 2.3 Hz), 6.26-6.22 (1H, m), 4.93 (1H, d, J=11.0 Hz), 4.45 (2H, dd, J=8.3, 9.4 Hz), 4.32 (2H, s), 4.00-3.92 (2H, m), 3.68-3.62 (1H, m), 3.55-3.50 (1H, m), 3.48 (2H, t, J=4.7 Hz), 3.45-3.35 (3H, m), 3.26-3.26 (4H, m), 2.50-2.40 (1H, m), 2.02-1.96 (1H, m), 1.15 (1H, t, J=1.0 Hz), 0.88 (1H, t, J=7.3 Hz);

Example 101: (12R,14S)-4-cyclopropanecarbonyl-12-(2-methoxyethoxy)-16-oxa-7,10,20,21,24-pentaazapentacyclo[15.5.2.1²,6.0¹°,¹4.0²°,²³]pentacosa-1(23),2,4,6(25),17(24),18,21-heptaen-11-one

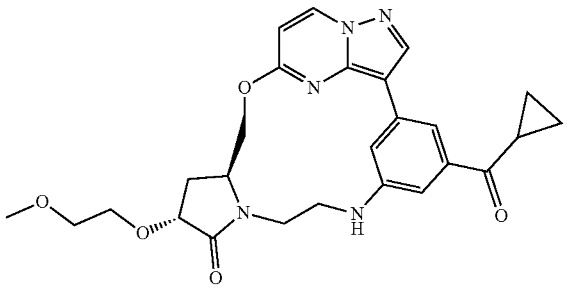 [SMILES: COCCO[C@@H]1C[C@H]2COc3ccn4ncc(c4n3)-c3cc(cc(C(=O)C4CC4)c3)NCCN2C1=O]

Step 1

Into a sealed tube, to a suspension under argon of Intermediate I33 (64 mg, 0.11 mmol) in dry Toluene (0.22 mL) were added Cyclopropane-methanol (10 μL, 0.13 mmol), Acetone (40 μL, 0.55 mmol) and TMP (37 μL, 0.22 mmol). The mixture was degassed by bubbling argon for 10 min and then Triphos (8 mg, 0.01 mmol) and $Ni(OTf)_2$ (4 mg, 0.01 mmol) were added. The tube was sealed and heated at 140° C. with a sand bath pre-heated at 140° C. The reaction was stirred at 140° C. for 48 h. Upon complete conversion of the starting material, monitored by LCMS, the layers were separated. The aqueous layer was extracted with EtOAc (2×10 mL) and the combined organic layers were dried over anhydrous sodium sulfate, filtered and evaporated under reduced pressure. The reaction was restarted in the same conditions over the crude. The mixture was warmed to 140° C. overnight. Upon completion, monitored by LCMS, the reaction was cooled at rt and the mixture was diluted with water and ethyl acetate. The layers were separated. The aqueous layer was extracted with EtOAc (2×10 mL) and the combined organic layers were dried over anhydrous sodium sulfate, filtered and evaporated under reduced pressure. The residue was purified by preparative HPLC: Column Waters XSELECT C18 19*100 mm, 5 μm, A: (NH4)2CO3 aq. 2 g/L, B: ACN, 19 ml/min, rt, 40% B to 45% B in 7 min. The residue (~15 mg) was purified a second time by Preparative TLC 0.5 mm using Cyclohexane/(EtOAc/EtOH 3:1) 1:1 as eluent to afford the expected product as a pale yellow solid (11 mg, 16%).

LCMS (MA) RT=2.15 min, m/z=492.4 $(M+H)^+$.

LCMS (MC) RT=2.15 min, m/z=492.4 $(M+H)^+$.

$^1$H NMR (400 MHz, $CDCl_3$) 8.54 (1H, d, J=7.4 Hz), 8.42 (1H, s), 8.10 (1H, Is), 7.62-7.60 (1H, m), 7.16-7.14 (1H, m), 6.45 (1H, d, J=7.4 Hz), 5.13-5.07 (1H, m), 4.54-4.47 (1H, m), 4.40-4.34 (1H, m), 4.35-4.31 (1H, m), 4.27-4.21 (1H, m), 3.90-3.56 (6H, m), 3.43 (3H, s), 3.33-3.27 (1H, m), 2.74-2.62 (2H, m), 2.28-2.21 (1H, m), 1.30-1.25 (2H, m), 1.10-1.05 (2H, m)

Example 102: (12R,14S)-4-ethenyl-12-ethoxy-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaen-11-one

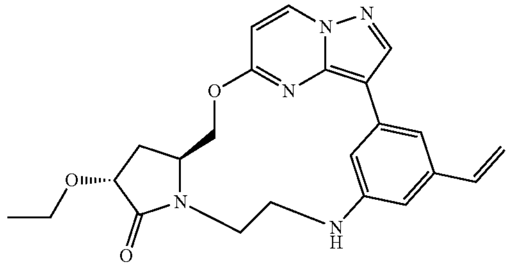 [SMILES: C=Cc1cc2cc(c1)-c1cnn3ccc(nc13)OC[C@@H]1C[C@@H](OCC)C(=O)N1CCN2]

Step 1

To a solution of Intermediate I30 (2.38 g, 3.47 mmol) in TFA (43 mL) was added Anisole (15.168 mL, 138.86 mmol). The reaction mixture was stirred at 130° C. for 2 h. Upon complete conversion, monitored by LCMS, the mixture was allowed to cooled at room temperature and the solvent was evaporated under reduced pressure. The residue was purified by flash column chromatography using Cyclohexane/EtOAc (100/0 to 0/100) as eluent to afford the title compound as a brown solid (1.96 g, 95% yield).

LCMS (MA) RT=2.35 min, m/z=595.2 $(M+H)^+$.

Step 2

To a suspension of the title compound from Step 1 (250 mg, 0.42 mmol) in DCM (20 mL) were added Triethylamine (0.09 mL, 0.63 mmol), then N-Phenylbis(Trifluoromethanesulfonimide) (165 mg, 0.46 mmol) portionwise. Upon complete conversion, monitored by LCMS, the reaction mixture was diluted with water. The layers were separated. The aqueous layer was extracted with DCM (2×15 mL). The combined organic layer was dried over anhydrous sodium sulfate, filtered and evaporated under reduced pressure to afford the title compound as a grey foam (430 mg), which was directly engaged in the next step without further purification.

LCMS (MA) RT=2.86 min, m/z=727.1 $(M+H)^+$.

Step 3

To a suspension of the title compound from Step 2 (305 mg, 0.42 mmol) in DMF (3.4 mL) were added Cesium carbonate (274 mg, 0.84 mmol) and then 4-Methylbenzenethiol (62 mg, 0.50 mmol). The reaction was stirred at rt for 45 min. Upon complete conversion, monitored by LCMS, the mixture was diluted with water and ethyl acetate. The layers were separated. The aqueous layer was extracted with EtOAc (2×15 mL). The combined organic layers were dried over anhydrous Sodium sulfate, filtered and evaporated under reduced pressure. The residue was purified on silica gel column using DCM/MeOH (100:0 to 95:5) as eluent to afford the title compound as a white solid (169 mg, 74% yield).

LCMS (MA) RT=2.69 min, m/z=542.1 $(M+H)^+$.

Step 4

Into a sealed tube, to a suspension of the title compound from Step 3 (100 mg, 0.18 mmol) in dry 1,4-Dioxane (3 mL) was added Lithium chloride (23 mg, 0.55 mmol) and the mixture was degassed by bubbling Argon for 10 min. Tributyl(vinyl)stannane (65 μL, 0.22 mmol) and $Pd(PPh_3)_4$ (21 mg, 0.02 mmol) were added and the reaction was stirred at 100° C. with a sand bath for 3 h. Upon complete conversion, monitored by LCMS, the mixture was cooled to rt. The mixture was diluted with water and ethyl acetate and the layers were separated. The aqueous layer was extracted with EtOAc (2×15 mL) and the combined organic layers were dried over anhydrous sodium sulfate, filtered and evaporated under reduced pressure. The residue was purified by preparative HPLC: Column Waters XSelect C18 19*100 mm, 5 μm, $[(NH_4)_2CO_3$ aq 2 g/L/ACN], 19 ml/min, rt, 40% B to 60% B in 7 min to afford the expected product as a beige solid (71 mg, 55% yield).

LCMS (MA) RT=2.36 min, m/z=420.2 $(M+H)^+$.

LCMS (MC) RT=2.35 min, m/z=420.2 $(M+H)^+$.

$^1$H NMR (400 MHz, DMSO) 8.98 (1H, d, J=7.6 Hz), 8.56 (1H, s), 7.76 (1H, Is), 7.08-7.07 (1H, m), 6.68-6.61 (2H, m), 6.53-6.52 (1H, m), 6.09 (1H, t, J=5.9 Hz), 5.79 (1H, dd, J=1.1, 17.7 Hz), 5.22 (1H, dd, J=1.1, 10.8 Hz), 4.93 (1H, d, J=10.6 Hz), 4.48-4.39 (2H, m), 3.95 (1H, t, J=10.9 Hz), 3.91-3.83 (1H, m), 3.61-3.49 (2H, m), 3.43-3.36 (1H, m), 3.26-3.18 (2H, m), 2.44 (1H, dd, J=8.1, 12.4 Hz), 2.01-1.93 (1H, m), 1.15 (3H, t, J=7.0 Hz).

Example 105 and 106: E1-(8R*,12R,14S)-4,12-dimethoxy-8-methyl-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaen-11-one/E2-(8R*,12R,14S)-4,12-dimethoxy-8-methyl-16-oxa-7,10,20,21,24-pentaazapentacyclo[15.5.2.1$^{2}$,6.0$^{1o}$,$^{1}$4.0$^{2o}$,$^{23}$]pentacosa-1(23),2,4,6(25),17(24),18,21-heptaen-11-one

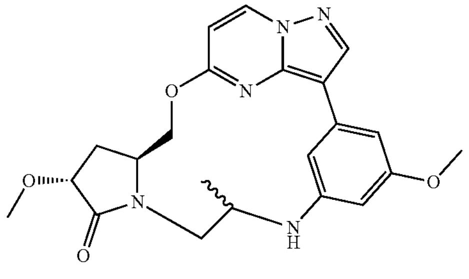

-continued

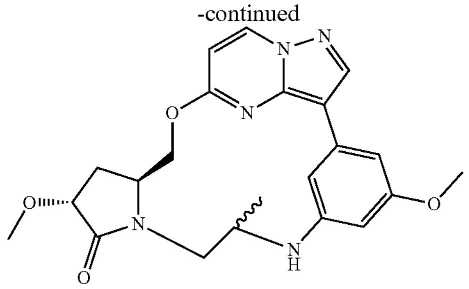

Step 1

To a suspension Sodium hydride, 60% in oil (3.2 g, 80.0 mmol) in dry THE (25 mL) was added at 0° C. a solution of Pyrrolidine P1 (9.25 g, 40.0 mmol) in THE (25 mL). After 30 min, 3-bromo-5-chloro-pyrazolo[1,5-a]pyrimidine (9.3 g, 40.01 mmol) was added and the mixture was stirred at 0° C. for 15 min, and then at rt for 4 h. The mixture was carefully diluted with water and EtOAc (250 ml) was added. The layers were separated. The aqueous layer was extracted with EtOAc (2×100 mL). The combined organic layer was dried over anhydrous sodium sulfate, filtered and evaporated under reduced pressure to afford the title compound as a yellow oil (17 g, 99% yield).

LCMS (MA) RT=2.84 min, m/z=429.1 $(M+H)^+$.

Step 2

To a suspension of title compound from Step 1 (3.33 g, 7.79 mmol) in Acetonitrile (10 mL) was added HCl in 1,4-Dioxane 4M (9.75 mL, 38.9 mmol). The mixture was stirred at room temperature for 1 h. The solvent was evaporated under reduced pressure to afford the title compound as a yellow foam (2.83 g, quant.). The crude was used in the next step without further purification.

LCMS (MA) RT=1.29 min, m/z=329.1 $(M+H)^+$.

Step 3

To a solution of the title compound from Step 2 (2.46 g, 6.76 mmol) in DCM (60 ml) was added Triethylamine (2.83 mL, 20.28 mmol) it was left stirring for 5 min then was added 2-(tert-Butyldimethylsilyloxy)propanal (2.54 g, 8.11 mmol). After 15 min Sodium triacetoxyborohydride (2.15 g, 10.14 mmol) was added. The reaction mixture was left stirring at rt for 3 hr. Upon complete conversion, monitored by LCMS, the reaction mixture was diluted in DCM (60 mL), and water solution was extracted with Dichloromethane. The organic layer was washed with saturated Brine, dried over anhydrous sodium sulfate, and concentrated under reduced pressure. The residue was purified by silica gel column chromatography using Cyclohexane/EtOAc (100/0 to 6/4) as eluent to afford the title compound as a colorless oil (2.66 g, 78% yield).

LCMS (MA) RT=2.37 min, m/z=501.2 $(M+H)^+$.

Step 4

To a solution of the title compound from Step 3 (3.06 g, 6.12 mmol) in Dioxane/Water (30/7 mL) was added Aniline A3 (1.98 g, 7.96 mmol), Tetrakis(triphenylphosphine)palladium(0) (139 mg, 0.12 mmol), Xphos (114 mg, 0.24 mmol) and Potassium phosphate tribasic (3.9 g, 18.36 mmol).

The reaction mixture was degassed by bubbling under argon for 15 min and stirred at 90° C. for 4 h. Upon complete conversion, monitored by LCMS, the mixture was allowed to cooled to room temperature and was diluted with water and EtOAc. Layers were separated. The combined organic layer was dried over anhydrous sodium sulfate, filtered and concentrated under reduced pressure. The residue was purified by silica gel column chromatography using Cyclohexane/EtOAc-EtOH (3:1) (100:0 to 6:4) as eluent to afford the title compound as a yellow oil (3.21 g, 97% yield).

LCMS (MA) RT=2.04 min, m/z=542.4 $(M+H)^+$.

Step 5

To a solution of the title compound from Step 4 (3.21 g, 5.9 mmol) in Acetonitrile (45 mL) was added Pyridine (0.62 mL, 7.7 mmol) then 2-nitrobenzenesulfonyl chloride (1.44 g, 6.5 mmol) portionwise. The reaction mixture was stirred at room temperature for 2 h. Upon complete conversion, monitored by LCMS, the solvent was evaporated under reduced pressure. The residue was purified by silica gel column chromatography using Cyclohexane/EtOAc-EtOH (3:1) (100:0 to 6:4) as eluent to afford the title compound as a yellow foam (3.8 g, 88% yield).

LCMS (MA) RT=2.49 min, m/z=727.3 $(M+H)^+$.

Step 6

To a solution of the title compound from Step 5 (3.8 g, 5.23 mmol) in THE (100 mL) was added a solution of TBAF (5.75 mL, 5.75 mmol). The reaction mixture was stirred at room temperature for 72 h. Upon complete conversion, monitored by LCMS, the solvent was evaporated under reduced pressure. The residue was purified by silica gel column chromatography using DCM/MeOH (100/0 to 9/1) as eluent to afford the title compound as a yellow foam (3.62 g, contain traces of TBAF).

LCMS (MA) RT=1.78 min, m/z=613.3 $(M+H)^+$.

Step 7

A solution of the title compound from Step 6 (3.31 g, 5.4 mmol) in THE (30 ml) and a solution of DIAD (3.18 mL, 16.2 mmol) in Toluene (30 mL) were added slowly dropwise (over 1 hr) simultaneously to a solution of Triphenylphosphine (4.25 g, 16.2 mmol) in Toluene (300 mL) heated at 90° C. The reaction mixture was heated at 90° C. for 1 h. Upon complete conversion, monitored by LCMS, solvent was removed under reduced pressure. The residue was purified by silica gel column chromatography using DCM/MeOH (100/0 to 9/1) as eluent. A second flash chromatography was performed using Cyclohexane/EtOAc-EtOH (3:1) (100/0 to 3/7) as eluent to afford the title compound as a cream foam (700 mg, 1.17 mmol, 22% yield).

LCMS (MA) RT=2.05 min, m/z=595.2 $(M+H)^+$.

Step 8

To a solution of the title compound from Step 7 (700 mg, 1.17 mmol) in Acetonitrile/Water (60 mL/20 mL) was added Sodium bicarbonate (0.983 g, 11.7 mmol). The reaction mixture was stirred 30 min at 45° C. and then Iodine (1.9 g, 8.77 mmol) was added. The reaction mixture was stirred at 45° C. for 3 h. Upon complete conversion, monitored by LCMS, the reaction mixture was quenched by saturated Sodium thiosulfate solution (100 mL). The mixture was mixed with DCM (200 mL) extracted with water (100 mL) and Brine (100 mL). The organic layer were combined, dried over anhydrous sodium sulfate, filtered and evaporated under reduced pressure. The residue was purified by silica gel column chromatography using DCM/MeOH (100/0 to 9/1) as eluent to afford the title compound as a cream solid (0.5 g, 0.82 mmol, 70%).

LCMS (MA) RT=2.50/2.58 min, m/z=609.2 $(M+H)^+$.

Step 9

To a suspension of the title compound from Step 8 (0.5 g, 0.82 mmol) in THE/Acetonitrile (40 mL/4 mL) was added Cesium carbonate (0.534 g, 1.64 mmol) and 4-Methylbenzenethiol (0.122 g, 0.98 mmol). The reaction mixture was stirred at room temperature overnight. The mixture was filtered and evaporated under reduced pressure. The residue was purified by silica gel column chromatography using DCM/MeOH (100:0 to 90:10) as eluent to afford the title compound as a cream solid (0.18 g, 52% yield).

LCMS (MA) RT=2.90 min, m/z=424.4 $(M+H)^+$.

Step 10

The mixture of 2 diastereoisomers obtained on Step 9 was separated by chiral preparative HPLC using the following conditions: Column Daicel IA 19×250 mm, 5um (C7/IPA) (75/25)+0.1% DEA 19 ml/min, RT 30 min Example 105 as E1-(8R*,12R,14S)-4,12-dimethoxy-8-methyl-16-oxa-7,10,20,21,24-pentaazapentacyclo[15.5.2.$1^{2}$,6.$0^{1o}$,$^{1}$4.$0^{2o}$,$^{23}$]pentacosa-1(23),2,4,6(25),17(24),18,21-heptaen-11-one (10 mg, 5.8% yield) as white solid LCMS (MA) RT=2.10 min, m/z=424.3 $(M+H)^+$.

LCMS (MC) RT=2.11 min, m/z=424.3 $(M+H)^+$.

Chiral HPLC Method RT=11.838 min, ee 99.5%

$^1$H NMR (400 MHz, $CDCl_3$) 8.53-8.50 (1H, m), 8.33-8.31 (1H, m), 7.57 (1H, s), 6.62-6.61 (1H, m), 6.43-6.39 (1H, m), 6.12-6.11 (1H, m), 5.12 (1H, d, J=11.0 Hz), 4.52 (1H, d, J=9.9 Hz), 4.25 (1H, dd, J=8.3, 9.8 Hz), 3.85-3.84 (6H, m), 3.66-3.60 (5H, m), 2.68 (1H, dd, J=7.7, 12.8 Hz), 2.13-2.06 (1H, m), 1.37 (3H, d, J=5.7 Hz).

Example 106 as E2-(8R*,12R,14S)-4,12-dimethoxy-8-methyl-16-oxa-7,10,20,21,24-pentaazapentacyclo[15.5.2.$1^{2}$,6.$0^{1o}$,$^{1}$4.$0^{2o}$,$^{23}$]pentacosa-1(23),2,4,6(25),17(24),18,21-heptaen-11-one (25 mg, 14.7% yield) as white solid LCMS (MA) RT=2.17 min, m/z=424.2 $(M+H)^+$.

LCMS (MC) RT=2.11 min, m/z=424.2 $(M+H)^+$.

Chiral HPLC Method RT=15.825 min, ee 99.5%

$^1$H NMR (400 MHz, $CDCl_3$) 8.53-8.50 (1H, m), 8.37 (1H, s), 8.10 (1H, s), 6.65 (1H, s), 6.44-6.41 (1H, m), 6.16-6.14 (1H, m), 5.46-5.43 (1H, m), 4.43-4.38 (1H, m), 4.24 (1H, dd, J=7.3, 10.2 Hz), 3.93-3.80 (6H, m), 3.72-3.62 (5H, m), 2.65 (1H, dd, J=7.4, 12.3 Hz), 2.20-2.12 (1H, m), 1.48-1.45 (3H, d, J=6.8 Hz).

Example 109: (12R,14S)-12-methoxy-4-(1,2,4-oxadiazol-5-yl)-16-oxa-7,10,20,21,24-pentaazapentacyclo[15.5.2.$1^{2}$,6.$0^{1o}$,$^{1}$4.$0^{2o}$,$^{23}$]pentacosa-1(23),2(25),3,5,17(24),18,21-heptaen-11-one

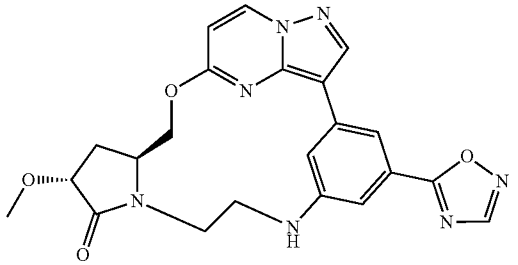 [SMILES: CO[C@@H]1C[C@H]2COc3ccn4ncc(c4n3)-c3cc(cc(-c4ncno4)c3)NCCN2C1=O]

Step 1

To a solution of Intermediate I23 (1.10 g, 1.87 mmol) in Methanol (17.6 mL) was added Sodium hydroxide solution 1M (2.052 mL, 2.05 mmol) and Hydrogen peroxide solution 30% (0.212 mL, 2.05 mmol). The reaction mixture was stirred at 40° C. for 1 h. Upon complete conversion, monitored by LCMS, solvent was removed under reduced pressure. The crude was diluted with Water (20 mL) and EtOAc (20 mL). The aqueous layer was extracted with EtOAc (2×10 mL) and the combined organic layer was washed with Brine (2×20 mL), dried over $Na_2SO_4$, filtered and concentrated under reduced pressure. The residue was purified by flash column chromatography using DCM/MeOH (100/0 to 95/5) as eluant to afford the title compound as a yellow solid (0.19 g, 17% yield).

LCMS (MA) RT=2.02 min, m/z=608.1 $(M+H)^+$.

Step 2

To a stirred solution of the title compound from Step 1 (0.19 g, 0.32 mmol) in 1,4-Dioxane (1.3 mL) was added Dimethoxy-N,N-dimethylmethanamine (0.05 mL, 0.38 mmol). The reaction mixture was stirred at 50° C. for 2 h. Upon complete conversion, monitored by LCMS, the reaction mixture was concentrated under vacuum to afford the title compound as a yellow solid (0.168 g, 80% Yield). The crude was directly engaged in the next step without further purification.

LCMS (MA) RT=2.10 min, m/z=663.2 $(M+H)^+$.

Step 3

To a stirred solution of the title compound from Step 2 (0.168 g, 0.25 mmol) in ethanol (5 mL) was added Hydroxylamine hydrochloride (0.021 g, 0.30 mmol). The reaction mixture was stirred at 90° C. for 4 days, then solvent was evaporated under reduced pressure. The residue was purified by flash column chromatography using Cyclohexane/EtOAc (100/0 to 0/100) as eluent to afford the title compound as a white solid (0.105 g, 65% yield).

LCMS (MA) RT=2.43 min, m/z=633.2 $(M+H)^+$.

Step 4

The title compound from Step 3 (0.105 g, 0.17 mmol) and Cesium carbonate (0.108 g, 0.33 mmol) were dissolved in DMF (3.7 mL). 4-Methylbenzenethiol (0.025 g, 0.20 mmol) was added and the mixture was stirred at rt overnight. Upon complete conversion, monitored by LCMS, the reaction mixture was filtered and the solvent was evaporated under vacuum. The residue was purified by flash column chromatography using Cyclohexane/EtOAc (100/0 to 0/100) as eluent to afford the expected product as a white solid (36 mg, 48% yield).

LCMS (MA) RT=2.87 min, m/z=448.4 $(M+H)^+$.

LCMS (MC) RT=2.05 min, m/z=448.4 $(M+H)^+$.

$^1$H NMR (400 MHz, DMSO) 9.09 (1H, s), 9.04-9.01 (1H, m), 8.68 (1H, s), 8.10 (1H, s), 7.63 (1H, s), 7.26 (1H, s), 6.70 (1H, d, J=7.6 Hz), 6.65-6.55 (1H, m), 4.97 (1H, d, J=10.8 Hz), 4.51-4.49 (1H, m), 4.35 (1H, t, J=8.7 Hz), 4.05-3.94 (1H, m), 3.59-3.53 (1H, m), 3.40-3.37 (1H, m), 3.33-3.29 (6H, m), 2.01-1.93 (1H, m);

Example 119: (12R,14S)-12-methoxy-4-(1-methyl-1H-1,2,3-triazol-4-yl)-16-oxa-7,10,20,21,24-pentaazapentacyclo[15.5.2.1$^2$,6.0$^{1o}$,$^1$4.0$^{2o}$,$^{23}$]pentacosa-1(23),2,4,6(25),17(24),18,21-heptaen-11-one

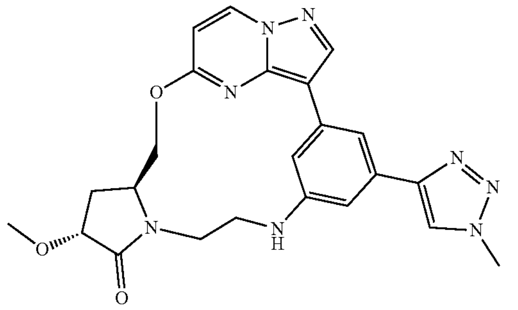

Step 1

To a solution of Intermediate I32 (0.50 g, 0.71 mmol) in THE (3.5 mL) was added Tetrabutylammonium fluoride 1 M in THE (0.780 mL, 0.78 mmol) dropwise at room temperature. The resulting reaction mixture was stirred 16 hours at room temperature. Upon complete conversion, monitored by LCMS, the reaction mixture was poured into ice water and stirred for 20 min. The aqueous phase was extracted with EtOAc (2×15 mL) and the combined organic phase was washed with saturated Brine (15 mL), dried over anhydrous sodium sulfate and concentrated in vacuo. The residue was purified by flash chromatography on silica gel column using Cyclohexane/EtOAc (30/70) as eluent to afford the title compound as a light brown solid (0.151 g, 36% yield).

LCMS (MA) RT=2.46 min, m/z=404.4 $(M+H)^+$.

Step 2

To a solution of the title compound from Step 1 (0.05 g, 0.08 mmol) in Water (0.18 mL) and tert-Butanol (0.05 mL) were added Methyl iodide (6 uL, 0.10 mmol), Sodium azide (6 mg, 0.09 mmol), CuI (3 mg, 0.02 mmol) and Sodium L-ascorbate (3 mg, 0.02 mmol) The reaction mixture was stirred and heated to 75° C. overnight. LCMS showed the reaction was incomplete, therefore further Methyl iodide (6 uL, 0.10 mmol), Sodium azide (6 mg, 0.09 mmol), CuI (3 mg, 0.02 mmol) and Sodium L-ascorbate (3 mg, 0.02 mmol) in Water (0.18 mL) and tert-Butanol (0.05 mL) were added. The reaction mixture was stirred and heated at 75° C. for 24 h. Upon 75% conversion, monitored by LCMS, the mixture was then diluted with Dichloromethane and filtered off. The aqueous layer was extracted with Dichloromethane and the combined organic layer was washed with Brine, dried over Sodium sulfate, filtered and evaporated under vacuum to afford the title compound as a solid (36 mg, 66% yield). The crude was directly engaged in the next step without further purification.

LCMS (MA) RT=2.16 min, m/z=646.4 $(M+H)^+$.

Step 3

The title compound from Step 2 (36 mg, 0.06 mmol) and Cesium carbonate (0.04 g, 0.11 mmol) were suspended in N,N-Dimethylformamide (1 mL). 4-Methylbenzenethiol (0.01 g, 0.07 mmol) was added and the mixture was stirred at room temperature for 2 hours. Upon complete conversion, monitored by LCMS, the reaction mixture was poured into Water then diluted with Ethyl acetate. The suspension was filtered off and the organic layer was washed with Brine, dried over $Na_2SO_4$, filtered and the solvent was removed under reduced pressure. The residue was purified by flash chromatography on silica gel column using DCM/MeOH (95/5) as eluent to afford the expected product as an off-white solid (20 mg, 78% yield).

LCMS (MA) RT=1.80 min, m/z=461.4 $(M+H)^+$.

LCMS (MC) RT=1.80 min, m/z=461.4 $(M+H)^+$.

$^1$H NMR (400 MHz, $CDCl_3$) 8.54-8.51 (1H, m), 8.42 (1H, s), 7.90 (1H, s), 7.79 (1H, s), 7.46 (1H, s), 7.02 (1H, s), 6.44-6.41 (1H, m), 5.11 (1H, d, J=10.8 Hz), 4.54 (1H, t, J=8.3 Hz), 4.19-4.18 (4H, m), 3.91-3.72 (2H, m), 3.65 (4H, s), 3.37-3.29 (1H, m), 2.66 (1H, dd, J=8.3, 13.2 Hz), 2.19-2.11 (1H, m), 1.29-1.27 (1H, m);

Example 120: (12R,14S)-4-methoxy-12-(oxetan-2-ylmethoxy)-16-oxa-7,10,20,21,24-pentaazapentacyclo[15.5.2.1$^2$,6.0$^{1o}$,$^1$4.0$^{2o}$,$^{23}$]pentacosa-1(23),2,4,6(25),17(24),18,21-heptaen-11-one

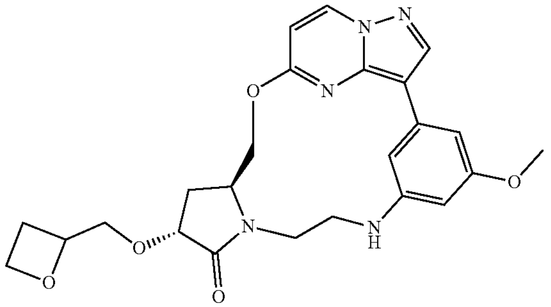 [SMILES: COc1cc2cc(c1)-c1cnn3ccc(nc13)OC[C@@H]1C[C@@H](OCC3CCO3)C(=O)N1CCN2]

Step 1

Into a sealed tube, to a suspension of Intermediate I27 (400 mg, 0.69 mmol) in dry THE (0.8 mL) were added n-Tetrabutylammonium bromide (78 mg, 0.24 mmol) and aqueous Sodium hydroxide solution 32% w (1.30 mL, 10.35 mmol). The mixture was stirred for 30 min and 2-(Bromomethyl)oxetane (520 mg, 3.45 mmol) was added. The reaction was stirred at 80° C. for 2 h. Upon complete conversion, monitored by LCMS, the reaction was stopped and cooled to rt. The mixture was diluted with Ethyl acetate and Water. The layers were separated and the aqueous layer was extracted with EtOAc (2×15 mL). The combined organic layer was dried over anhydrous Sodium sulfate, filtered and evaporated under reduced pressure. The residue was purified by preparative HPLC: Column Waters XSELECT C18 19*100 mm, 5 μm, A: (NH4)2CO3 aq. 2 g/L, B: CAN 19 ml/min, rt 30% B to 45% B in 7 min. The expected fractions were collected and evaporated under reduced pressure. A second purification was performed by preparative TLC 0.25 mm using DCM/MeOH (9:1) as eluent. The compound was scratched and silica was dissolved with DCM/MeOH 8:2. The suspension was filtered and the solvent was evaporated under reduced pressure to afford the expected product as a beige solid (7 mg, 0.02 mmol, 2%).

LCMS (MA) RT=1.99 min, m/z=466.4 $(M+H)^+$.

LCMS (MC) RT=1.99 min, m/z=466.4 $(M+H)^+$.

$^1$H NMR (400 MHz, $CDCl_3$) 8.51 (1H, d, J=7.4 Hz), 8.32 (1H, s), 7.55 (1H, Is), 6.61-6.59 (1H, m), 6.41 (1H, d, J=7.6 Hz), 6.11-6.09 (1H, m), 5.12-5.07 (1H, m), 5.07-5.00 (1H, m), 4.74-4.68 (1H, m), 4.65-4.59 (1H, m), 4.52-4.44 (2H, m), 4.20 (1H, dd, J=3.2, 11.2 Hz), 3.93 (1H, dd, J=6.6, 11.3 Hz), 3.89-3.81 (1H, m), 3.84 (3H, s), 3.77-3.71 (1H, m), 3.67-3.60 (1H, m), 3.60-3.52 (1H, m), 3.32-3.24 (1H, m), 2.76-2.63 (2H, m), 2.58-2.50 (1H, m), 2.24-2.17 (1H, m);

Example 139: (12R,14S)-18-(2-hydroxyethoxy)-4-methoxy-12-(2-methoxyethoxy)-16-oxa-7,10,20,21,24-pentaazapentacyclo[15.5.2.1$^{2}$,6.0$^{1°}$,$^{1}$4.0$^{2°}$,$^{23}$]pentacosa-1(23),2,4,6(25),17(24),18,21-heptaen-11-one

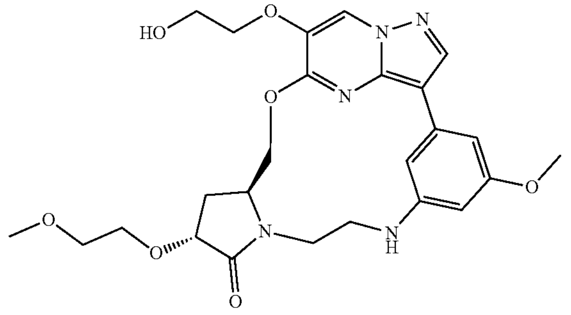

Following the general synthetic scheme 1, as depicted for the synthesis of Example 1, (12R,14S)-18-(benzyloxy)-4-methoxy-12-(2-methoxyethoxy)-7-(2-nitrobenzenesulfonyl)-16-oxa-7,10,20,21,24-pentaazapentacyclo[15.5.2.12, 6.010,14.020,23]pentacosa-1(23),2(25),3,5,17(24),18,21-heptaen-11-one was obtained as Intermediate I34 using Scaffold S3, Pyrrolidine P7 and Aniline A3.

Step 1

To a solution of Intermediate I34 (5.46 g, 7.34 mmol) in TFA (92 mL) was added Anisole (32.06 mL, 7.34 mmol). The reaction mixture was stirred at 110° C. overnight. Upon complete conversion, monitored by LCMS, the mixture was allowed to cooled at room temperature and the solvent was evaporated under reduced pressure. The residue was purified by flash column chromatography using DCM/MeOH (100/0 to 95/5) as eluent to afford the title compound as a brown solid (4.66 g, 97% Yield).

LCMS (MA) RT=2.30 min, m/z=655.2 (M+H)$^+$.

Step 2

To a suspension of the title compound from Step 1 in DMF (2 mL) was added Potassium carbonate (63 mg, 0.46 mmol) and 2-(2-Bromoethoxy)oxane (0.028 mL, 0.18 mmol). The reaction mixture was stirred at 80° C. for 60 min. The reaction mixture was filtered and concentrate under reduce pression to afford the title compound as a light brown solid (120 mg, 100% yield). The crude was directly engaged in the next step without further purification.

LCMS (MA) RT=2.66 min, m/z=783.3 (M+H)$^+$.

Step 3

The title compound from Step 2 (0.12 g, 0.15 mmol) and Cesium carbonate (0.10 g, 0.31 mmol) were suspended in N,N-Dimethylformamide (1 mL). 4-Methylbenzenethiol (0.023 g, 0.18 mmol) was added and the mixture was stirred at room temperature for 2 hours. Upon complete conversion, monitored by LCMS, the reaction mixture was poured into water then diluted with Ethyl acetate. The suspension was filtered. The organic layer was washed with Brine, dried over Sodium sulfate, filtered and the solvent was removed under reduced pressure. The residue was purified by flash chromatography using DCM/MeOH (95/5) as eluent to afford to afford the title compound as a beige solid (70 mg, 76% yield).

LCMS (MA) RT=1.99 min, m/z=466.4 (M+H)$^+$.

Step 4

To a solution of the title compound from Step 3 (0.067 g, 0.11 mmol) in MeOH (1.3 mL) and Water (0.2 mL) was added p-Toluenesulfonic acid monohydrate (0.107 g, 0.56 mmol) and the reaction mixture was stirred at 65° C. for 16 h. Upon complete conversion, monitored by LCMS, the reaction mixture was dissolved in Ethyl acetate then a saturated aqueous solution of Sodium hydrogen carbonate was added. After separation, the aqueous layer was extracted with Ethyl acetate (2×). The combined organic layer was washed with Brine, dried over Sodium sulfate, filtered and evaporated under reduced pressure to afford the expected product as a light yellow solid (31 mg, 54% yield).

LCMS (MA) RT=1.81 min, m/z=514.4 (M+H)$^+$.

LCMS (MC) RT=1.80 min, m/z=514.3 (M+H)$^+$.

$^1$H NMR (400 MHz, DMSO) 8.77 (1H, s), 8.36-8.35 (1H, m), 7.43-7.43 (1H, m), 6.52 (1H, d, J=0.8 Hz), 6.07-6.01 (2H, m), 4.99-4.92 (2H, m), 4.46 (2H, t, J=8.8 Hz), 4.13-3.90 (4H, m), 3.77 (2H, s), 3.72 (2H, s), 3.65 (1H, s), 3.58-3.51 (1H, m), 3.48 (2H, t, J=4.8 Hz), 3.43-3.36 (1H, m), 3.27-3.26 (6H, m), 2.46 (1H, dd, J=7.5, 12.9 Hz), 2.00-1.96 (1H, m);

Example 142: (12R,14S)-4,12-dimethoxy-9-methyl-16-oxa-7,10,20,21,24-pentaazapentacyclo[15.5.2.1$^{2}$,6.0$^{1°}$,$^{1}$4.0$^{2°}$,$^{23}$]pentacosa-1(23),2(25),3,5,17(24),18,21-heptaen-11-one

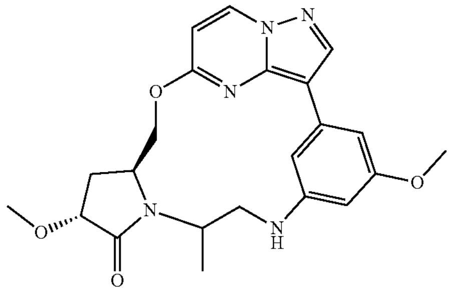

Step 1

To a solution of Pyrrolidine P1 (5.97 g, 25.81 mmol) in dry DMF (83 mL) was added Sodium hydride, 60% in Mineral oil (1.72 g, 43.02 mmol) at 0° C. After 30 min 3-Bromo-5-chloropyrazolo[1,5-a]pyrimidine (5.00 g, 21.51 mmol) was added and the mixture was stirred at rt for 1 h. Upon complete conversion, monitored by LCMS, Water was carefully added dropwise at 0° C. and the mixture was extracted with EtOAc (3×50 mL). The combined organic layers were washed with Brine, dried over $Na_2SO_4$, filtered and concentrated under vacuum. The residue was purified by flash chromatography using Cyclohexane/EtOAc (100/0 to 60/40) as eluent to afford the title compound as an orange oil (5.55 g, 60% yield).

LCMS (MA) RT=2.72 min, m/z=427.1/429.1 (M+H)$^+$.

Step 2

To a suspension of the title compound from Step 1 (5.55 g, 12.99 mmol) in Acetonitrile (130 mL) was added Hydrogen Chloride solution 4M in 1,4-Dioxane (16.24 mL, 64.97 mmol). The reaction mixture was stirred overnight. Upon complete conversion, monitored by LCMS, the solvent was removed under reduced pressure to afford the title compound as a yellow solid (4.84 g, quantitative yield). The crude was directly engaged in the next step without further purification.

LCMS (MA) RT=1.17 min, m/z=327.2/329.2 (M+H)$^+$.

Step 3

To a solution of the title compound from Step 2 (4.72 g, 14.44 mmol) in Acetonitrile (114 mL) was added Potassium carbonate (5.99 g, 43.32 mmol) and Ethyl 2-bromopropanoate (5.23 g, 28.88 mmol). The reaction mixture was stirred at 50° C. overnight. Upon complete conversion, monitored by LCMS, aqueous 1N NaOH solution was added and the reaction mixture was stirred for 10 minutes. Water and Ethyl acetate were added to the mixture and extracted with Ethyl acetate. The organic layer was dried over anhydrous Sodium sulfate, filtered and evaporated under reduced pressure. The residue was purified by flash chromatography using Cyclohexane/EtOAc (100/0 to 70/30) as eluent to afford the title compound as a yellow oil (4.729 g, 77% yield).

LCMS (MA) RT=1.72/1.83 min, m/z=427.1/429.1 $(M+H)^+$.

Step 4

To a suspension of the title compound from Step 3 (4.73 g, 11.07 mmol) in a mixture of EtOH/THF (60 mL/60 mL) cooled at 0° C. were added Sodium borohydride (1.26 g, 33.20 mmol) and Calcium chloride (1.84 g, 16.60 mmol). The solution was allowed to reach room temperature and stirred for 4 h at rt. The reaction mixture was quenched by addition of Water and aqueous HCl 1M until pH=4. EtOAc was added and the layers were separated. The aqueous layer was extracted with EtOAc. The combined organic layer was dried over Sodium sulfate, filtered and concentrated in vacuo. The residue was purified by column chromatography using Cyclohexane/AE (100/0 to 0/100) as eluent to afford the title compound as a yellow oil (1.23 g, 29% yield).

LCMS (MA) RT=1.21/1.24 min, m/z=385.3/385.3 $(M+H)^+$.

Step 5

To a solution of the title compound from Step 4 (1.23 g, 3.20 mmol) in DMF (18 mL) was added imidazole (0.653 g, 9.59 mmol) and tert-Butyldimethylsilyl chloride (1.44 g, 9.59 mmol). The reaction mixture was stirred at room temperature overnight. Upon complete conversion, monitored by LCMS, an aqueous saturated solution of $NaHCO_3$ was added and the mixture was extracted with Ethyl acetate. The combined organic layer was dried over anhydrous Sodium sulfate, filtered and concentrated under reduced pressure. The residue was purified by Flash chromatography using Cyclohexane/EtOAc (100/0 to 70/30) as eluent to afford the title compound as a yellow oil (1.279 g, 80% Yield).

LCMS (MA) RT=2.20/2.25 min, m/z=499.2/501.2 $(M+H)^+$.

Step 6

A mixture of the title compound from Step 5 (1.18 g, 2.36 mmol), Aniline A3 (0.76 g, 3.07 mmol), Xphos (0.045 g, 0.09 mmol), and $K_3PO_4$ (1.50 g, 7.08 mmol) were dissolved in 1,4-Dioxane/Water (15 mL/5 mL) and degassed with Argon during 15 min. Tetrakis(triphenylphosphine)palladium(0) (0.055 g, 0.05 mmol) was added and the reaction mixture was stirred at 110° C. for 1 h. Upon complete conversion, monitored by LCMS, the reaction mixture was cooled down and filtered over Celite then solvent was evaporated. The residue was purified by column chromatography using Cyclohexane/EtOAc (100/0 to 40/60) as eluent to afford the title compound as a yellow oil (1.33 g, quantitative yield).

LCMS (MA) RT=2.00/2.04 min, m/z=542.5 $(M+H)^+$.

Step 7

To a solution of the title compound from Step 6 (1.28 g, 2.36 mmol) in Acetonitrile (33 mL) were added Pyridine (0.29 mL, 3.54 mmol) and 2-Nitrobenzene-1-sulfonyl chloride (0.68 g, 3.07 mmol). The reaction mixture was stirred at rt overnight. Upon complete conversion, monitored by LCMS, the solvent was removed under reduced pressure and the residue was poured into water (40 mL) and EtOAc (80 mL). The aqueous layer was extracted with EtOAc (3×40 mL) and the organic layer was washed with Brine (2×40 mL), dried over $Na_2SO_4$, filtered and concentrated under reduced pressure to afford the title compound as a red solid (1.88 g, quantitative yield). The crude was directly engaged in the next step without further purification.

LCMS (MA) RT=2.38 min, m/z=727.5 $(M+H)^+$.

Step 8

To a solution of the title compound from Step 7 (1.73 g, 2.37 mmol) in THF (21 mL) was added Tetrabutylammonium fluoride 1M in THF (4.749 mL, 4.75 mmol) at room temperature. The resulting reaction mixture was stirred at rt for 2 h. Upon complete conversion, monitored by LCMS, the reaction mixture was diluted with saturated Ammonium chloride solution and extracted with Ethyl acetate twice. The combined organic layer was dried over anhydrous Sodium sulfate and concentrated in vacuo. The residue was purified by column chromatography using DCM/MeOH (100/0 to 95/5) as eluent to afford the title compound as a brown solid (1.653 g, quantitative yield).

LCMS (MA) RT=1.80 min, m/z=613.3 $(M+H)^+$.

Step 9

A solution of the title compound from Step 8 (1.45 g, 2.37 mmol) in Me-THF (71 ml) and DIAD (1.399 ml, 7.12 mmol) in Toluene (71 ml) were simultaneously added dropwise to a solution of Triphenylphosphine (1.87 g, 7.12 mmol) in Toluene (237 ml) at 90° C. for 1.5 h. Upon complete conversion, monitored by LCMS, solvent was removed under reduced pressure. The residue was purified by column chromatography using Cyclohexane/EtOAc (100/0 to 50/50). The desired fractions were collected and evaporated. The residue was triturated in Diethylether to afford the title compound as a yellow oil (1.52 g, 37% yield).

LCMS (MA) RT=2.76 min, m/z=595.4 $(M+H)^+$.

Step 10

To a mixture of the title compound from Step 9 (1.41 g, 2.37 mmol) in THF/$H_2O$ (185 mL/49 mL) was added Sodium bicarbonate (3.99 g, 47.49 mmol) and Iodine (9.04 g, 35.62 mmol). The reaction mixture was stirred at 60° C. for 1 h. Upon complete conversion, monitored by LCMS, the reaction mixture was quenched by saturated Sodium thiosulfate solution then extracted by Ethyl acetate. The organic layer was dried over anhydrous Sodium sulfate, filtered and evaporated under reduced pressure. The residue was purified by column chromatography using Cyclohexane/EtOAc (100/0 to 30/70) as eluent to afford the title compound as a yellow solid (0.539 g, 37% yield).

LCMS (MA) RT=2.62 min, m/z=609.3 $(M+H)^+$.

Step 11

To a solution of the title compound from Step 10 (0.54 g, 0.89 mmol) in DMF (20 mL) were added Lithium hydroxide (0.127 g, 5.31 mmol) and DL-cysteine (0.13 g, 1.06 mmol) and the mixture was stirred at rt overnight. Upon complete conversion, monitored by LCMS, Water was added and the resulting mixture was extracted by Ethyl acetate. The organic layer sequentially washed with a saturated Sodium bicarbonate solution and saturated Brine, dried over $Na_2SO_4$, filtered and concentrated to dryness. The crude was triturated in Acetonitrile to afford the expected product as a white solid (0.201 g, 54% yield).

LCMS (MA) RT=2.10 min, m/z=424.4 $(M+H)^+$.

LCMS (MC) RT=2.10 min, m/z=424.4 $(M+H)^+$.

$^1$H NMR (400 MHz, DMSO) 8.97 (1H, dd, J=7.6, 9.7 Hz), 8.60 (0.63H, s), 8.47 (0.37H, s), 7.99 (0.63H, s), 7.22 (0.37H, s), 6.67-6.60 (1.63H, m), 6.48 (0.37H, dd, J=1.0, 2.2 Hz), 6.21 (0.37H, t, J=5.8 Hz), 6.14-6.02 (1.63H, m), 5.28 (0.63H, d, J=11.6 Hz), 4.87-4.83 (0.37H, m), 4.52-4.47 (0.37H, m), 4.36 (0.63H, dd, J=7.3, 10.2 Hz), 4.21 (1H, t, J=8.6 Hz), 4.12-3.98 (1.37H, m), 3.73-3.72 (4H, m), 3.64-3.55 (0.63H, m), 3.45-3.41 (4H, m), 2.47-2.30 (1H, m), 2.03-1.95 (1H, m), 1.45 (1.11H, d, J=6.8 Hz), 1.28 (1.89H, d, J=6.8 Hz);

Example 146: (12R,14S)-4-ethynyl-18-methoxy-12-(2-methoxyethoxy)-16-oxa-7,10,20,21,24-pentaaza-pentacyclo[15.5.2.1$^{2}$,6.0$^{10}$,$^{14}$.0$^{20}$,$^{23}$]pentacosa-1(23),2,4,6(25),17(24),18,21-heptaen-11-one

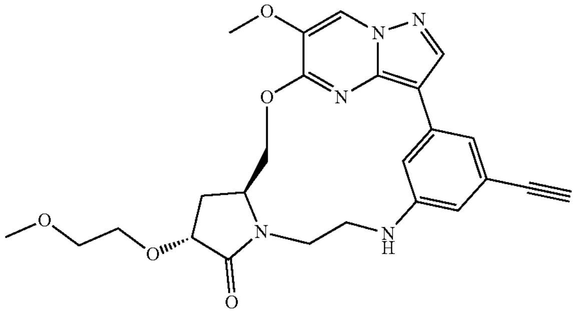 [SMILES: C#Cc1cc2cc(c1)-c1cnn3cc(OC)c(nc13)OC[C@@H]1C[C@@H](OCCOC)C(=O)N1CCN2]

Following the general synthetic scheme 1, as depicted for the synthesis of Example 1, (12R,14S)-4-(benzyloxy)-18-methoxy-12-(2-methoxyethoxy)-7-(2-nitrobenzenesulfonyl)-16-oxa-7,10,20,21,24-pentaazapentacyclo[15.5.2.12,6.010,14.020,23]pentacosa-1(23),2(25),3,5,17(24),18,21-heptaen-11-one was obtained as Intermediate I35 using Scaffold S2, Pyrrolidine P7 and Aniline A9.

LCMS (MA) RT=2.77 min, m/z=745.3 (M+H)$^+$.

Step 1

To a solution of Intermediate I35 (80 mg, 0.107 mmol) in TFA (1 mL) was added Anisole (0.5 mL, 4.30 mmol). The reaction mixture was stirred at 130° C. for 40 min. Upon complete conversion, monitored by LCMS, the mixture was allowed to cooled at room temperature and the solvent was evaporated under reduced pressure. The residue was purified by flash column chromatography using DCM/Methanol (100/0 to 98/2) as eluent to afford the title compound as a pale brown solid (65 mg, 93% Yield).

LCMS (MA) RT=2.20 min, m/z=655.2 (M+H)$^+$.

Step 2

To a solution of Triethylamine (0.02 mL, 0.148 mmol) and the title compound from Step 1 (65 mg, 0.099 mmol) in Dichloromethane (5 mL) was added portionwise N-Phenyl-bis(trifluoromethanesulfonimide) (39 mg, 0.109 mmol), and the reaction mixture was stirred at room temperature for 5 h. Upon complete conversion, monitored by LCMS, Water (5 mL) was added to the reaction solution. Thereafter, the reaction solution was extracted with Dichloromethane (3×5 mL), the combined organic layer was washed with Brine (10 mL), dried over anhydrous Sodium sulfate, and concentrated under reduced pressure to afford the title compound as a yellowish amorphous solid (80 mg, postulated, qt.). The crude was directly engaged in the next step further without purification.

LCMS (MA) RT=2.77 min, m/z=787.2 (M+H)$^+$.

Step 3

To a solution of the title compound from Step 2 (80 mg, 0.099 mmol postulated) in DMF (1 mL) were added Cesium carbonate (64 mg, 0.148 mmol) and then 4-Methylbenzenethiol (15 mg, 0.119 mmol). The reaction was stirred at rt for 45 min. Upon complete conversion, monitored by LCMS, the mixture was diluted with Water (3 mL) and Ethyl acetate (3 mL). The layers were separated. The aqueous layer was extracted with EtOAc (2×3 mL) and the combined organic layer was dried over anhydrous Sodium sulfate, filtered and evaporated under reduced pressure. The residue was purified on silica gel column chromatography using DCM/MeOH (100:0 to 97.5:2.5) as eluent to afford the title compound as a yellowish amorphous solid (40 mg, 67% Yield over two steps).

LCMS (MA) RT=2.54 min, m/z=602.3 (M+H)$^+$.

Step 4

In a microwave reactor, a solution of the title compound from Step 3 (15 mg, 0.025 mmol) in dry Acetonitrile/DMF (1.4:0.15 mL) was degassed by bubbling argon for 10 min. Then, were added cesium carbonate (24 mg, 0.075 mmol), bis(acetonitrile)dichloropalladium(II) (0.6 mg, 0.0025 mmol), Xphos (2.4 mg, 0.005 mmol) and Triethylsilylacetylene (0.022 mL, 0.125 mmol).

The reaction mixture was stirred at 100° c. under microwave irradiation for 1 h. LCMS showed full conversion with main formation of the expected compound.

The reaction was repeated with the title compound from Step 3 (15 mg, 0.025 mmol) using similar conditions, but microwave irradiation was maintained for 3 h. Both reaction mixtures were combined, filtrated over Celite and concentrated in vacuo. To afford the title compound as a dark brown amorphous solid (34 mg, qt. postulated). The crude was directly engaged in the next step without further purification.

LCMS (MA) RT=3.29 min, m/z=592.4 (M+H)$^+$.

Step 5

To a solution of title compound from Step 4 (34 mg, 0.050 mmol postulated) in Methanol (1 mL) was added Potassium carbonate (34 mg, 0.250 mmol). The reaction mixture was stirred at 50° C. 3 h. Upon complete conversion, monitored by LCMS, the reaction mixture was cooled down to room temperature then quenched with Water (2 mL) and diluted with Ethyl acetate (2 mL). The two layers were separated and the aqueous layer was extracted three times with Ethyl acetate (3×3 mL). The combined organic layer was washed with Brine (3 mL), dried over Sodium sulfate, filtered and concentrated in vacuo. The crude residue was purified by preparative TLC using Ethyl acetate/Methanol (95:5). The expected fraction was scratched, extracted with Dichloromethane/Methanol 9:1, filtered off and concentrated in vacuo to afford the expected product as a brownish amorphous solid (4 mg, 17% over two steps).

LCMS (MA) RT=2.26 min, m/z=478.2 (M+H)$^+$.

LCMS (MC) RT=2.16 min, m/z=478.3 (M+H)$^+$.

$^1$H NMR (400 MHz, $CDCl_3$) 8.24-8.17 (2H, m), 7.86-7.86 (1H, m), 7.15-7.13 (1H, m), 6.67 (1H, s), 5.12 (1H, d, J=10.6 Hz), 4.53-4.48 (1H, m), 4.36 (1H, t, J=8.7 Hz), 4.21-4.13 (1H, m), 3.96 (3H, s), 3.93-3.79 (3H, m), 3.69-3.55 (5H, m), 3.43-3.41 (3H, m), 3.29-3.23 (1H, m), 3.06 (1H, s), 2.76-2.70 (1H, m), 2.26-2.18 (1H, m).

RIPK2 AlphaLISA® Assay (Amplified Luminescent Proximity Homogeneous Assay)

A non-specific kinase inhibitor (CZC-8004 Cayman #916603-07-1) bound to an acceptor bead (#6772001 PerkinElmer) was mixed to the recombinant hRIPK2 protein (kinase domain aa 1-299-His-tagged—Life Technologies PR7829A) and a Ni2+-tagged donor beads (#AS101D PerkinElmer). In the presence of an inhibitor, the compound beads displacement from hRIPK2 was followed by signal loss. In a 384-well ProxiPlate@ (Perkin Elmer, 6008280) add:

2 μL RIPK2 inhibitor (in DMSO 0.8%).

2 μL human recombinant RIPK2 (10 nM diluted in AlphaLISA buffer 1×).

4 μL Mix of donor Compound-beads 1/1000 and acceptor Ni2+-beads 1/1000 in AlphaLISA buffer 1×.

Homogenize using a microtiter plate shaker and incubate for 2 h at 23° C.

Read using EnVision®-Alpha Reader (PerkinElmer) according to manufacturer specifications.

+ indicates an $IC_{50}$ between 100 nM and 11 uM, ++ indicates an $IC_{50}$ of between 10 nM and 100 nM, and +++ indicates an $IC_{50}$<10 nM; ND=Not determined

| Ex ID | Activity |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | ++ |
| 15 | ++ |
| 16 | +++ |
| 17 | +++ |
| 18 | +++ |
| 19 | +++ |
| 20 | +++ |
| 21 | ++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | ++ |
| 45 | + |
| 46 | ++ |
| 47 | +++ |
| 48 | + |
| 49 | ++ |
| 50 | ++ |
| 51 | + |
| 52 | +++ |
| 53 | +++ |
| 54 | +++ |
| 55 | +++ |
| 56 | +++ |
| 57 | +++ |
| 58 | +++ |
| 59 | +++ |

-continued

| Ex ID | Activity |
|---|---|
| 60 | +++ |
| 61 | + |
| 62 | +++ |
| 63 | +++ |
| 64 | ++ |
| 65 | +++ |
| 66 | +++ |
| 67 | +++ |
| 68 | +++ |
| 69 | +++ |
| 70 | +++ |
| 71 | +++ |
| 72 | +++ |
| 73 | ++ |
| 74 | ++ |
| 75 | ++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | + |
| 86 | +++ |
| 87 | + |
| 88 | +++ |
| 89 | +++ |
| 90 | +++ |
| 91 | +++ |
| 92 | +++ |
| 93 | + |
| 94 | +++ |
| 95 | +++ |
| 96 | +++ |
| 97 | +++ |
| 98 | +++ |
| 99 | +++ |
| 100 | ++ |
| 101 | + |
| 102 | +++ |
| 103 | ++ |
| 104 | +++ |
| 105 | +++ |
| 106 | ++ |
| 107 | ++ |
| 108 | + |
| 109 | +++ |
| 110 | +++ |
| 111 | +++ |
| 112 | +++ |
| 113 | ++ |
| 114 | +++ |
| 115 | +++ |
| 116 | +++ |
| 117 | +++ |
| 118 | +++ |
| 119 | ++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |

-continued

| Ex ID | Activity |
|---|---|
| 137 | +++ |
| 138 | +++ |
| 139 | +++ |
| 140 | +++ |
| 141 | +++ |
| 142 | ++ |
| 143 | +++ |
| 144 | +++ |
| 145 | +++ |
| 146 | +++ |
| 147 | +++ |

Comparative Table Between Representative Compounds from WO2016/042087 and Representative Compounds from Present Patent Application Properties

| Example ID | Assay A | Assay B | Assay C |
|---|---|---|---|
| Example O4 of WO2016042087 | + | + | ++ |
| Example O11 of WO2016042087 | + | + | + |
| Example 1 | ND | +++ | +++ |
| Example 55 | ND | +++ | +++ |
| Example 67 | ND | +++ | +++ |
| Example 3 | +++ | ++ | +++ |
| Example 54 | +++ | ++ | +++ |
| Example 79 | +++ | +++ | ++ |

Human protein binding free fraction data legend: + indicates F % below 0.1%, ++ indicates F % of between 0.1-1%, and +++ indicates F % above 1%; ND=Not determined Human Clint data legend: + indicates hCl above 18 ug/min/mg prot, ++ indicates hCl between 6-18 ug/min/mg prot, and +++ indicates hCl equal or below 5 ug/min/mg prot; ND=Not determined hERG q-patch inhibition data legend: + indicates an IC50 below 11 uM, ++ indicates an IC50 of between 1-10 uM, and +++ indicates an IC50 above 10 uM; ND=Not determined Human Clint protocol: Pooled liver microsomes (Sekisui Xenotech) were diluted at 0.5 mg/mL in 50 mM phosphate buffer, pH 7.4 then pre-incubated with 0.5 μM 00945 for 7 min at 37° C. The reactions were initiated by adding prewarmed cofactor (0.44 mM NADPH). Aliquots of samples were taken at 0, 5, 10, 20 and 45 min and the reactions stopped by addition of cold acetonitrile containing an internal standard. Samples were centrifuged at 3000 g for 10 min at 4° C. and then supernatants were analyzed by LC/MS/MS for the amount of parent compound remaining.

Human protein binding protocol: Compound was added to plasma or brain homogenate and incubated at 2 μM at 37° C. in the RED plate (Thermo n° 96009, cut-off 8000 Da) against PBS buffer. After 4 h, aliquots of plasma and buffer side were transferred to a well containing acetonitrile with an internal standard. After protein precipitation, samples were centrifuged and supernatant was injected in LC/MS/MS. Standards were prepared in the same matrix and treated as samples.

A fraction unbound ($fu_{plasma}$) was determined for each plasma sample as follows:

$$fu_{plasma}(\%) = \frac{C_{buffer}}{C_{plasma}} \times 100\%$$

hERG q-patch assay protocol: The potential for test compound to inhibit the hERG potassium channel was determined using the Charles River ChanTest® hERG-HEK stably transfected cell line on the Sophion Qube automated electrophysiology platform. The assay was performed at room temperature and recordings of the hERG tail current from a population of cells were made using multi-hole QChips.

REFERENCES

Becker et al., Curr. Rheum. Reports 2005 7:427-433
Brooks, The Oncologist 2013 1:e3-e5
Cai et al., Oncology Reports 2018 39:2915-2923
Chen et al., J. Pathol. 2020 250 2:170-182
Chin et al., Curr. Med. Chem. 2005 4 1:35-42
Duggan et al., Scientific reports 2017 7:1578
Franca et al., Scand. J. Rheumatol. 2016 45:8-12
Gambino et al., Assay Drug. Dev. Technol. 2017 15 1:30-43
Girardin et al., EMBO Rep. 2001 2:736-742
Haile et al., J. Med. Chem. 2019 14:6482-6494
Hollenbach et al., JBC, 2005, 280: 14981-8
Hysi et al., Hum. Mol. Genet. 2005 14:935-941
Inaki et al., Genome Research 2014 24: 1559
Inohara et al., J Biol Chem 2000 36:27823-31
Jaafar et al., Biochem. Biophys. Res. Commun. 2018 1:115-121
Kabesh et al., J. Allergy Clin. Immunol. 2003 4:813-7
Lesage et al., Am. J. Hum. Genet. 2002 70:845-857
Liu et al., Cell. Biochem. Biophys. 2015 72 3:681-5
Maloney et al., JACS 2017 4 (S1):S150
McGovern et al., Hum. Mol. Genet. 2005 14:1245-1250
Mertins et al., Nature 2016 7605:55-62
Miceli-Richard et al., Nature Genetics 2001 29:19-20
Negroni et al., Inflamm. Bowel Dis. 2009 8:1145-1154
Singel et al., Breast Cancer Res. 2014 16:R28
Som et al., World J. Clin. Cases 2019 4:405-418
Strober et al., Nat. Rev. Immunol. 2006 1:9-20
Stronati et al., Digestive and Liver Disease 2010 12:848-853
Tigno-Aranjuez et al., Genes Dev. 2010 1:2666-77
Uehara et al., Diag. Path. 2009 4:23
Vieira et al., J. Immunol. 2012 10:5116-5122
Wiken et al., J. Clin. Immunol. 2009 29:78-89
Wu et al., Mol. Cell. Proteomics 2011 10: 1-14
Yamamoto et al., Microbes & Infections 2009 12:912-918
Yang et al., PLoS One 2012 8:e40196
Zare et al., Cancers 2018 10:184
Zhao et al., Biochem. Biophys. Res. Commun. 2017 2:1151-1158
Zhou et al., Obesity 2015 7:1394-1400

The invention claimed is:

1. A compound according to Formula (I):

(I)

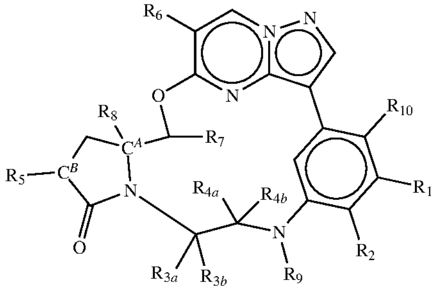

or a stereoisomer, tautomer, racemate, salt, hydrate, N-oxide form, or solvate thereof, wherein:

$R_1$ is selected from -halo, —O—$C_{1-6}$alkyl, -alkynyl, —$C_{1-6}$alkyl, —$C_{3-6}$-cycloalkyl, —C(O)—$C_{1-6}$-alkyl, —C(O)—$C_{1-6}$cycloalkyl, —C(O)-$Het_2$, —C(O)—$NR_aR_b$, -$Het_1$ and —CN, wherein:

each —$C_{1-6}$alkyl in $R_1$ is optionally substituted with one or more substituents selected from -D, -halo, —O—$C_{1-3}$alkyl, —$C_{3-6}$-cycloalkyl, -Ph, -$Het_1$, -$Het_2$, and —OH;

the -alkynyl in $R_1$ is optionally substituted with one substituent selected from —$C_{1-6}$alkyl, and —$CH_2$—O—$C_{1-6}$alkyl;

R2 and $R_{10}$ are each independently selected from —H, and -halo;

$R_{3a}$, $R_{3b}$, $R_{4a}$, $R_{4b}$, $R_7$, and $R_8$ are each independently selected from —H, and —$C_{1-6}$alkyl, wherein:

each —$C_{1-6}$alkyl in $R_{3a}$, $R_{3b}$, $R_{4a}$, $R_{4b}$, $R_7$, and $R_8$ is optionally substituted with one or more —O—$C_{1-6}$ alkyl;

when $R_{3a}$ and/or $R_{3b}$ is —$C_{1-6}$alkyl, then $R_{4a}$ and $R_{4b}$ are each —H; and when $R_{4a}$ and/or $R_{4b}$ is —$C_{1-6}$alkyl, then $R_3$ and $R_{3b}$ are each —H;

$R_5$ is selected from —OH, —$NR_cR_d$, —NHC(O)$R_c$, —NC(O)$R_cR_d$, —NC(O)O$R_c$, —NHS($O_2$)$R_c$, -halo, —O—$C_{1-6}$alkyl, —O—$C_{3-5}$-cycloalkyl, —O-$Het_2$, —$C_{1-6}$alkyl, and —CN, wherein:

each —$C_{1-6}$alkyl in $R_5$ is optionally substituted with one or more substituents selected from -D, —OH, —$C_{1-6}$alkyl, —$C_{3-5}$-cycloalkyl, —O—$C_{1-6}$alkyl and -$Het_2$;

$R_6$ is selected from —H, -halo, —$C_{1-6}$alkyl, —O—$C_{1-6}$ alkyl, —O-$Het_4$, and -$Het_3$, wherein:

each —$C_{1-6}$alkyl in $R_6$ is optionally substituted with one or more substituents selected from -D, and —O—$C_{1-6}$alkyl;

$R_9$ is selected from —H, —$C_{1-6}$alkyl, —C(O)—$C_{1-6}$alkyl, and —C(O)—O—$C_{1-6}$alkyl;

$C^A$ and $C^B$ are carbon atoms;

$R_a$ is selected from —H, and —$C_{1-6}$alkyl, wherein:

the —$C_{1-6}$alkyl in $R_a$ is optionally substituted with one or more substituents selected from -D, and —$C_{1-6}$ alkyl;

$R_b$ is selected from —H, —$C_{1-6}$alkyl, and —O—$C_{1-6}$ alkyl, wherein:

each —$C_{1-6}$alkyl in $R_b$ is optionally substituted with one or more substituents selected from -D, —$C_{1-6}$ alkyl, and —$C_{3-5}$-cycloalkyl;

$R_c$ and $R_d$ are each independently selected from —H, and —$C_{1-6}$alkyl, wherein:

each —$C_{1-6}$alkyl in $R_c$ and $R_d$ is optionally substituted with one or more substituents selected from -D, and —$C_{1-6}$alkyl;

$Het_1$ and $Het_3$ are each independently a 5 or 6-membered aromatic heterocycle having from 1 to 3 heteroatoms selected from O, N and S, wherein:

each $Het_1$ and each $Het_3$ are optionally substituted with from 1 to 3 —$C_{1-6}$alkyl; and each —$C_{1-6}$alkyl in $Het_1$ and $Het_3$ is optionally substituted with one or more substituents selected from -D, -halo, —O—$C_{1-3}$alkyl, and —OH;

$Het_2$ is a 4-to-6-membered saturated heterocycle having from 1 to 3 heteroatoms selected from O and N, wherein:

each $Het_2$ is optionally substituted with from 1 to 3—$C_{1-6}$alkyl;

each —$C_{1-6}$alkyl in $Het_2$ is optionally substituted with one or more substituents selected from -D, -halo, —O—$C_{1-3}$alkyl, and —OH; and $Het_4$ is a 4-to-10-membered saturated heterocycle having from 1 to 3 heteroatoms selected from O and N, wherein:

each $Het_4$ is optionally substituted with from 1 to 3—$C_{1-6}$alkyl; and each —$C_{1-6}$alkyl in $Het_4$ is optionally substituted with one or more substituents selected from -D, -halo, —O—$C_{1-3}$alkyl, and —OH.

2. The compound according to claim 1, wherein:

$R_1$ is selected from -halo, —O—$C_{1-6}$alkyl, -alkynyl, —$C_{1-6}$alkyl, —$C_{3-6}$-cycloalkyl, —C(O)—$C_{1-6}$-alkyl, —C(O)—$C_{1-6}$cycloalkyl, —C(O)-$Het_2$, —C(O)—$NR_aR_b$, -$Het_1$, and —CN, wherein:

each —$C_{1-6}$alkyl in $R_1$ is optionally substituted with one or more substituents selected from -D, -halo, —O—$C_{1-3}$alkyl, —$C_{3-6}$-cycloalkyl, -Ph, -$Het_1$, -$Het_2$, and —OH;

$R_5$ is selected from —OH, —$NR_cR_a$, —NHC(O)$R_c$, -halo, —O—$C_{1-6}$alkyl, —O—$C_{3-5}$-cycloalkyl, —O-$Het_2$, —$C_{1-6}$alkyl, and —CN, wherein:

each —$C_{1-6}$alkyl in $R_5$ is optionally substituted with one or more substituents selected from -D, —OH, —$C_{1-6}$alkyl, —$C_{3-5}$-cycloalkyl, —O—$C_{1-6}$alkyl and -$Het_2$;

$R_a$ is selected from —H, and —$C_{1-6}$alkyl;

$R_b$ is selected from —H, —$C_{1-6}$alkyl, and —O—$C_{1-6}$ alkyl;

$R_c$ and $R_a$ are each independently selected from —H, and —$C_{1-6}$alkyl;

$Het_1$ and $Het_3$ are each independently a 5 or 6-membered aromatic heterocycle having from 1 to 3 heteroatoms selected from O and N, wherein:

each $Het_1$ and each $Het_3$ is optionally substituted with from 1 to 3 —$C_{1-6}$alkyl; and $Het_2$ is a 4 to 6-membered saturated heterocycle having from 1 to 3 O atoms.

3. The compound according to claim 1, wherein:

$R_1$ is selected from -halo, —O—$C_{1-6}$alkyl, -alkynyl, —$C_{1-6}$alkyl, —$C_{3-6}$-cycloalkyl, —C(O)—$C_{1-6}$-alkyl, —C(O)—$C_{1-6}$cycloalkyl, —C(O)-$Het_2$, —C(O)—$NR_aR_b$, $Het_1$ and —CN, wherein:

each —$C_{1-6}$alkyl in $R_1$ is optionally substituted with one or more substituents selected from -D, -halo, —O—$C_{1-3}$alkyl, —$C_{3-6}$-cycloalkyl, -Ph, -$Het_1$, -$Het_2$, and —OH;

$R_{3a}$, $R_{3b}$, $R_{4a}$, $R_{4b}$, $R_7$, and $R_8$ are each —H;

$R_5$ is selected from —OH, -halo, —O—$C_{1-6}$alkyl, —O—$C_{3-5}$-cycloalkyl, and —$C_{1-6}$alkyl, wherein:

each —$C_{1-6}$alkyl in $R_5$ is optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -halo, —$C_{1-6}$alkyl, O—$C_{1-6}$ alkyl, —O-$Het_4$, and -$Het_3$, wherein:

each —$C_{1-6}$alkyl in $R_6$ is optionally substituted with one or more —O—$C_{1-6}$alkyl;

$R_a$ is selected from —H, and —$C_{1-6}$alkyl;

$R_b$ is selected from —H, —$C_{1-6}$alkyl, and —O—$C_{1-6}$ alkyl;

$Het_1$ and $Het_3$ are each independently a 5 or 6-membered aromatic heterocycle having from 1 to 3 heteroatoms selected from O and N, wherein:

each $Het_1$ and each $Het_3$ is optionally substituted with from 1 to 3 —$C_{1-6}$alkyl; and $Het_2$ is a 4 to 6-membered saturated heterocycle having from 1 to 3 O atoms.

4. The compound according to claim 1, wherein:

$R_1$ is selected from -halo, —O—$C_{1-6}$alkyl, -alkynyl, $C_{1-6}$alkyl, —$C_{3-6}$-cycloalkyl, —C(O)—$C_{1-6}$-alkyl, —C(O)—$NR_aR_b$, -$Het_1$ and —CN, wherein:

each —$C_{1-6}$alkyl in $R_1$ is optionally substituted with one or more substituents selected from -D, -halo, and —O—$C_{1-3}$alkyl;

$R_2$ is selected from —H, and -halo;

$R_{10}$ is —H;

$R_{3a}$, $R_{3b}$, $R_{4a}$, $R_{4b}$, $R_7$, and $R_8$ are each —H;

$R_5$ is selected from —OH, -halo, —O—$C_{1-6}$alkyl, —O—$C_{3-5}$-cycloalkyl, and —$C_{1-6}$alkyl, wherein:

each —$C_{1-6}$alkyl in $R_5$ is optionally substituted with one or more substituents selected from -D, —OH, —$C_{1-6}$alkyl, —$C_{3-5}$-cycloalkyl, and —O—$C_{1-6}$alkyl;

$R_6$ is selected from —H, -halo, —$C_{1-6}$alkyl, —O—$C_{1-6}$ alkyl, —O-$Het_4$, and -$Het_3$, wherein:

each —$C_{1-6}$alkyl in $R_6$ is optionally substituted with one or more —O—$C_{1-6}$alkyl;

$R_9$ is —H;

$R_a$ is selected from —H, and —$C_{1-6}$alkyl;

$R_b$ is selected from —H, —$C_{1-6}$alkyl, and —O—$C_{1-6}$ alkyl;

$Het_1$ is a 5-membered aromatic heterocycle having from 1 to 3 heteroatoms selected from O and N; and $Het_1$ is optionally substituted with from 1 to 3—$C_{1-6}$alkyl.

5. The compound according to claim 1, selected from the group consisting of compounds (1), (2), (3), (4), (5), (6), (7), (8), (9), (10), (11), (12), (13), (14), (15), (16), (17), (18), (19), (20), (21), (22), (23), (24), (25), (26), (27), (28), (29), (30), (31), (32), (33), (34), (35), (36), (37), (38), (39), (40), (41), (42), (43), (44), (45), (46), (47), (48), (49), (50), (51), (52), (53), (54), (55), (56), (57), (58), (59), (60), (61), (62), (63), (64), (65), (66), (67), (68), (69), (70), (71), (72), (73), (74), (75), (76), (77), (78), (79), (80), (81), (82), (83), (84), (85), (86), (87), (88), (89), (90), (91), (92), (93), (94), (95), (96), (97), (98), (99), (100), (101), (102), (103), (104), (105), (106), (107), (108), (109), (110), (111), (112), (113), (114), (115), (116), (117), (118), (119), (120), (121), (122), (123), (124), (125), (126), (127), (128), (129), (130), (131), (132), (133), (134), (135), (136), (137), (138), (139), (140), (141), (142), (143), (144), (145), (146), and (147):

(1)

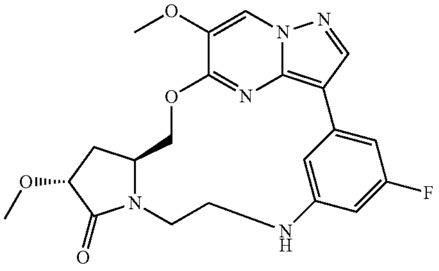

-continued (2)

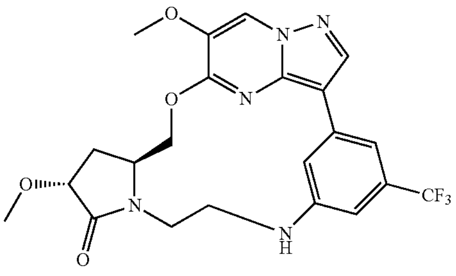

(3)

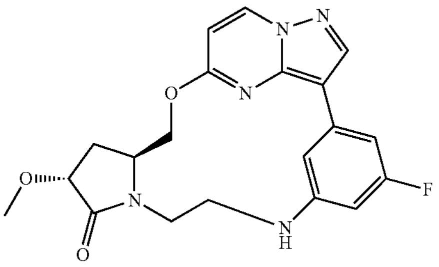

(4)

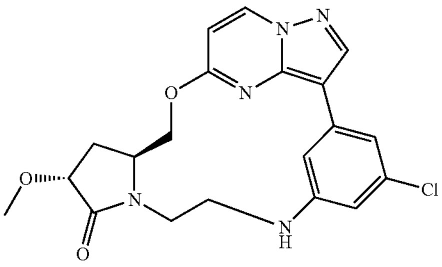

(5)

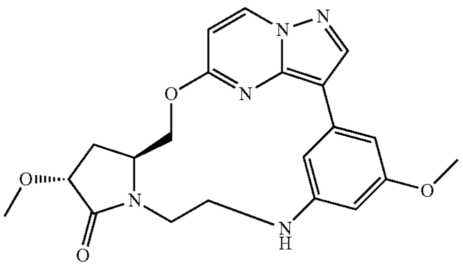

(6)

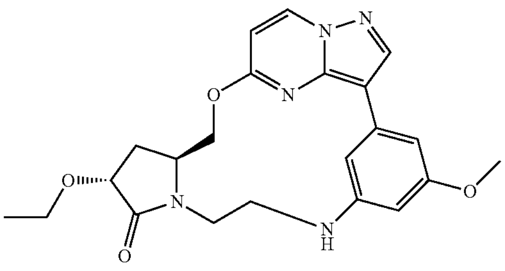

-continued
(7)
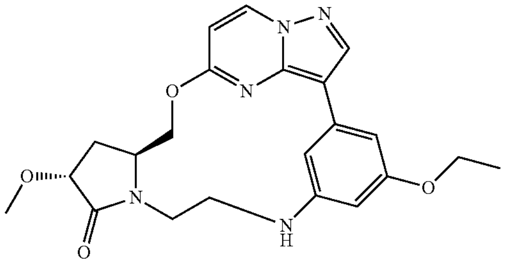
(8)
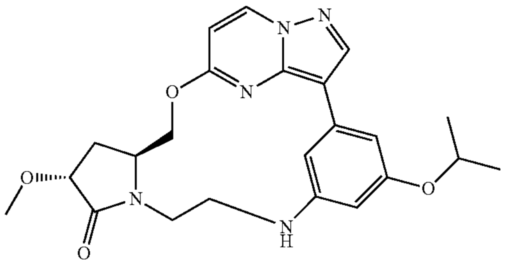
(9)
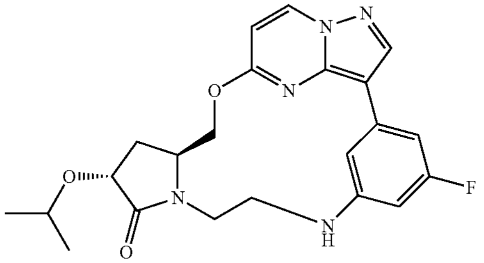
(10)
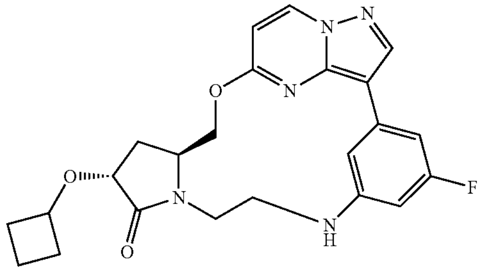
(11)
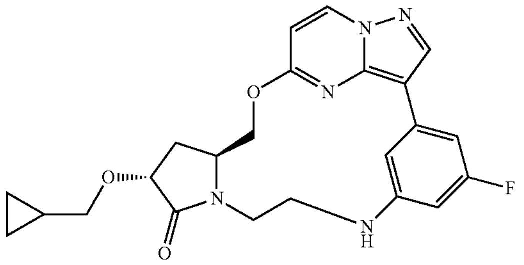
-continued
(12)
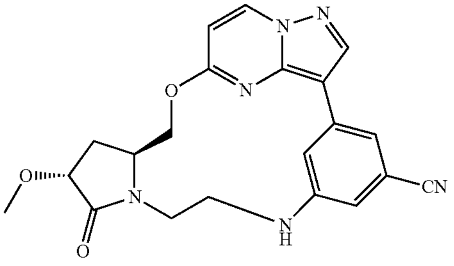
(13)
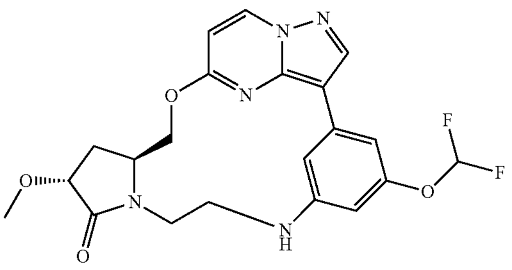
(14)
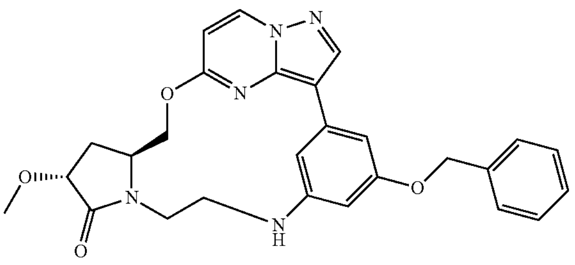
(15)
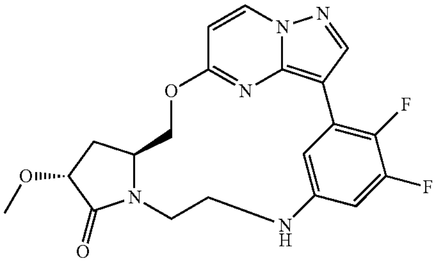
(16)
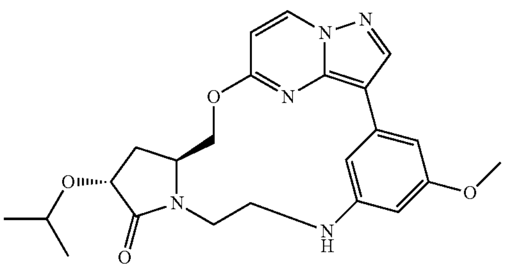

-continued
(17)
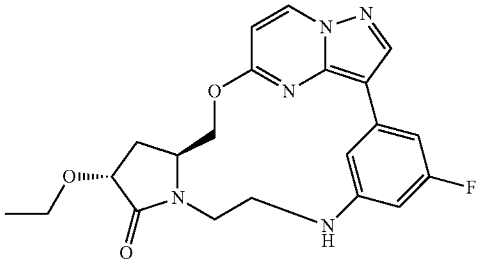
(18)
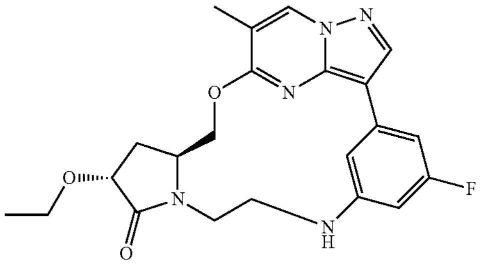
(19)
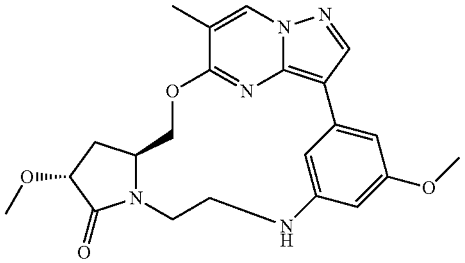
(20)
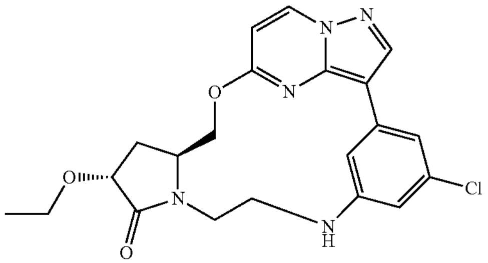
(21)
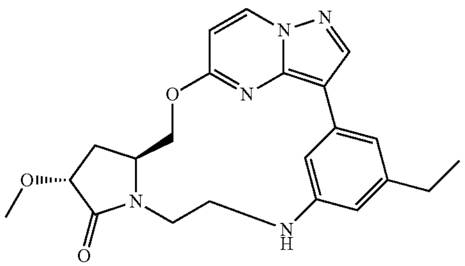
(22)
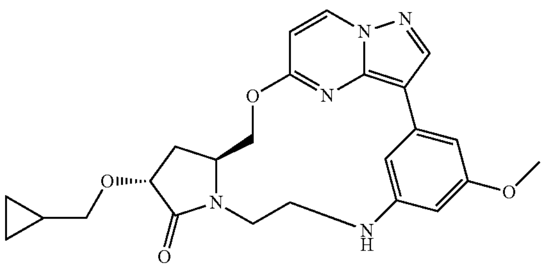
-continued
(23)
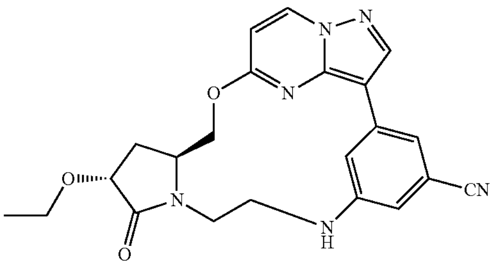
(24)
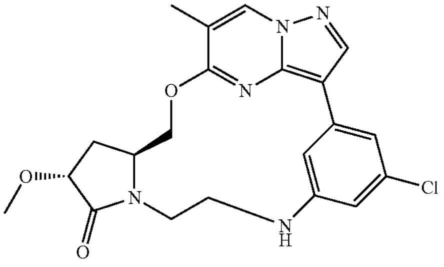
(25)
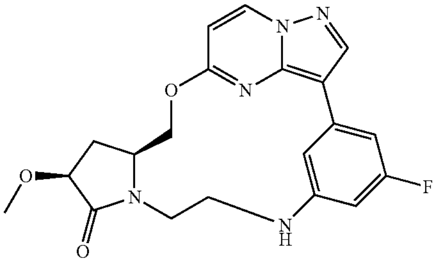
(26)
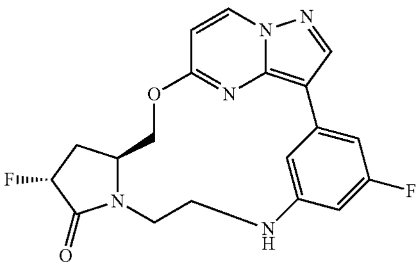
(27)
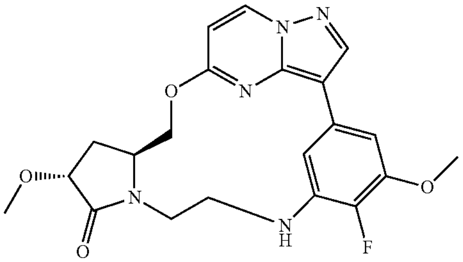

-continued
(28)
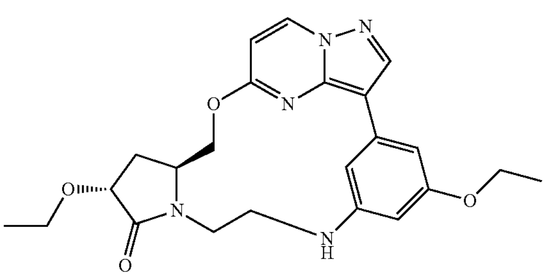
(29)
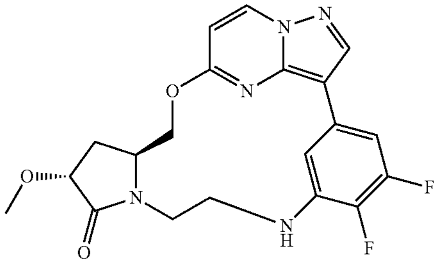
(30)
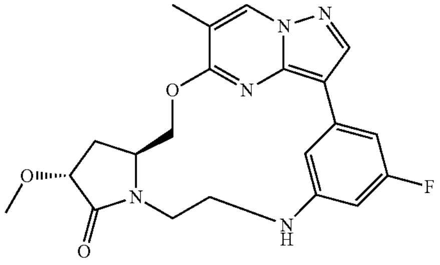
(31)
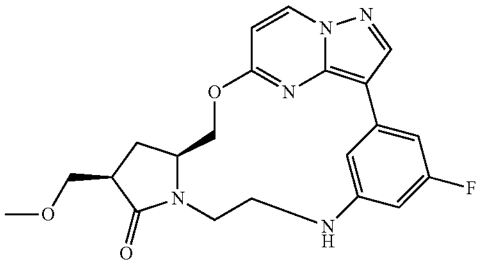
(32)
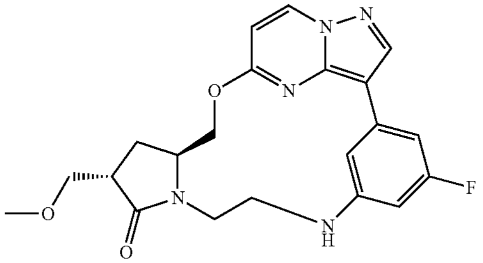
(33)
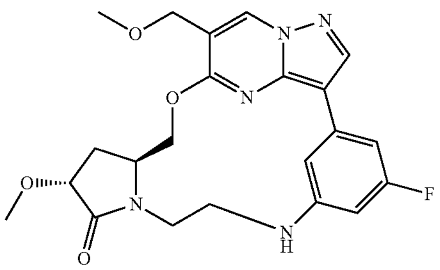
-continued
(34)
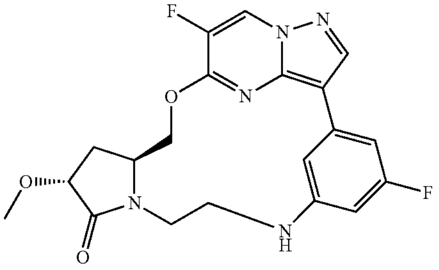
(35)
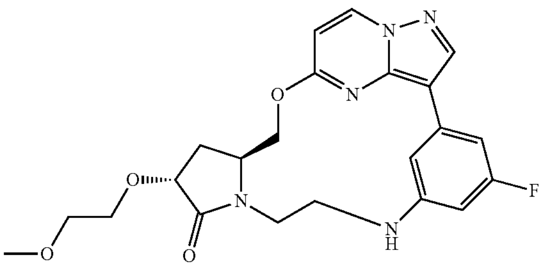
(36)
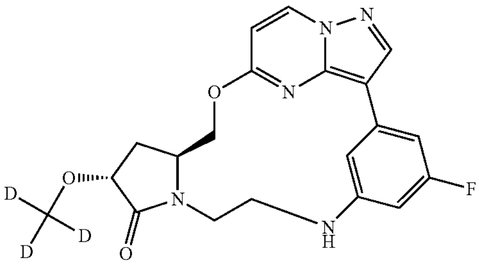
(37)
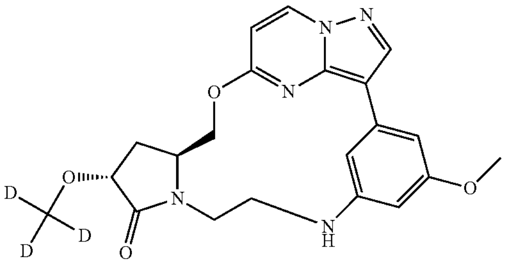
(38)
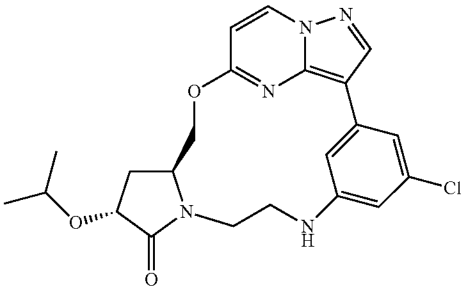

-continued
(39)
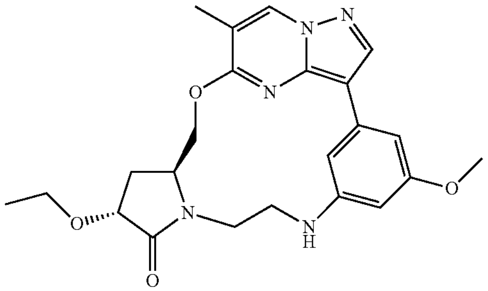
(40)
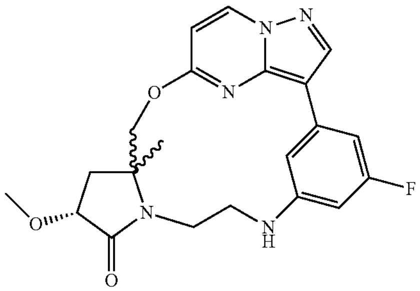
(41)
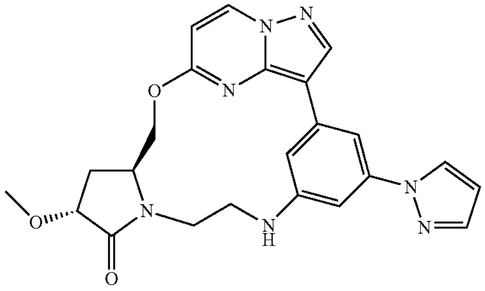
(42)
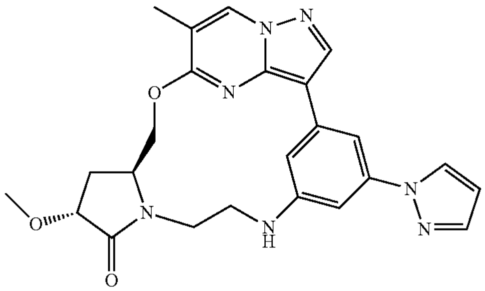
(43)
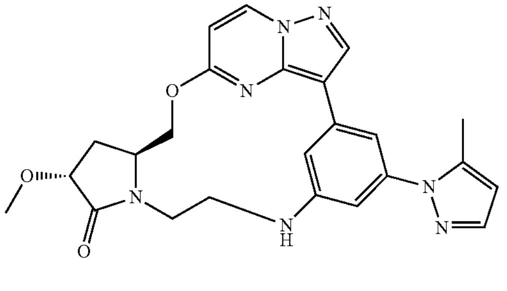
-continued
(44)
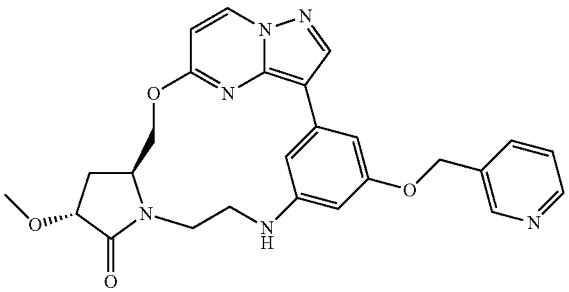
(45)
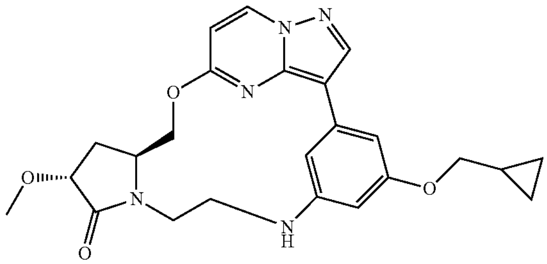
(46)
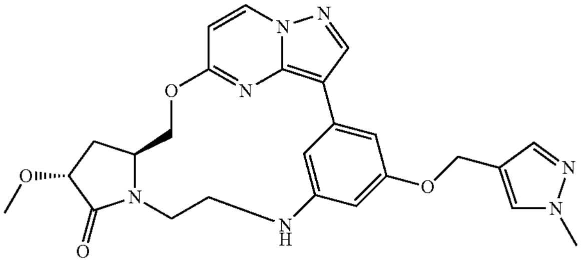
(47)
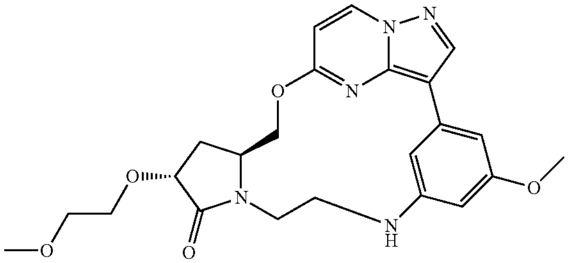
(48)
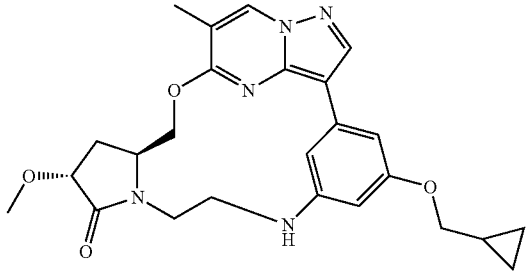

-continued
(49)
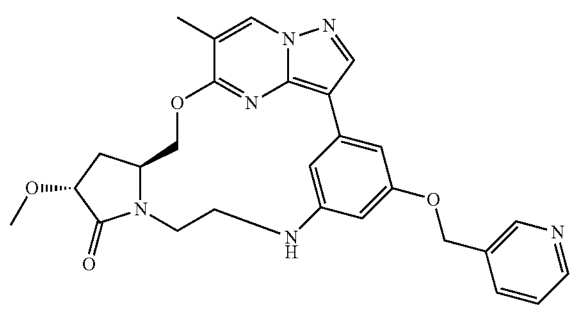
(50)
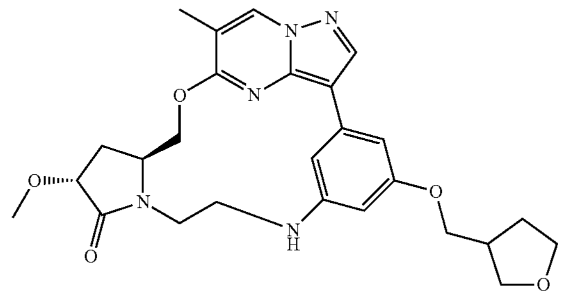
(51)
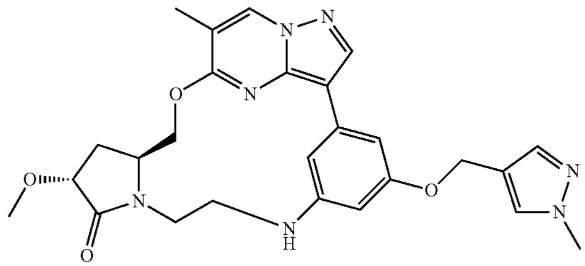
(52)
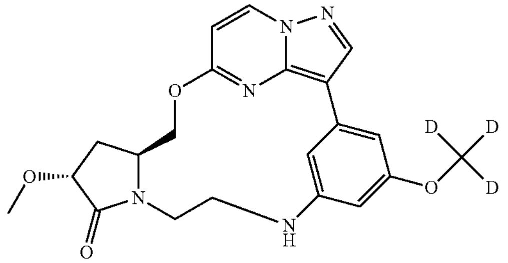
(53)
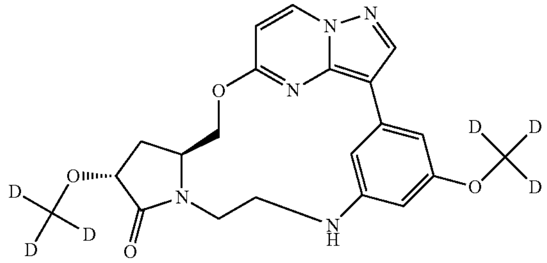
-continued
(54)
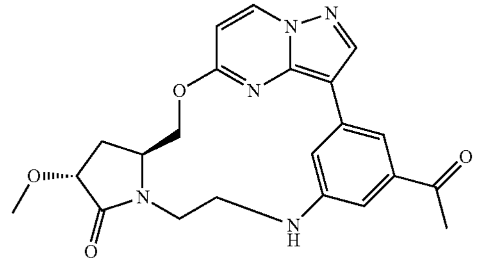
(55)
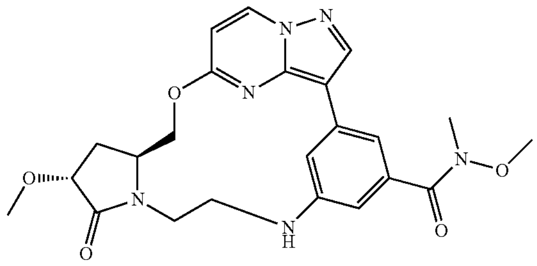
(56)
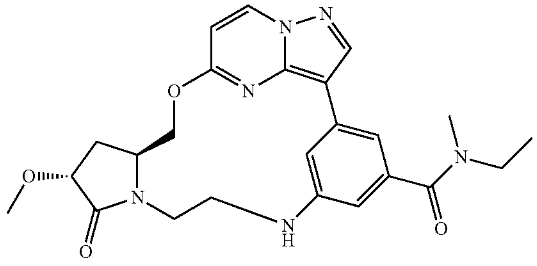
(57)
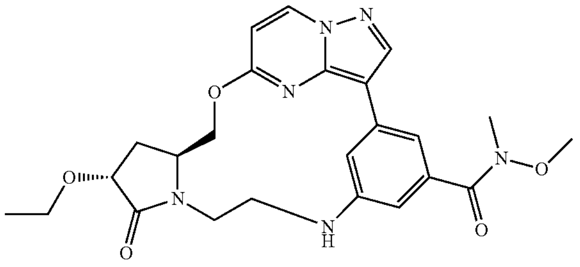
(58)
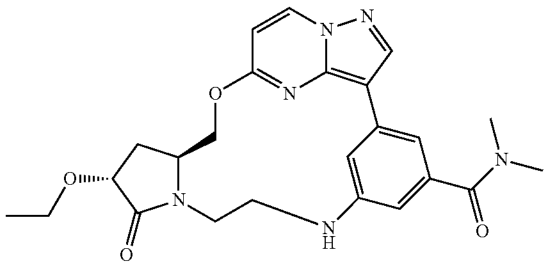

-continued
(59)
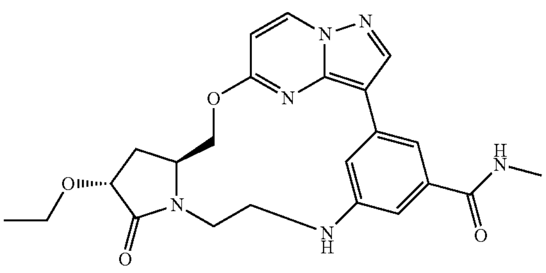
(60)
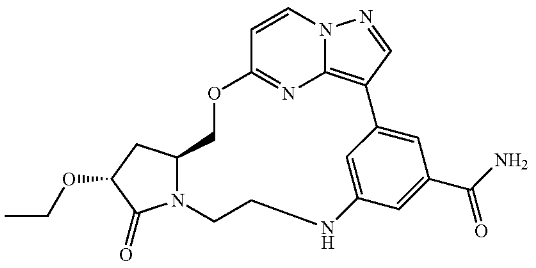
(61)
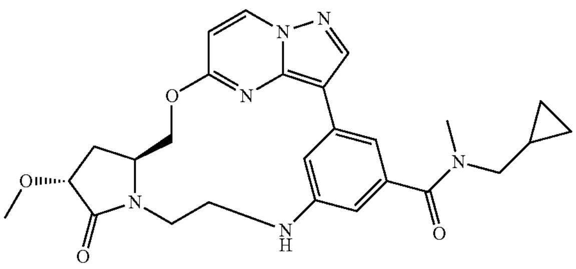
(62)
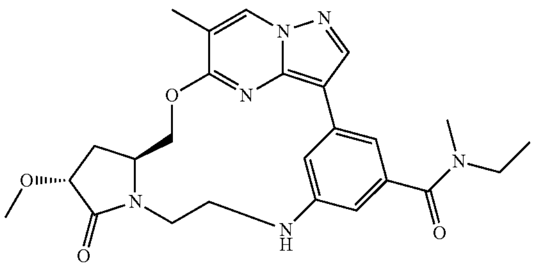
(63)
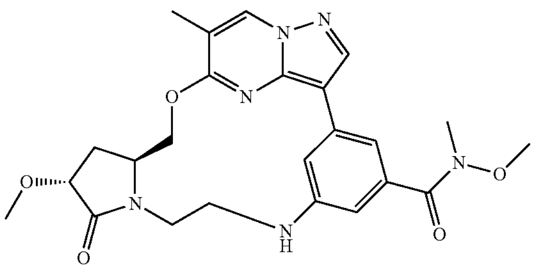
-continued
(64)
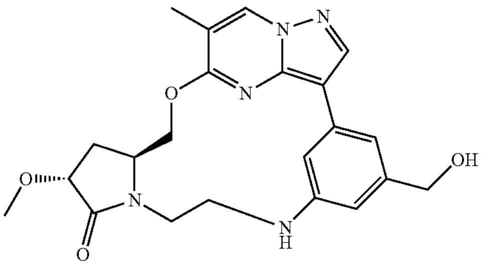
(65)
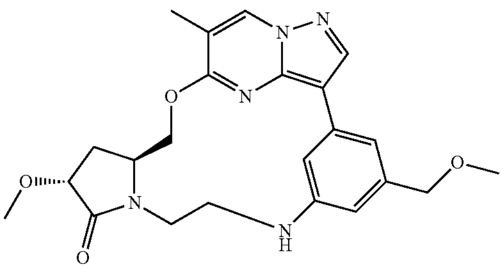
(66)
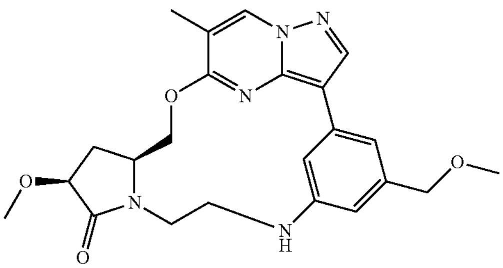
(67)
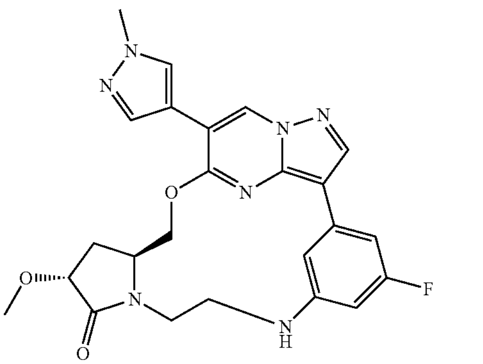
(68)
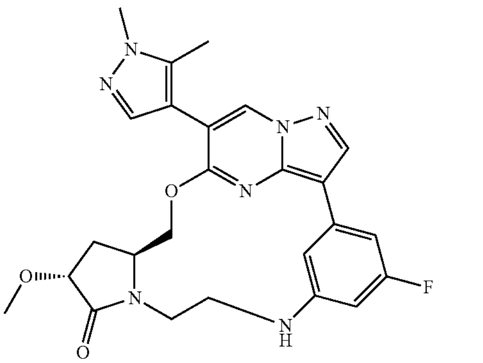

-continued
(69)
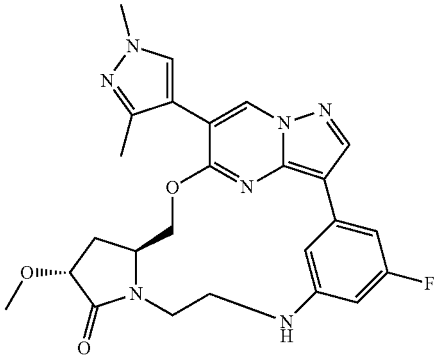
(70)
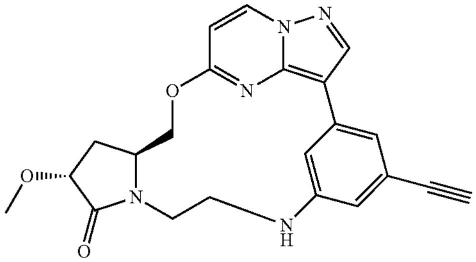
(71)
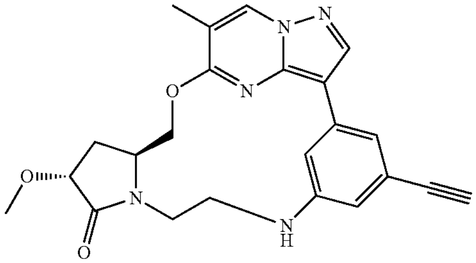
(72)
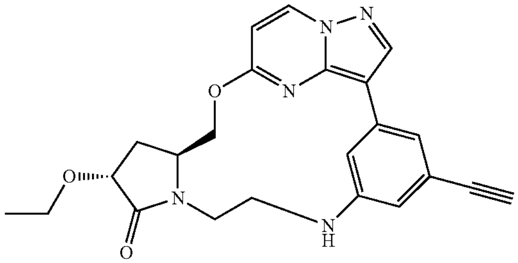
(73)
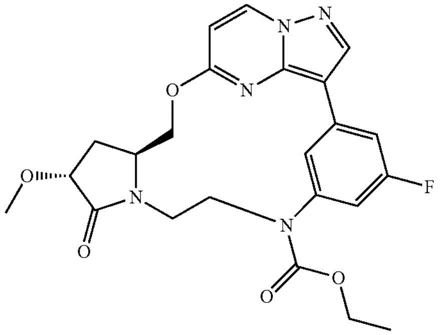
-continued
(74)
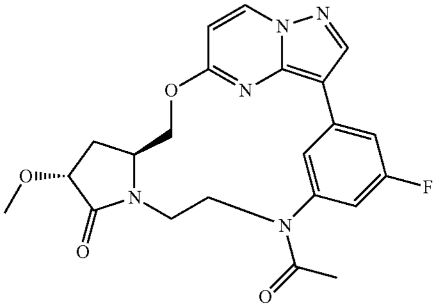
(75)
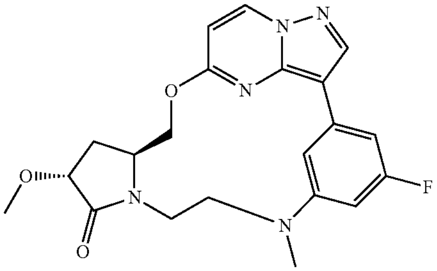
(76)
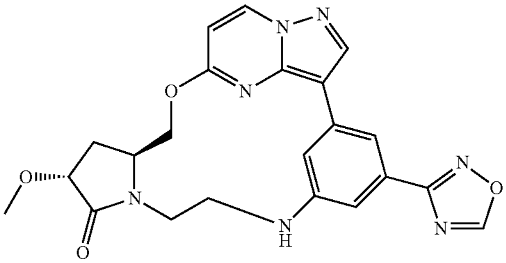
(77)
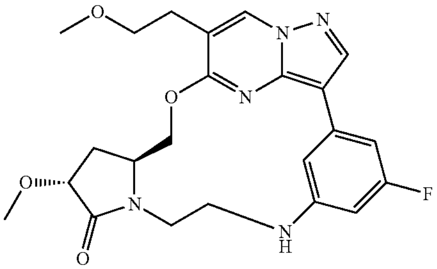
(78)
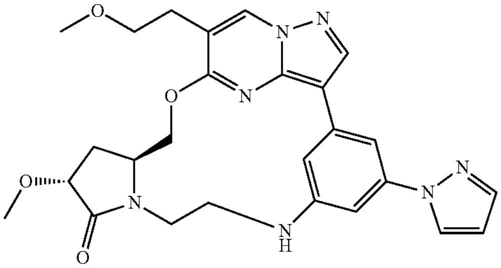

-continued
(79)
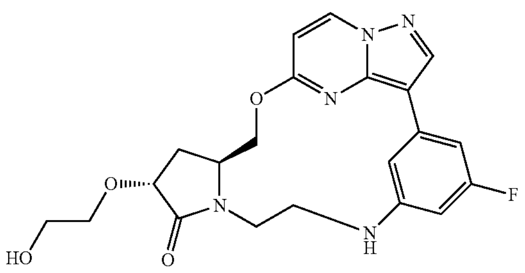
(80)
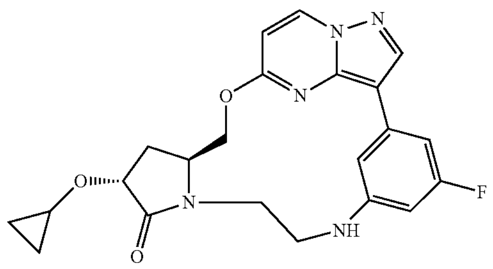
(81)
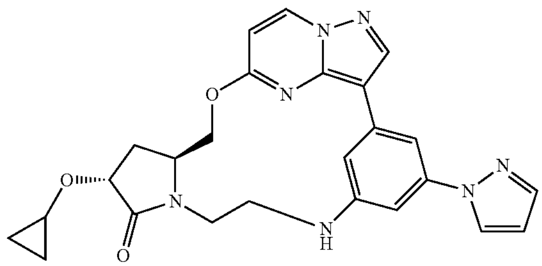
(82)
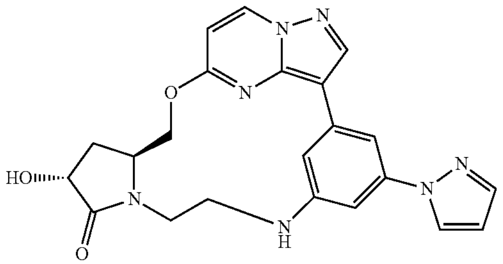
(83)
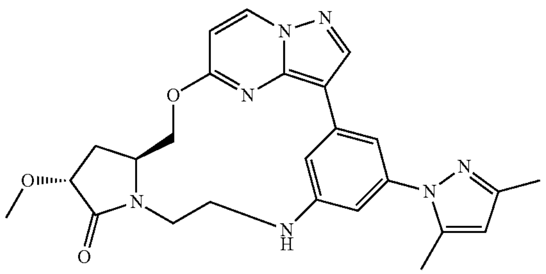
-continued
(84)
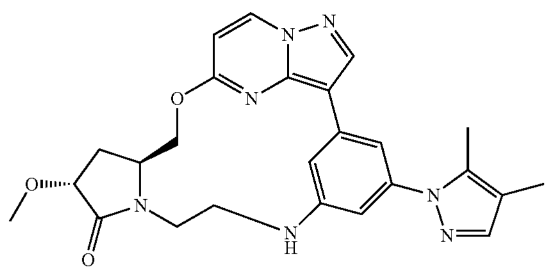
(85)
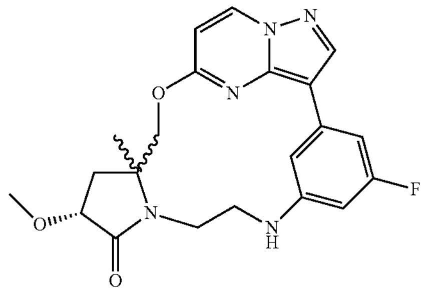
(86)
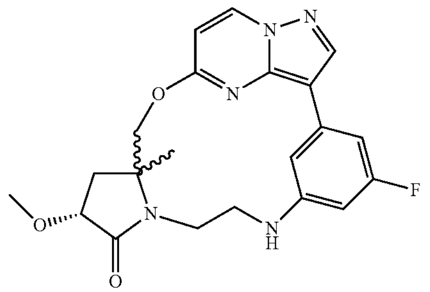
(87)
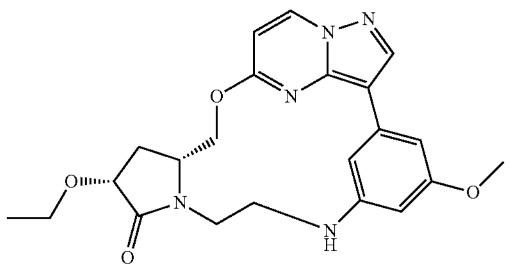
(88)
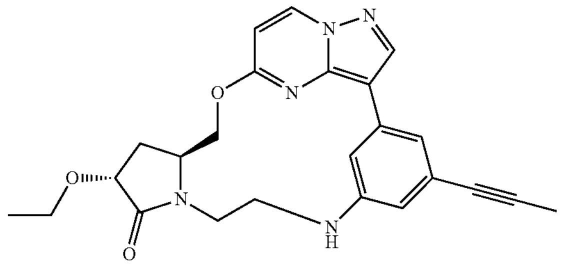

-continued
(89)
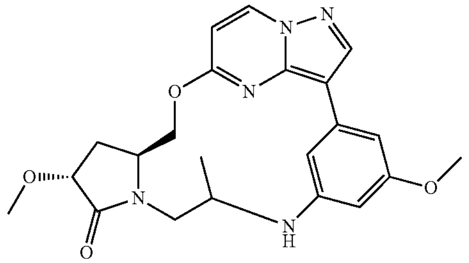
(90)
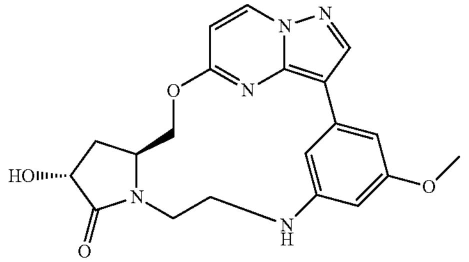
(91)
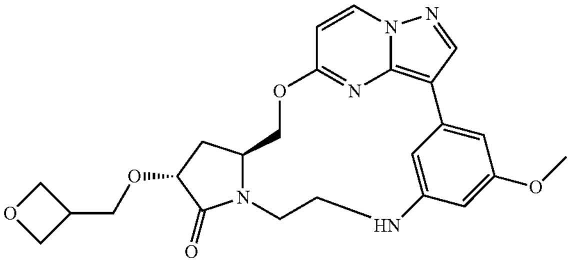
(92)
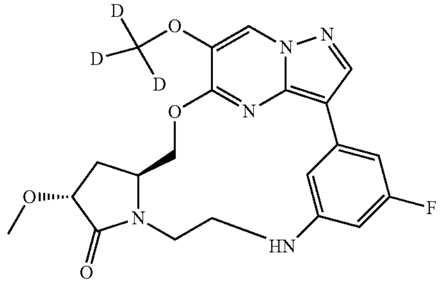
(93)
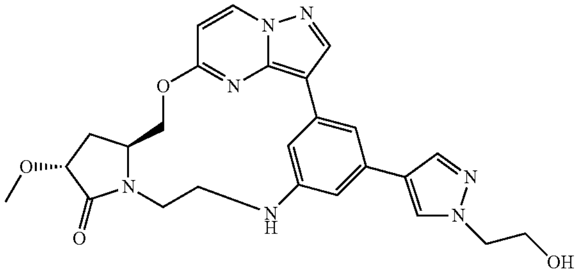
-continued
(94)
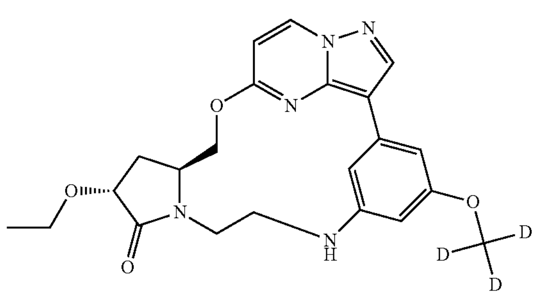
(95)
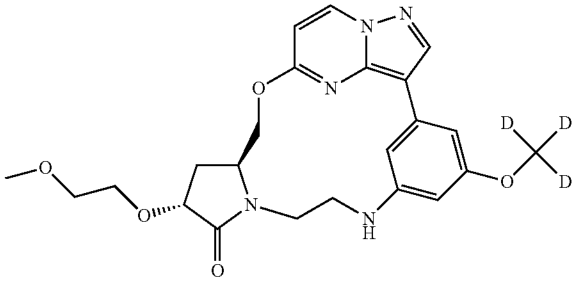
(96)
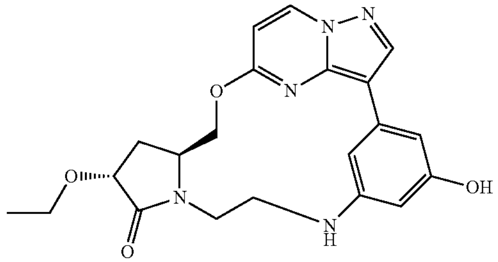
(97)
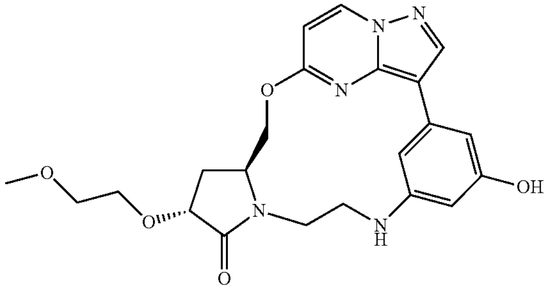
(98)
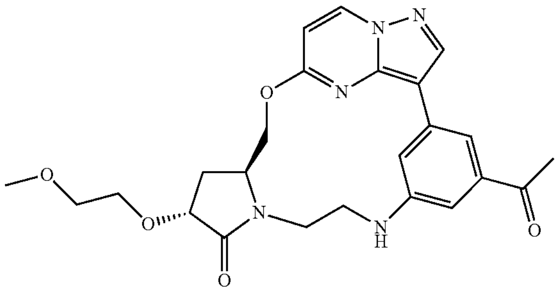

-continued
(99)
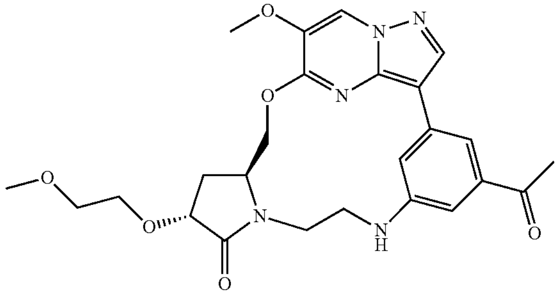
(100)
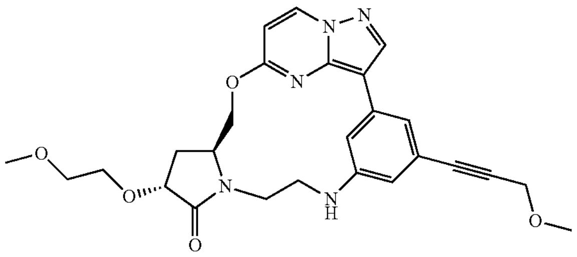
(101)
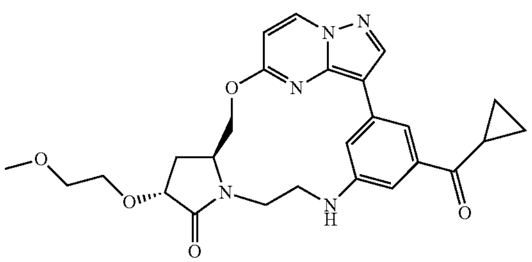
(102)
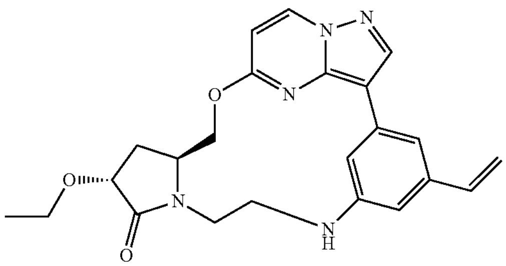
(103)
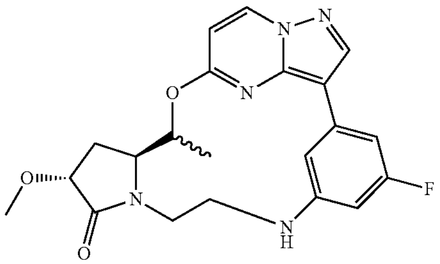
-continued
(104)
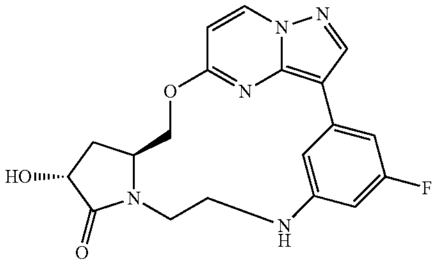
(105)
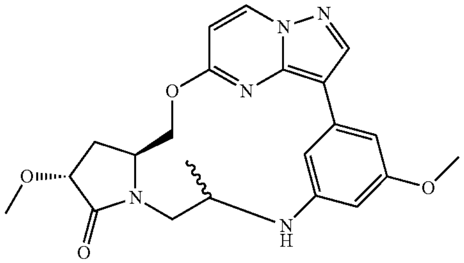
(106)
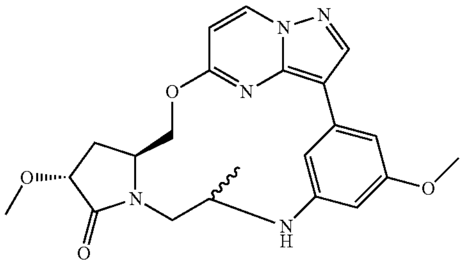
(107)
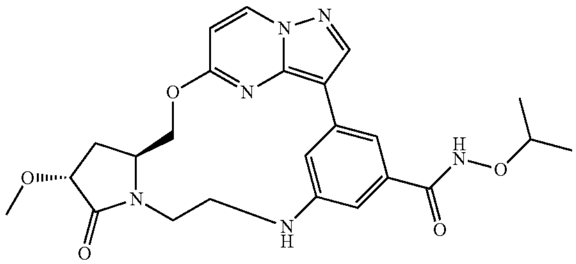
(108)
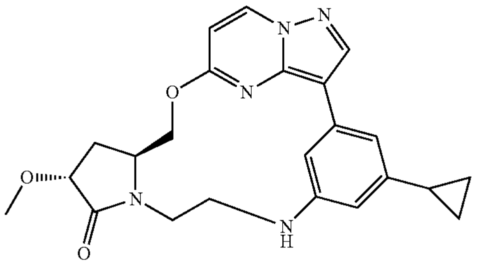

-continued
(109)
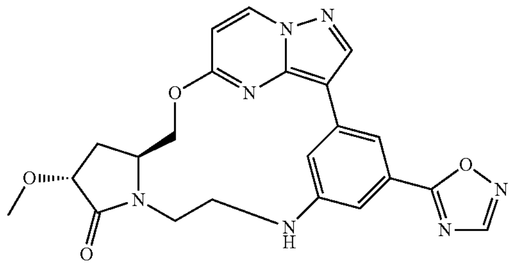
(110)
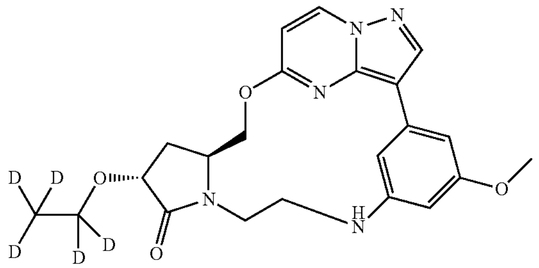
(111)
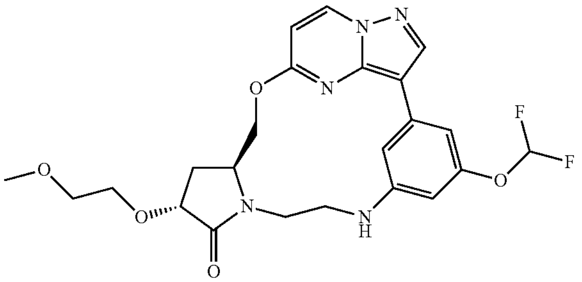
(112)
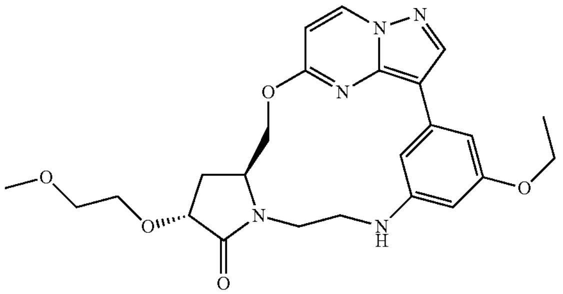
(113)
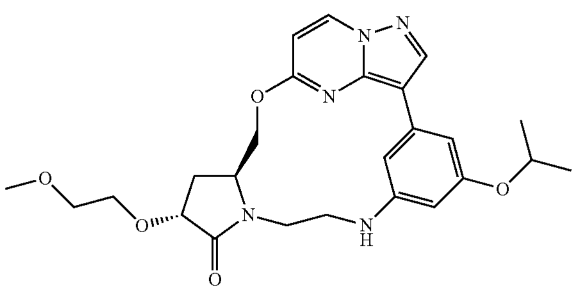
-continued
(114)
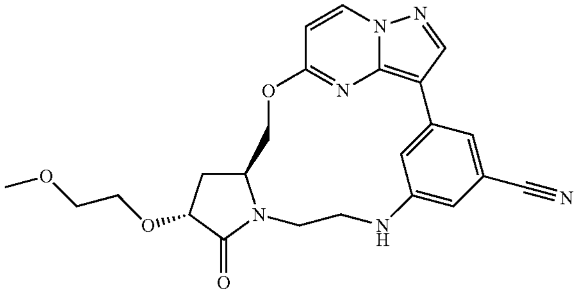
(115)
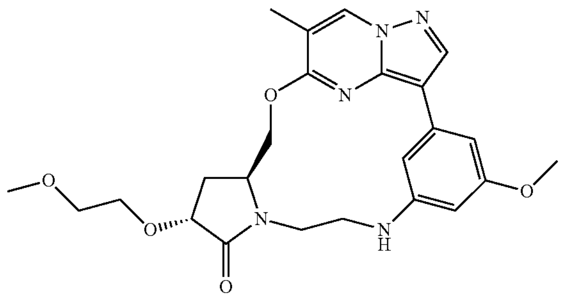
(116)
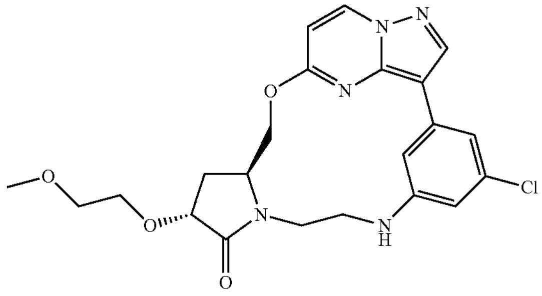
(117)
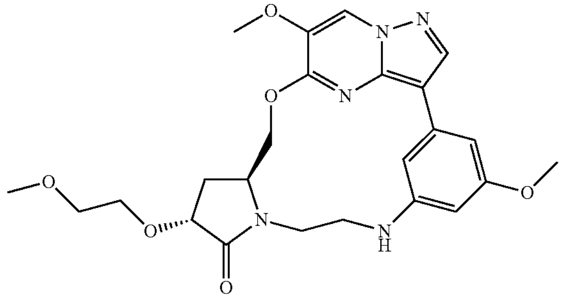
(118)
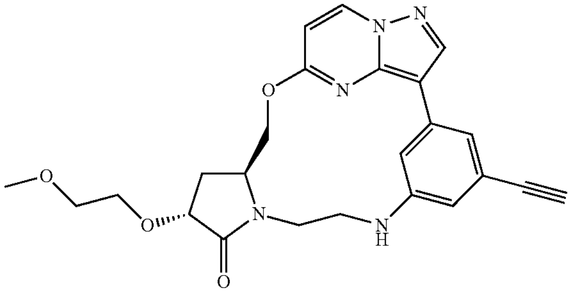

-continued
(119)
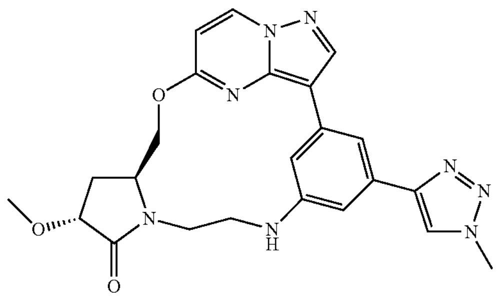
(120)
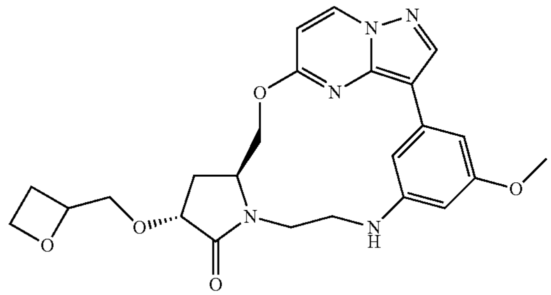
(121)
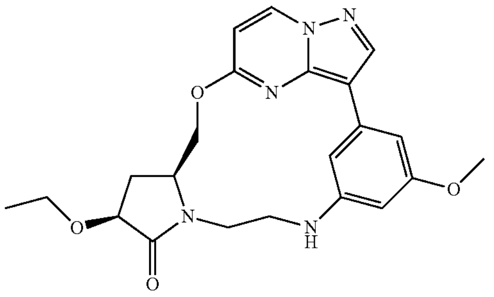
(122)
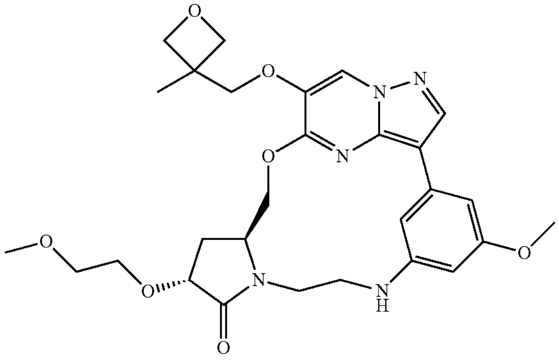
-continued
(123)
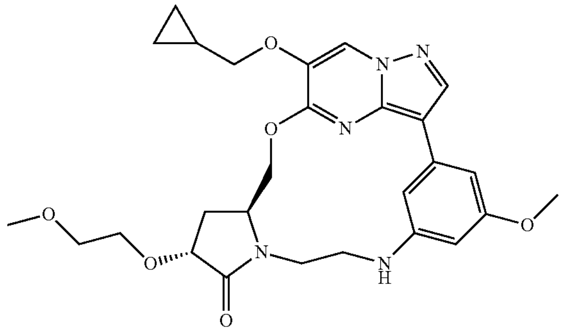
(124)
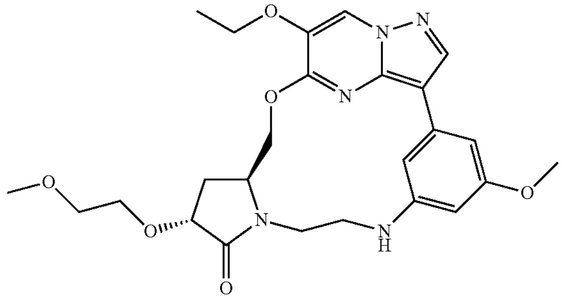
(125)
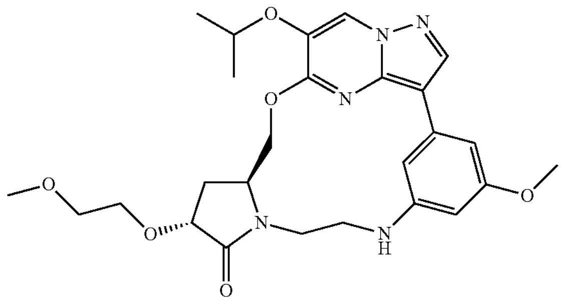
(126)
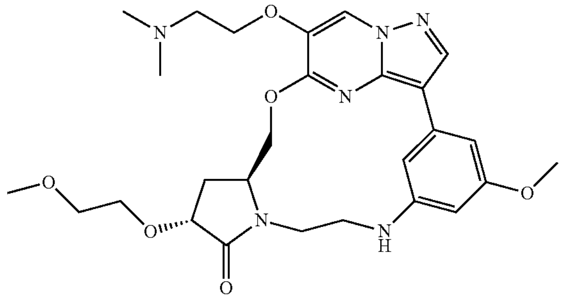

-continued
(127)
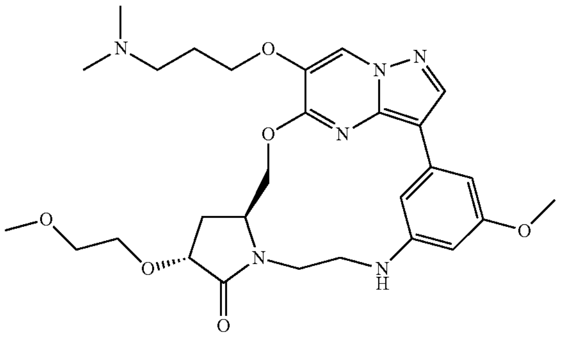
(128)
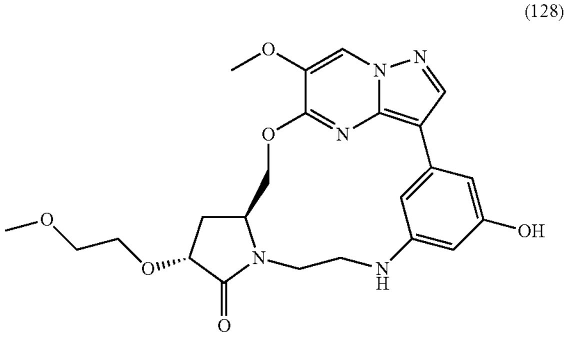
(129)
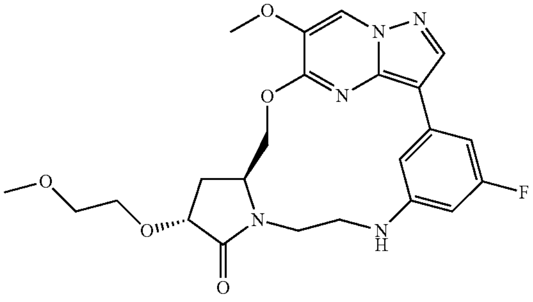
(130)
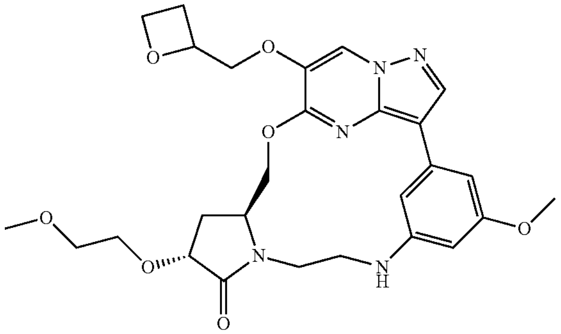
-continued
(131)
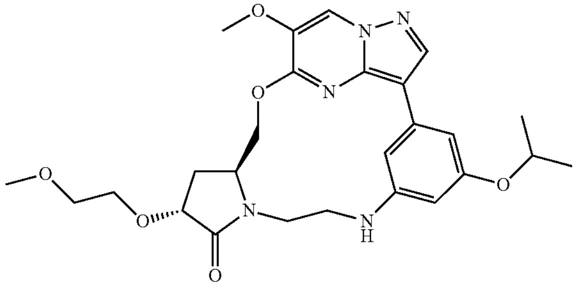
(132)
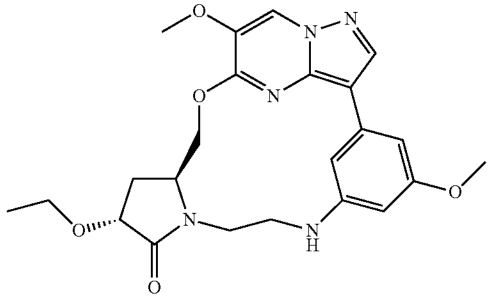
(133)
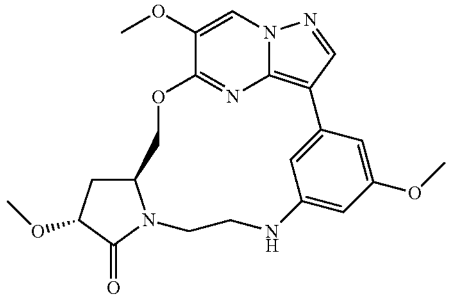
(134)
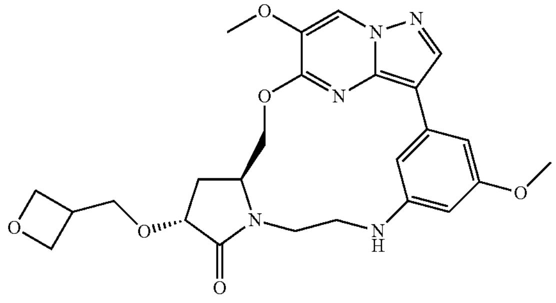
(135)
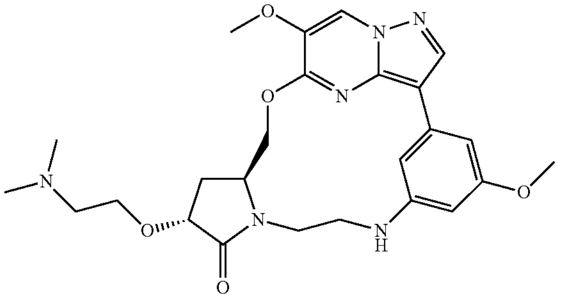

-continued
(136)
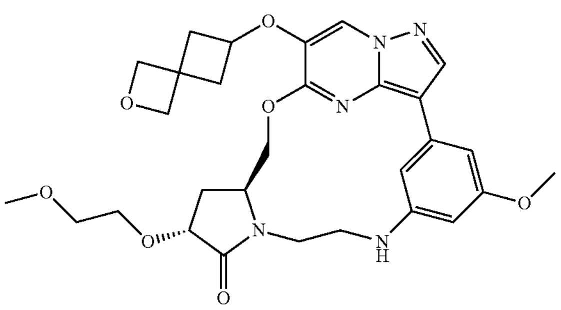
(137)
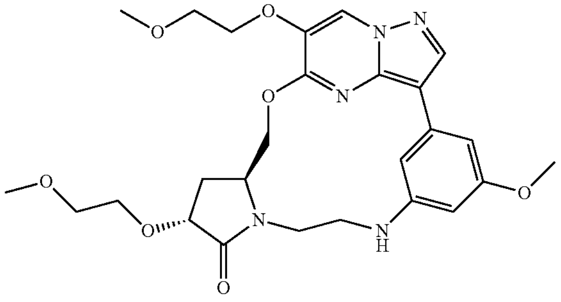
(138)
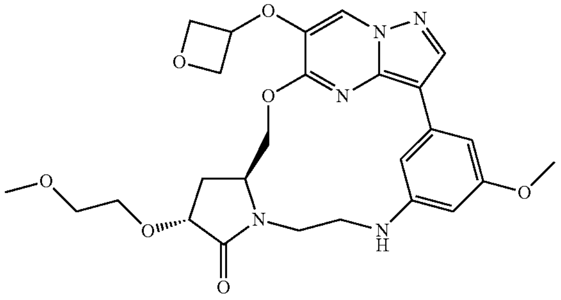
(139)
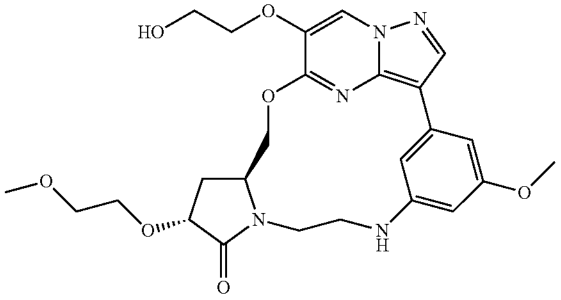
(140)
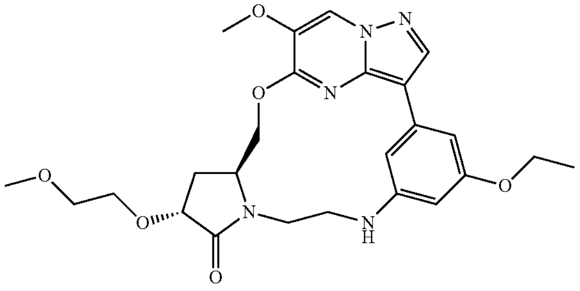
-continued
(141)
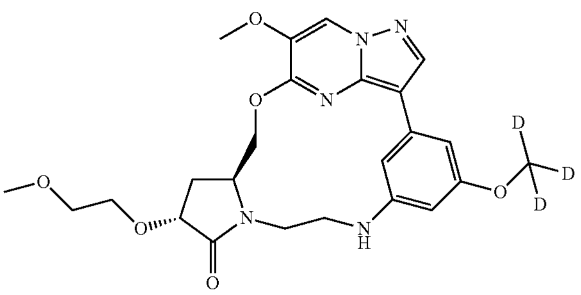
(142)
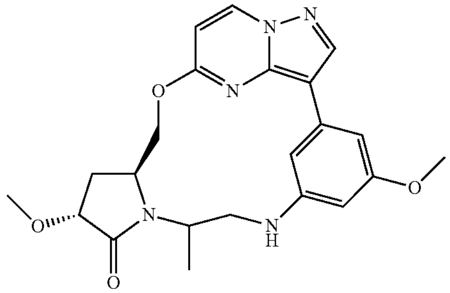
(143)
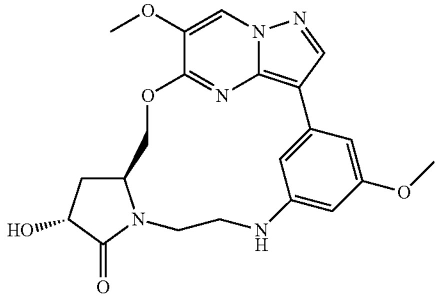
(144)
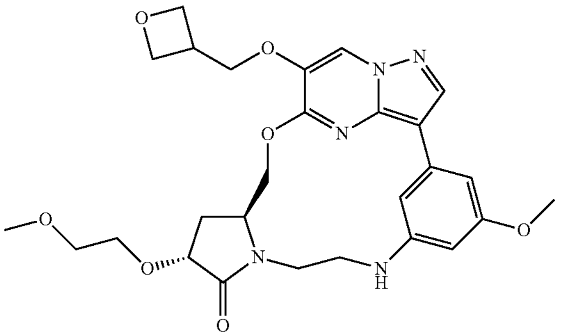
(145)
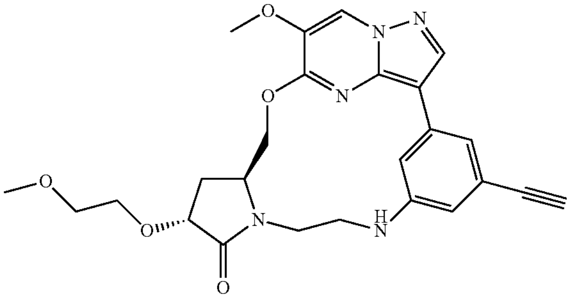

-continued (146)

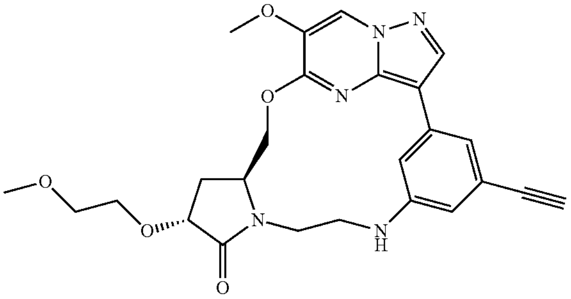

(147)

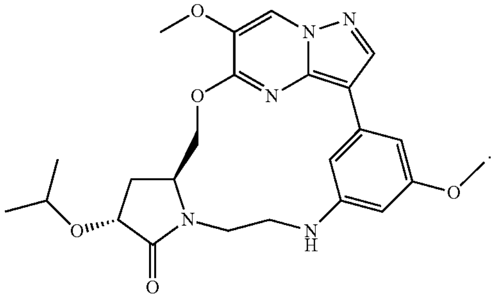

6. The compound according to claim 1, wherein carbon atom $C^A$ is in the S-$_{configuration}$.

7. A compound according to claim 1, wherein the carbon atom $C^B$ is in the R-$_{configuration}$.

8. A pharmaceutical composition comprising a compound according to claim 1 in combination with at least one pharmaceutically acceptable carrier, diluent, excipient, or adjuvant.

9. A method for treating a RIP2-kinase associated disease, the method comprising administering to a subject in need thereof an effective amount of the compound according to claim 1, optionally in combination with at least one pharmaceutically acceptable carrier, diluent, excipient, or adjuvant, wherein the RIP2-kinase associated disease is an inflammatory disorder selected from the group consisting of Crohn's disease and ulcerative colitis.

10. A method of inhibiting RIP-2 kinase in a cell, the method comprising contacting the cell with a compound according to claim 1.

* * * * *